(12) United States Patent
Hermann et al.

(10) Patent No.: US 8,901,124 B2
(45) Date of Patent: Dec. 2, 2014

(54) PYRIDAZINE AMIDE COMPOUNDS USEFUL AS SYK INHIBITORS

(71) Applicant: Hoffmann-La Roche Inc., Nutley, NJ (US)

(72) Inventors: Johannes Cornelius Hermann, Jersey City, NJ (US); Joshua Kennedy-Smith, New York, NY (US); Matthew C. Lucas, Lexington, MA (US); Fernando Padilla, Verona, NJ (US); Michael Soth, Glen Rock, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/738,098

(22) Filed: Jan. 10, 2013

(65) Prior Publication Data
US 2013/0178478 A1    Jul. 11, 2013

Related U.S. Application Data

(60) Provisional application No. 61/584,859, filed on Jan. 10, 2012, provisional application No. 61/696,855, filed on Sep. 5, 2012.

(51) Int. Cl.
| | | |
|---|---|---|
| *A61K 31/50* | (2006.01) | |
| *C07D 403/02* | (2006.01) | |
| *A61K 45/06* | (2006.01) | |
| *C07D 471/04* | (2006.01) | |
| *C07D 401/14* | (2006.01) | |
| *C07D 403/12* | (2006.01) | |
| *A61K 31/501* | (2006.01) | |
| *C07D 405/14* | (2006.01) | |
| *C07D 237/24* | (2006.01) | |
| *C07D 401/12* | (2006.01) | |

(52) U.S. Cl.
CPC ............. *C07D 471/04* (2013.01); *A61K 45/06* (2013.01); *A61K 31/50* (2013.01); *C07D 401/14* (2013.01); *C07D 403/12* (2013.01); *A61K 31/501* (2013.01); *C07D 405/14* (2013.01); *C07D 237/24* (2013.01); *C07D 401/12* (2013.01)
USPC ........ 514/247; 544/238; 546/113; 546/268.1; 548/306.1; 548/373.1; 549/356

(58) Field of Classification Search
CPC .............................. A61K 31/50; C07D 403/02
USPC ................ 514/247; 544/238; 546/113, 268.1; 548/306.1, 373.1; 549/356
See application file for complete search history.

(56) References Cited

U.S. PATENT DOCUMENTS

| | | |
|---|---|---|
| 7,902,197 B2 | 3/2011 | Elworthy et al. |
| 7,932,254 B2 | 4/2011 | DuBois et al. |
| 7,939,531 B2 | 5/2011 | Bamberg et al. |
| 8,008,298 B2 | 8/2011 | Bamberg et al. |
| 8,119,636 B2 | 2/2012 | Du Bois et al. |
| 2011/0230414 A1 | 9/2011 | Hendricks et al. |
| 2011/0230462 A1 | 9/2011 | Hendricks et al. |
| 2011/0288067 A1 | 11/2011 | Hendricks et al. |
| 2011/0288097 A1 | 11/2011 | Hendricks et al. |

FOREIGN PATENT DOCUMENTS

| | | |
|---|---|---|
| EP | 1184376 | 3/2002 |
| WO | 2007/038314 | 4/2007 |
| WO | 2009/077334 | 6/2009 |
| WO | 2009/136995 | 11/2009 |
| WO | 2010/068258 | 6/2010 |
| WO | 2010/070008 | 6/2010 |

OTHER PUBLICATIONS

International Search Report for PCT/EP2013/050136 dated Mar. 4, 2013.
Leonard et al., "JAKS and STATS: biological implications" Annual Rev. Immunol 16:293-322 (1998).
Turner et al., "Perinatal lethality and blocked B-cell developement in mice lacking the tyrosine kinase Syk:" Nature 378:298-302 (1995).
Cheng et al., "Syk tryosine kinase required for mouse viability and B-cell development" Nature 378:303-306 (1995).

*Primary Examiner* — Douglas M Willis

(57) ABSTRACT

The present invention relates to the use of novel triazolopyridine derivatives of formula I:

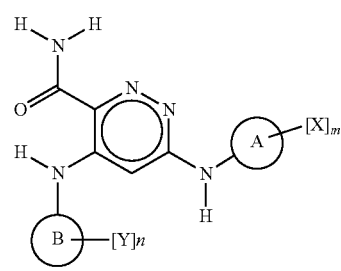

wherein all variable substituents are defined as described herein, which are SYK inhibitors and are useful for the treatment of auto-immune and inflammatory diseases.

13 Claims, No Drawings

PYRIDAZINE AMIDE COMPOUNDS USEFUL AS SYK INHIBITORS

PRIORITY TO RELATED APPLICATIONS

This application is entitled to the benefit of U.S. provisional patent application Ser. No. 61/696,855 filed on Sep. 5, 2012, and U.S. provisional patent application Ser. No. 61/584,859 filed Jan. 10, 2012.

FIELD OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma. SYK binds to the phosphorylated gamma chain of FcγRI via its SH2 domains and is essential for downstream signaling. SYK deficient mast cells demonstrate defective degranulation, arachidonic acid and cytokine secretion. This also has been shown for pharmacologic agents that inhibit SYK activity in mast cells. Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the therapeutic treatment of auto-immune and inflammatory diseases by targeting the SYK pathway or by inhibition of SYK kinase.

SUMMARY OF THE INVENTION

The application provides a compound of Formula I

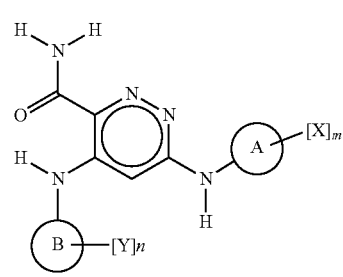

wherein:
  A is cycloalkyl or heterocycloalkyl;
    each X is independently amino, C(=O)NHR, C(=O)R, C(=O)OR, OR,
    NHC(=O)R, CH$_2$NHR, lower alkyl, hydroxy lower alkyl, or hydroxy lower alkyl amino;
    each R is independently H, or R';
    each R' is independently lower alkyl, heterocycloalkyl, phenyl, heteroaryl, heteroaryl lower alkyl, or bicyclic heteroaryl, optionally substituted with one or more R";
    each R" is independently hydroxy, lower alkyl amido, carboxy, oxo, lower alkoxy, lower alkyl amino, or lower dialkyl amino;
  m is 0, 1, or 2;
  B is phenyl or monocyclic or bicyclic heteroaryl;
    each Y is independently halo, lower alkyl, lower alkoxy, lower haloalkyl, lower hydroxyalkyl, heteroaryl, lower alkyl sulfonyl, cycloalkyl, heteroaryl, or heterocycloalkyl; and
  n is 0, 1, or 2;
or a pharmaceutically acceptable salt thereof.

The application provides a method for treating an inflammatory or autoimmune condition comprising administering to a patient in need thereof a therapeutically effective amount of the compound of Formula I.

The application provides a pharmaceutical composition comprising the compound of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

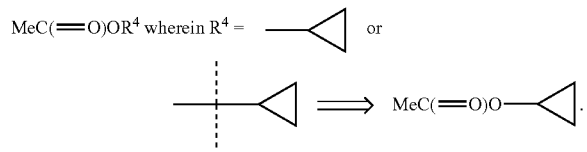

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH—Δ—C(—OH)=CH—), amide/imidic acid (—C(=O)—NH—Δ—C(—OH)=N—) and amidine (—C(=NR)—NH—Δ—C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term-(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe— or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "carboxy-alkyl" as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK

The Formula I, as represented herein:

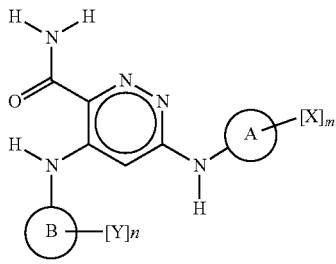

is intended to include formulae with the following resonance arrangements in the pyridazine ring:

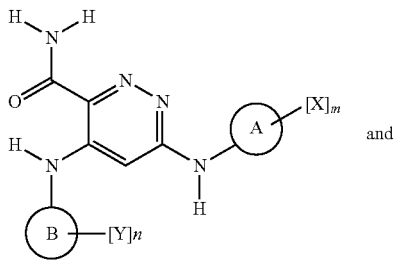

The application provides a compound of Formula I

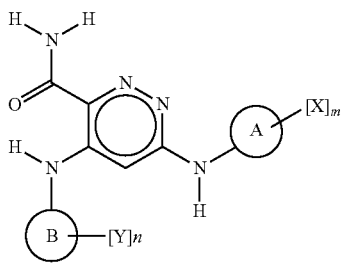

wherein:
A is cycloalkyl or heterocycloalkyl;
each X is independently amino, C(=O)NHR, C(=O)R, C(=O)OR, OR, NHC(=O)R, CH$_2$NHR, lower alkyl, hydroxy lower alkyl, or hydroxy lower alkyl amino;
each R is independently H, or R';
each R' is independently lower alkyl, heterocycloalkyl, phenyl, heteroaryl, heteroaryl lower alkyl, or bicyclic heteroaryl, optionally substituted with one or more R'';
each R'' is independently hydroxy, lower alkyl amido, carboxy, oxo, lower alkoxy, lower alkyl amino, or lower dialkyl amino;
m is 0, 1, or 2;
B is phenyl or monocyclic or bicyclic heteroaryl;
each Y is independently halo, lower alkyl, lower alkoxy, lower haloalkyl, lower hydroxyalkyl, heteroaryl, lower alkyl sulfonyl, cycloalkyl, heteroaryl, or heterocycloalkyl; and
n is 0, 1, or 2;
or a pharmaceutically acceptable salt thereof.

The application provides a compound of Formula I, wherein B is pyridyl.

The application provides a compound of Formula I, wherein A is cyclohexyl or tetrahydro pyranyl.

The application provides a compound of Formula I, wherein A is cyclohexyl.

The application provides a compound of Formula I, wherein A is tetrahydro pyranyl.

The application provides a compound of Formula I, wherein A is cyclohexyl or tetrahydro pyranyl and B is pyridyl.

The application provides a compound of Formula I, wherein A is cyclohexyl and B is pyridyl.

The application provides a compound of Formula I, wherein A is tetrahydro pyranyl and B is pyridyl.

The application provides a compound of Formula I, wherein m is 1.

The application provides a compound of Formula I, wherein A is cyclohexyl, B is pyridyl, and m is 1.

The application provides a compound of Formula I, wherein A is tetrahydro pyranyl, B is pyridyl, and m is 1.

The application provides a compound of Formula I, wherein X is amino.

The application provides a compound of Formula I, wherein A is cyclohexyl, B is pyridyl, m is 1, and X is amino.

The application provides a compound of Formula I, wherein A is tetrahydro pyranyl, B is pyridyl, m is 1, and X is amino.

The application provides a compound of Formula I, wherein n is 1.

The application provides a compound of Formula I, wherein A is cyclohexyl, B is pyridyl, m is 1, X is amino, and n is 1.

The application provides a compound of Formula I, wherein A is tetrahydro pyranyl, B is pyridyl, m is 1, X is amino, and n is 1.

The application provides a compound of Formula I, wherein Y is lower alkyl, cycloalkyl, heteroaryl, or lower alkyl sulfonyl.

The application provides a compound of Formula I, wherein Y is lower alkyl.

The application provides a compound of Formula I, wherein A is cyclohexyl, B is pyridyl, m is 1, X is amino, n is 1, and Y is lower alkyl.

The application provides a compound of Formula I, wherein A is tetrahydro pyranyl, B is pyridyl, m is 1, X is amino, n is 1, and Y is lower alkyl.

The application provides a compound of Formula I, wherein n is 2.

The application provides a compound of Formula I, wherein A is cyclohexyl, B is pyridyl, m is 1, X is amino, and n is 2.

The application provides a compound of Formula I, wherein A is tetrahydro pyranyl, B is pyridyl, m is 1, X is amino, and n is 2.

The application provides a compound of Formula I, wherein one Y is lower alkyl and the other is halo or lower alkyl.

The application provides a compound of Formula I, wherein A is cyclohexyl, B is pyridyl, m is 1, X is amino, n is 2, one Y is lower alkyl and the other is halo or lower alkyl.

The application provides a compound of Formula I, wherein A is tetrahydro pyranyl, B is pyridyl, m is 1, X is amino, n is 2, one Y is lower alkyl and the other is halo or lower alkyl.

The application provides a compound of Formula I, wherein B is pyrrolo[2,3-b]pyridinyl or pyrazolyl.

The application provides a compound of Formula I, wherein B is pyrrolo[2,3-b]pyridinyl.

The application provides a compound of Formula I, wherein B is pyrazolyl.

The application provides a compound of Formula I, wherein A is cyclohexyl, B is pyrrolo[2,3-b]pyridinyl, m is 1, X is amino, n is 1, and Y is lower alkyl.

The application provides a compound of Formula I, wherein A is cyclohexyl, B is pyrazolyl, m is 1, X is amino, n is 1, and Y is lower alkyl.

The application provides a compound selected from the group consisting of:

6-(cis-2-Amino-cyclohexylamino)-4-(6-methyl-pyridin-2-ylamino)-pyridazine-3-carboxylic acid amide;
6-(cis-2-Amino-cyclohexylamino)-4-(6-ethyl-pyridin-2-ylamino)-pyridazine-3-carboxylic acid amide;
6-((3R,4R)-3-Amino-tetrahydro-pyran-4-ylamino)-4-(6-methyl-pyridin-2-ylamino)-pyridazine-3-carboxylic acid amide;
6-((1 S,2R)-2-Amino-cyclohexylamino)-4-(6-[1,2,3]triazol-1-yl-pyridin-2-ylamino)-pyridazine-3-carboxylic acid amide;
6-(cis-2-Amino-cyclohexylamino)-4-(5-methanesulfonyl-pyridin-2-ylamino)-pyridazine-3-carboxylic acid amide;
6-((1R,2S)-2-Amino-cyclohexylamino)-4-p-tolylamino-pyridazine-3-carboxylic acid amide;
6-((1R,2S)-2-Amino-cyclohexylamino)-4-(6-isopropyl-pyridin-2-ylamino)-pyridazine-3-carboxylic acid amide;
6-((3R,4R)-3-Amino-tetrahydro-pyran-4-ylamino)-4-(5,6-dimethyl-pyridin-2-ylamino)-pyridazine-3-carboxylic acid amide;
6-((1R,2S)-2-Amino-cyclohexylamino)-4-(1-methyl-1H-pyrazol-3-ylamino)-pyridazine-3-carboxylic acid amide;
6-((1R,2S)-2-Amino-cyclohexylamino)-4-(6-methyl-pyridin-2-ylamino)-pyridazine-3-carboxylic acid amide;
6-((1R,2S)-2-Amino-cyclohexylamino)-4-(1-methyl-1H-pyrrolo[2,3-b]pyridin-6-ylamino)-pyridazine-3-carboxylic acid amide;
6-((1R,2S)-2-Amino-cyclohexylamino)-4-(6-cyclopropyl-pyridin-2-ylamino)-pyridazine-3-carboxylic acid amide;
6-((1R,2S)-2-Amino-cyclohexylamino)-4-(5-fluoro-6-methyl-pyridin-2-ylamino)-pyridazine-3-carboxylic acid amide;
6-((1S,2R)-2-Amino-cyclohexylamino)-4-(6-ethyl-pyridin-2-ylamino)-pyridazine-3-carboxylic acid amide;
6-((1R,2S)-2-Amino-cyclohexylamino)-4-(5,6-dimethyl-pyridin-2-ylamino)-pyridazine-3-carboxylic acid amide;
6-((1R,2S)-2-Amino-cyclohexylamino)-4-(5-chloro-6-methyl-pyridin-2-ylamino)-pyridazine-3-carboxylic acid amide;
6-((1R,2S)-2-Amino-cyclohexylamino)-4-(5,6-dimethoxy-pyridin-2-ylamino)-pyridazine-3-carboxylic acid amide;
6-((1R,2S)-2-aminocyclohexylamino)-4-(4,6-dimethylpyridin-2-ylamino)pyridazine-3-carboxamide 2,2,2-trifluoroacetate;
6-((1R,2S)-2-aminocyclohexylamino)-4-(6-tert-butylpyridin-2-ylamino)pyridazine-3-carboxamide;
6-(cyclohexylamino)-4-(6-cyclopropylpyridin-2-ylamino)pyridazine-3-carboxamide;
6-((1R,2S)-2-aminocyclohexylamino)-4-(6-cyclobutylpyridin-2-ylamino)pyridazine-3-carboxamide;
6-((1R,2S)-2-aminocyclohexylamino)-4-(1-methyl-1H-benzo[d]imidazol-4-ylamino)pyridazine-3-carboxamide;
4-(6-(2H-1,2,3-triazol-2-yl)pyridin-2-ylamino)-6-((1R,2S)-2-aminocyclohexylamino)pyridazine-3-carboxamide;
6-((1R,2S)-2-aminocyclohexylamino)-4-(6,7-dihydro-5H-cyclopenta[b]pyridin-2-ylamino)pyridazine-3-carboxamide;
6-((1R,2S)-2-Amino-cyclohexylamino)-4-(6-isopropyl-5-methyl-pyridin-2-ylamino)-pyridazine-3-carboxylic acid amide;
6-((1R,2S)-2-aminocyclohexylamino)-4-(6-propylpyridin-2-ylamino)pyridazine-3-carboxamide;
6-((3R,4R)-3-Amino-tetrahydro-pyran-4-ylamino)-4-(6-isopropyl-5-methyl-pyridin-2-ylamino)-pyridazine-3-carboxylic acid amide;
6-((1R,2S)-2-aminocyclohexylamino)-4-(3,5-dimethylphenylamino)pyridazine-3-carboxamide;
6-((3R,4R)-3-aminotetrahydro-2H-pyran-4-ylamino)-4-(6-tert-butylpyridin-2-ylamino)pyridazine-3-carboxamide;
6-((1R,2S)-2-aminocyclohexylamino)-4-(6-ethoxypyridin-2-ylamino)pyridazine-3-carboxamide;
6-((1R,2S)-2-aminocyclohexylamino)-4-(5-methoxy-6-propylpyridin-2-ylamino)pyridazine-3-carboxamide;
6-((1R,2S)-2-aminocyclohexylamino)-4-(6-isopropyl-5-methoxypyridin-2-ylamino)pyridazine-3-carboxamide;
4-(6-(1H-pyrazol-1-yl)pyridin-2-ylamino)-6-((1R,2S)-2-aminocyclohexylamino)pyridazine-3-carboxamide;
6-((3R,4R)-3-aminotetrahydro-2H-pyran-4-ylamino)-4-(6-isopropyl-5-methoxypyridin-2-ylamino)pyridazine-3-carboxamide;
6-((1R,2S)-2-aminocyclohexylamino)-4-(6-isopropyl-4-methylpyridin-2-ylamino)pyridazine-3-carboxamide;
6-((1R,2S)-2-aminocyclohexylamino)-4-(6-(2-cyanopropan-2-yl)pyridin-2-ylamino)pyridazine-3-carboxamide;
6-((1R,2S)-2-aminocyclohexylamino)-4-(6-(2-hydroxypropan-2-yl)pyridin-2-ylamino)pyridazine-3-carboxamide;
6-((1R,2S)-2-aminocyclohexylamino)-4-(4-methyl-6-propylpyridin-2-ylamino)pyridazine-3-carboxamide;
6-((3R,4R)-3-aminotetrahydro-2H-pyran-4-ylamino)-4-(4-methyl-6-propylpyridin-2-ylamino)pyridazine-3-carboxamide;
6-((3R,4R)-3-aminotetrahydro-2H-pyran-4-ylamino)-4-(5-methoxy-6-propylpyridin-2-ylamino)pyridazine-3-carboxamide;
6-((3R,4R)-3-aminotetrahydro-2H-pyran-4-ylamino)-4-(5-fluoro-6-isopropylpyridin-2-ylamino)pyridazine-3-carboxamide;
6-((3R,4R)-3-aminotetrahydro-2H-pyran-4-ylamino)-4-(5-isopropyl-6-methoxypyridin-2-ylamino)pyridazine-3-carboxamide; and
6-((3R,4R)-3-aminotetrahydro-2H-pyran-4-ylamino)-4-(6-isopropoxypyridin-2-ylamino)pyridazine-3-carboxamide.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

The application provides a pharmaceutical composition comprising the compound of Formula I, admixed with at least one pharmaceutically acceptable carrier, excipient or diluent.

The application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The application provides the use of the compound of formula I for the manufacture of a medicament useful for the treatment of disorders associated with Syk.

The application provides the use of the compound of formula I for the manufacture of a medicament useful for the treatment of rheumatoid arthritis.

A compound, method, or composition as described herein.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of triazolopyridine compounds according to generic Formula I.

TABLE I

| Compound | Nomenclature | Structure |
|---|---|---|
| I-1 | 6-(cis-2-Amino-cyclohexylamino)-4-(6-methyl-pyridin-2-ylamino)-pyridazine-3-carboxylic acid amide | 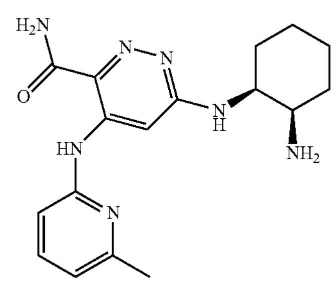 [SMILES: Cc1cccc(Nc2cc(N[C@H]3CCCC[C@H]3N)nnc2C(N)=O)n1] |
| I-2 | 6-(cis-2-Amino-cyclohexylamino)-4-(6-ethyl-pyridin-2-ylamino)-pyridazine-3-carboxylic acid amide | 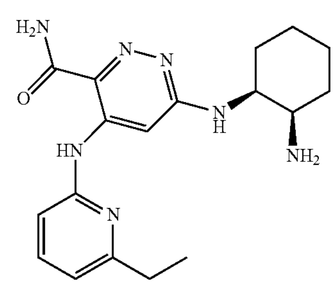 [SMILES: CCc1cccc(Nc2cc(N[C@H]3CCCC[C@H]3N)nnc2C(N)=O)n1] |

TABLE I-continued

| Compound | Nomenclature | Structure |
|---|---|---|
| I-3 | 6-((3R,4R)-3-Amino-tetrahydro-pyran-4-ylamino)-4-(6-methyl-pyridin-2-ylamino)-pyridazine-3-carboxylic acid amide | 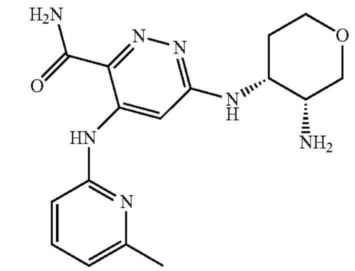 [SMILES: Cc1cccc(Nc2cc(N[C@@H]3CCOC[C@@H]3N)nnc2C(N)=O)n1] |
| I-4 | 6-((1S,2R)-2-Amino-cyclohexylamino)-4-(6-[1,2,3]triazol-1-yl-pyridin-2-ylamino)-pyridazine-3-carboxylic acid amide | 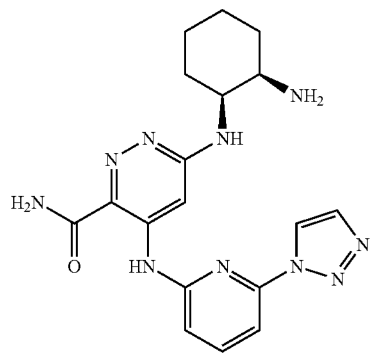 [SMILES: NC(=O)c1nnc(N[C@H]2CCCC[C@H]2N)cc1Nc1cccc(-n2ccnn2)n1] |
| I-5 | 6-(cis-2-Amino-cyclohexylamino)-4-(5-methanesulfonyl-pyridin-2-ylamino)-pyridazine-3-carboxylic acid amide | 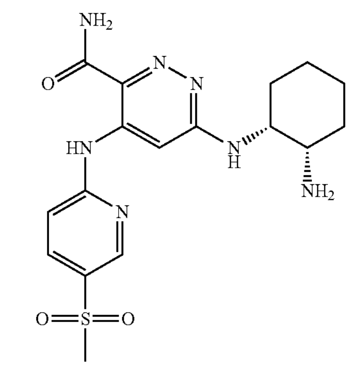 [SMILES: CS(=O)(=O)c1ccc(Nc2cc(N[C@@H]3CCCC[C@@H]3N)nnc2C(N)=O)nc1] |
| I-6 | 6-((1R,2S)-2-Amino-cyclohexylamino)-4-p-tolylamino-pyridazine-3-carboxylic acid amide | 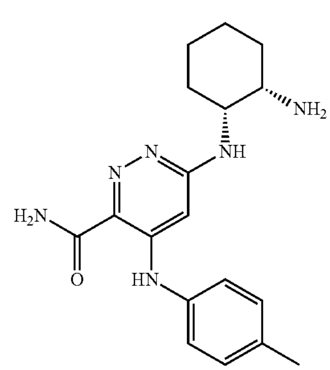 [SMILES: Cc1ccc(Nc2cc(N[C@@H]3CCCC[C@@H]3N)nnc2C(N)=O)cc1] |

TABLE I-continued

| Compound | Nomenclature | Structure |
|---|---|---|
| I-7 | 6-((1R,2S)-2-Amino-cyclohexylamino)-4-(6-isopropyl-pyridin-2-ylamino)-pyridazine-3-carboxylic acid amide | 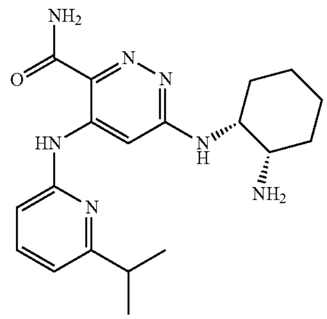 [SMILES: CC(C)c1cccc(Nc2cc(N[C@@H]3CCCC[C@@H]3N)nnc2C(N)=O)n1] |
| I-8 | 6-((3R,4R)-3-Amino-tetrahydro-pyran-4-ylamino)-4-(5,6-dimethyl-pyridin-2-ylamino)-pyridazine-3-carboxylic acid amide | 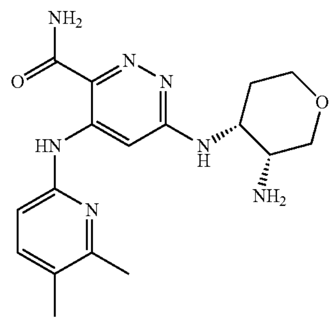 [SMILES: Cc1ccc(Nc2cc(N[C@@H]3CCOC[C@@H]3N)nnc2C(N)=O)nc1C] |
| I-9 | 6-((1R,2S)-2-Amino-cyclohexylamino)-4-(1-methyl-1H-pyrazol-3-ylamino)-pyridazine-3-carboxylic acid amide | 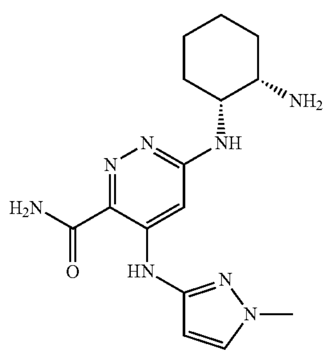 [SMILES: Cn1ccc(Nc2cc(N[C@@H]3CCCC[C@@H]3N)nnc2C(N)=O)n1] |
| I-10 | 6-((1R,2S)-2-Amino-cyclohexylamino)-4-(6-methyl-pyridin-2-ylamino)-pyridazine-3-carboxylic acid amide | 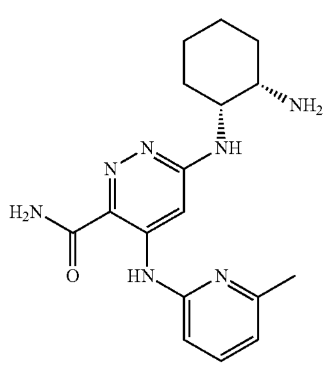 [SMILES: Cc1cccc(Nc2cc(N[C@@H]3CCCC[C@@H]3N)nnc2C(N)=O)n1] |

TABLE I-continued

| Compound | Nomenclature | Structure |
|---|---|---|
| I-11 | 6-((1R,2S)-2-Amino-cyclohexylamino)-4-(1-methyl-1H-pyrrolo[2,3-b]pyridin-6-ylamino)-pyridazine-3-carboxylic acid amide | 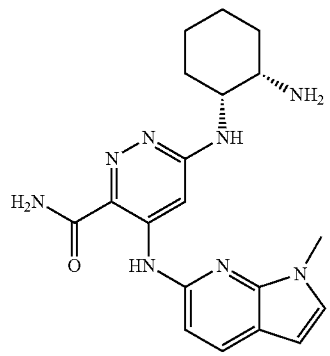 [SMILES: Cn1ccc2ccc(Nc3cc(N[C@@H]4CCCC[C@@H]4N)nnc3C(N)=O)nc21] |
| I-12 | 6-((1R,2S)-2-Amino-cyclohexylamino)-4-(6-cyclopropyl-pyridin-2-ylamino)-pyridazine-3-carboxylic acid amide | 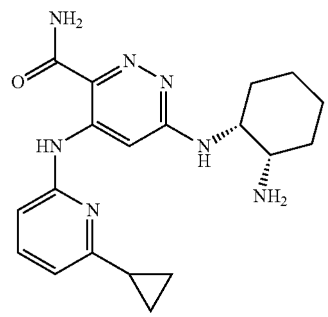 [SMILES: NC(=O)c1nnc(N[C@@H]2CCCC[C@@H]2N)cc1Nc1cccc(C2CC2)n1] |
| I-13 | 6-((1R,2S)-2-Amino-cyclohexylamino)-4-(5-fluoro-6-methyl-pyridin-2-ylamino)-pyridazine-3-carboxylic acid amide | 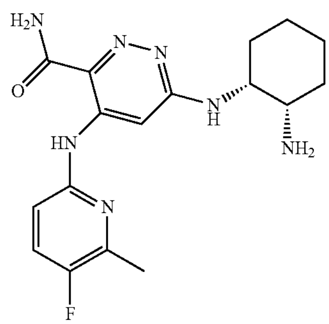 [SMILES: Cc1nc(Nc2cc(N[C@@H]3CCCC[C@@H]3N)nnc2C(N)=O)ccc1F] |
| I-14 | 6-((1S,2R)-2-Amino-cyclohexylamino)-4-(6-ethyl-pyridin-2-ylamino)-pyridazine-3-carboxylic acid amide | 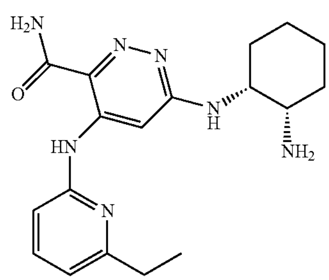 [SMILES: CCc1cccc(Nc2cc(N[C@@H]3CCCC[C@@H]3N)nnc2C(N)=O)n1] |
| I-15 | 6-((1R,2S)-2-Amino-cyclohexylamino)-4-(5,6-dimethyl-pyridin-2-ylamino)-pyridazine-3-carboxylic acid amide | 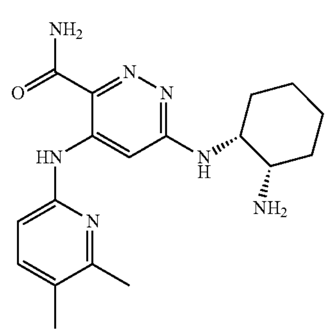 [SMILES: Cc1ccc(Nc2cc(N[C@@H]3CCCC[C@@H]3N)nnc2C(N)=O)nc1C] |

TABLE I-continued

| Compound | Nomenclature | Structure |
|---|---|---|
| I-16 | 6-((1R,2S)-2-Amino-cyclohexylamino)-4-(5-chloro-6-methyl-pyridin-2-ylamino)-pyridazine-3-carboxylic acid amide | 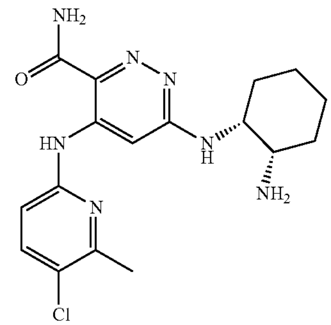 [SMILES: Cc1nc(Nc2cc(N[C@@H]3CCCC[C@@H]3N)nnc2C(N)=O)ccc1Cl] |
| I-17 | 6-((1R,2S)-2-Amino-cyclohexylamino)-4-(5,6-dimethoxy-pyridin-2-ylamino)-pyridazine-3-carboxylic acid amide | 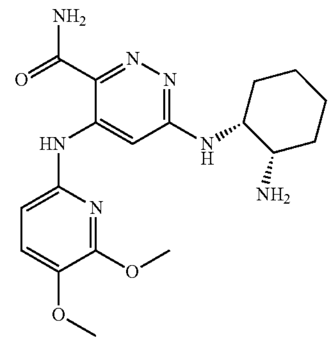 [SMILES: COc1ccc(Nc2cc(N[C@@H]3CCCC[C@@H]3N)nnc2C(N)=O)nc1OC] |
| I-18 | 6-((1R,2S)-2-aminocyclohexylamino)-4-(4,6-dimethylpyridin-2-ylamino)pyridazine-3-carboxamide 2,2,2-trifluoroacetate | 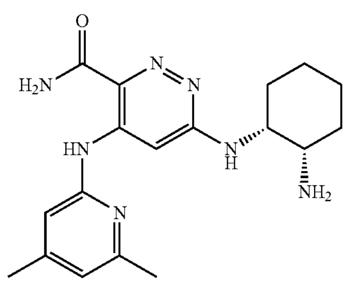 [SMILES: Cc1cc(C)nc(Nc2cc(N[C@@H]3CCCC[C@@H]3N)nnc2C(N)=O)c1] |
| I-19 | 6-((1R,2S)-2-aminocyclohexylamino)-4-(6-tert-butylpyridin-2-ylamino)pyridazine-3-carboxamide | 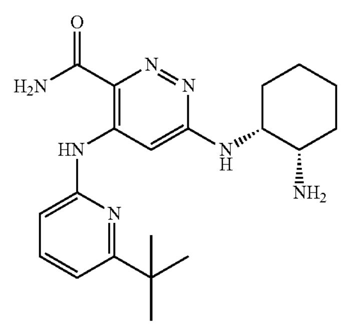 [SMILES: CC(C)(C)c1cccc(Nc2cc(N[C@@H]3CCCC[C@@H]3N)nnc2C(N)=O)n1] |
| I-20 | 6-(cyclohexylamino)-4-(6-cyclopropylpyridin-2-ylamino)pyridazine-3-carboxamide | 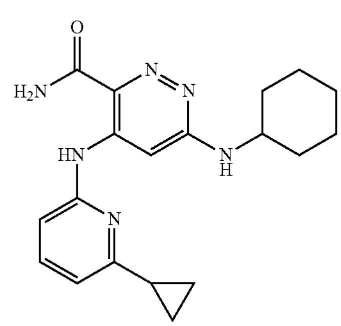 [SMILES: NC(=O)c1nnc(NC2CCCCC2)cc1Nc1cccc(C2CC2)n1] |

TABLE I-continued

| Compound | Nomenclature | Structure |
|---|---|---|
| I-21 | 6-((1R,2S)-2-aminocyclohexylamino)-4-(6-cyclobutylpyridin-2-ylamino)pyridazine-3-carboxamide | 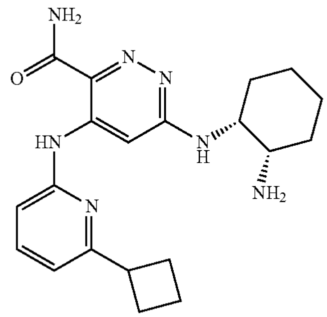 [SMILES: NC(=O)c1nnc(N[C@@H]2CCCC[C@@H]2N)cc1Nc1cccc(C2CCC2)n1] |
| I-22 | 6-((1R,2S)-2-aminocyclohexylamino)-4-(1-methyl-1H-benzo[d]imidazol-4-ylamino)pyridazine-3-carboxamide | 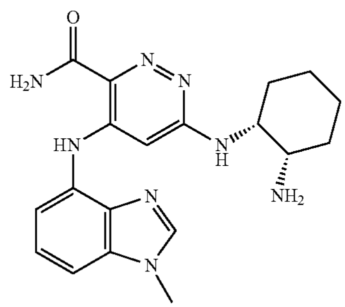 [SMILES: Cn1cnc2c(Nc3cc(N[C@@H]4CCCC[C@@H]4N)nnc3C(N)=O)cccc21] |
| I-23 | 4-(6-(2H-1,2,3-triazol-2-yl)pyridin-2-ylamino)-6-((1R,2S)-2-aminocyclohexylamino)pyridazine-3-carboxamide | 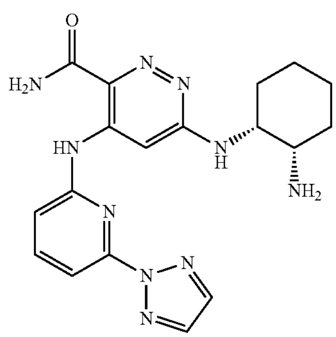 [SMILES: NC(=O)c1nnc(N[C@@H]2CCCC[C@@H]2N)cc1Nc1cccc(-n2nccn2)n1] |
| I-24 | 6-((1R,2S)-2-aminocyclohexylamino)-4-(6,7-dihydro-5H-cyclopenta[b]pyridin-2-ylamino)pyridazine-3-carboxamide | 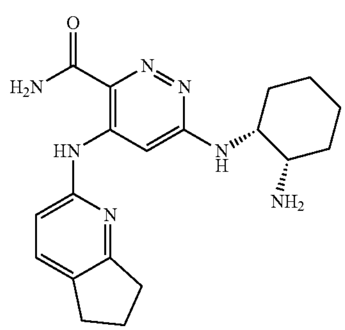 [SMILES: NC(=O)c1nnc(N[C@@H]2CCCC[C@@H]2N)cc1Nc1ccc2c(n1)CCC2] |
| I-25 | 6-((1R,2S)-2-Amino-cyclohexylamino)-4-(6-isopropyl-5-methyl-pyridin-2-ylamino)-pyridazine-3-carboxylic acid amide | 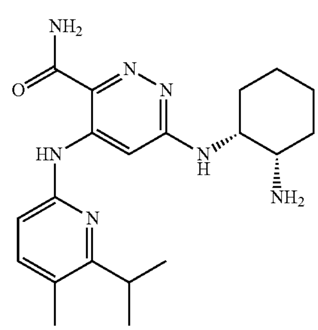 [SMILES: Cc1ccc(Nc2cc(N[C@@H]3CCCC[C@@H]3N)nnc2C(N)=O)nc1C(C)C] |

TABLE I-continued

| Compound | Nomenclature | Structure |
|---|---|---|
| I-26 | 6-((1R,2S)-2-aminocyclohexylamino)-4-(6-propylpyridin-2-ylamino)pyridazine-3-carboxamide | 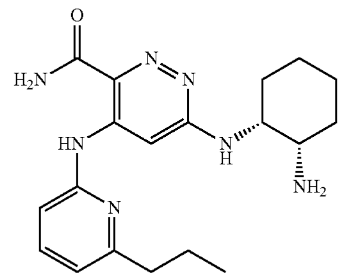 [SMILES: CCCc1cccc(Nc2cc(N[C@@H]3CCCC[C@@H]3N)nnc2C(N)=O)n1] |
| I-27 | 6-((3R,4R)-3-Amino-tetrahydro-pyran-4-ylamino)-4-(6-isopropyl-5-methyl-pyridin-2-ylamino)-pyridazine-3-carboxylic acid amide | 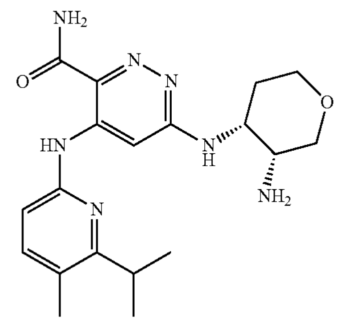 [SMILES: Cc1ccc(Nc2cc(N[C@@H]3CCOC[C@@H]3N)nnc2C(N)=O)nc1C(C)C] |
| I-28 | 6-((1R,2S)-2-aminocyclohexylamino)-4-(3,5-dimethylphenylamino)pyridazine-3-carboxamide | 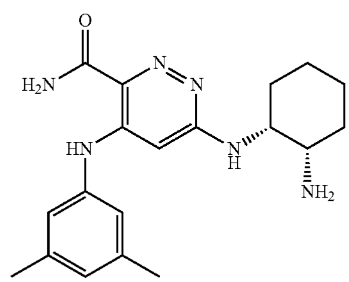 [SMILES: Cc1cc(C)cc(Nc2cc(N[C@@H]3CCCC[C@@H]3N)nnc2C(N)=O)c1] |
| I-29 | 6-((3R,4R)-3-aminotetrahydro-2H-pyran-4-ylamino)-4-(6-tert-butylpyridin-2-ylamino)pyridazine-3-carboxamide | 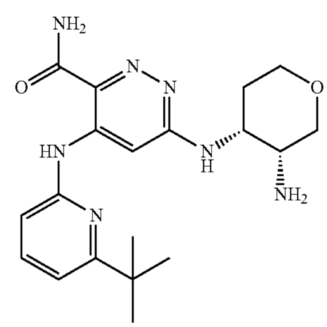 [SMILES: CC(C)(C)c1cccc(Nc2cc(N[C@@H]3CCOC[C@@H]3N)nnc2C(N)=O)n1] |
| I-30 | 6-((1R,2S)-2-aminocyclohexylamino)-4-(6-ethoxypyridin-2-ylamino)pyridazine-3-carboxamide | 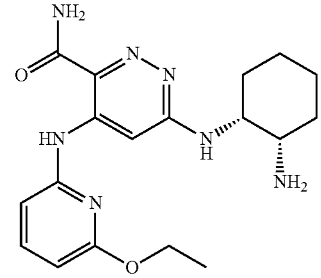 [SMILES: CCOc1cccc(Nc2cc(N[C@@H]3CCCC[C@@H]3N)nnc2C(N)=O)n1] |

TABLE I-continued

| Compound | Nomenclature | Structure |
|---|---|---|
| I-31 | 6-((1R,2S)-2-aminocyclohexylamino)-4-(5-methoxy-6-propylpyridin-2-ylamino)pyridazine-3-carboxamide | 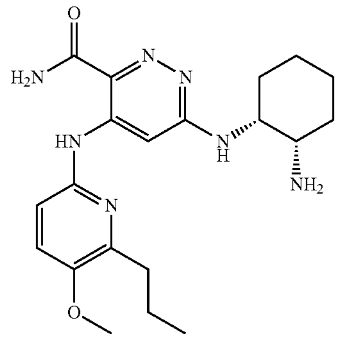 [SMILES: CCCc1nc(Nc2cc(N[C@@H]3CCCC[C@@H]3N)nnc2C(N)=O)ccc1OC] |
| I-32 | 6-((1R,2S)-2-aminocyclohexylamino)-4-(6-isopropyl-5-methoxypyridin-2-ylamino)pyridazine-3-carboxamide | 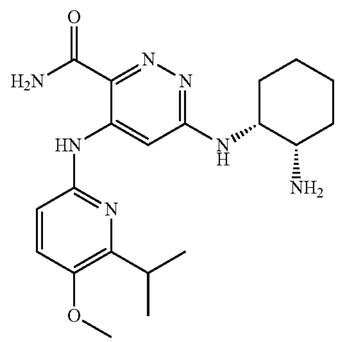 [SMILES: COc1ccc(Nc2cc(N[C@@H]3CCCC[C@@H]3N)nnc2C(N)=O)nc1C(C)C] |
| I-33 | 4-(6-(1H-pyrazol-1-yl)pyridin-2-ylamino)-6-((1R,2S)-2-aminocyclohexylamino)pyridazine-3-carboxamide | 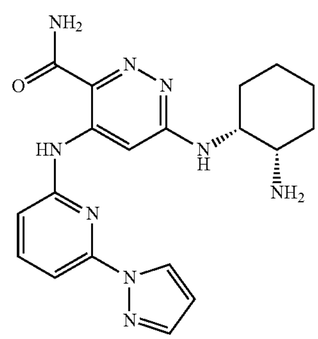 [SMILES: NC(=O)c1nnc(N[C@@H]2CCCC[C@@H]2N)cc1Nc1cccc(-n2cccn2)n1] |
| I-34 | 6-((3R,4R)-3-aminotetrahydro-2H-pyran-4-ylamino)-4-(6-isopropyl-5-methoxypyridin-2-ylamino)pyridazine-3-carboxamide | 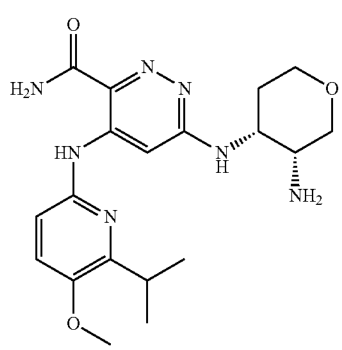 [SMILES: COc1ccc(Nc2cc(N[C@@H]3CCOC[C@@H]3N)nnc2C(N)=O)nc1C(C)C] |

TABLE I-continued

| Compound | Nomenclature | Structure |
| --- | --- | --- |
| I-35 | 6-((1R,2S)-2-aminocyclohexylamino)-4-(6-isopropyl-4-methylpyridin-2-ylamino)pyridazine-3-carboxamide | 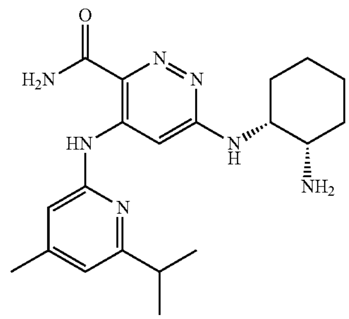 [SMILES: Cc1cc(Nc2cc(N[C@@H]3CCCC[C@@H]3N)nnc2C(N)=O)nc(C(C)C)c1] |
| I-36 | 6-((1R,2S)-2-aminocyclohexylamino)-4-(6-(2-cyanopropan-2-yl)pyridin-2-ylamino)pyridazine-3-carboxamide | 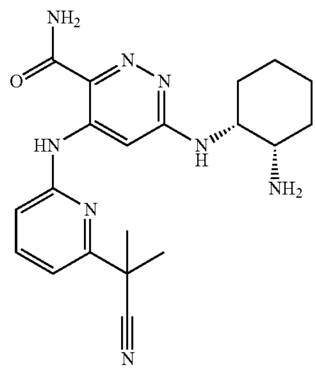 [SMILES: CC(C)(C#N)c1cccc(Nc2cc(N[C@@H]3CCCC[C@@H]3N)nnc2C(N)=O)n1] |
| I-37 | 6-((1R,2S)-2-aminocyclohexylamino)-4-(6-(2-hydroxypropan-2-yl)pyridin-2-ylamino)pyridazine-3-carboxamide | 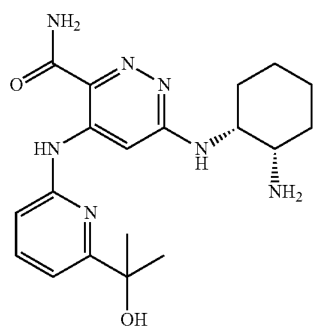 [SMILES: CC(C)(O)c1cccc(Nc2cc(N[C@@H]3CCCC[C@@H]3N)nnc2C(N)=O)n1] |
| I-38 | 6-((1R,2S)-2-aminocyclohexylamino)-4-(4-methyl-6-propylpyridin-2-ylamino)pyridazine-3-carboxamide | 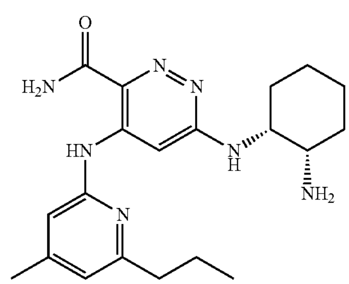 [SMILES: CCCc1cc(C)cc(Nc2cc(N[C@@H]3CCCC[C@@H]3N)nnc2C(N)=O)n1] |
| I-39 | 6-((3R,4R)-3-aminotetrahydro-2H-pyran-4-ylamino)-4-(4-methyl-6-propylpyridin-2-ylamino)pyridazine-3-carboxamide | 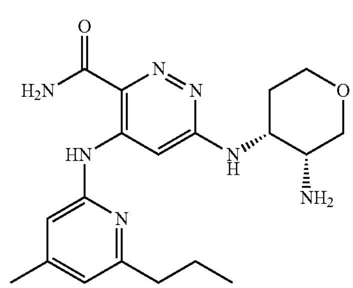 [SMILES: CCCc1cc(C)cc(Nc2cc(N[C@@H]3CCOC[C@@H]3N)nnc2C(N)=O)n1] |

TABLE I-continued

| Compound Nomenclature | | Structure |
|---|---|---|
| I-40 | 6-((3R,4R)-3-aminotetrahydro-2H-pyran-4-ylamino)-4-(5-methoxy-6-propylpyridin-2-ylamino)pyridazine-3-carboxamide | 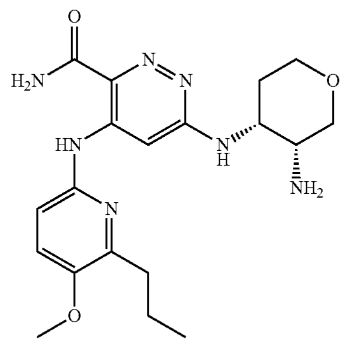 [SMILES: CCCc1nc(Nc2cc(N[C@@H]3CCOC[C@@H]3N)nnc2C(N)=O)ccc1OC] |
| I-41 | 6-((3R,4R)-3-aminotetrahydro-2H-pyran-4-ylamino)-4-(5-fluoro-6-isopropylpyridin-2-ylamino)pyridazine-3-carboxamide | 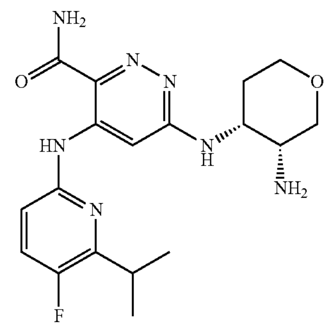 [SMILES: CC(C)c1nc(Nc2cc(N[C@@H]3CCOC[C@@H]3N)nnc2C(N)=O)ccc1F] |
| I-42 | 6-((3R,4R)-3-aminotetrahydro-2H-pyran-4-ylamino)-4-(5-isopropyl-6-methoxypyridin-2-ylamino)pyridazine-3-carboxamide | 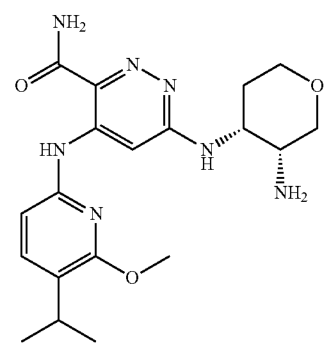 [SMILES: COc1nc(Nc2cc(N[C@@H]3CCOC[C@@H]3N)nnc2C(N)=O)ccc1C(C)C] |
| I-43 | 6-((3R,4R)-3-aminotetrahydro-2H-pyran-4-ylamino)-4-(6-isopropoxypyridin-2-ylamino)pyridazine-3-carboxamide | 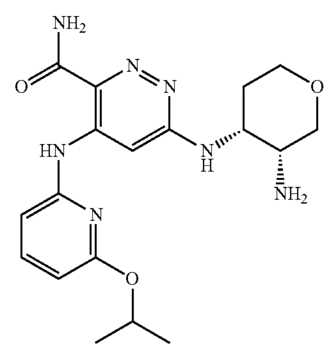 [SMILES: CC(C)Oc1cccc(Nc2cc(N[C@@H]3CCOC[C@@H]3N)nnc2C(N)=O)n1] |

Synthesis
General Scheme

The compounds of generic Formula I

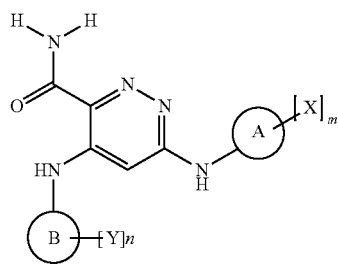

wherein:
- A is cycloalkyl or heterocycloalkyl;
  - each X is independently amino, C(=O)NHR, C(=O)R, C(=O)OR, OR, NHC(=O)R, CH$_2$NHR, lower alkyl, hydroxy lower alkyl, or hydroxy lower alkyl amino;
  - each R is independently H, or R';
  - each R' is independently lower alkyl, heterocycloalkyl, phenyl, heteroaryl, heteroaryl lower alkyl, or bicyclic heteroaryl, optionally substituted with one or more R";
  - each R" is independently hydroxy, lower alkyl amido, carboxy, oxo, lower alkoxy, lower alkyl amino, or lower dialkyl amino;
- m is 0, 1, or 2;
- B is heteroaryl;
  - each Y is independently halo, lower alkyl, lower alkoxy, lower haloalkyl, lower hydroxyalkyl, heteroaryl, lower alkyl sulfonyl, or heterocycloalkyl; and
- n is 0, 1, or 2;

or a pharmaceutically acceptable salt thereof, may be synthesized following the general scheme below:

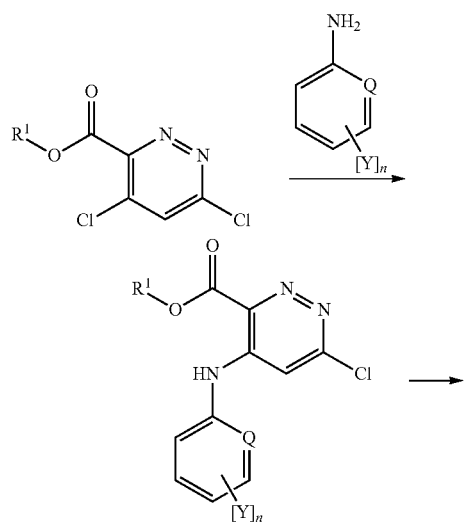

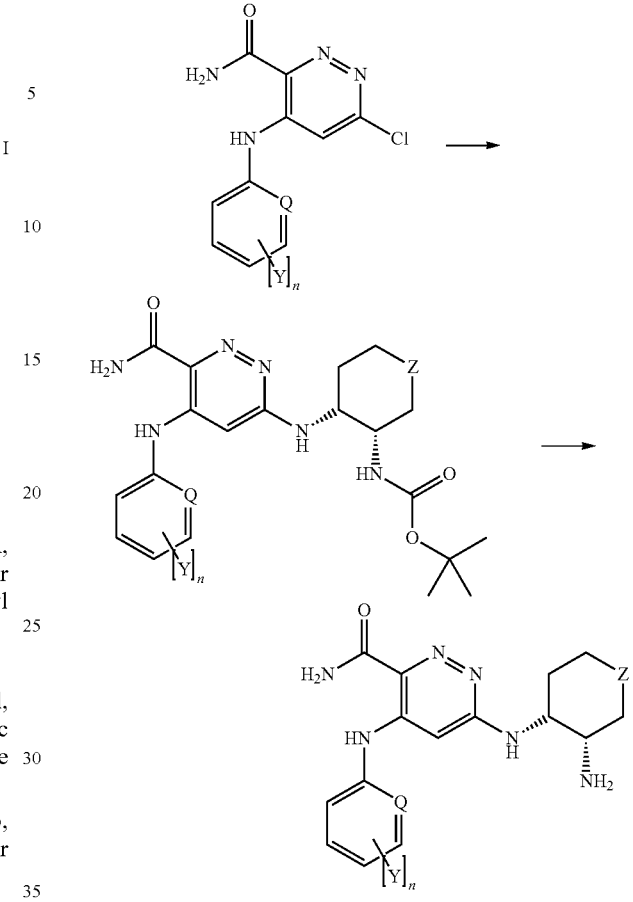

wherein Y is as defined above, Q can be CH or N, Z can be CH$_2$ or O, and R$^1$ can be lower alkyl.

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalene-sulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 h.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The application provides a method for treating an inflammatory or autoimmune condition comprising administering to a patient in need thereof a therapeutically effective amount of the compound of Formula I.

The application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The application provides a method for treating an inflammatory condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The application provides a method for treating an inflammatory condition comprising co-administering to a patient in need thereof a therapeutically effective amount of an anti-inflammatory compound in combination with the compound of Formula I.

The application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl) palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-P-(di-tert-butylphosphino)ferrocene (Q-Phos), room temperature (ambient temperature, rt or RT), sec-Butyllithium (sBuLi), tert-butyldimethylsilyl or $t$-$BuMe_2Si$ (TBDMS), tetra-n-butylammonium fluoride (TBAF), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

General Conditions.

Unless otherwise stated, all temperatures including melting points (i.e., MP) are in degrees Celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The preceding abbreviations may be used in the Preparations and Examples. All names were generated using Autonom or ChemDraw.

The following preparations and examples are given to enable those skilled in the art to more clearly understand and to practice the present invention. They should not be considered as limiting the scope of the invention, but merely as being illustrative and representative thereof.

PREPARATIVE EXAMPLES

Example 1

6-(cis-2-Amino-cyclohexylamino)-4-(6-methyl-pyridin-2-ylamino)-pyridazine-3-carboxylic acid amide

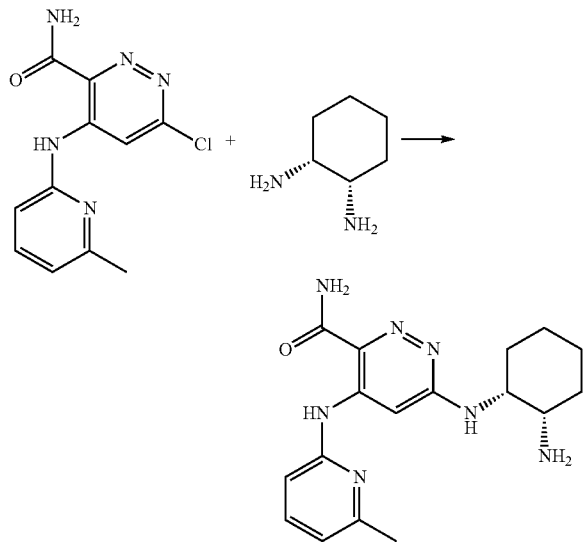

A mixture of 6-chloro-4-(6-methylpyridin-2-ylamino)pyridazine-3-carboxamide (0.0996 g, 0.378 mmol), N-methylpyrrolidinone (2 mL), and racemic cis-cyclohexane-1,2-diamine (0.270 mL, 2.29 mmol) was stirred at 150° C. for 15 h, then concentrated to a dark orange oil. Purification by chromatography (silica, 0 to 10% of a 20:1 mixture of methanol: NH$_4$OH in dichloromethane) afforded an orange solid. The solid was triturated with a mixture of methanol (1 mL) and diethyl ether (10 mL), then filtered and dried to afford 6-(cis-2-amino-cyclohexylamino)-4-(6-methyl-pyridin-2-ylamino)-pyridazine-3-carboxylic acid amide (0.041 g, 32%) as a light tan solid. $^1$H NMR (300 MHz, DMSO-d$_6$) δ ppm 1.33 (d, J=9.06 Hz, 2H), 1.47-1.79 (m, 6H), 2.13 (br. s., 2H), 3.16 (d, J=3.02 Hz, 1H), 3.89 (br. s., 1H), 6.74 (d, J=8.31 Hz, 1H), 6.79-6.89 (m, 2H), 7.52-7.67 (m, 2H), 8.09 (s, 1H), 8.35 (br. s., 1H), 11.59 (s, 1H) (peak for the pyridyl methyl group, 3H, assumed to be coincident with DMSO solvent peak). MS (EI/CI) m/z: 342 [M+H].

Example 2

6-(cis-2-Amino-cyclohexylamino)-4-(6-methyl-pyridin-2-ylamino)-pyridazine-3-carboxylic acid amide

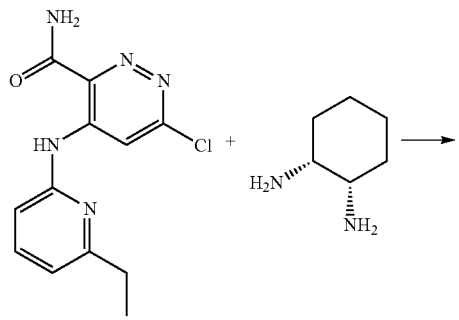

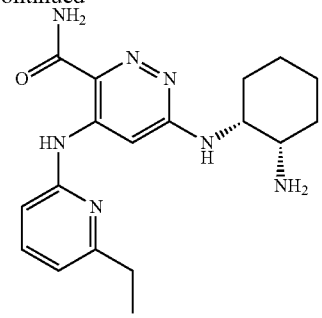

A mixture of 6-chloro-4-(6-ethylpyridin-2-ylamino)pyridazine-3-carboxamide (0.0448 g, 0.161 mmol), N-methylpyrrolidinone (1 mL) and racemic cis-cyclohexane-1,2-diamine (0.115 mL, 0.977 mmol) was stirred at 150° C. for 19 h, then cooled and concentrated in vacuo. Purification by chromatography (silica, 0 to 10% of a 20:1 mixture of methanol: NH$_4$OH in dichloromethane) afforded a yellow solid. This solid was triturated with diethyl ether (5 mL), filtered, and dried to give racemic 6-(cis-2-amino-cyclohexylamino)-4-(6-ethyl-pyridin-2-ylamino)-pyridazine-3-carboxylic acid (0.0264 g, 46%) as an off-white solid. $^1$H NMR (300 MHz, DMSO-d$_6$) δ ppm 1.26 (t, J=7.55 Hz, 5H), 1.43-1.79 (m, 8H), 2.74 (q, J=7.43 Hz, 2H), 3.11 (br. s., 1H), 3.78 (br. s., 1H), 6.71-6.81 (m, 2H), 6.85 (d, J=7.55 Hz, 1H), 7.55-7.68 (m, 2H), 8.07 (s, 1H), 8.36 (br. s., 1H), 11.65 (s, 1H). MS (EI/CI) m/z: 356 [M+H].

Example 3

6-((3R,4R)-3-Amino-tetrahydro-pyran-4-ylamino)-4-(6-methyl-pyridin-2-ylamino)-pyridazine-3-carboxylic acid amide

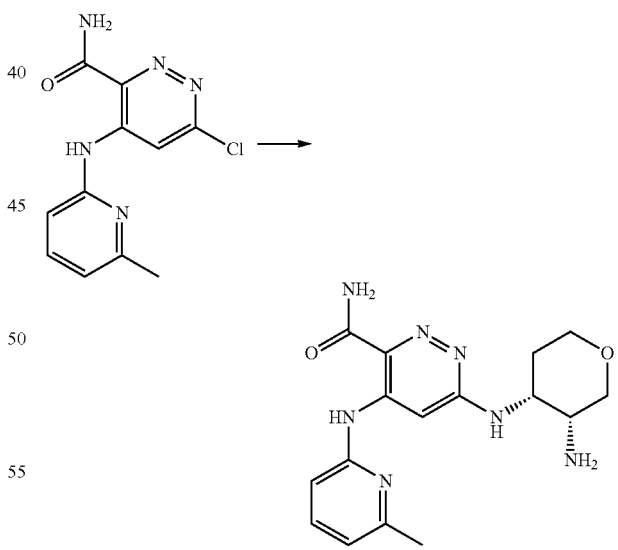

Step 1

6-Chloro-4-(6-methyl-pyridin-2-ylamino)-pyridazine-3-carboxylic acid amide (150 mg, 0.57 mmol) and tert-butyl (3R,4R)-4-aminotetrahydro-2H-pyran-3-ylcarbamate (185 mg, 0.85 mmol) were dissolved in 1,4-dioxane (2.8 mL) and N,N-diisopropylethylamine (0.25 mL, 1.4 mmol). The reaction mixture was stirred at 150° C. for 4 d. Further tert-butyl (3R,4R)-4-aminotetrahydro-2H-pyran-3-ylcarbamate (50 mg, 0.23 mmol) and N,N-diisopropylethylamine (0.04 mL, 0.23 mmol) was added in four portions (every 36 h for 144 h). The mixture was cooled, and then water and ethyl acetate were added. The aqueous layer was extracted with ethyl acetate, and the combined organic layers were washed with sodium chloride solution and dried over sodium sulfate. After concentration, the residue was purified by chromatography (silica, 0 to 7% methanol in dichloromethane) to give {(3R, 4R)-4-[6-carbamoyl-5-(6-methyl-pyridin-2-ylamino)-pyridazin-3-ylamino]-tetrahydro-pyran-3-yl}-carbamic acid tert-butyl ester (60 mg, 18%) as a clear amorphous residue. This was 83% pure and was used directly without further purification. MS (EI/CI) m/z: 444 [M+H].

Step 2 tert-butyl (3R,4R)-4-(6-carbamoyl-5-(6-methylpyridin-2-ylamino)pyridazin-3-ylamino)tetrahydro-2H-pyran-3-ylcarbamate (60 mg, 83% pure, 0.112 mmol) was dissolved in dichloromethane (0.85 mL) and cooled to 0° C. Trifluoroacetic acid (0.35 mL, 4.49 mmol) was added drop-wise, then the mixture was warmed to room temperature. After 3 h, the mixture was concentrated in vacuo then water, sodium bicarbonate solution and ethyl acetate were added. The aqueous phase was extracted with ethyl acetate. Sodium chloride was added to the aqueous layer and it was further extracted with ethyl acetate. The combined organic extracts were washed with saturated aqueous sodium chloride solution, dried over sodium sulfate, filtered, and concentrated in vacuo. Purification by chromatography (silica, 0-10% methanol in dichloromethane) gave 6-((3R,4R)-3-amino-tetrahydropyran-4-ylamino)-4-(6-methyl-pyridin-2-ylamino)-pyridazine-3-carboxylic acid amide (11 mg, 28%) as an off-white solid. $^1$H NMR (300 MHz, DMSO-$d_6$) δ ppm 11.61 (s, 1H) 8.39 (br. s., 1H) 8.12 (s, 1H) 7.65 (br. s., 1H) 7.60 (t, J=7.7 Hz, 1H) 6.95 (d, J=7.2 Hz, 1H) 6.85 (d, J=7.6 Hz, 1H) 6.75 (d, J=8.3 Hz, 1H) 4.10 (br. s., 1H) 3.79-3.89 (m, 1H) 3.66-3.75 (m, 1H) 3.49-3.57 (m, 1H) 3.37-3.47 (m, 1H) 3.00-3.08 (m, 1H) 1.94-2.12 (m, 1H) 1.76-1.92 (m, 1H) 1.63-1.73 (m, 1H). MS (EI/CI) m/z: 344 [M+H].

Example 4

6-((1S,2R)-2-Amino-cyclohexylamino)-4-(6-[1,2,3]triazol-1-yl-pyridin-2-ylamino)-pyridazine-3-carboxylic acid amide

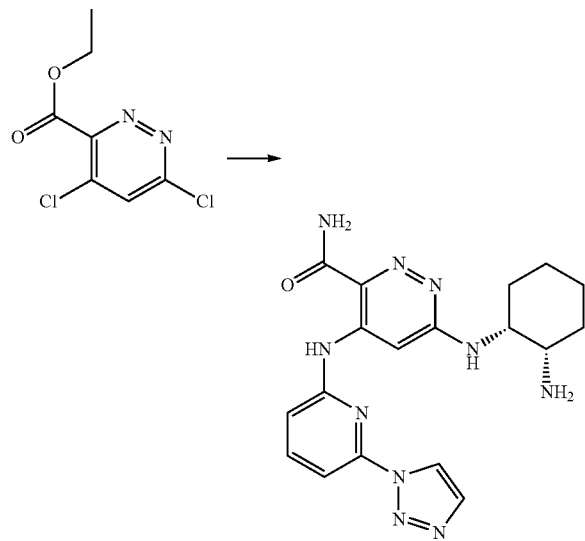

Step 1

6-(di-tert-butyloxycarbonyl-amino)-2-bromopyridine (1.26 g, 3.4 mmol), copper powder (1.29 g, 6.75 mmol), 1H-1,2,3-triazole (4.66 g, 67.5 mmol) and potassium hydroxide (0.38 g, 6.75 mmol) were combined and stirred at 130° C. for 16 h. After cooling the mixture was adsorbed on to silica gel and purified twice by chromatography (silica, 0 to 7% methanol in dichloromethane) then (silica, 25 to 100% ethyl acetate in hexanes) to give firstly 6-[1,2,3]triazol-1-yl-pyridin-2-ylamine (203 mg, 37%) as a white solid, and then 6-[1,2,3]triazol-2-yl-pyridin-2-ylamine (219 mg, 40%) as a white solid. 6-[1,2,3]triazol-1-yl-pyridin-2-ylamine: $^1$H NMR (300 MHz, CHLOROFORM-d) δ ppm 8.49 (d, J=1.1 Hz, 1H) 7.80 (d, J=1.1 Hz, 1H) 7.60-7.68 (m, 1H) 7.51 (d, J=7.2 Hz, 1H) 6.53 (d, J=7.9 Hz, 1H); MS (EI/CI) m/z: 162 [M+H]; 6-[1,2,3]triazol-2-yl-pyridin-2-ylamine: $^1$H NMR (300 MHz, CHLOROFORM-d) δ ppm 7.86 (s, 2H) 7.62 (t, J=7.9 Hz, 1H) 7.40 (d, J=7.9 Hz, 1H) 6.52 (d, J=7.9 Hz, 1H); MS (EI/CI) m/z: 162 [M+H].

Step 2

4,6-Dichloro-pyridazine-3-carboxylic acid ethyl ester (200 mg, 0.905 mmol) and 6-[1,2,3]triazol-1-yl-pyridin-2-ylamine (147 mg, 0.914 mmol) were dissolved in 1,4-dioxane (6 mL) and the solution was purged with argon. Tris(dibenzylideneacetone)dipalladium (83 mg, 0.09 mmol), Xantphos (105 mg, 0.18 mmol), and cesium carbonate (884 mg, 2.7 mmol) were added and the reaction mixture was heated to 100° C. for 1 h. The reaction mixture was cooled, diluted with saturated aqueous sodium bicarbonate solution, then extracted with ethyl acetate. The combined organic extracts were washed with saturated aqueous sodium chloride solution, dried over sodium sulfate, filtered and concentrated in vacuo. Purification by chromatography (silica, 25 to 100% ethyl acetate in hexanes) gave 6-chloro-4-(6-[1,2,3]triazol-1-yl-pyridin-2-ylamino)-pyridazine-3-carboxylic acid ethyl ester (48 mg, 15%) as a light yellow solid. $^1$H NMR (300 MHz, CHLOROFORM-d) δ ppm 9.34-9.43 (m, 1H) 8.54-8.57 (m, 1H) 8.43 (d, J=1.1 Hz, 1H) 7.87-7.97 (m, 3H) 7.60 (dd, J=7.4, 1.3 Hz, 1H) 4.55 (q, J=7.2 Hz, 2H) 1.50 (t, J=7.2 Hz, 3H); MS (EI/CI) m/z: 346 [M+H].

Step 3

6-Chloro-4-(6-[1,2,3]triazol-1-yl-pyridin-2-ylamino)-pyridazine-3-carboxylic acid ethyl ester (48 mg, 0.139 mmol) was suspended in 7M ammonia in methanol (23 mL). After 4 h, the reaction mixture was concentrated in vacuo to give 6-chloro-4-(6-[1,2,3]triazol-1-yl-pyridin-2-ylamino)-pyridazine-3-carboxylic acid amide (44 mg, 100%) as an off-white solid which was used directly in the next step without purification. MS (EI/CI) m/z: 317 [M+H].

Step 4

6-Chloro-4-(6-[1,2,3]triazol-1-yl-pyridin-2-ylamino)-pyridazine-3-carboxylic acid amide (44 mg, 0.139 mmol) was dissolved in N-methylpyrrolidinone (0.9 mL). cis-Cyclohexane-1,2-diamine (95 mg, 0.834 mmol) was added and the mixture was warmed to 150° C. After 16 h the mixture was cooled and concentrated in vacuo. The residue obtained was diluted with saturated aqueous sodium bicarbonate solution, then extracted with ethyl acetate. The combined organic extracts were washed with saturated aqueous sodium chloride solution, dried over sodium sulfate, filtered, and concentrated in vacuo. Purification by chromatography (silica, 0:0:10 to 0.1:1:10 ammonium hydroxide:methanol:dichloromethane) gave 6-(cis-2-amino-cyclohexylamino)-4-(6-[1,2,3]triazol-1-yl-pyridin-2-ylamino)-pyridazine-3-carboxylic acid amide (13 mg, 23%) as a brown solid. $^1$H NMR (300 MHz, DMSO-$d_6$) δ ppm 10.33 (s, 1H) 9.13 (d, J=8.3 Hz, 1H) 8.84 (d, J=1.1 Hz, 1H) 8.16-8.26 (m, 1H) 8.03 (d, J=0.8 Hz, 1H) 7.96 (d, J=7.9 Hz, 1H) 7.67 (s, 1H) 7.51-7.57 (m, 1H) 7.51-7.57 (m, 1H) 7.43-7.50 (m, 1H) 3.60 (br. s., 1H) 2.96-3.03 (m, 1H) 1.21-1.64 (m, 8H); MS (EI/CI) m/z: 395 [M+H].

Example 5

6-(cis-2-Amino-cyclohexylamino)-4-(5-methane-sulfonyl-pyridin-2-ylamino)-pyridazine-3-carboxylic acid amide Step 1

Methyl 6-chloro-4-(5-(methylsulfonyl)pyridin-2-ylamino)pyridazine-3-carboxylate

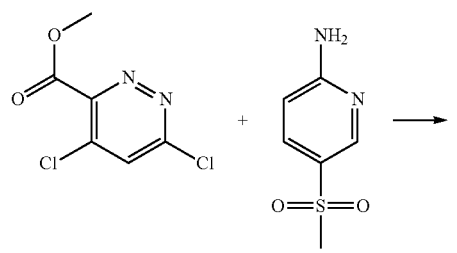

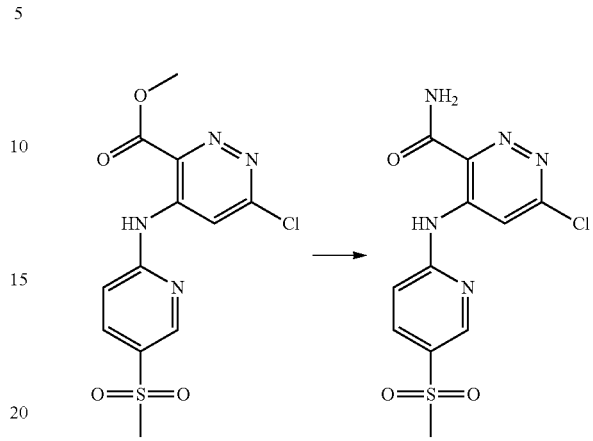

A flask was charged with methyl 4,6-dichloropyridazine-3-carboxylate (200 mg, 0.966 mmol), 5-(methylsulfonyl)pyridin-2-amine (183 mg, 1.06 mmol), Pd$_2$(dba)$_3$ (88.5 mg, 0.097 mmol), xantphos (112 mg, 0.193 mmol) and cesium carbonate (944 mg, 2.9 mmol). 1,4-Dioxane (6.0 mL) was added and argon was bubbled through it while sonicating the flask for 5 min. The flask was sealed and heated at 100° C. for 1 h. After cooling the mixture was filtered through celite and the filter cake washed with CH$_2$Cl$_2$. The filtrates were concentrated in vacuo then purified by chromatography (spherical silica 20-45 μM, 23 g, Versaflash Supelco, 0 to 100% ethyl acetate in hexanes, 30 min) to give methyl 6-chloro-4-(5-(methylsulfonyl)pyridin-2-ylamino)pyridazine-3-carboxylate (62 mg, 19%) as a light yellow solid. $^1$H NMR (400 MHz, CHLOROFORM-d) δ ppm 11.18 (s, 1H) 9.31 (s, 1H) 8.98 (d, J=2.27 Hz, 1H) 8.19 (dd, J=8.59, 2.53 Hz, 1H) 7.09 (dd, J=8.84, 0.76 Hz, 1H) 4.15 (s, 3H) 3.15 (s, 3H). LCMS (EI/CI) m/z: 342.9 [M+H].

Step 2

6-Chloro-4-(5-(methylsulfonyl)pyridin-2-ylamino) pyridazine-3-carboxamide

Methyl 6-chloro-4-(5-(methylsulfonyl)pyridin-2-ylamino)pyridazine-3-carboxylate (62 mg, 0.181 mmol) was suspended in ammonia (7M in methanol, 3.94 g, 5 mL, 35.0 mmol). The reaction vessel was sealed. After 18 h, the mixture was concentrated in vacuo to give 6-chloro-4-(5-(methylsulfonyl)pyridin-2-ylamino)pyridazine-3-carboxamide (60 mg, 100%) as an off-white solid that was used directly in the next step without further purification.

Step 3

6-(cis-2-Aminocyclohexylamino)-4-(5-(methylsulfonyl)pyridin-2-ylamino)pyridazine-3-carboxamide

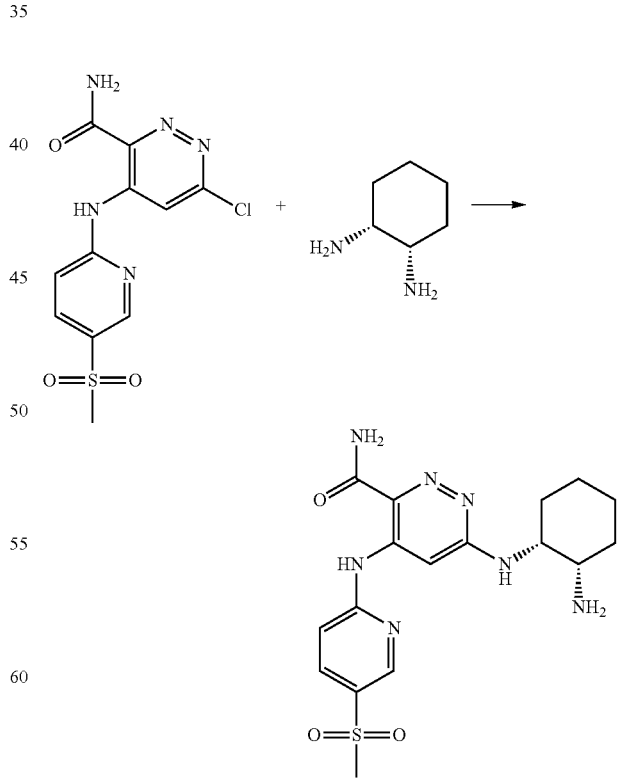

A mixture of 6-chloro-4-(5-(methylsulfonyl)pyridin-2-ylamino)pyridazine-3-carboxamide (60 mg, 0.183 mmol), cis-cyclohexane-1,2-diamine (125 mg, 1.1 mmol) and N-methyl-2-pyrrolidinone (2 mL) was heated to 150° C. After 18 h, the reaction mixture was cooled and concentrated in vacuo. Purification by chromatography (spherical silica 20-45 uM, 23 g, Versaflash Supelco, 0 to 5% MeOH containing 10% NH₄OH in CH₂Cl₂, 20 min) gave a solid residue. This residue was dissolved in MeOH and CH₂Cl₂, then precipitated by addition of cyclohexane. The solid formed was obtained by decantation of the mother liquor, then dried to give 6-(cis-2-aminocyclohexylamino)-4-(5-(methylsulfonyl)pyridin-2-ylamino)pyridazine-3-carboxamide (19 mg, 45.6 μmol, 25%) as a beige solid. ¹H NMR (300 MHz, DMSO-d₆) δ ppm 12.21 (s, 1H) 8.73 (d, J=2.27 Hz, 1H) 8.48 (br. s., 1H) 8.16 (s, 1H) 8.12 (dd, J=8.69, 2.64 Hz, 1H) 7.75 (br. s., 1H) 7.14 (d, J=8.69 Hz, 1H) 7.03 (d, J=7.93 Hz, 1H) 4.06 (br. s., 1H) 3.26 (s, 3H) 3.09 (br. s., 1H) 1.24-1.78 (m, 10H). LCMS (EI/CI) m/z: 406 [M+H].

Example 6

6-((1R,2S)-2-Amino-cyclohexylamino)-4-p-tolylamino-pyridazine-3-carboxylic acid amide

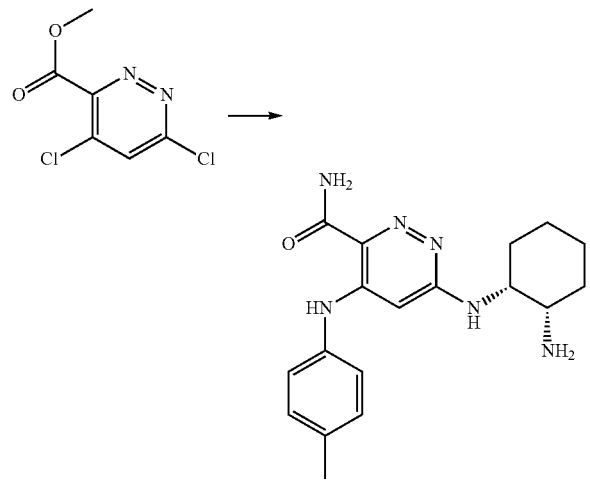

Step 1

6-Chloro-4-p-tolylamino-pyridazine-3-carboxylic acid methyl ester 4,6-Dichloro-pyridazine-3-carboxylic acid methyl ester (200 mg, 0.966 mmol), p-toluidine (104 mg, 0.966 mmol) and N,N-diisopropylethylamine (0.34 mL, 1.93 mmol) were dissolved in N,N-dimethylacetamide (2.4 mL), then heated at 110° C. for 1 h. The reaction mixture was cooled, then poured into ethyl acetate and water. The aqueous layer was extracted with ethyl acetate, and then the combined organic layers were washed with saturated aqueous sodium chloride solution, dried over sodium sulfate, filtered, and concentrated in vacuo. Purification by chromatography (silica, 0 to 50% ethyl acetate in hexanes) gave 6-chloro-4-p-tolylamino-pyridazine-3-carboxylic acid methyl ester (214 mg, 79%) as an off-white solid. ¹H NMR (300 MHz, CHLOROFORM-d) δ ppm 9.61 (br. s., 1H) 7.23-7.32 (m, 2H) 7.13 (d, J=7.9 Hz, 2H) 6.96 (s, 1H) 4.08 (s, 3H) 2.41 (s, 3H); LCMS (EI/CI) m/z: 278 [M+H].

Step 2

6-Chloro-4-p-tolylamino-pyridazine-3-carboxylic acid amide

6-Chloro-4-p-tolylamino-pyridazine-3-carboxylic acid methyl ester (210 mg, 0.756 mmol) was suspended in 7M ammonia in methanol (7 mL). After 3.5 h, the reaction mixture was concentrated in vacuo to give 6-chloro-4-(6-[1,2,3]triazol-1-yl-pyridin-2-ylamino)-pyridazine-3-carboxylic acid amide (199 mg, 100%) as an off-white solid which was used directly in the next step without purification. MS (EI/CI) m/z: 263 [M+H].

Step 3

[(1S,2R)-2-(6-Carbamoyl-5-p-tolylamino-pyridazin-3-ylamino)-cyclohexyl]-carbamic acid tert-butyl ester 6-Chloro-4-p-tolylamino-pyridazine-3-carboxylic acid amide (199 mg, 0.758 mmol) and tert-butyl (1S,2R)-2-aminocyclohexylcarbamate (325 mg, 1.52 mmol) were dissolved in N-methylpyrrolidinone (4.7 mL). The reaction mixture was heated at 150° C. for 16 h, then additional tert-butyl (1S,2R)-2-aminocyclohexylcarbamate (550 mg, 2.57 mmol total) was added in three portions over 6 d. The reaction mixture was cooled, diluted with ethyl acetate and saturated aqueous sodium bicarbonate solution, and extracted with ethyl acetate. The combined organic extracts were washed with water and brine, then dried (sodium sulfate), filtered, and concentrated in vacuo. The residue obtained was purified by chromatography (silica, 0 to 5% methanol in dichloromethane) to give [(1S,2R)-2-(6-carbamoyl-5-p-tolylamino-pyridazin-3-ylamino)-cyclohexyl]-carbamic acid tert-butyl ester (26 mg, 8%) as a light brown amorphous residue. LCMS (EI/CI) m/z: 441 [M+H].

Step 4

6-((1R,2S)-2-Amino-cyclohexylamino)-4-p-tolylamino-pyridazine-3-carboxylic acid amide

[(1S,2R)-2-(6-carbamoyl-5-p-tolylamino-pyridazin-3-ylamino)-cyclohexyl]-carbamic acid tert-butyl ester (26 mg, 0.059 mmol) was dissolved in dichloromethane (0.6 mL) then cooled to 0° C. Trifluoroacetic acid (0.27 mL, 3.54 mmol) was added drop-wise then the reaction mixture was warmed to 25° C. After 4 h, the mixture was cooled in an ice bath and neutralized with sodium bicarbonate solution. The mixture was extracted with ethyl acetate, and the combined organic layers washed with brine, dried (sodium sulfate), filtered, and concentrated in vacuo. Purification by chromatography (silica, 0 to 80% of a 0.1:0.01 solution of methanol:NH₄OH in dichloromethane) gave 6-((1R,2S)-2-amino-cyclohexylamino)-4-p-tolylamino-pyridazine-3-carboxylic acid amide (15 mg, 72%) as an off-white solid. ¹H NMR (300 MHz, DMSO-d₆) δ ppm 10.30 (s, 1H) 8.20-8.30 (m, 1H) 7.44-7.55 (m, 1H) 7.17-7.27 (m, 2H) 7.07-7.17 (m, 2H) 6.59 (d, J=7.9 Hz, 1H) 6.33 (s, 1H) 3.95-4.09 (m, 1H) 2.93-3.06 (m, 1H) 2.30 (s, 3H) 1.19-1.68 (m, 9H); LCMS (EI/CI) m/z: 341 [M+H].

Example 7

6-((1R,2S)-2-Amino-cyclohexylamino)-4-(6-isopropyl-pyridin-2-ylamino)-pyridazine-3-carboxylic acid amide Step 1

Methyl 6-chloro-4-(6-isopropylpyridin-2-ylamino)pyridazine-3-carboxylate

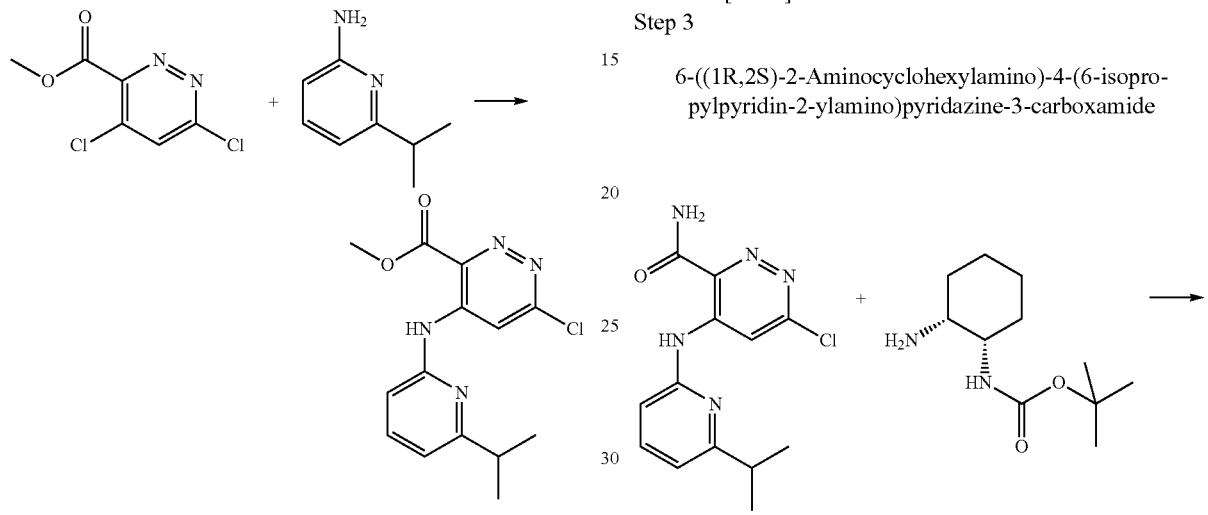

A stirred solution of methyl 4,6-dichloropyridazine-3-carboxylate (255 mg, 1.23 mmol) and 6-isopropylpyridin-2-amine (252 mg, 1.85 mmol) in acetonitrile (8.0 mL) was heated at 140° C. for 21 h. After cooling to room temperature the reaction mixture was concentrated in vacuo, then the residue purified by chromatography (silica, 20-45 μm, 80 g, Thomson, 0 to 10% acetone in dichloromethane, 20 min) to give methyl 6-chloro-4-(6-isopropylpyridin-2-ylamino)pyridazine-3-carboxylate (113 mg, 30%) as a yellow solid. $^1$H NMR (400 MHz, CHLOROFORM-d) δ ppm 10.64 (br. s., 1H) 9.39 (s, 1H) 7.63 (t, J=7.83 Hz, 1H) 6.94 (d, J=7.58 Hz, 1H) 6.78 (d, J=8.08 Hz, 1H) 4.12 (s, 3H) 3.01-3.19 (m, 1H) 1.31-1.42 (m, 6H). LCMS (EI/CI) m/z: 307 [M+H].

Step 2

6-Chloro-4-(6-isopropylpyridin-2-ylamino)pyridazine-3-carboxamide

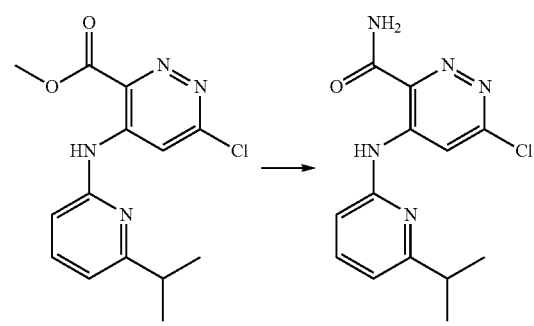 [SMILES: COC(=O)c1nnc(Cl)cc1Nc1cccc(C(C)C)n1 ; CC(C)c1cccc(Nc2cc(Cl)nnc2C(N)=O)n1]

Methyl 6-chloro-4-(6-isopropylpyridin-2-ylamino)pyridazine-3-carboxylate (99 mg, 322 μmol) was added to a pressure tube followed by ammonia (7M in methanol, 3.94 g, 5 mL, 35.0 mmol). The mixture was heated to 50° C. for 18 h, and then additional 7 N ammonia in methanol (7.5 mL) was added. After 24 h, the mixture was cooled, filtered and dried to afford 6-chloro-4-(6-isopropylpyridin-2-ylamino)pyridazine-3-carboxamide (103 mg, 100%) as a yellow solid. $^1$H NMR (400 MHz, CHLOROFORM-d) δ ppm 11.58 (br. s., 1H) 9.41 (s, 1H) 8.20 (br. s., 1H) 7.60 (t, J=7.83 Hz, 1H) 6.90 (d, J=7.33 Hz, 1H) 6.77 (d, J=8.08 Hz, 1H) 5.72 (br. s., 1H) 3.01-3.16 (m, 1H) 1.37 (d, J=6.82 Hz, 6H). LCMS (EI/CI) m/z: 292 [M+H].

Step 3

6-((1R,2S)-2-Aminocyclohexylamino)-4-(6-isopropylpyridin-2-ylamino)pyridazine-3-carboxamide

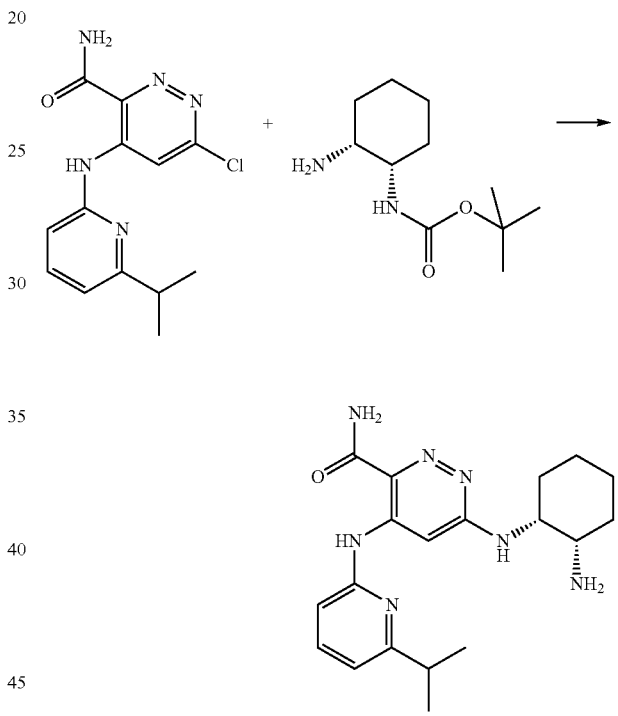

To a solution of 6-chloro-4-(6-isopropylpyridin-2-ylamino)pyridazine-3-carboxamide (102 mg, 350 μmol) in N-methyl-2-pyrrolidinone (6 ml) was added tert-butyl (1S,2R)-2-aminocyclohexylcarbamate (150 mg, 699 μmol) and the mixture heated to 150° C. for 3 d. Additional tert-butyl (1S,2R)-2-aminocyclohexylcarbamate (150 mg, 699 μmol) was added and the reaction heated to 150° C. for an additional 2 d, then cooled, concentrated, and purified by chromatography (silica, 50 μm, 40 g, Analogix, 96:3.8:0.2 to 84:15.2:0.8; dichloromethane:MeOH:NH$_4$OH) to give a mixture of tert-butyl (1S,2R)-2-(6-carbamoyl-5-(6-isopropylpyridin-2-ylamino)pyridazin-3-ylamino)cyclohexylcarbamate and 6-((1R,2S)-2-aminocyclohexylamino)-4-(6-isopropylpyridin-2-ylamino)pyridazine-3-carboxamide (33 mg). This mixture was dissolved in dichloromethane (2 mL) then TFA (370 mg, 250 μL, 3.24 mmol) was added. After 18 h, the mixture was concentrated in vacuo and the residue obtained was purified by chromatography (spherical silica, 20-45 μm, 25 g, Versaflash Supelco, 96:3.8:0.2 to 84:15.2:0.8 dichloromethane:MeOH:NH₄OH, 25 min gradient to afford 6-((1R,2S)-2-aminocyclohexylamino)-4-(6-isopropylpyridin-2-ylamino)pyridazine-3-carboxamide (12 mg, 9%) as a brown solid. ¹H NMR (400 MHz, CHLOROFORM-d) δ ppm 11.35 (br. s., 1H) 8.33 (s, 1H) 7.96 (br. s., 1H) 7.44 (t, J=7.83 Hz, 1H) 6.70 (d, J=7.58 Hz, 1H) 6.61 (d, J=8.08 Hz, 1H) 5.61 (br. s., 1H) 5.31 (br. s., 1H) 3.75 (br. s., 1H) 3.19 (d, J=3.28 Hz, 1H) 2.89-3.01 (m, 1H) 1.32-1.80 (m, 8H) 1.27 (d, J=6.82 Hz, 6H). LCMS (EI/CI) m/z: 370 [M+H].

Example 8

6-((3R,4R)-3-Amino-tetrahydro-pyran-4-ylamino)-4-(5,6-dimethyl-pyridin-2-ylamino)-pyridazine-3-carboxylic acid amide Step 1

Ethyl 6-chloro-4-(5,6-dimethylpyridin-2-ylamino)pyridazine-3-carboxylate

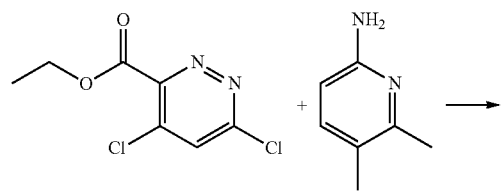

A pressure tube was charged with ethyl 4,6-dichloropyridazine-3-carboxylate (300 mg, 1.36 mmol), 5,6-dimethylpyridin-2-amine (249 mg, 2.04 mmol) in acetonitrile (8 mL) and the mixture was heated in an oil bath at 140° C. for 18 h. After cooling to room temperature, the mixture was concentrated in vacuo, adsorbed on silica gel and then purified by chromatography (silica, 50 μm, 80 g column from Analogix, 0% to 10% acetone in dichloromethane, 20 min) to afford ethyl 6-chloro-4-(5,6-dimethylpyridin-2-ylamino)pyridazine-3-carboxylate (150 mg, 36%) as a yellow solid. ¹H NMR (400 MHz, DMSO-d₆) δ ppm 10.20 (s, 1H) 8.86 (s, 1H) 7.57 (d, J=8.08 Hz, 1H) 6.97 (d, J=8.08 Hz, 1H) 4.40 (q, J=7.24 Hz, 2H) 2.42 (s, 3H) 2.23 (s, 3H) 1.35 (t, J=7.20 Hz, 3H); LCMS (EI/CI) m/z: 307 [M+H].

Step 2

6-Chloro-4-(5,6-dimethylpyridin-2-ylamino)pyridazine-3-carboxamide

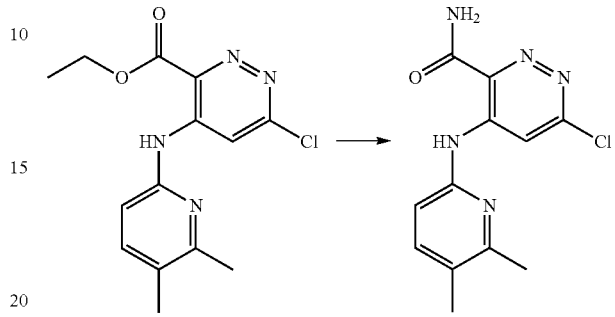

A pressure tube was charged with ethyl 6-chloro-4-(5,6-dimethylpyridin-2-ylamino)pyridazine-3-carboxylate (133 mg, 434 μmol) and 7N ammonia in methanol (9.44 g, 12 mL, 84.0 mmol). The mixture was heated in an oil bath at 50° C. for 18 h. After cooling to room temperature the reaction mixture was concentrated in vacuo to afford 6-chloro-4-(5,6-dimethylpyridin-2-ylamino)pyridazine-3-carboxamide (160 mg, 100%) as a yellow solid. ¹H NMR (400 MHz, CHLOROFORM-d) δ ppm 11.48 (br. s., 1H) 9.18 (s, 1H) 8.17 (br. s., 1H) 7.43 (d, J=8.34 Hz, 1H) 6.74 (d, J=7.83 Hz, 1H) 5.67 (br. s., 1H) 2.53 (s, 3H) 2.28 (s, 3H); LCMS (EI/CI) m/z: 278 [M+H]. This material was used directly in the next step without further purification.

Step 3

6-((3R,4R)-3-Aminotetrahydro-2H-pyran-4-ylamino)-4-(5,6-dimethylpyridin-2-ylamino)pyridazine-3-carboxamide

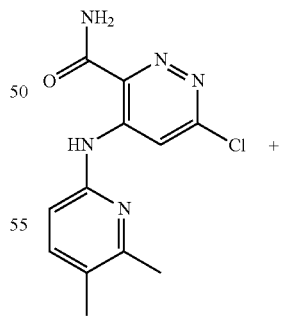 +

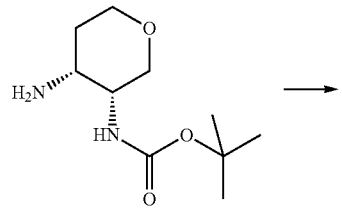

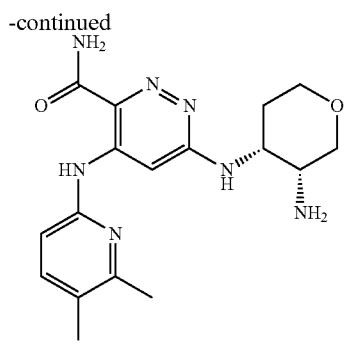

6-Chloro-4-(5,6-dimethylpyridin-2-ylamino)pyridazine-3-carboxamide (120 mg, 432 mmol) and tert-butyl (3R,4R)-4-aminotetrahydro-2H-pyran-3-ylcarbamate (187 mg, 864 μmol) in N-methyl-2-pyrrolidinone (6 mL) was heated at 150° C. for 1.5 d. After solvent evaporation, the residue was dissolved in dichloromethane (2 mL) and TFA (370 mg, 250 μL, 3.24 mmol). The mixture was stirred at room temperature for 3 h, then the solvent was evaporated and the residue was purified by chromatography (spherical silica, 20-45 μm, 11 g, Versaflash from Supelco, 97:2.75:0.15 to 87:12.35:0.65 dichloromethane:MeOH:NH$_4$OH, 20 min) to afford a brown solid. The brown solid was dissolved in dichloromethane and 10 mL of cyclohexane was added. After standing, a solid precipitate formed. The supernatant was decanted and the solid residue was dried under vacuum to give 6-((3R,4R)-3-aminotetrahydro-2H-pyran-4-ylamino)-4-(5,6-dimethylpyridin-2-ylamino)pyridazine-3-carboxamide (18 mg, 12% over two steps) as a brown solid. $^1$H NMR (400 MHz, CHLOROFORM-d) δ ppm 11.23 (br. s., 1H) 8.29 (s, 1H) 8.03 (br. s., 1H) 7.36 (d, J=8.08 Hz, 1H) 6.67 (d, J=8.08 Hz, 1H) 5.68-5.79 (m, 1H) 5.39 (br. s., 1H) 4.02 (d, J=7.33 Hz, 1H) 3.88 (d, J=11.12 Hz, 1H) 3.69 (d, J=11.62 Hz, 1H) 3.55 (t, J=11.49 Hz, 1H) 3.10 (br. s., 1H) 2.49 (s, 3H) 2.25 (s, 3H) 2.02 (d, J=12.38 Hz, 1H) 1.42-1.84 (m, 3H); LCMS (EI/CI) m/z: 358 [M+H].

Example 9

6-((1R,2S)-2-Amino-cyclohexylamino)-4-(1-methyl-1H-pyrazol-3-ylamino)-pyridazine-3-carboxylic acid amide

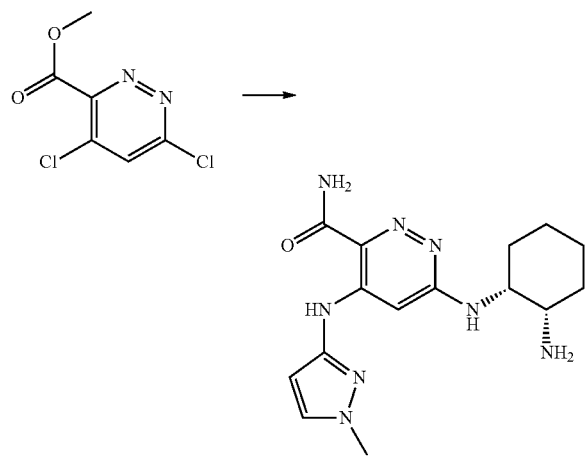

Step 1

6-Chloro-4-(1-methyl-1H-pyrazol-3-ylamino)-pyridazine-3-carboxylic acid methyl ester 4,6-Dichloro-pyridazine-3-carboxylic acid methyl ester (165 mg, 0.8 mmol) and 1-methyl-1H-pyrazol-3-amine (81 mg, 0.837 mmol) were dissolved in of N-methylpyrrolidinone (3.2 mL). The reaction was heated at 110° C. for 2 h, then cooled and concentrated in vacuo. The residue was diluted with water and then extracted with ethyl acetate. The combined organic extracts were washed with brine, dried (sodium sulfate), filtered and concentrated in vacuo. Purification by chromatography (silica, 10 to 70% ethyl acetate in hexanes) gave 6-chloro-4-(1-methyl-1H-pyrazol-3-ylamino)-pyridazine-3-carboxylic acid methyl ester (69 mg, 32%) as a light brown solid. $^1$H NMR (300 MHz, CHLOROFORM-d) δ ppm 10.09 (br. s., 1H) 8.24 (s, 1H) 7.34 (d, J=2.3 Hz, 1H) 6.02 (d, J=2.3 Hz, 1H) 4.08 (s, 3H) 3.91 (s, 3H); LCMS (EI/CI) m/z: 268 [M+H].

Step 2

6-Chloro-4-(1-methyl-1H-pyrazol-3-ylamino)-pyridazine-3-carboxylic acid amide

6-Chloro-4-(1-methyl-1H-pyrazol-3-ylamino)-pyridazine-3-carboxylic acid methyl ester (75 mg, 0.28 mmol) was suspended in 7M ammonia in methanol (3 mL). After 16 h, the reaction mixture was concentrated in vacuo to give 6-chloro-4-(1-methyl-1H-pyrazol-3-ylamino)-pyridazine-3-carboxylic acid amide (70 mg, 100%) as an off-white solid which was used directly in the next step without purification. $^1$H NMR (300 MHz, DMSO-d$_6$) δ ppm 11.39 (s, 1H) 8.77 (br. s., 1H) 8.24 (s, 1H) 8.13 (br. s., 1H) 7.72 (d, J=2.3 Hz, 1H) 6.18 (d, J=2.3 Hz, 1H) 3.84 (s, 3H); LCMS (EI/CI) m/z: 253 [M+H].

Step 3

{(1S,2R)-2-[6-Carbamoyl-5-(1-methyl-1H-pyrazol-3-ylamino)-pyridazin-3-ylamino]-cyclohexyl}-carbamic acid tert-butyl ester 6-Chloro-4-(1-methyl-1H-pyrazol-3-ylamino)-pyridazine-3-carboxylic acid amide (60 mg, 0.237 mmol) and tert-butyl (1S,2R)-2-aminocyclohexylcarbamate (102 mg, 0.475 mmol) were dissolved in N-methylpyrrolidinone (1.5 mL). The reaction mixture was heated at 150° C. for 16 h, then additional tert-butyl (1S,2R)-2-aminocyclohexylcarbamate (100 mg, 0.47 mmol total) was added in three portions over 6 d. The reaction mixture was cooled, diluted with ethyl acetate and water, and extracted with ethyl acetate. The combined organic extracts were washed with water and brine, and then dried (sodium sulfate), filtered, and concentrated in vacuo. The residue obtained was purified by chromatography (silica, 0 to 7% methanol in dichloromethane) to give {(1S,2R)-2-[6-carbamoyl-5-(1-methyl-1H-pyrazol-3-ylamino)-pyridazin-3-ylamino]-cyclohexyl}-carbamic acid tert-butyl ester (18 mg, 17%) as a brown amorphous residue. $^1$H NMR (300 MHz, CHLOROFORM-d) δ ppm 10.68-10.80 (m, 1H) 7.89-8.06 (m, 1H) 7.34-7.37 (m, 1H) 7.25 (d, J=2.3 Hz, 1H) 5.93 (d, J=2.3 Hz, 1H) 5.56-5.64 (m, 1H) 5.02-5.14 (m, 1H) 3.91-4.01 (m, 1H) 3.86 (s, 3H) 1.55 (br. s., 8H) 1.40 (s, 9H); LCMS (EI/CI) m/z: 431 [M+H].

Step 4

6-((1R,2S)-2-Amino-cyclohexylamino)-4-(1-methyl-1H-pyrazol-3-ylamino)-pyridazine-3-carboxylic acid amide {(1S,2R)-2-[6-carbamoyl-5-(1-methyl-1H-pyrazol-3-ylamino)-pyridazin-3-ylamino]-cyclohexyl}-carbamic acid tert-butyl ester (34 mg, 0.079 mmol) was dissolved in dichloromethane (1 mL) then cooled to 0° C. Trifluoroacetic acid (0.5 mL, 6.49 mmol) was added drop-wise then the reaction mixture was warmed to 25° C. After 4 h, the mixture was cooled in an ice bath and neutralized with sodium bicarbonate solution. The mixture was extracted with ethyl acetate, and the combined organic layers washed with brine, dried (sodium sulfate), filtered, and concentrated in vacuo. Purification by chromatography (silica, 0 to 80% of a 0.1:0.01 solution of methanol:NH$_4$OH in dichloromethane) gave 6-((1R,2S)-2-amino-cyclohexylamino)-4-(1-methyl-1H-pyrazol-3-ylamino)-pyridazine-3-carboxylic acid amide (5 mg, 20%) as a brown solid. $^1$H NMR (300 MHz, DMSO-d$_6$) δ ppm 10.84-10.89 (m, 1H) 8.23-8.32 (m, 1H) 7.66 (d, J=2.3 Hz, 1H) 7.48-7.59 (m, 1H) 7.10 (s, 1H) 6.73 (d, J=7.9 Hz, 1H) 6.05 (d, J=2.3 Hz, 1H) 3.91-4.05 (m, 1H) 3.01-3.11 (m, 1H) 1.46-1.72 (m, 6H) 1.25-1.36 (m, 2H); LCMS (EI/CI) m/z: 331 [M+H].

Example 10

6-((1R,2S)-2-Amino-cyclohexylamino)-4-(6-methyl-pyridin-2-ylamino)-pyridazine-3-carboxylic acid amide

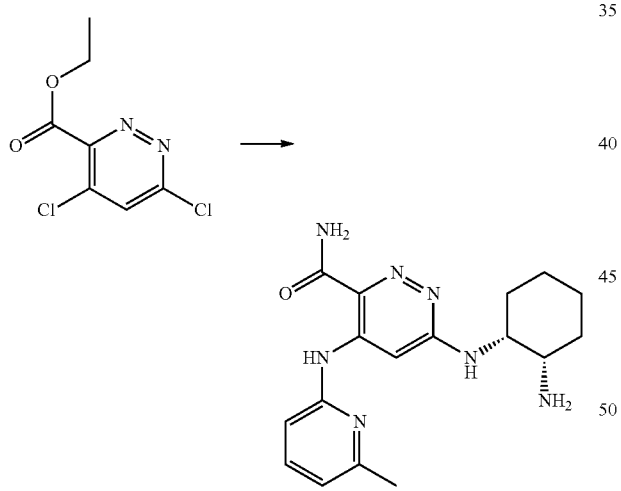

Step 1

6-Chloro-4-(6-methyl-pyridin-2-ylamino)-pyridazine-3-carboxylic acid ethyl ester 4,6-Dichloro-pyridazine-3-carboxylic acid ethyl ester (300 mg, 1.36 mmol) and 6-methylpyridin-2-amine (176 mg, 1.63 mmol) were dissolved in acetonitrile (4.1 mL), then heated at 140° C. for 16 h. A second portion of 6-methylpyridin-2-amine (73 mg, 0.67 mmol) was added. After a further 2 d at 140° C. the reaction mixture was cooled and concentrated in vacuo. Purification by chromatography (silica, 5 to 40% ethyl acetate in hexanes) gave 6-chloro-4-(6-methyl-pyridin-2-ylamino)-pyridazine-3-carboxylic acid ethyl ester (146 mg, 36%) as a light yellow oil. $^1$H NMR (300 MHz, CHLOROFORM-d) δ ppm 10.68 (br. s., 1H) 9.21 (s, 1H) 7.59 (t, J=7.7 Hz, 1H) 6.90 (d, J=7.6 Hz, 1H) 6.76 (d, J=7.9 Hz, 1H) 4.57 (q, J=7.2 Hz, 2H) 2.57 (s, 3H) 1.51 (t, J=7.0 Hz, 3H); LCMS (EI/CI) m/z: 315 [M+Na].

Step 2

6-Chloro-4-(6-methyl-pyridin-2-ylamino)-pyridazine-3-carboxylic acid amide

6-Chloro-4-(6-methyl-pyridin-2-ylamino)-pyridazine-3-carboxylic acid ethyl ester (137 mg, 0.468 mmol) was suspended in 7M ammonia in methanol (3 mL). After 4 h, the reaction mixture was concentrated in vacuo to give 6-chloro-4-(6-methyl-pyridin-2-ylamino)-pyridazine-3-carboxylic acid amide (123 mg, 100%) as an off-white solid which was used directly in the next step without purification. LCMS (EI/CI) m/z: 264 [M+H].

Step 3

{(1S,2R)-2-[6-Carbamoyl-5-(6-methyl-pyridin-2-ylamino)-pyridazin-3-ylamino]-cyclohexyl}-carbamic acid tert-butyl ester 6-Chloro-4-(6-methyl-pyridin-2-ylamino)-pyridazine-3-carboxylic acid amide (130 mg, 0.49 mmol), N,N-diisopropylethylamine (0.17 mL, 0.986 mmol) and tert-butyl (1S,2R)-2-aminocyclohexylcarbamate (211 mg, 0.986 mmol) were dissolved in N-methylpyrrolidinone (2 mL) and heated at 150° C. for 2 d. The reaction mixture was cooled and concentrated in vacuo, then diluted with water, and extracted with ethyl acetate. The combined organic extracts were washed with brine, dried (sodium sulfate), filtered and concentrated in vacuo. Purification by chromatography (silica, 0 to 5% methanol in dichloromethane) gave {(1S,2R)-2-[6-carbamoyl-5-(6-methyl-pyridin-2-ylamino)-pyridazin-3-ylamino]-cyclohexyl}-carbamic acid tert-butyl ester (78 mg, 35%) as a light brown amorphous residue. LCMS (EI/CI) m/z: 442 [M+H].

Step 4

6-((1R,2S)-2-amino-cyclohexylamino)-4-(6-methyl-pyridin-2-ylamino)-pyridazine-3-carboxylic acid amide {(1S,2R)-2-[6-Carbamoyl-5-(6-methyl-pyridin-2-ylamino)-pyridazin-3-ylamino]-cyclohexyl}-carbamic acid tert-butyl ester (188 mg, 0.426 mmol) was dissolved in dichloromethane (4 mL) then cooled to 0° C. Trifluoroacetic acid (2 mL, 25 mmol) was added drop-wise then the reaction mixture was warmed to 25° C. After 4 h, the mixture was cooled in an ice bath and neutralized with sodium bicarbonate solution. The mixture was extracted with ethyl acetate, and the combined organic layers washed with brine, dried (sodium sulfate), filtered, and concentrated in vacuo. Purification by chromatography (silica, 0 to 100% of a 0.1:0.01 solution of methanol:NH$_4$OH in dichloromethane) gave 6-((1R,2S)-2-amino-cyclohexylamino)-4-(6-methyl-pyridin-2-ylamino)-pyridazine-3-carboxylic acid amide (61 mg, 42%) as a light brown solid. $^1$H NMR (400 MHz, DMSO-d$_6$) d ppm 11.61 (s, 1H) 8.35-8.44 (m, 1H) 8.10 (s, 1H) 7.61 (br. s, 1H) 7.61 (t, J=7.3 Hz, 1H) 6.81-6.89 (m, 1H) 6.85 (d, J=7.3 Hz, 1H) 6.76 (d, J=8.1 Hz, 1H) 3.76-3.99 (m, 2H) 3.11-3.18

(m, 1H) 2.48-2.49 (m, 3H) 1.49-1.77 (m, 7H) 1.27-1.38 (m, 2H); LCMS (EI/CI) m/z: 342 [M+H].

Example 11

6-((1R,2S)-2-Amino-cyclohexylamino)-4-(1-methyl-1H-pyrrolo[2,3-b]pyridin-6-ylamino)-pyridazine-3-carboxylic acid amide

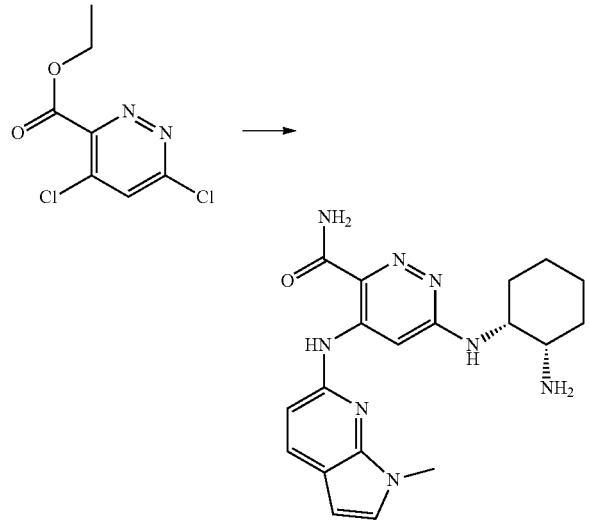

Step 1

(3-Methyl-pyridin-2-yl)-carbamic acid tert-butyl ester

3-Methylpyridin-2-amine (20 g, 185 mmol) was dissolved in ethyl acetate (30 mL) and added drop-wise to a solution of di-tert-butyldicarbonate (64.6 g, 296 mmol) in hexanes (72 mL) at 60° C. After 3 h, the mixture was cooled to 25° C. After 16 h, hexanes (70 mL) were added. After 2 h, the solid precipitate was filtered, the cake rinsed with hexanes, and then dried to give (3-methyl-pyridin-2-yl)-carbamic acid tert-butyl ester (27.4 g, 71%) as a white solid. $^1$H NMR (400 MHz, CHLOROFORM-d) δ ppm 8.24-8.29 (m, 1H) 7.49-7.54 (m, 1H) 7.00-7.07 (m, 1H) 2.30 (s, 3H) 1.52 (s, 9H); LCMS (EI/CI) m/z: 209 [M+H].
Step 2

1H-pyrrolo[2,3-b]pyridine (3-Methyl-pyridin-2-yl)-carbamic acid tert-butyl ester (5 g, 24 mmol) was dissolved in tetrahydrofuran (96 mL) and cooled in an ice-salt bath to −15° C. Butyl lithium solution (1.6 M in hexanes, 30 mL, 48 mmol) was added drop wise over 30 min. After an additional 1 h, N,N-dimethylformamide (1.9 mL, 34.5 mmol) was added and the reaction mixture warmed to 25° C. over 16 h. The reaction mixture was added very slowly to approximately 150 mL of 6M HCl solution. The resulting mixture was warmed to 55° C. for 2 h, then cooled, the phases separated, and ethyl acetate was added to the aqueous layer. 6M sodium hydroxide solution was slowly added until the pH 6, then the layers were separated and the aqueous layer was extracted once more with ethyl acetate. The combined ethyl acetate extracts were washed with sodium chloride solution, dried (sodium sulfate), filtered, and concentrated in vacuo to give 1H-pyrrolo[2,3-b]pyridine (3.8 g, 134%) as a brown semisolid. This was used directly in the next step without further purification. $^1$H NMR (300 MHz, CHLOROFORM-d) δ ppm 10.86 (br. s., 1H) 8.28 (dd, J=4.9, 1.5 Hz, 1H) 7.98 (dd, J=7.7, 1.7 Hz, 1H) 7.36 (d, J=3.4 Hz, 1H) 7.10 (dd, J=7.9, 4.9 Hz, 1H) 6.51 (d, J=3.4 Hz, 1H); LCMS (EI/CI) m/z: 119 [M+H].
Step 3

1H-pyrrolo[2,3-b]pyridine 7-oxide, 3-chlorobenzoic acid complex 1H-pyrrolo[2,3-b]pyridine (2.8 g, 24 mmol) was dissolved in ethyl acetate (24 mL) and cooled to 0° C. A solution of 3-chloroperbenzoic acid (77%, 6.7 g, 30.1 mmol) in ethyl acetate (24 mL) was added drop-wise then the reaction mixture warmed to 25° C. over 16 h. The reaction mixture was cooled to 0° C., filtered, and the solids dried to give crude 1H-pyrrolo[2,3-b]pyridine 7-oxide, 3-chlorobenzoic acid complex (4.1 g, 58%) as an off-white solid. This was used directly in the next step without purification. LCMS (EI/CI) m/z: 135 [M+H].
Step 4

1H-Pyrrolo[2,3-b]pyridin-6-ylamine

1H-Pyrrolo[2,3-b]pyridine 7-oxide, 3-chlorobenzoic acid complex (1.5 g, 5.16 mmol) was suspended in acetonitrile (10 mL). Dimethyl sulfate (0.54 mL, 5.68 mmol) was added and the reaction mixture was warmed to 60° C. After 16 h, the mixture was transferred to a thick-walled pressure tube and 7M ammonia in methanol solution (11 mL) was added. The tube was sealed and warmed to 55° C. After 16 h, the solvent was evaporated and the residue was taken up in dichloromethane and 10% sodium carbonate solution. The aqueous layer was extracted with dichloromethane, and then the combined organic layers were washed successively with saturated aqueous sodium bicarbonate solution, water and brine. The organic phase was dried (sodium sulfate), filtered, and concentrated in vacuo. Purification by chromatography (silica, 10 to 80% ethyl acetate in hexanes) gave 1H-pyrrolo[2,3-b]pyridin-6-ylamine (316 mg, 46%) as a white solid. $^1$H NMR (400 MHz, CHLOROFORM-d) δ ppm 8.73 (br. s., 1H) 7.70 (d, J=8.3 Hz, 1H) 6.99 (d, J=3.5 Hz, 1H) 6.38 (d, J=8.3 Hz, 1H) 6.36 (d, J=3.5 Hz, 1H) 3.82 (br. s., 2H).
Step 5

2-(1H-pyrrolo[2,3-b]pyridin-6-yl)-isoindole-1,3-dione

1H-Pyrrolo[2,3-b]pyridin-6-ylamine (0.12 g, 0.9 mmol) was suspended in acetic acid (1.5 mL), then phthalic anhydride (133 mg, 0.9 mmol) and sodium acetate (118 mg, 1.44 mmol) were added and the mixture heated to 120° C. After 3 h, the mixture was concentrated in vacuo, the residue obtained dissolved in ethyl acetate, and then cooled to 0° C. Ice-water and sodium bicarbonate solution were added then the aqueous layer was extracted with ethyl acetate. The aqueous layer was adjusted to pH 6 with 1M HCl solution and was extracted twice more with ethyl acetate. The combined organic layers were dried over sodium sulfate then concentrated in vacuo. Purification by chromatography (silica, 20 to 70% ethyl acetate in hexanes) gave 2-(1H-pyrrolo[2,3-b]pyridin-6-yl)-isoindole-1,3-dione (179 mg, 75%) as a light brown solid. $^1$H NMR (300 MHz, DMSO-$d_6$) δ ppm 11.91 (br. s., 1H) 8.15 (d, J=7.9 Hz, 1H) 7.90-8.05 (m, 4H) 7.59-

7.65 (m, 1H) 7.21 (d, J=7.9 Hz, 1H) 6.54-6.60 (m, 1H); LCMS (EI/CI) m/z: 264 [M+H].

Step 6

2-(1-Methyl-1H-pyrrolo[2,3-b]pyridin-6-yl)-isoindole-1,3-dione 2-(1H-Pyrrolo[2,3-b]pyridin-6-yl)-isoindole-1,3-dione (179 mg, 0.68 mmol) was suspended in acetonitrile (3.4 mL). Iodomethane (53 µL, 0.843 mmol) and cesium carbonate (443 mg, 1.36 mmol) were then added. After 16 h, water was added and the aqueous layer was extracted with ethyl acetate. The combined organic extracts were dried (sodium sulfate), filtered and concentrated in vacuo to give 2-(1-methyl-1H-pyrrolo[2,3-b]pyridin-6-yl)-isoindole-1,3-dione (0.22 g, 117%) as a light brown solid, which was used directly in the next step without further purification. LCMS (EI/CI) m/z: 278 [M+H].

Step 7

1-Methyl-1H-pyrrolo[2,3-b]pyridin-6-ylamine 2-(1-Methyl-1H-pyrrolo[2,3-b]pyridin-6-yl)-isoindole-1,3-dione (220 mg, 0.793 mmol) was dissolved in ethanol (4 mL), then hydrazine (0.5 mL, 15.9 mmol) was added. After 16 h, the mixture was concentrated in vacuo and partitioned between ethyl acetate and water. The aqueous layer was extracted twice more with ethyl acetate, then the combined organic extracts were washed with brine, dried (sodium sulfate), filtered, and concentrated in vacuo. Purification by chromatography (silica, 10 to 50% ethyl acetate in hexanes) gave 1-methyl-1H-pyrrolo[2,3-b]pyridin-6-ylamine (115 mg, 98%) as an off-white solid. $^1$H NMR (300 MHz, CHLOROFORM-d) δ ppm 7.67 (d, J=8.3 Hz, 1H) 6.87 (d, J=3.4 Hz, 1H) 6.35 (d, J=8.3 Hz, 1H) 6.30 (d, J=3.4 Hz, 1H) 4.38 (br. s., 2H) 3.76 (s, 3H); LCMS (EI/CI) m/z: 148 [M+H].

Step 8

6-Chloro-4-(1-methyl-1H-pyrrolo[2,3-b]pyridin-6-ylamino)-pyridazine-3-carboxylic acid ethyl ester 4,6-Dichloro-pyridazine-3-carboxylic acid ethyl ester (195 mg, 0.882 mmol) and 1-methyl-1H-pyrrolo[2,3-b]pyridin-6-ylamine (156 mg, 1.06 mmol) were dissolved in acetonitrile (2.7 mL), then heated at 140° C. for 2 d. The reaction mixture was cooled and concentrated in vacuo. The residue was diluted with water and then extracted with ethyl acetate. The combined organic extracts were washed with brine, dried (sodium sulfate), filtered and concentrated in vacuo. Purification by chromatography (silica, 5 to 70% ethyl acetate in hexanes) gave 6-chloro-4-(1-methyl-1H-pyrrolo[2,3-b]pyridin-6-ylamino)-pyridazine-3-carboxylic acid ethyl ester (52 mg, 18%) as a light yellow solid. $^1$H NMR (400 MHz, CHLOROFORM-d) δ ppm 10.78 (s, 1H) 9.34 (s, 1H) 7.90 (d, J=8.3 Hz, 1H) 7.14 (d, J=3.3 Hz, 1H) 6.74 (d, J=8.3 Hz, 1H) 6.45 (d, J=3.5 Hz, 1H) 4.58 (d, J=7.1 Hz, 2H) 3.90 (s, 3H) 1.52 (t, J=7.2 Hz, 3H); LCMS (EI/CI) m/z: 332 [M+H].

Step 9

6-Chloro-4-(1-methyl-1H-pyrrolo[2,3-b]pyridin-6-ylamino)-pyridazine-3-carboxylic acid amide 6-Chloro-4-(1-methyl-1H-pyrrolo[2,3-b]pyridin-6-ylamino)-pyridazine-3-carboxylic acid ethyl ester (52 mg, 0.157 mmol) was suspended in 7M ammonia in methanol (2 mL). After 2 h, the reaction mixture was concentrated in vacuo to give 6-chloro-4-(1-methyl-1H-pyrrolo[2,3-b]pyridin-6-ylamino)-pyridazine-3-carboxylic acid amide (47 mg, 100%) as a light yellow solid which was used directly in the next step without purification. $^1$H NMR (400 MHz, DMSO-d$_6$) δ ppm 12.07 (s, 1H) 9.24 (s, 1H) 8.85 (br. s., 1H) 8.21 (br. s., 1H) 7.99 (d, J=8.3 Hz, 1H) 7.42 (d, J=3.3 Hz, 1H) 6.81 (d, J=8.3 Hz, 1H) 6.45 (d, J=3.3 Hz, 1H) 3.83 (s, 3H); LCMS (EI/CI) m/z: 303 [M+H].

Step 10

{(1S,2R)-2-[6-Carbamoyl-5-(1-methyl-1H-pyrrolo[2,3-b]pyridin-6-ylamino)-pyridazin-3-ylamino]-cyclohexyl}-carbamic acid tert-butyl ester 6-Chloro-4-(1-methyl-1H-pyrrolo[2,3-b]pyridin-6-ylamino)-pyridazine-3-carboxylic acid amide (42 mg, 0.139 mmol), and tert-butyl (1S,2R)-2-aminocyclohexylcarbamate (89 mg, 0.416 mmol) were dissolved in N-methylpyrrolidinone (1.4 mL) and heated at 150° C. for 36 h. Additional tert-butyl (1S,2R)-2-aminocyclohexylcarbamate (35 mg, 0.16 mmol) was added and the heating continued for 16 h more. The reaction mixture was cooled and concentrated in vacuo, then diluted with water, and extracted with ethyl acetate. The combined organic extracts were washed with brine, dried (sodium sulfate), filtered and concentrated in vacuo. Purification by chromatography (silica, 0 to 5% methanol in dichloromethane) gave {(1S,2R)-2-[6-carbamoyl-5-(1-methyl-1H-pyrrolo[2,3-b]pyridin-6-ylamino)-pyridazin-3-ylamino]-cyclohexyl}-carbamic acid tert-butyl ester (12 mg, 18%) as a light brown amorphous residue. LCMS (EI/CI) m/z: 481 [M+H].

Step 11

6-((1R,2S)-2-Amino-cyclohexylamino)-4-(1-methyl-1H-pyrrolo[2,3-b]pyridin-6-ylamino)-pyridazine-3-carboxylic acid amide {(1S,2R)-2-[6-Carbamoyl-5-(1-methyl-1H-pyrrolo[2,3-b]pyridin-6-ylamino)-pyridazin-3-ylamino]-cyclohexyl}-carbamic acid tert-butyl ester (23 mg, 0.048 mmol) was dissolved in dichloromethane (1 mL) then cooled to 0° C. Trifluoroacetic acid (0.5 mL, 6.5 mmol) was added drop-wise then the reaction mixture was warmed to 25° C. After 2 h, the mixture was cooled in an ice bath and neutralized with sodium bicarbonate solution. The mixture was extracted with ethyl acetate, and the combined organic layers washed with brine, dried (sodium sulfate), filtered, and concentrated in vacuo. Purification by chromatography (silica, 0 to 100% of a 0.1:0.01 solution of methanol:NH$_4$OH in dichloromethane) gave 6-((1R,2S)-2-amino-cyclohexylamino)-4-(1-methyl-1H-pyrrolo[2,3-b]pyridin-6-ylamino)-pyridazine-3-carboxylic acid amide (5.8 mg, 32%) as a light brown solid. $^1$H NMR (400 MHz, DMSO-d$_6$) δ ppm 11.74-11.82 (m, 1H) 8.35-8.44 (m, 1H) 8.14 (s, 1H) 7.90 (d, J=8.3 Hz, 1H) 7.60-7.67 (m, 1H) 7.32 (d, J=3.3 Hz, 1H) 6.80 (d, J=7.6 Hz, 1H) 6.66 (d, J=8.3 Hz, 1H) 6.40 (d, J=3.3 Hz, 1H) 3.86 (s, 3H) 3.11-3.17 (m, 1H) 1.50-1.75 (m, 8H) 1.23-1.36 (m, 3H); LCMS (EI/CI) m/z: 381 [M+H].

Example 12

6-((1R,2S)-2-Aminocyclohexylamino)-4-(6-cyclopropylpyridin-2-ylamino)pyridazine-3-carboxamide Step 1

Ethyl 6-chloro-4-(6-cyclopropylpyridin-2-ylamino)pyridazine-3-carboxylate

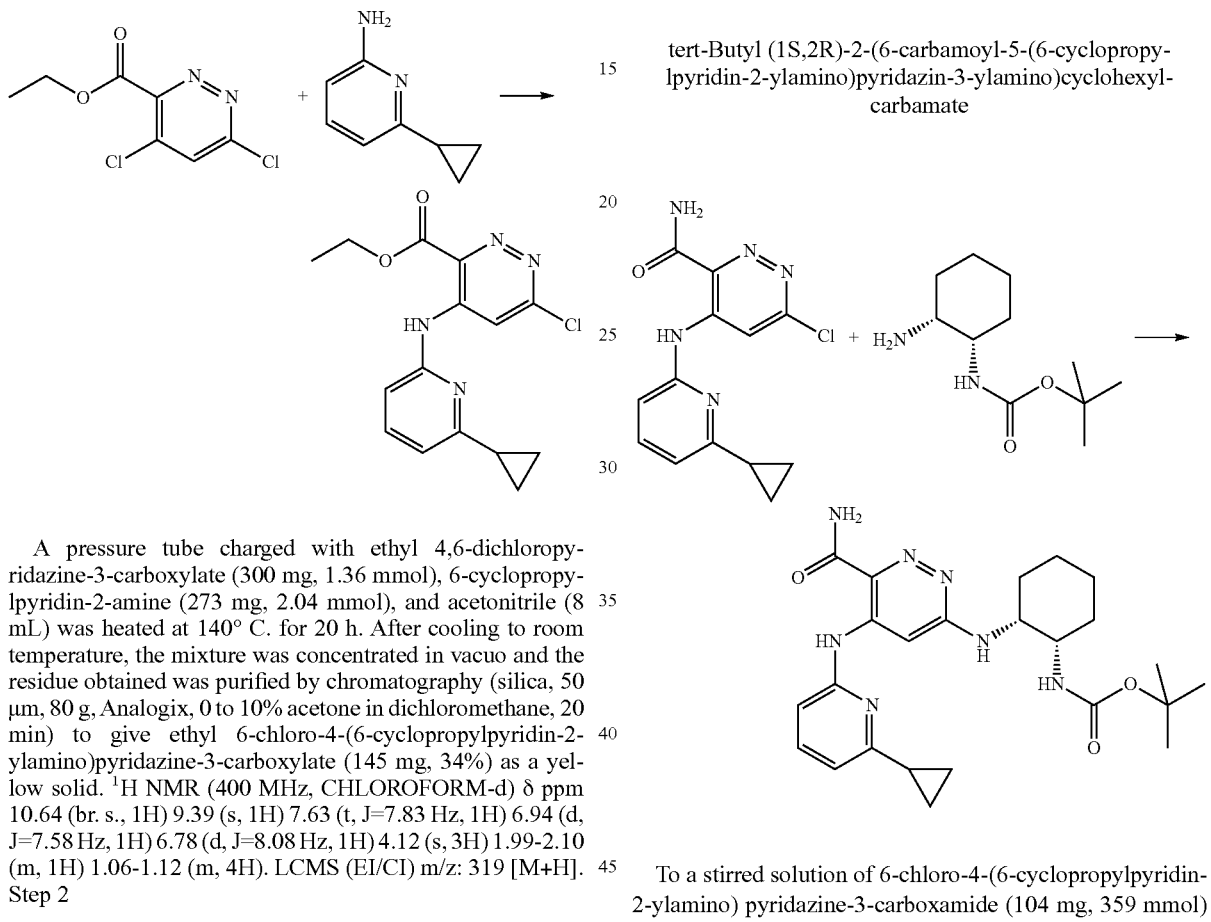

A pressure tube charged with ethyl 4,6-dichloropyridazine-3-carboxylate (300 mg, 1.36 mmol), 6-cyclopropylpyridin-2-amine (273 mg, 2.04 mmol), and acetonitrile (8 mL) was heated at 140° C. for 20 h. After cooling to room temperature, the mixture was concentrated in vacuo and the residue obtained was purified by chromatography (silica, 50 µm, 80 g, Analogix, 0 to 10% acetone in dichloromethane, 20 min) to give ethyl 6-chloro-4-(6-cyclopropylpyridin-2-ylamino)pyridazine-3-carboxylate (145 mg, 34%) as a yellow solid. $^1$H NMR (400 MHz, CHLOROFORM-d) δ ppm 10.64 (br. s., 1H) 9.39 (s, 1H) 7.63 (t, J=7.83 Hz, 1H) 6.94 (d, J=7.58 Hz, 1H) 6.78 (d, J=8.08 Hz, 1H) 4.12 (s, 3H) 1.99-2.10 (m, 1H) 1.06-1.12 (m, 4H). LCMS (EI/CI) m/z: 319 [M+H].

Step 2

6-Chloro-4-(6-cyclopropylpyridin-2-ylamino)pyridazine-3-carboxamide

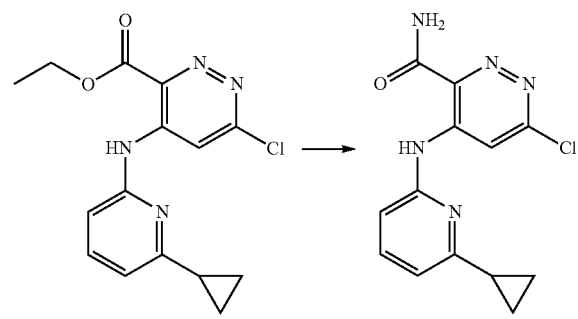 [SMILES: CCOC(=O)c1nnc(Cl)cc1Nc1cccc(C2CC2)n1 ; NC(=O)c1nnc(Cl)cc1Nc1cccc(C2CC2)n1]

Ethyl 6-chloro-4-(6-cyclopropylpyridin-2-ylamino)pyridazine-3-carboxylate (140 mg, 439 µmol) and ammonia (7M in methanol, 9.44 g, 12 mL, 84.0 mmol) were heated at 50° C. in a sealed tube for 21 h. After cooling to room temperature, concentration in vacuo gave 6-chloro-4-(6-cyclopropylpyridin-2-ylamino)pyridazine-3-carboxamide (112 mg, 88%) as a yellow solid. $^1$H NMR (300 MHz, CHLOROFORM-d) δ ppm 11.51 (br. s., 1H) 9.16 (s, 1H) 8.16 (br. s., 1H) 7.52 (t, J=7.74 Hz, 1H) 6.86-6.96 (m, 1H) 6.68 (d, J=7.93 Hz, 1H) 5.65 (br. s., 1H) 1.99-2.10 (m, 1H) 1.06-1.12 (m, 4H). LCMS (EI/CI) m/z: 290 [M+H]. The crude product was used directly in the next step without further purification.

Step 3 tert-Butyl (1S,2R)-2-(6-carbamoyl-5-(6-cyclopropylpyridin-2-ylamino)pyridazin-3-ylamino)cyclohexylcarbamate

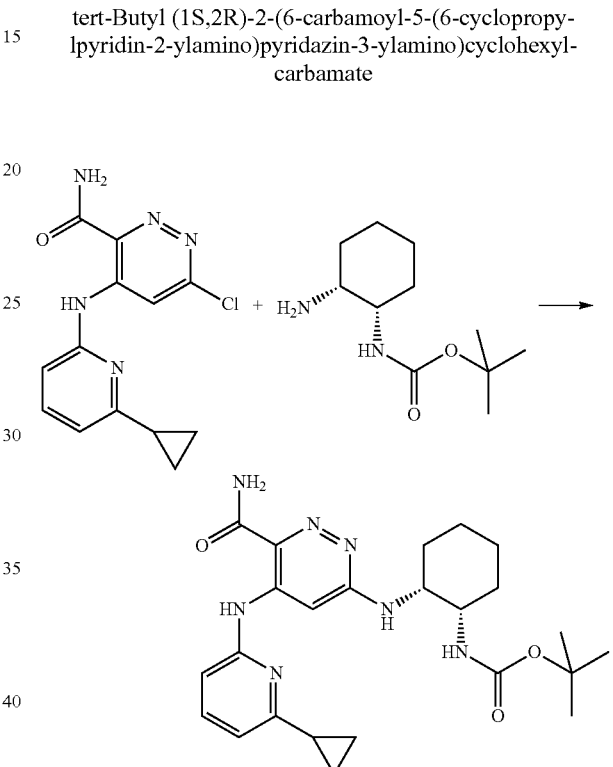

To a stirred solution of 6-chloro-4-(6-cyclopropylpyridin-2-ylamino) pyridazine-3-carboxamide (104 mg, 359 mmol) in N-methyl-2-pyrrolidinone (5 mL) was added DMAP (47 mg, 377 µmol) and tert-butyl (1S,2R)-2-aminocyclohexylcarbamate (154 mg, 718 µmol). The mixture was heated to 150° C. for 1.5 days, then a stream of N$_2$ was blown into the flask while heating at 140° C. to evaporate the volatile solvents. The residue obtained was then purified by chromatography (silica, 50 µm, 60 g, Analogix, 97:2.75:0.15 to 84:15.2:0.8 dichloromethane:MeOH:NH$_4$OH, 30 min) to afford tert-butyl (1S,2R)-2-(6-carbamoyl-5-(6-cyclopropylpyridin-2-ylamino)pyridazin-3 ylamino)cyclohexylcarbamate (126 mg, containing some residual NMP) as a brown viscous oil. $^1$H NMR (300 MHz, CHLOROFORM-d) δ ppm 11.43 (br. s., 1H) 8.17 (br. s., 1H) 8.03 (br. s., 1H) 7.44 (br. s., 1H) 7.03 (br. s., 1H) 6.80 (br. s., 1H) 6.60 (br. s., 1H) 5.76 (br. s., 1H) 5.49 (br. s., 1H) 3.82 (br. s., 1H) 3.24 (br. s., 1H) 2.03 (br. s., 1H) 1.32-1.91 (m, 8H) 1.45 (s., 9H) 1.05 (d, J=16.62 Hz, 4H). LCMS (EI/CI) m/z: 468 [M+H]. This was used directly in the next step without further purification.

Step 4

6-((1R,2S)-2-Aminocyclohexylamino)-4-(6-cyclopropylpyridin-2-ylamino)pyridazine-3-carboxamide

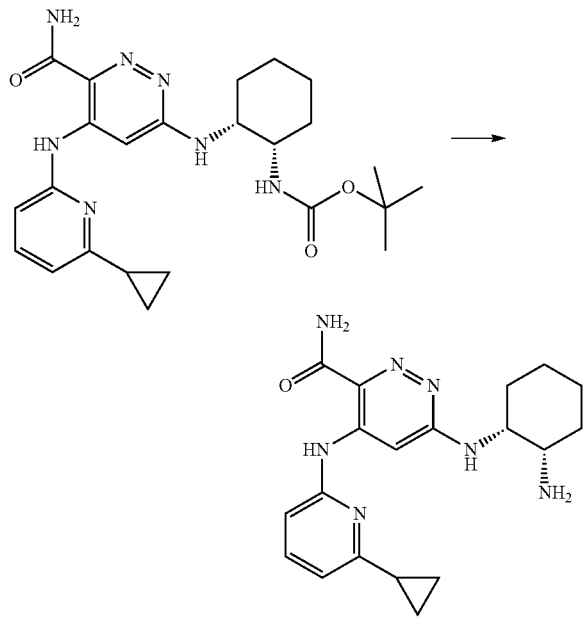

To a solution of tert-butyl (1S,2R)-2-(6-carbamoyl-5-(6-cyclopropylpyridin-2-ylamino)pyridazin-3-ylamino)cyclohexylcarbamate (25 mg, 53.5 µmol) in dichloromethane (4 mL) was added TFA (370 µg, 0.25 µL, 3.24 µmol). After 6 h, the mixture was concentrated in vacuo, then purified by flash chromatography (spherical silica, 20-45 µm, 25 g, Versaflash from Supelco, 97:2.75:0.15 to 84:15.2:0.8 dichloromethane:MeOH:NH$_4$OH, 30 min) to give 6-((1R,2S)-2-aminocyclohexylamino)-4-(6-cyclopropylpyridin-2-ylamino)pyridazine-3-carboxamide (13 mg, 10%, two steps) as a brown solid. $^1$H NMR (300 MHz, CHLOROFORM-d) δ ppm 11.43 (br. s., 1H) 8.17 (br. s., 1H) 8.03 (br. s., 1H) 7.44 (br. s., 1H) 7.03 (br. s., 1H) 6.80 (br. s., 1H) 6.60 (br. s., 1H) 5.76 (br. s., 1H) 5.49 (br. s., 1H) 3.82 (br. s., 1H) 3.24 (br. s., 1H) 2.03 (br. s., 1H) 1.32-1.91 (m, 8H) 1.05 (d, J=16.62 Hz, 4H). LCMS (EI/CI) m/z: 368 [M+H].

Example 13

6-((1R,2S)-2-Aminocyclohexylamino)-4-(5-fluoro-6-methylpyridin-2-ylamino pyridazine-3-carboxamide Step 1

Ethyl 6-chloro-4-(5-fluoro-6-methylpyridin-2-ylamino) pyridazine-3-carboxylate

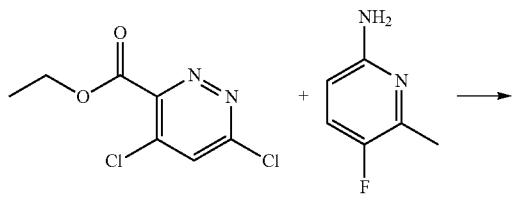

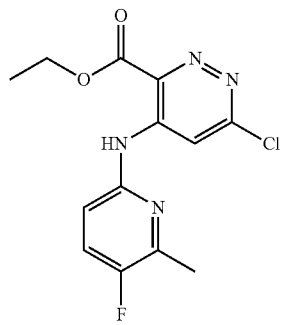

A pressure tube was charged with ethyl 4,6-dichloropyridazine-3-carboxylate (300 mg, 1.36 mmol), 5-fluoro-6-methylpyridin-2-amine (257 mg, 2.04 mmol), and acetonitrile (8 mL) and then heated at 140° C. for 3 d. After cooling to room temperature the reaction mixture was concentrated in vacuo and the residue purified by chromatography (silica, 50 µm, 80 g, Analogix, 0 to 10% acetone in dichloromethane, 25 min) to afford ethyl 6-chloro-4-(5-fluoro-6-methylpyridin-2-ylamino)pyridazine-3-carboxylate (69 mg, 16%) as a yellow solid. $^1$H NMR (400 MHz, CHLOROFORM-d) δ ppm 10.72 (br. s., 1H) 9.06 (s, 1H) 7.38 (s, 1H) 6.74-6.85 (m, 1H) 4.58 (q, J=7.07 Hz, 2H) 2.56 (d, J=3.03 Hz, 3H) 1.53 (t, J=7.07 Hz, 3H) 1.27 (s, 1H). LCMS (EI/CI) m/z: 311 [M+H].

Step 2

6-Chloro-4-(5-fluoro-6-methylpyridin-2-ylamino) pyridazine-3-carboxamide

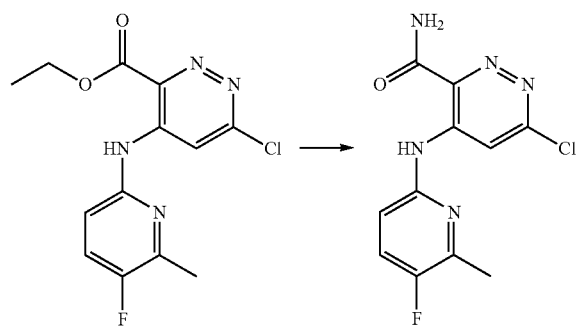 [SMILES: CCOC(=O)c1nnc(Cl)cc1Nc1ccc(F)c(C)n1 ; Cc1nc(Nc2cc(Cl)nnc2C(N)=O)ccc1F]

Ethyl 6-chloro-4-(5-fluoro-6-methylpyridin-2-ylamino) pyridazine-3-carboxylate (111.2 mg, 358 µmol) was added to a pressure tube containing ammonia 7M in methanol (9.44 g, 12 mL, 84.0 mmol). The reaction mixture was heated to 50° C. for 6 h, then was concentrated in vacuo to give 6-chloro-4-(5-fluoro-6-methylpyridin-2-ylamino) pyridazine-3-carboxamide (110 mg 100%) as a yellow solid. $^1$H NMR (300 MHz, CHLOROFORM-d) δ ppm 11.67 (br. s., 1H) 9.10 (s, 1H) 8.17 (br. s., 1H) 7.35 (t, J=8.50 Hz, 1H) 6.79 (dd, J=8.69, 3.02 Hz, 1H) 5.67 (br. s., 1H) 2.54 (d, J=3.02 Hz, 3H). LCMS (EI/CI) m/z: 282 [M+H]. The crude product was used in the next step without further purification.

Step 3 tert-Butyl (1S,2R)-2-(6-carbamoyl-5-(5-fluoro-6-methylpyridin-2-ylamino)pyridazin-3-ylamino)cyclohexylcarbamate

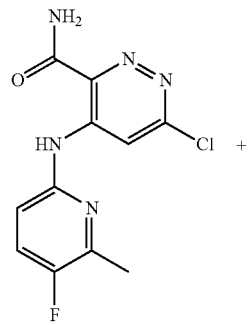

To a solution of 6-chloro-4-(5-fluoro-6-methylpyridin-2-ylamino) pyridazine-3-carboxamide (109 mg, 387 μmol) in N-methyl-2-pyrrolidinone (2.4 mL) was added DMAP (50.7 mg, 406 μmol) and tert-butyl (1S,2R)-2-aminocyclohexylcarbamate (166 mg, 774 μmol) and the mixture was heated to 150° C. for 1.5 d. A steam of $N_2$ was blown into the mixture while still heating at 140° C. to evaporate the NMP, then the reaction mixture was purified by chromatography (silica, 50 μm, 40 g, Analogix, 97:2.75:0.15 to 84:15.2:0.8 dichloromethane:MeOH:NH$_4$OH, 30 min) to provide tert-butyl (1S,2R)-2-(6-carbamoyl-5-(5-fluoro-6-methylpyridin-2-ylamino)pyridazin-3-ylamino)cyclohexylcarbamate (82 mg, 23%) as a brown oil. $^1$H NMR (400 MHz, CHLOROFORM-d) δ ppm 11.43 (s, 1H) 8.24 (s, 1H) 8.08 (br. s., 2H) 7.22-7.37 (m, 1H) 6.66-6.77 (m, 1H) 5.64 (d, J=3.28 Hz, 1H) 4.02 (br. s., 2H) 2.49 (d, J=3.03 Hz, 3H) 1.67-1.92 (m, 2H) 1.35-1.65 (m, 8H). LCMS (EI/CI) m/z: 460 [M+H].

Step 4

6-((1R,2S)-2-Aminocyclohexylamino)-4-(5-fluoro-6-methylpyridin-2-ylamino pyridazine-3-carboxamide To a solution of tert-butyl (1S,2R)-2-(6-carbamoyl-5-(5-fluoro-6-methylpyridin-2-ylamino)pyridazin-3-ylamino)cyclohexylcarbamate (40 mg, 87.0 μmol) in dichloromethane (3.2 mL) was added TFA (592 μg, 0.400 μL, 5.19 μmol) and the mixture was stirred at room temperature for 3 h. The mixture was concentrated in vacuo then purified by chromatography (spherical silica, 20-45 μm, 23 g, Versaflash from Supelco, 99:0.95:0.05 to 90:9.5:0.5 dichloromethane:MeOH:NH$_4$OH, 25 min) to give 6-((1R,2S)-2-aminocyclohexylamino)-4-(5-fluoro-6-methylpyridin-2-ylamino pyridazine-3-carboxamide (10 mg, 32% yield) as a light brown solid. $^1$H NMR (400 MHz, DMSO-d$_6$) δ ppm 11.65 (s, 1H) 8.38 (br. s., 1H) 7.97 (s, 1H) 7.54-7.69 (m, 2H) 6.75-6.94 (m, 2H) 3.15 (d, J=3.03 Hz, 1H) 2.47 (d, J=2.78 Hz, 3H) 1.44-1.84 (m, 8H) 1.33 (br. s., 2H). LCMS (EI/CI) m/z: 360 [M+H].

Example 14

6-((1R,2S)-2-Amino-cyclohexylamino)-4-(6-ethylpyridin-2-ylamino)-pyridazine-3-carboxylic acid amide -continued

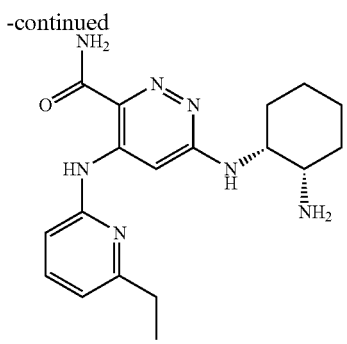

Step 1

6-Chloro-4-(6-ethyl-pyridin-2-ylamino)-pyridazine-3-carboxylic acid ethyl ester 4,6-Dichloro-pyridazine-3-carboxylic acid ethyl ester (500 mg, 2.26 mmol) and 6-ethylpyridin-2-amine 415 mg, 3.39 mmol) were dissolved in acetonitrile (7 mL), then heated at 140° C. for 3 d. The reaction mixture was cooled and concentrated in vacuo. Purification by chromatography (silica, 5 to 50% ethyl acetate in hexanes) gave 6-chloro-4-(6-ethyl-pyridin-2-ylamino)-pyridazine-3-carboxylic acid ethyl ester (246 mg, 35%) as a light brown solid. $^1$H NMR (400 MHz, CHLOROFORM-d) δ ppm 10.68 (br. s., 1H) 9.30 (s, 1H) 7.61 (t, J=7.8 Hz, 1H) 6.91 (d, J=7.3 Hz, 1H) 6.77 (d, J=7.8 Hz, 1H) 4.57 (q, J=7.2 Hz, 2H) 2.86 (q, J=7.6 Hz, 2H) 1.52 (t, J=7.1 Hz, 3H) 1.38 (t, J=7.5 Hz, 3H); LCMS (EI/CI) m/z: 307 [M+H].

Step 2

6-Chloro-4-(6-ethyl-pyridin-2-ylamino)-pyridazine-3-carboxylic acid amide

6-Chloro-4-(6-ethyl-pyridin-2-ylamino)-pyridazine-3-carboxylic acid ethyl ester (241 mg, 0.786 mmol) was suspended in 7M ammonia in methanol (9 mL). After 3 h, the reaction mixture was concentrated in vacuo to give 6-chloro-4-(6-ethyl-pyridin-2-ylamino)-pyridazine-3-carboxylic acid amide (218 mg, 100%) as an off-white solid which was used directly in the next step without purification. LCMS (EI/CI) m/z: 278 [M+H].

Step 3

{(1S,2R)-2-[6-Carbamoyl-5-(6-ethyl-pyridin-2-ylamino)-pyridazin-3-ylamino]-cyclohexyl}-carbamic acid tert-butyl ester 6-Chloro-4-(6-ethyl-pyridin-2-ylamino)-pyridazine-3-carboxylic acid amide (218 mg, 0.785 mmol), and tert-butyl (1S,2R)-2-aminocyclohexylcarbamate (336 mg, 1.57 mmol) were dissolved in N-methylpyrrolidinone (4 mL) and heated at 150° C. for 40 h. Additional tert-butyl (1S,2R)-2-aminocyclohexylcarbamate (168 mg, 0.78 mmol) was added and the heating continued for 16 h more. The reaction mixture was cooled and concentrated in vacuo, then diluted with water, and extracted with ethyl acetate. The combined organic extracts were washed with brine, dried (sodium sulfate), filtered and concentrated in vacuo. Purification by chromatography (silica, 0 to 5% methanol in dichloromethane) gave {(1S,2R)-2-[6-carbamoyl-5-(6-ethyl-pyridin-2-ylamino)-pyridazin-3-ylamino]-cyclohexyl}-carbamic acid tert-butyl ester (167 mg, 46%) as a light brown amorphous residue. $^1$H NMR (300 MHz, CHLOROFORM-d) δ ppm 11.44 (s, 1H) 8.47 (s, 1H) 7.97-8.03 (m, 1H) 7.52 (t, J=7.6 Hz, 1H) 7.22-7.26 (m, 1H) 6.78 (d, J=7.2 Hz, 1H) 6.70 (d, J=7.9 Hz, 1H) 5.38-5.43 (m, 1H) 4.92-5.00 (m, 1H) 3.97-4.08 (m, 2H) 2.80 (q, J=7.6 Hz, 2H) 1.58-1.96 (m, 8H) 1.41 (s, 9H) 1.31-1.39 (m, 3H); LCMS (EI/CI) m/z: 456 [M+H].

Step 4

6-((1R,2S)-2-Amino-cyclohexylamino)-4-(6-ethyl-pyridin-2-ylamino)-pyridazine-3-carboxylic acid amide {(1S,2R)-2-[6-Carbamoyl-5-(6-ethyl-pyridin-2-ylamino)-pyridazin-3-ylamino]-cyclohexyl}-carbamic acid tert-butyl ester (167 mg, 0.367 mmol) was dissolved in dichloromethane (4 mL) then cooled to 0° C. Trifluoroacetic acid (2 mL, 26 mmol) was added drop-wise then the reaction mixture was warmed to 25° C. After 5 h, the mixture was cooled in an ice bath and neutralized with sodium bicarbonate solution. The mixture was extracted with ethyl acetate, and the combined organic layers washed with brine, dried (sodium sulfate), filtered, and concentrated in vacuo. Purification by chromatography (silica, 5 to 80% of a 0.1:0.01 solution of methanol:NH$_4$OH in dichloromethane) gave 6-((1R,2S)-2-amino-cyclohexylamino)-4-(6-ethyl-pyridin-2-ylamino)-pyridazine-3-carboxylic acid amide (66 mg, 50%) as a light brown solid. $^1$H NMR (400 MHz, DMSO-d$_6$) δ ppm 11.66 (s, 1H) 8.35-8.40 (m, 1H) 8.09 (s, 1H) 7.63 (dd, J=8.2, 7.5 Hz, 1H) 7.62 (br. s., 1H) 6.86 (d, J=7.6 Hz, 1H) 6.79 (d, J=7.6 Hz, 1H) 6.76 (d, J=7.8 Hz, 1H) 3.73-3.86 (m, 1H) 3.10-3.15 (m, 1H) 2.75 (q, J=7.6 Hz, 2H) 1.48-1.73 (m, 7H) 1.27 (t, J=7.7 Hz, 3H) 1.24-1.37 (m, 2H); LCMS (EI/CI) m/z: 356 [M+H].

Example 15

6-((1R,2S)-2-Amino-cyclohexylamino)-4-(5,6-dimethyl-pyridin-2-ylamino)-pyridazine-3-carboxylic acid amide

Step 1

Ethyl 6-chloro-4-(5,6-dimethylpyridin-2-ylamino) pyridazine-3-carboxylate

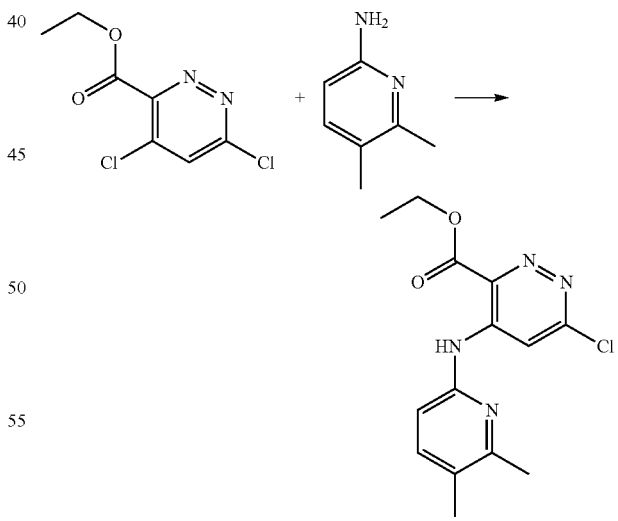

A heavy walled sealable tube was charged with ethyl 4,6-dichloropyridazine-3-carboxylate (300 mg, 1.36 mmol) and 5,6-dimethylpyridin-2-amine (249 mg, 2.04 mmol). To the mixture was added acetonitrile (8.00 mL) and the reaction mixture was heated with stirring in an oil bath at 140° C. for 20 h. After cooling to room temperature the residue was suspended in dichloromethane and purified by flash chromatography (silica 20-45 μM, 40 g, Thomson) eluting with 0 to 10% over 20 min, acetone/dichloromethane to give ethyl 6-chloro-4-(5,6-dimethylpyridin-2-ylamino)pyridazine-3-carboxylate (195 mg, 46.8%) as an off-white solid. $^1$H NMR (CHLOROFORM-d) δ: 10.54 (s, 1H), 9.14 (s, 1H), 7.41 (d, J=8.3 Hz, 1H), 6.70 (d, J=8.3 Hz, 1H), 4.55 (q, J=7.2 Hz, 2H), 2.50 (s, 3H), 2.26 (s, 3H), 1.50 (t, J=7.2 Hz, 3H); LC-MS 307.0 [M+H]$^+$.

Step 2

6-Chloro-4-(5,6-dimethylpyridin-2-ylamino)pyridazine-3-carboxamide

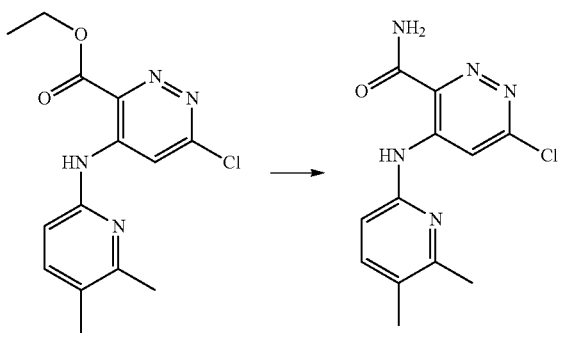 [SMILES: CCOC(=O)c1nnc(Cl)cc1Nc1ccc(C)c(C)n1 ; Cc1ccc(Nc2cc(Cl)nnc2C(N)=O)nc1C]

In a 50 mL round bottom flask, ethyl 6-chloro-4-(5,6-dimethylpyridin-2-ylamino)pyridazine-3-carboxylate (929 mg, 3.03 mmol) was suspended in ammonia 7M in methanol (7.87 g, 10.0 mL, 70.0 mmol). The flask was sealed and stirred for 2 h at room temperature. Solvents evaporated and solid residue dried in high vacuum to give 6-chloro-4-(5,6-dimethylpyridin-2-ylamino)pyridazine-3-carboxamide (841 mg, 100% yield) as an off-white solid. $^1$H NMR (CHLOROFORM-d) δ: 11.37 (br. s., 1H), 9.11 (s, 1H), 8.09 (br. s., 1H), 7.32 (d, J=8.3 Hz, 1H), 6.63 (d, J=8.1 Hz, 1H), 5.59 (br. s., 1H), 2.43 (s, 3H), 2.19 (s, 3H); LC-MS 278.0 [M+H]$^+$.

Step 3

6-((1R,2S)-2-Aminocyclohexylamino)-4-(5,6-dimethylpyridin-2-ylamino)pyridazine-3-carboxamide

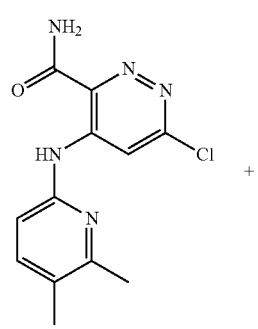

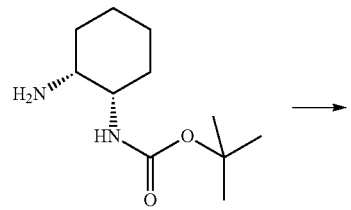

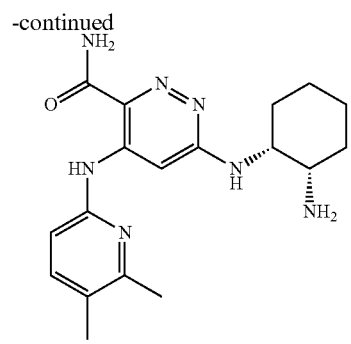

6-Chloro-4-(5,6-dimethylpyridin-2-ylamino)pyridazine-3-carboxamide (841 mg, 3.03 mmol) was dissolved in NMP (2 mL) and to this solution was added tert-butyl (1S,2R)-2-aminocyclohexylcarbamate (649 mg, 3.03 mmol) and the reaction mixture heated in an oil bath with stirring at 120° C. for 24 h. A second equivalent of tert-butyl (1S,2R)-2-aminocyclohexylcarbamate (649 mg, 3.03 mmol) was added and reaction continued for 72 h. The mixture was cooled, then the NMP solvent was distilled off under high vacuum. The residue was dissolved in dichloromethane containing few drops of methanol and passed through a silica plug eluting with 5% of a 9:1 MeOH:NH$_4$OH solution in CH$_2$Cl$_2$ to yield tert-butyl (1S,2R)-2-(6-carbamoyl-5-(5,6-dimethylpyridin-2-ylamino)pyridazin-3-ylamino)cyclohexylcarbamate mixed with 6-chloro-4-(5,6-dimethylpyridin-2-ylamino)pyridazine-3-carboxamide. The mixture was suspended in CH$_2$Cl$_2$ (3 mL) then TFA (1.48 g, 13.0 mmol) was added and mixture stirred at room temperature for 18 h. The mixture was concentrated in vacuo and the residue obtained was purified by chromatography (spherical silica 20-45 uM, 50 g, Versaflash Supelco, 0 to 10% of a 9:1 MeOH:NH$_4$OH solution in CH$_2$Cl$_2$, 20 min) to give 6-((1R,2S)-2-aminocyclohexylamino)-4-(5,6-dimethylpyridin-2-ylamino)pyridazine-3-carboxamide (550 mg, 49% yield over two steps) as an off-white solid. $^1$H NMR (DMSO-d$_6$) δ: 11.48 (s, 1H), 8.36 (br. s., 1H), 8.05 (s, 1H), 7.60 (br. s., 1H), 7.47 (d, J=8.1 Hz, 1H), 6.80 (d, J=8.1 Hz, 1H), 6.73 (d, J=8.1 Hz, 1H), 3.87 (br. s., 1H), 3.15 (br. s., 1H), 2.45 (s, 3H), 2.20 (s, 3H), 1.44-1.79 (m, 8H), 1.32 (br. s., 2H); LC-MS 356.1 [M+H]$^+$.

Example 16

6-((1R,2S)-2-Amino-cyclohexylamino)-4-(5-chloro-6-methyl-pyridin-2-ylamino)-pyridazine-3-carboxylic acid amide Step 1

Methyl 6-chloro-4-(5-chloro-6-methylpyridin-2-ylamino)pyridazine-3-carboxylate

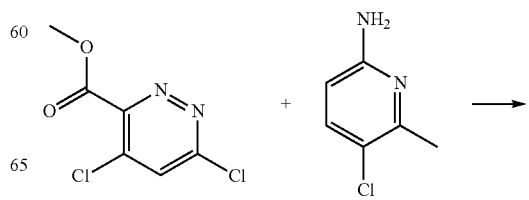

Step 3

6-((1R,2S)-2-Aminocyclohexylamino)-4-(5-chloro-6-methylpyridin-2-ylamino)pyridazine-3-carboxamide

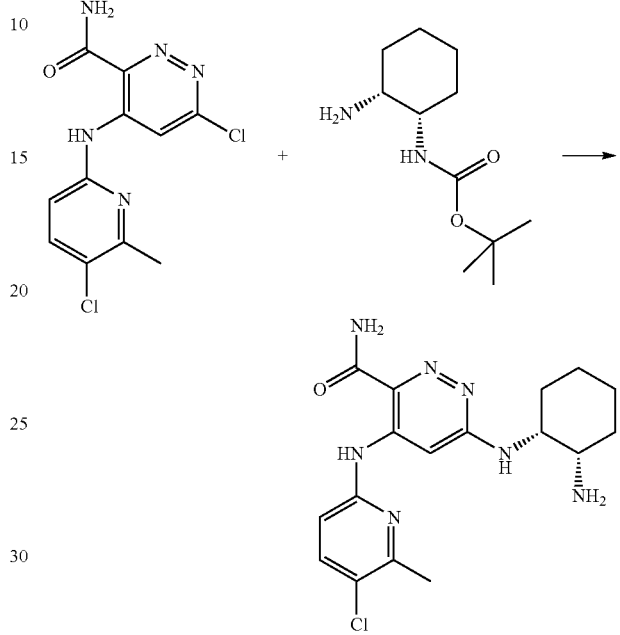

A pressure tube was charged with methyl 4,6-dichloropyridazine-3-carboxylate (2 g, 9.66 mmol) and 5-chloro-6-methylpyridin-2-amine (2.76 g, 19.3 mmol). To the mixture was added acetonitrile (12 mL) and the reaction mixture heated with stirring at 130° C. for 1.5 days. After cooling to room temperature, the acetonitrile was removed in vacuo. The residue obtained was purified by chromatography (silica, 80 g, 50 μm from Analogix, 0% to 5% acetone in dichloromethane over 20 min., holding at 5% for 5 min, then increasing the gradient from 5% to 10% over the next 20 min) to give methyl 6-chloro-4-(5-chloro-6-methylpyridin-2-ylamino)pyridazine-3-carboxylate (618 mg, 20%) as an orange solid. $^1$H NMR (400 MHz, CHLOROFORM-d) δ ppm 10.70 (br. s., 1H), 9.18 (s, 1H), 7.63 (d, J=8.34 Hz, 1H), 6.78 (d, J=8.34 Hz, 1H), 4.12 (s, 3H), 2.66 (s, 3H), 1.58 (br. s., 1H); LC-MS 313 [M+H]$^+$.

Step 2

6-Chloro-4-(5-chloro-6-methylpyridin-2-ylamino)pyridazine-3-carboxamide

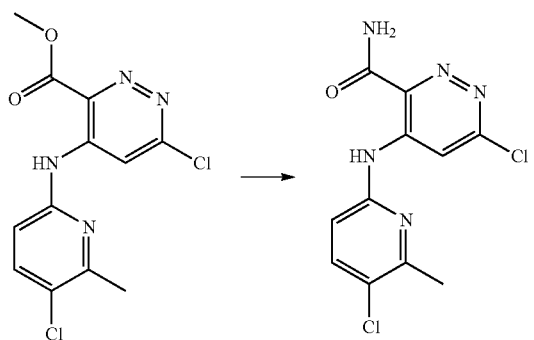 [SMILES: COC(=O)c1nnc(Cl)cc1Nc1ccc(Cl)c(C)n1 ; Cc1nc(Nc2cc(Cl)nnc2C(N)=O)ccc1Cl]

A pressure tube was charged with methyl 6-chloro-4-(5-chloro-6-methylpyridin-2-ylamino)pyridazine-3-carboxylate (600 mg, 1.92 mmol) and an ammonia solution in methanol (7M, 20 mL, 140 mmol). The reaction mixture was heated to 50° C. and was stirred for 18 h. The mixture was cooled and concentrated in vacuo to give 6-chloro-4-(5-chloro-6-methylpyridin-2-ylamino)pyridazine-3-carboxamide (665 mg crude, 116%) as a yellow solid. $^1$H NMR (400 MHz, CHLOROFORM-d) d ppm 11.69 (br. s., 1H), 9.18 (s, 1H), 8.20 (br. s., 1H), 7.61 (d, J=8.59 Hz, 1H), 6.77 (d, J=8.59 Hz, 1H), 5.71 (br. s., 1H), 2.65 (s, 3H). LC-MS 298 [M+H]$^+$. This material was used directly in the next step without further purification.

A pressure tube was charged with 6-chloro-4-(5-chloro-6-methylpyridin-2-ylamino)pyridazine-3-carboxamide (600 mg, 2.01 mmol), tert-butyl (1S,2R)-2-aminocyclohexylcarbamate (863 mg, 4.03 mmol) and NMP (6 mL) to give a yellow suspension. The reaction mixture was stirred at 140° C. for 2.5 days. After cooling to room temperature, the NMP was distilled off using a Kugelrohr to afford a brown, viscous oil. This crude material was dissolved in dichloromethane and methanol and adsorbed onto silica gel. Purification by chromatography (spherical silica 20-45 m, 50 g, Versaflash column from Supelco, eluting from 100% dichloromethane to 84:15.2:0.8 dichloromethane/methanol/NH$_4$OH), to give tert-butyl (1S,2R)-2-(6-carbamoyl-5-(5-chloro-6-methylpyridin-2-ylamino)pyridazin-3-ylamino)cyclohexylcarbamate (242.3 mg) as a brown solid. The product was then dissolved in dichloromethane (3 mL) and TFA (2.96 g, 2 mL, 26.0 mmol) was added. The mixture was stirred at room temperature for 2 h. The excess TFA and the dichloromethane were removed in vacuo and the residue obtained was purified by chromatography (spherical silica 20-45 μm, 50 g, Versaflash from Supelco, eluting with a gradient of 0.05:0.95:99 NH$_4$OH:methanol:dichloromethane up to 0.6:11.4:88 NH$_4$OH:methanol:dichloromethane over 40 min) to give 6-((1R,2S)-2-aminocyclohexylamino)-4-(5-chloro-6-methylpyridin-2-ylamino)pyridazine-3-carboxamide (152 mg, 4%) as a light brown solid. $^1$H NMR (400 MHz, DMSO-d$_6$) δ ppm 11.77 (br. s., 1H), 8.42 (br. s., 1H), 8.05 (br. s., 1H), 7.59-7.80 (m, 2H), 6.78-6.99 (m, 2H), 3.18 (br. s., 1H), 2.57 (br. s., 4H), 1.21-1.42 (m, 2H), 1.20-1.81 (m, 8H), LC-MS 376 [M+H]$^+$.

Example 17

6-((1R,2S)-2-Amino-cyclohexylamino)-4-(5-chloro-6-methyl-pyridin-2-ylamino)-pyridazine-3-carboxylic acid amide Step 1

2-Diazo-3-oxo-pentanedioic acid dimethyl ester

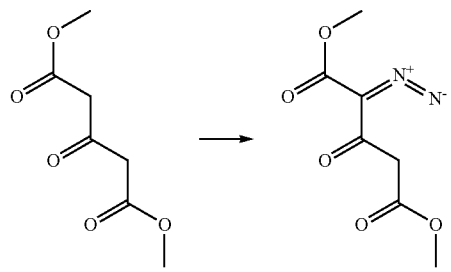

To a stirred solution of dimethyl 3-oxopentanedioate (50.0 g, 287.1 mmol) and triethylamine (47.8 mL, 344.5 mmol) in acetonitrile (1.2 L) at 0° C. was added 4-acetamidobenzene sulfonyl azide (69.0 g, 287.1 mmol) portion wise. After addition was completed, the reaction mixture was stirred at room temperature for 1 h (silica TLC; ethyl acetate:hexane=1:4, Rf=0.3; showed KMnO4 activity). The reaction mixture was filtered, and the filtrate was concentrated to get a viscous mass, which was diluted with n-hexane (3 L). The unwanted solid byproduct was removed by filtration then filtrate was concentrated under reduced pressure to give 2-diazo-3-oxo-pentanedioic acid dimethyl ester (50.0 g, 87% crude yield) as a light yellow liquid, which was directly used for next step without further purification.

Step 2

4,6-Dihydroxy-pyridazine-3-carboxylic acid methyl ester

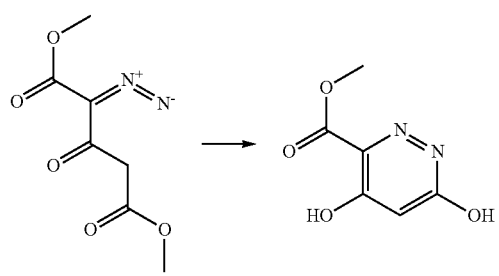

A mixture of 2-diazo-3-oxo-pentanedioic acid dimethyl ester (50.0 g, 249.8 mmol) and triphenylphosphine (65.5 g, 249.8 mmol) in diethyl ether (500 mL) was stirred at room temperature for 24 h. The organic solvent was removed under vacuum and then acetic acid (500 mL) and water (50 mL) were added to the residue and the mixture was refluxed for 10 h. The reaction mixture was concentrated under reduced pressure to obtain a viscous residue. Trituration with ethyl acetate generated a yellow solid that was purified by chromatography (silica, 100-200 mesh, 1-5% methanol in dichloromethane) to give 4,6-dihydroxy-pyridazine-3-carboxylic acid methyl ester (12.8 g, 30%) as a yellow solid. LC-MS 169.2 [M+H]+.

Step 3

4,6-Dichloro-pyridazine-3-carboxylic acid methyl ester

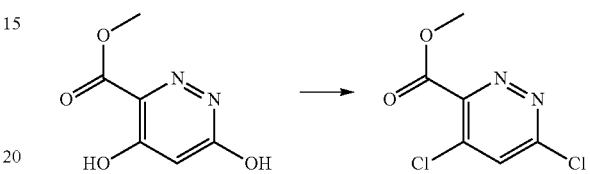

A mixture of 4,6-dihydroxy-pyridazine-3-carboxylic acid methyl ester (10.5 g, 61.7 mmol) and POCl3 (70 mL) was heated to 95° C. for 5 h. The excess POCl3 was removed under reduced pressure, then the crude residue was added to ice-water (250 mL) and extracted with ethyl acetate (3×100 mL). The combined extracts were dried then concentrated to give a crude residue which was purified by chromatography (silica, 100-200 mesh, 30% ethyl acetate in hexane) to give 4,6-dichloro-pyridazine-3-carboxylic acid methyl ester (9.2 g, 72%) as an off white solid. LC-MS: 207.0 [M+H]+.

Step 4

6-Chloro-4-(5,6-dimethoxy-pyridin-2-ylamino)-pyridazine-3-carboxylic acid methyl ester

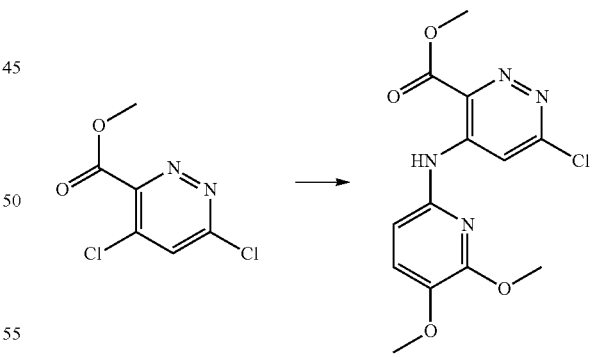

A mixture of 4,6-dichloro-pyridazine-3-carboxylic acid methyl ester (1.0 g, 4.83 mmol) and 5,6-dimethoxypyridin-2-amine (968 mg, 6.28 mmol) was dissolved in acetonitrile (5 mL) and heated at 70° C. for 16 h. The mixture was concentrated in vacuo and the crude mass obtained was purified by chromatography (silica, 100-200 mesh, 10-70% ethyl acetate in hexane) to give 6-chloro-4-(5,6-dimethoxy-pyridin-2-ylamino)-pyridazine-3-carboxylic acid methyl ester (830 mg, 53%) as a yellow solid. LC-MS: 325.2 [M+H]+.

Step 5

6-Chloro-4-(5,6-dimethoxy-pyridin-2-ylamino)-pyridazine-3-carboxylic acid amide

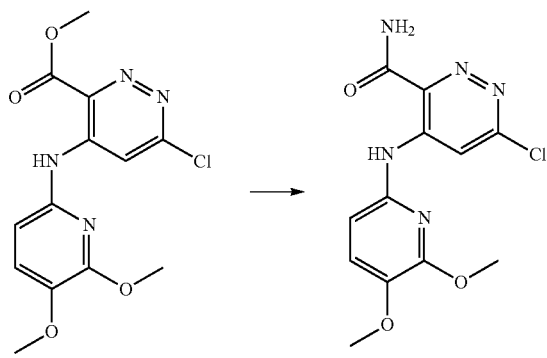 [SMILES: COC(=O)c1nnc(Cl)cc1Nc1ccc(OC)c(OC)n1 ; COc1ccc(Nc2cc(Cl)nnc2C(N)=O)nc1OC]

6-Chloro-4-(5,6-dimethoxy-pyridin-2-ylamino)-pyridazine-3-carboxylic acid methyl ester (1.7 g, 5.2 mmol) was suspended in ammonia in methanol (7N, 30.0 mL, 210 mmol) and the flask sealed. After stirring for 6 h at room temperature the mixture was concentrated in vacuo to give 6-chloro-4-(5,6-dimethoxy-pyridin-2-ylamino)-pyridazine-3-carboxylic acid amide (1.55 g, 96%) as a yellow powder. LC-MS: 310.4 [M+H]$^+$.

Step 6

6-((1R,2S)-2-Aminocyclohexylamino)-4-(5,6-dimethoxypyridin-2-ylamino)pyridazine-3-carboxamide

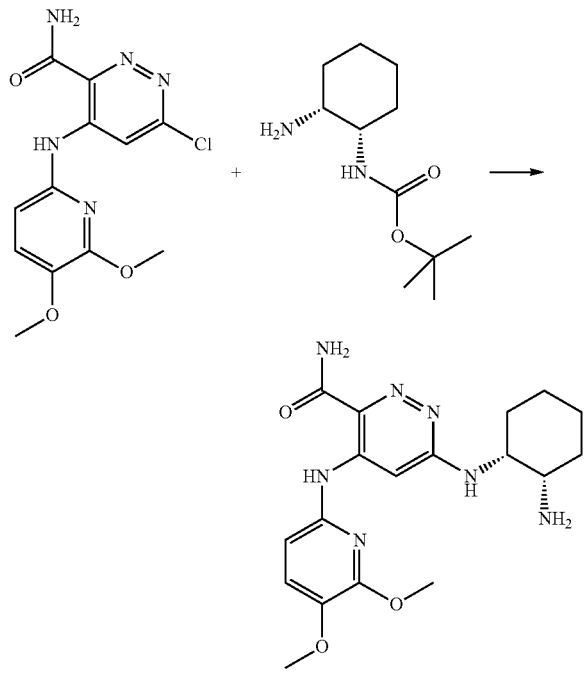

Method A

A pressure tube was charged with 6-chloro-4-(5,6-dimethoxypyridin-2-ylamino)pyridazine-3-carboxamide (310 mg, 1.00 mmol), tert-butyl (1S,2R)-2-aminocyclohexylcarbamate (429 mg, 2.00 mmol) and NMP (4 mL). The reaction mixture was stirred at 140° C. for 18 h, then the NMP was distilled using a Kugelrohr under high vacuum and at 120° C. to afford a brown viscous oil. The crude oil was dissolved in dichloromethane and methanol then adsorbed onto silica and purified by chromatography (spherical silica 20-45 μm, 11 g, Versaflash from Supelco, eluting with 100% dichloromethane to 88:11.4:0.6 dichloromethane:methanol:NH$_4$OH, 40 min) to give tert-butyl (1S,2R)-2-(6-carbamoyl-5-(5,6-dimethoxypyridin-2-ylamino)pyridazin-3-ylamino)cyclohexylcarbamate as a brown viscous oil (291.3 mg). This was dissolved in dichloromethane (2 mL) and TFA (740 mg, 500 μL, 6.49 mmol) was added. The reaction mixture was stirred at room temperature for 3 h. The TFA and the dichloromethane were removed in vacuo and the residue obtained was purified by chromatography (Spherical silica 20-45 μm, 50 g, Versaflash from Supelco, eluting with 0.1:1.9:98 NH$_4$OH:methanol:dichloromethane to 0.6:11.4:88 NH$_4$OH:methanol:dichloromethane, 40 min) to give 6-((1R,2S)-2-aminocyclohexylamino)-4-(5,6-dimethoxypyridin-2-ylamino)pyridazine-3-carboxamide (81 mg, 21%) as a light brown solid. $^1$H NMR (400 MHz, DMSO-d$_6$) δ ppm 11.33 (br. s., 1H), 8.34 (br. s., 1H), 7.59 (br. s., 1H), 7.46 (s, 1H), 7.35 (d, J=8.08 Hz, 1H), 6.70 (d, J=7.83 Hz, 1H), 6.57 (d, J=8.34 Hz, 1H), 3.95 (s, 3H), 3.76 (s, 3H), 3.10 (br. s., 1H), 2.03 (br. s., 2H), 1.18-1.78 (m, 8H), 0.98-1.12 (m, 1H); LC-MS 388 [M+H]$^+$.

Method B

To 6-chloro-4-(5,6-dimethoxypyridin-2-ylamino)pyridazine-3-carboxamide (500 mg, 1.6 mmol) and tert-butyl (1S,2R)-2-aminocyclohexylcarbamate (692 mg, 3.2 mmol) in NMP (1.5 mL), methoxy trimethylsilane (0.5 mL, 3.6 mmol) was added and the mixture heated to 150° C. for 65 h. The mixture was concentrated under high vacuum to obtain a sticky crude mass that was purified by chromatography (silica, 100-200 mesh, 1-10% methanol in dichloromethane) to give 6-((1R,2S)-2-amino-cyclohexylamino)-4-(5,6-dimethoxy-pyridin-2-ylamino)-pyridazine-3-carboxylic acid amide (220 mg 35%) as a yellow solid. LC-MS 388 [M+H]$^+$.

Example 18

6-((1R,2S)-2-aminocyclohexylamino)-4-(4,6-dimethylpyridin-2-ylamino)pyridazine-3-carboxamide Step 1

Ethyl 6-chloro-4-(4,6-dimethylpyridin-2-ylamino)pyridazine-3-carboxylate

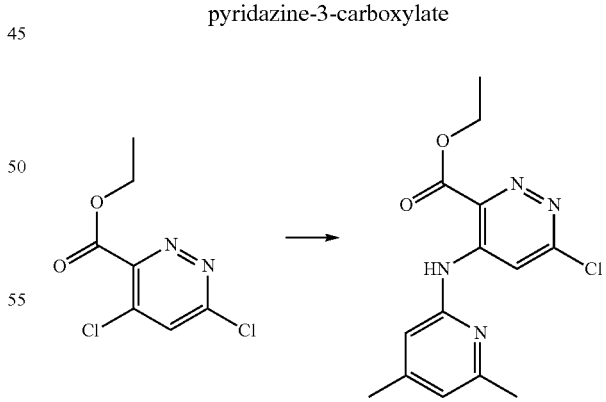

To a solution of ethyl 4,6-dichloropyridazine-3-carboxylate (790 mg, 3.57 mmol) in acetonitrile (11.9 mL) was added 4,6-dimethylpyridin-2-amine (873 mg, 7.15 mmol) and heated at 140° C. in a sealed vial for 20 h. The mixture was concentrated in vacuo then purified by chromatography (silica, 0-8% acetone in dichloromethane) to give ethyl 6-chloro-4-(4,6-dimethylpyridin-2-ylamino)pyridazine-3-carboxylate (165 mg, 538 μmol, 15%) as an off-white solid.

¹H NMR (400 MHz, CHLOROFORM-d) δ ppm 10.60 (s, 1H), 9.24 (s, 1H), 8.75 (s, 1H), 8.59 (s, 1H), 4.58 (q, J=7.1 Hz, 2H), 2.53 (s, 3H), 2.33 (s, 3H), 1.52 (t, J=7.1 Hz, 3H); MS (EI/CI) m/z: 306.1 [M+H].

Step 2

6-Chloro-4-(4,6-dimethylpyridin-2-ylamino)pyridazine-3-carboxamide

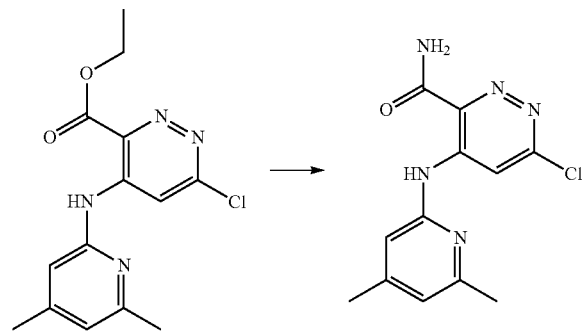 [SMILES: CCOC(=O)c1nnc(Cl)cc1Nc1cc(C)cc(C)n1 ; Cc1cc(C)nc(Nc2cc(Cl)nnc2C(N)=O)c1]

To a solution of ethyl 6-chloro-4-(4,6-dimethylpyridin-2-ylamino)pyridazine-3-carboxylate (165 mg, 538 μmol) in methanol (1 mL) was added ammonia in methanol (4.72 g, 6 mL, 42.0 mmol) and the mixture stirred at 50° C. for 16 h. The mixture was then concentrated in vacuo to give 6-chloro-4-(4,6-dimethylpyridin-2-ylamino)pyridazine-3-carboxamide (140 mg, 504 μmol, 94%) as a white solid. ¹H NMR (400 MHz, DMSO-d) δ ppm 11.92 (s, 1H), 9.13 (s, 1H), 8.86 (s, 1H), 8.21 (s, 1H), 6.84 (s, 1H), 6.76 (s, 1H), 2.45 (s, 3H), 2.29 (s, 3H); MS (EI/CI) m/z: 277.9 [M+H].

Step 3 tert-Butyl-(1S,2R)-2-(6-carbamoyl-5-(4,6-dimethylpyridin-2-ylamino)pyridazin-3-ylamino)cyclohexylcarbamate

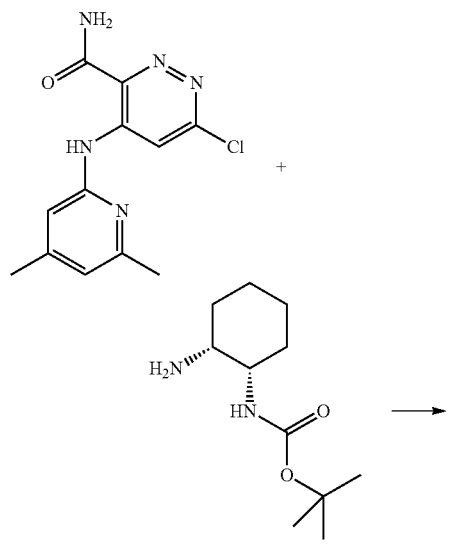

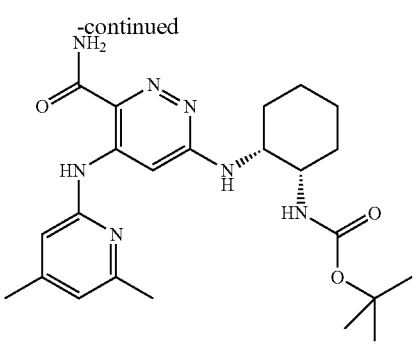

To a solution of 6-chloro-4-(4,6-dimethylpyridin-2-ylamino)pyridazine-3-carboxamide (140 mg, 504 μmol) in NMP (2.52 mL) was added tert-butyl (1S,2R)-2-aminocyclohexylcarbamate (216 mg, 1.01 mmol) and the mixture heated at 130° C. for 72 h. The reaction mixture was cooled and diluted with ethyl acetate and brine. The organic phase was washed with brine (2×) and water (1×), then the organic phase was concentrated in vacuo then purified by chromatography (silica, 40-100% ethyl acetate in hexanes) to give tert-butyl (1S,2R)-2-(6-carbamoyl-5-(4,6-dimethylpyridin-2-ylamino)pyridazin-3-ylamino)cyclohexylcarbamate (75 mg, 98.8 μmol, 20%) as an orange solid. MS (EI/CI) m/z: 456.2 [M+H].

Step 4

6-((1R,2S)-2-aminocyclohexylamino)-4-(4,6-dimethylpyridin-2-ylamino)pyridazine-3-carboxamide 2,2,2-trifluoroacetate

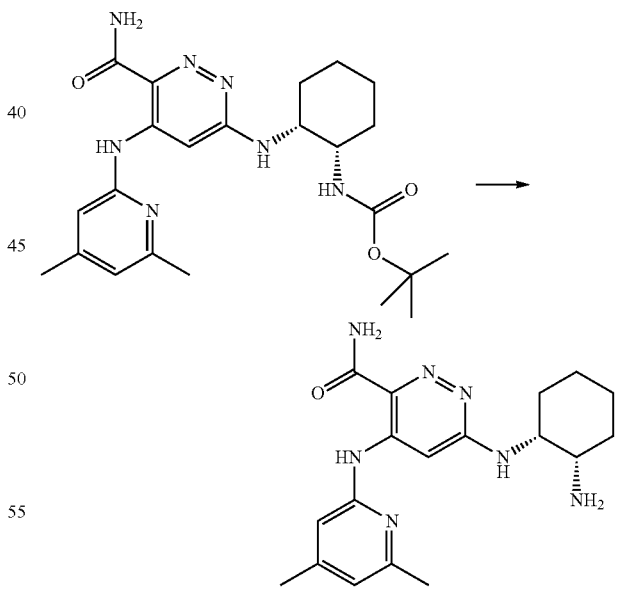

To a solution of tert-butyl (1S,2R)-2-(6-carbamoyl-5-(4,6-dimethylpyridin-2-ylamino)pyridazin-3-ylamino)cyclohexylcarbamate (75 mg, 165 μmol) in dichloromethane (5 mL) was added trifluoroacetic acid (1.88 g, 1.27 mL, 16.5 mmol) and the mixture stirred at room temperature for 16 h. The mixture was concentrated and then the residue was diluted with dichloromethane and neutralized with NH₄OH. Purification by chromatography (silica, 0-100% of a 10:0.5:

89.5 methanol:NH₄OH:dichloromethane in dichloromethane) followed by further purification by HPLC (C-18, 10-100% water in acetonitrile gradient) gave 6-((1R,2S)-2-aminocyclohexylamino)-4-(4,6-dimethylpyridin-2-ylamino)pyridazine-3-carboxamide 2,2,2-trifluoroacetate (33 mg, 70.3 µmol, 43%) as a fluffy off white solid. ¹H NMR (400 MHz, DMSO-d₆) δ ppm 11.66 (s, 1H), 8.38 (s, 1H), 8.25 (s, 1H), 7.86 (br. s, 1H), 7.40 (br. s, 2H), 6.76 (s, 1H), 6.65 (s, 1H), 4.40 (s., 1H), 3.63 (s, 1H), 2.48 (s, 3H), 1.58-1.86 (m, 8H), 1.46 (m, 2H); MS (EI/CI) m/z: 356.1 [M+H].

Example 19

6-((1R,2S)-2-aminocyclohexylamino)-4-(6-tert-butylpyridin-2-ylamino)pyridazine-3-carboxamide Step 1

Methyl 4-(6-tert-butylpyridin-2-ylamino)-6-chloropyridazine-3-carboxylate

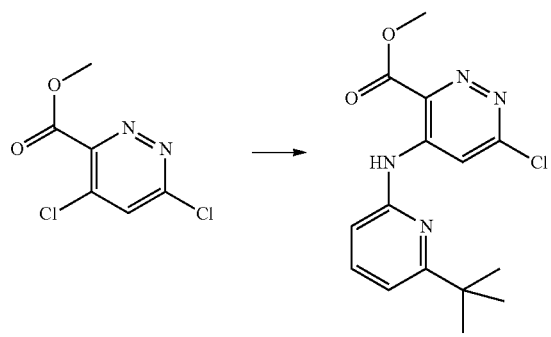 [SMILES: COC(=O)c1nnc(Cl)cc1Cl ; COC(=O)c1nnc(Cl)cc1Nc1cccc(C(C)(C)C)n1]

A mixture of methyl 4,6-dichloropyridazine-3-carboxylate (0.69 g, 3.33 mmol) and 6-tert-butylpyridin-2-amine (1.00 g, 6.67 mmol) was dissolved in acetonitrile (3 mL) and heated at 130° C. for 14 h The dark brown mixture was cooled, concentrated onto silica, and purified by chromatography (silica, 80 g, 0-20% acetone in dichloromethane, 40 min) to give methyl 4-(6-tert-butylpyridin-2-ylamino)-6-chloropyridazine-3-carboxylate (372 mg, 1.16 mmol, 35%) as a yellow solid. MS (EI/CI) m/z: 321.0 [M+H].

Step 2

4-(6-tert-Butylpyridin-2-ylamino)-6-chloropyridazine-3-carboxamide

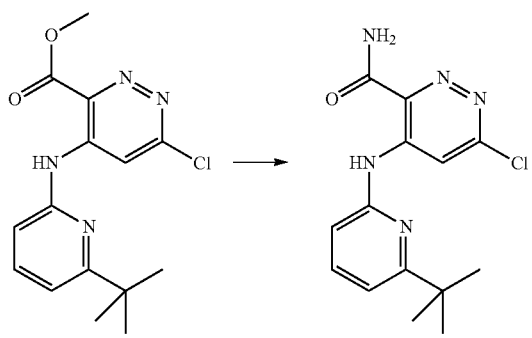 [SMILES: COC(=O)c1nnc(Cl)cc1Nc1cccc(C(C)(C)C)n1 ; CC(C)(C)c1cccc(Nc2cc(Cl)nnc2C(N)=O)n1]

Methyl 4-(6-tert-butylpyridin-2-ylamino)-6-chloropyridazine-3-carboxylate (360 mg, 1.12 mmol) was suspended in 7N ammonia in methanol (12 mL, 84.0 mmol) and stirred at room temperature for 16 h. The mixture was concentrated in vacuo to give 4-(6-tert-butylpyridin-2-ylamino)-6-chloropyridazine-3-carboxamide (317 mg, 1.03 mmol, 92%) as a yellow powder. MS (EI/CI) m/z: 306.0 [M+H]. This material was used directly in the next step without further purification.

Step 3 tert-Butyl (1S,2R)-2-(5-(6-tert-butylpyridin-2-ylamino)-6-carbamoylpyridazin-3-ylamino)cyclohexylcarbamate

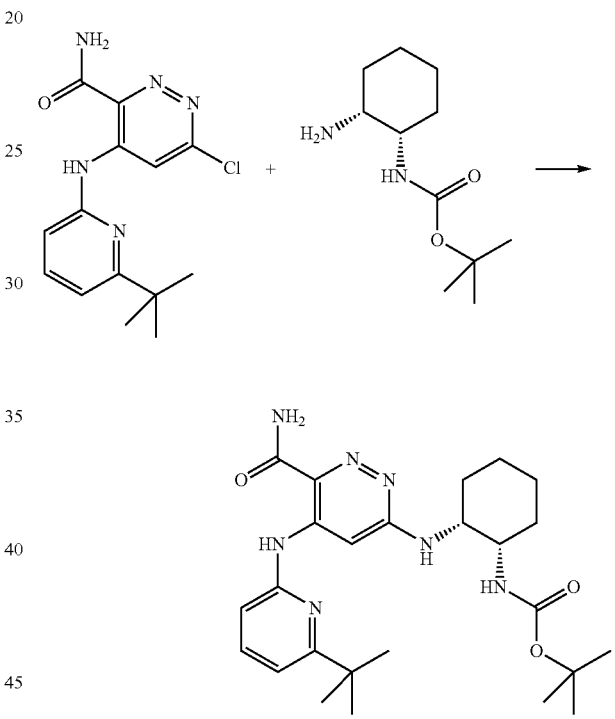

A stirred solution of 4-(6-tert-butylpyridin-2-ylamino)-6-chloropyridazine-3-carboxamide (317 mg, 1.04 mmol) and tert-butyl (1S,2R)-2-aminocyclohexylcarbamate (444 mg, 2.07 mmol) in NMP (4 mL) was heated at 140° C. for 24 h in a sealed tube. The mixture was concentrated in vacuo (Kugelrohr, high vacuum) to a brown solid. Purification by chromatography (silica, 40 g, 0-10% of a 9:1 MeOH solution in dichloromethane, 30 min) then a second purification by chromatography (silica, 24 g, 10% acetone in dichloromethane, 10 min, then 9:1:90 MeOH:NH₄OH:DCM, 10 min) gave tert-butyl (1S,2R)-2-(5-(6-tert-butylpyridin-2-ylamino)-6-carbamoylpyridazin-3-ylamino)cyclohexylcarbamate (197 mg, 407 µmol, 39%) as a brown viscous gum. MS (EI/CI) m/z: 484.2 [M+H]. This material contained small amounts of residual NMP and was used directly in the next step without further purification.

81

Step 4

6-((1R,2S)-2-Aminocyclohexylamino)-4-(6-tert-butylpyridin-2-ylamino)pyridazine-3-carboxamide

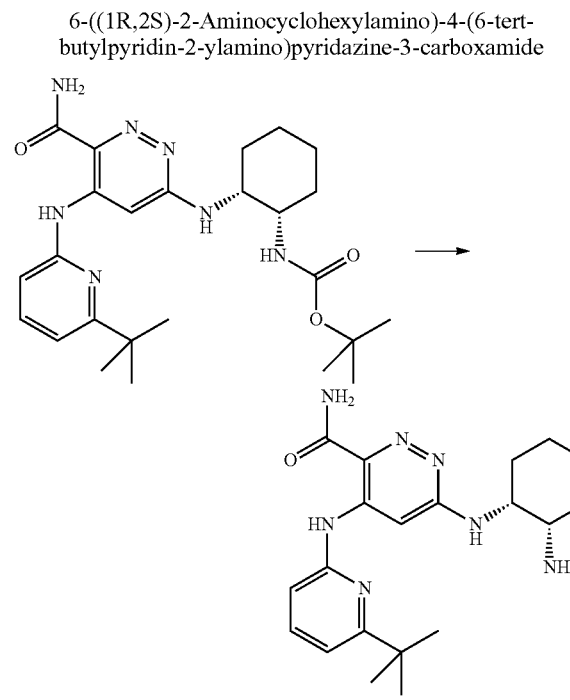

To a solution of tert-butyl (1S,2R)-2-(5-(6-tert-butylpyridin-2-ylamino)-6-carbamoylpyridazin-3-ylamino)cyclohexylcarbamate (192 mg, 397 µmol) in dichloromethane (2 mL) was added TFA (747 mg, 505 µL, 6.55 mmol). After 14 h, the mixture was concentrated in vacuo then purified by chromatography (spherical silica, 50 g, 0-20% of a 9:1 MeOH:NH$_4$OH solution in dichloromethane, 30 min) to give a pale brown gum. This was triturated with ethanol and concentrated to give a yellow solid. Trituration again with hot ethanol, followed by decanting of the supernatant, gave 6-((1R,2S)-2-aminocyclohexylamino)-4-(6-tert-butylpyridin-2-ylamino)pyridazine-3-carboxamide (57 mg, 149 µmol, 37%) as a cream powder after drying under high vacuum. $^1$H NMR (DMSO-d$_6$) δ: 11.80 (s, 1H), 8.39 (d, J=2.0 Hz, 1H), 7.98 (s, 1H), 7.55-7.76 (m, 2H), 6.96-7.09 (m, 1H), 6.77 (dd, J=8.1, 0.5 Hz, 1H), 6.70 (d, J=8.1 Hz, 1H), 3.67 (br. s., 1H), 3.03-3.12 (m, 1H), 1.45-1.72 (m, 8H), 1.22-1.41 (m, 11H); MS (EI/CI) m/z: 384.2 [M+H].

Example 20

6-(Cyclohexylamino)-4-(6-cyclopropylpyridin-2-ylamino)pyridazine-3-carboxamide

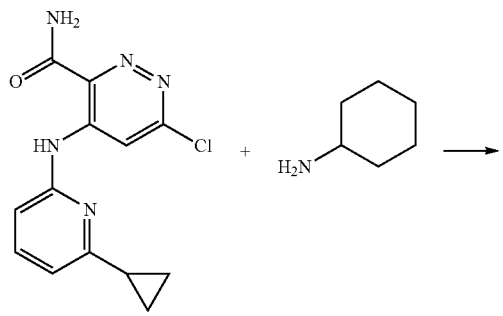

82

-continued

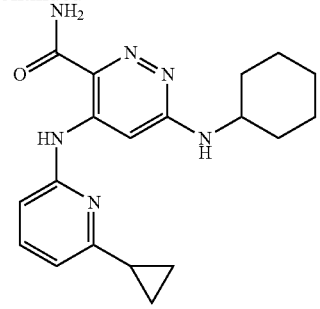

A suspension of 6-chloro-4-(6-cyclopropylpyridin-2-ylamino)pyridazine-3-carboxamide (100 mg, 345 µmol, prepared as described for example 12) and cyclohexylamine (342 mg, 395 µL, 3.45 mmol) in N-methyl-2-pyrrolidinone (0.5 mL) was heated at 130° C. for 14 h. The mixture was cooled and concentrated under high vacuum at 120° C. to remove all residual solvent and amine starting material. The brown solid obtained was purified by chromatography (silica, 11 g spherical, 0-20% acetone in dichloromethane, 20 min) to give 6-(cyclohexylamino)-4-(6-cyclopropylpyridin-2-ylamino)pyridazine-3-carboxamide (81 mg, 230 µmol, 67% yield) as a white solid. $^1$H NMR (DMSO-d$_6$) δ: 11.72 (br. s., 1H), 8.37 (br. s., 1H), 7.83 (s, 1H), 7.62 (br. s., 1H), 7.56 (t, J=7.7 Hz, 1H), 7.10 (d, J=7.8 Hz, 1H), 6.88 (d, J=7.3 Hz, 1H), 6.66 (d, J=8.1 Hz, 1H), 3.52-3.69 (m, 1H), 2.04-2.18 (m, 1H), 1.90-2.00 (m, 2H), 1.72-1.82 (m, 2H), 1.63 (d, J=12.6 Hz, 1H), 1.24-1.45 (m, 4H), 1.09-1.23 (m, 1H), 0.95-1.03 (m, 4H); MS (EI/CI) m/z: 353.1 [M+H].

Example 21

6-((1R,2S)-2-Aminocyclohexylamino)-4-(6-cyclobutylpyridin-2-ylamino)pyridazine-3-carboxamide Step 1

Methyl 6-chloro-4-(6-cyclobutylpyridin-2-ylamino)pyridazine-3-carboxylate

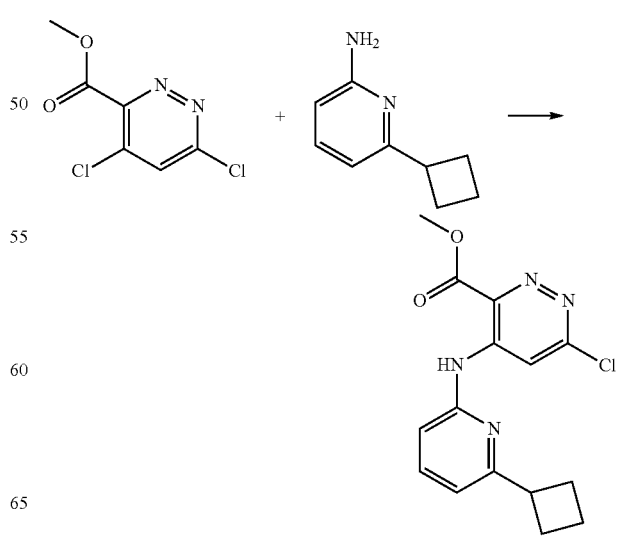

A heavy walled resealable tube was charged with methyl 4,6-dichloropyridazine-3-carboxylate (1.3 g, 6.28 mmol) and 6-cyclobutylpyridin-2-amine (931 mg, 6.28 mmol) in acetonitrile (6.00 mL). The tube was heated with stirring in an oil bath at 80° C. for 48 h. Solvent was evaporated under vacuum, the residue was dissolved in dichloromethane and then purified by flash chromatography (spherical silica 20-45 μM, 50 g, Versaflash Supelco) eluting with 0 to 10% over 20 min dichloromethane/acetone to give methyl 6-chloro-4-(6-cyclobutylpyridin-2-ylamino)pyridazine-3-carboxylate (350 mg, 17.5% yield) as a light yellow solid. $^1$H NMR (CHLOROFORM-d) δ: 10.62 (s, 1H), 9.49 (s, 1H), 7.59 (t, J=7.9 Hz, 1H), 6.85 (d, J=7.6 Hz, 1H), 6.73 (d, J=8.3 Hz, 1H), 4.10 (s, 3H), 3.67 (quin, J=8.6 Hz, 1H), 2.24-2.58 (m, 4H), 1.85-2.22 (m, 2H); LC-MS 319.0 [M+H]$^+$.

Step 2

6-Chloro-4-(6-cyclobutylpyridin-2-ylamino)pyridazine-3-carboxamide

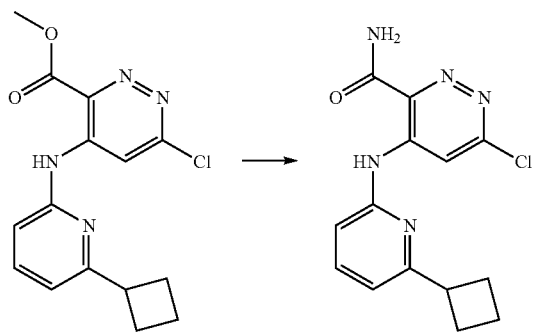 [SMILES: COC(=O)c1nnc(Cl)cc1Nc1cccc(C2CCC2)n1 ; NC(=O)c1nnc(Cl)cc1Nc1cccc(C2CCC2)n1]

In a 100 mL round bottom flask, methyl 6-chloro-4-(6-cyclobutylpyridin-2-ylamino)pyridazine-3-carboxylate (350 mg, 1.1 mmol) was suspended in ammonia 7M in methanol (7.87 g, 10.0 mL, 70.0 mmol). The flask was sealed and stirred at room temperature for 18 h. The solid formed was separated by filtration and dried in high vacuum to give 6-chloro-4-(6-cyclobutylpyridin-2-ylamino)pyridazine-3-carboxamide (281 mg, 84.3% yield) as a white solid. $^1$H NMR (DMSO-d$_6$) δ: 11.95 (s, 1H), 9.34 (s, 1H), 8.85 (s, 1H), 8.20 (s, 1H), 7.69 (t, J=7.7 Hz, 1H), 6.91 (dd, J=7.7, 3.6 Hz, 2H), 3.66 (quin, J=8.6 Hz, 1H), 2.19-2.40 (m, 4H), 1.78-2.15 (m, 2H); LC-MS 304.1 [M+H]$^+$.

Step 3 tert-Butyl (1S,2R)-2-(6-carbamoyl-5-(6-cyclobutylpyridin-2-ylamino)pyridazin-3-ylamino)cyclohexylcarbamate

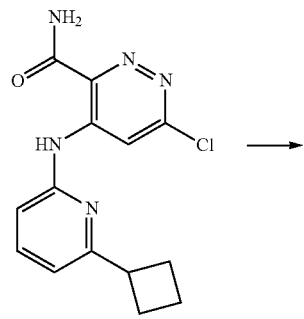

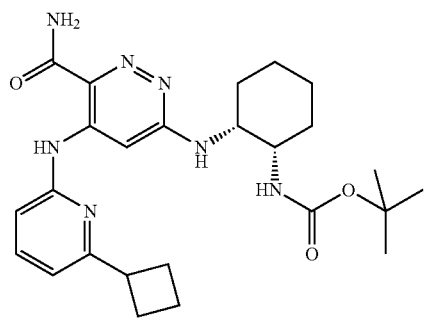

In a 25 mL round bottom flask, a solution of 6-chloro-4-(6-cyclobutylpyridin-2-ylamino)pyridazine-3-carboxamide (281 mg, 925 μmol) in N-methyl-2-pyrrolidinone (3.5 mL) was treated with tert-butyl (1S,2R)-2-aminocyclohexylcarbamate (397 mg, 1.85 mmol) and the mixture heated to 120° C. for 72 h. After cooling to room temperature the solvent was evaporated in high vacuum and residue was purified by flash column (spherical silica 20-45 μM, 80 g, Versaflash Supelco) eluting with 0 to 5% over 20 min (MeOH containing 10% NH$_4$OH)/CH$_2$Cl$_2$ to give tert-butyl (1S,2R)-2-(6-carbamoyl-5-(6-cyclobutylpyridin-2-ylamino)pyridazin-3-ylamino)cyclohexylcarbamate (112 mg, 25.1% yield) as a light brown foam. $^1$H NMR (CHLOROFORM-d) δ: 11.49 (br. s., 1H), 8.38 (s, 1H), 8.12 (d, J=3.0 Hz, 1H), 7.42 (t, J=7.9 Hz, 1H), 7.23 (s, 1H), 6.67 (d, J=7.2 Hz, 1H), 6.59 (d, J=7.9 Hz, 1H), 5.89-6.22 (m, 2H), 3.72-4.08 (m, 2H), 3.55 (quin, J=8.6 Hz, 1H), 1.76-2.11 (m, 4H), 1.19-1.74 (m, 19H); LC-MS 482.1 [M+H]$^+$.

Step 4

6-((1R,2S)-2-Aminocyclohexylamino)-4-(6-cyclobutylpyridin-2-ylamino)pyridazine-3-carboxamide

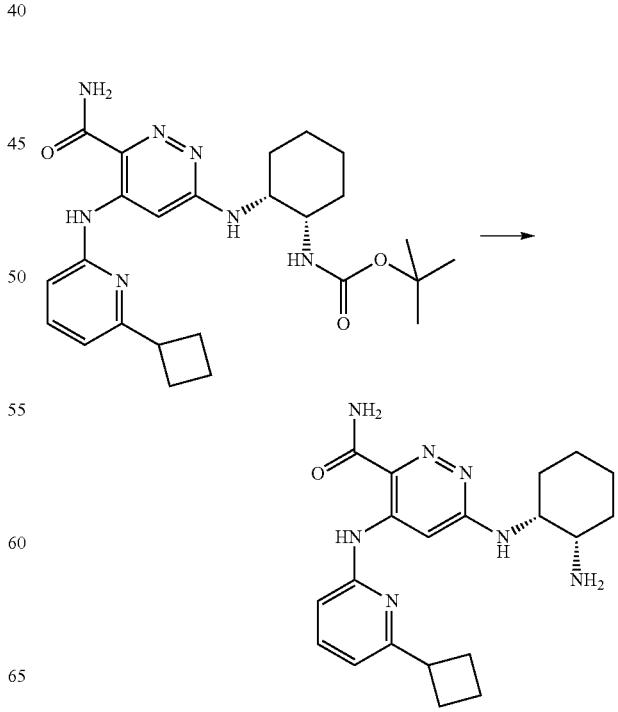

In a 25 mL round bottom flask, a solution of tert-butyl (1S,2R)-2-(6-carbamoyl-5-(6-cyclobutylpyridin-2-ylamino)pyridazin-3-ylamino)cyclohexylcarbamate (112 mg, 233 µmol) in CH$_2$Cl$_2$ (5.0 mL) was treated with TFA (2.22 g, 1.5 mL, 19.5 mmol) and the mixture stirred to room temperature for 18 h. Solvents evaporated and residue purified by flash chromatography (spherical silica 20-45 µM, 80 g, Versaflash Supelco) eluting with 0 to 10% over 30 min (MeOH containing 10% NH$_4$OH)/CH$_2$Cl$_2$ to give 6-((1R,2S)-2-aminocyclohexylamino)-4-(6-cyclobutylpyridin-2-ylamino)pyridazine-3-carboxamide (48 mg, 126 µmol, 54.1% yield) as an off-white solid. $^1$H NMR (CHLOROFORM-d) δ: 11.43 (br. s., 1H), 8.45 (s, 1H), 8.03 (br. s., 1H), 7.51 (t, J=7.7 Hz, 1H), 6.75 (d, J=7.2 Hz, 1H), 6.68 (d, J=7.9 Hz, 1H), 5.62 (d, J=8.3 Hz, 1H), 5.37 (br. s., 1H), 3.88 (br. s., 1H), 3.65 (quin, J=8.5 Hz, 1H), 3.22 (d, J=4.9 Hz, 1H), 2.27-2.51 (m, 4H), 1.99-2.22 (m, 1H), 1.94 (dd, J=11.1, 5.5 Hz, 1H), 1.07-1.84 (m, 10H); LC-MS 382.0 [M+H]$^+$.

Example 22

6-((1R,2S)-2-Aminocyclohexylamino)-4-(1-methyl-1H-benzo[d]imidazol-4-ylamino)pyridazine-3-carboxamide Step 1

Ethyl 6-chloro-4-(1-methyl-1H-benzo[d]imidazol-4-ylamino)pyridazine-3-carboxylate

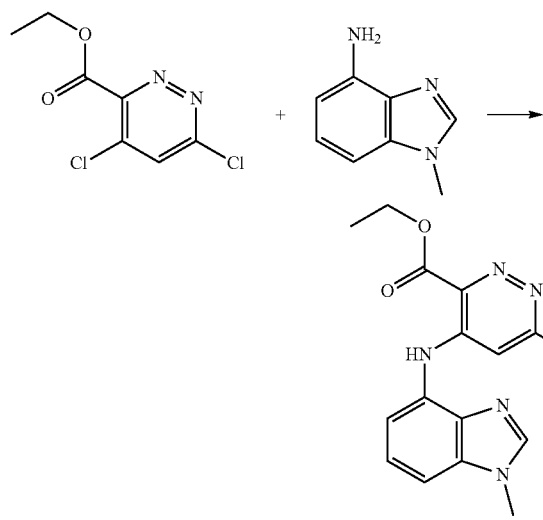

A heavy walled resealable tube, was charged with ethyl 4,6-dichloropyridazine-3-carboxylate (500 mg, 2.26 mmol) and 1-methyl-1H-benzo[d]imidazol-4-amine dihydrochloride (498 mg, 2.26 mmol) in acetonitrile (3.5 mL) with stirring. DIPEA (877 mg, 1.19 mL, 6.79 mmol) was added and the tube was heated with stirring in an oil bath at 80° C. for 24 h. Solvents evaporated and crude purified by flash chromatography (silica 20-45 µM, 80 g, Thomson, 0 to 20% acetone in dichloromethane, 20 min) to give ethyl 6-chloro-4-(1-methyl-1H-benzo[d]imidazol-4-ylamino)pyridazine-3-carboxylate (461 mg, 1.39 mmol, 61%) as a light yellow solid. $^1$H NMR (CHLOROFORM-d) δ: 10.42 (s, 1H), 7.92 (s, 1H), 7.30-7.45 (m, 2H), 7.23-7.28 (m, 1H), 7.20 (s, 1H), 4.59 (q, J=7.1 Hz, 2H), 3.91 (s, 3H), 1.51 (t, J=7.2 Hz, 3H); LC-MS 332.0 [M+H]$^+$.

Step 2

6-Chloro-4-(1-methyl-1H-benzo[d]imidazol-4-ylamino)pyridazine-3-carboxamide

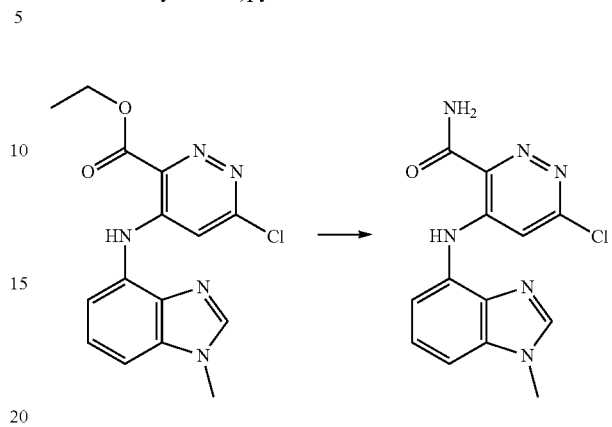

Ethyl 6-chloro-4-(1-methyl-1H-benzo[d]imidazol-4-ylamino)pyridazine-3-carboxylate (285 mg, 859 µmol) was suspended in ammonia (7M in methanol, 7.87 g, 10.0 mL, 70.0 mmol). The flask was sealed and stirred at room temperature for 18 h. The solvent was evaporated and the residue dried in high vacuum to give 6-chloro-4-(1-methyl-1H-benzo[d]imidazol-4-ylamino)pyridazine-3-carboxamide (260 mg, 100%) as an off-white solid. $^1$H NMR (DMSO-d$_6$) δ: 11.36 (s, 1H), 8.74 (s, 1H), 8.22 (s, 1H), 8.09 (s, 1H), 7.41-7.52 (m, 1H), 7.28-7.35 (m, 2H), 7.23 (s, 1H), 3.86 (s, 3H); LC-MS 303.0 [M+H]$^+$.

Step 3 tert-Butyl (1S,2R)-2-(6-carbamoyl-5-(6-cyclobutylpyridin-2-ylamino)pyridazin-3-ylamino)cyclohexylcarbamate

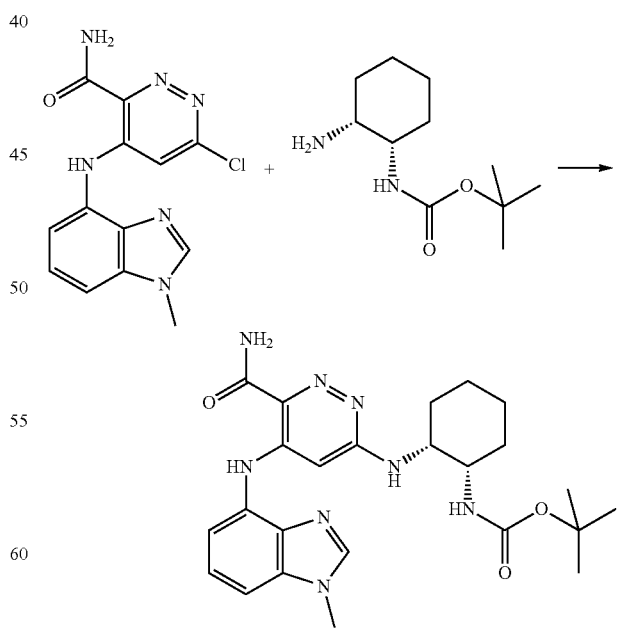

A solution of 6-chloro-4-(1-methyl-1H-benzo[d]imidazol-4-ylamino)pyridazine-3-carboxamide (260 mg, 859 µmol) in N-methyl-2-pyrrolidinone (3.0 mL) was treated with tert-butyl (1S,2R)-2-aminocyclohexylcarbamate (368 mg, 1.72 mmol), and the mixture was heated to 120° C. for 72 h. The solvent was evaporated under high vacuum and the residue was purified by chromatography (spherical silica 20-45 µM, 80 g, Versaflash Supelco, 0 to 5% of a 9:1 MeOH: NH₄OH solution in CH₂Cl₂, 20 min) to give tert-butyl (1S,2R)-2-(6-carbamoyl-5-(1-methyl-1H-benzo[d]imidazol-4-ylamino) pyridazin-3-ylamino)cyclohexylcarbamate (132 mg, 32%) as a light brown foam. ¹H NMR (CHLOROFORM-d) δ: 11.05 (s, 1H), 7.89 (d, J=2.6 Hz, 1H), 7.77 (s, 1H), 7.39 (br. s., 1H), 6.96-7.30 (m, 3H), 6.40 (br. s., 1H), 6.10-6.33 (m, 2H), 3.78 (br. s., 4H), 3.52 (br. s., 1H), 0.95-1.70 (m, 17H); LC-MS 481.0 [M+H]⁺.

Step 4

6-((1R,2S)-2-Aminocyclohexylamino)-4-(1-methyl-1H-benzo[d]imidazol-4-ylamino)pyridazine-3-carboxamide

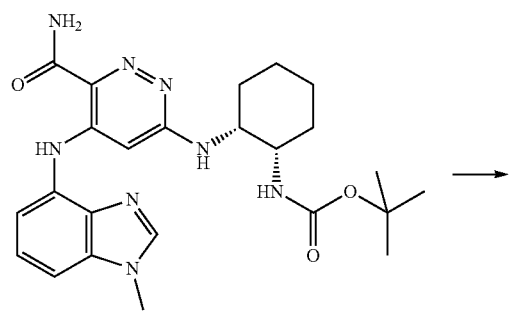

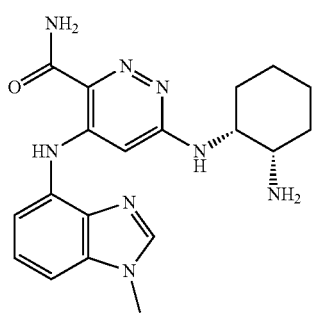

A solution of tert-butyl (1S,2R)-2-(6-carbamoyl-5-(1-methyl-1H-benzo[d]imidazol-4-ylamino)pyridazin-3-ylamino) cyclohexylcarbamate (132 mg, 275 µmol) in CH₂Cl₂ (5 mL) was treated with TFA (4.08 g, 2.76 mL, 35.8 mmol) and the reaction mixture stirred to room temperature for 18 h. The solvent was evaporated and the residue purified by chromatography (spherical silica 20-45 µM, 80 g, Versaflash Supelco, 0 to 10% of a 9:1 MeOH:NH₄OH solution in CH₂Cl₂, 30 min) to give 6-((1R,2S)-2-aminocyclohexylamino)-4-(1-methyl-1H-benzo[d]imidazol-4-ylamino)pyridazine-3-carboxamide (70 mg, 67%) as an off-white solid. ¹H NMR (DMSO-d₆) δ: 11.06 (s, 1H), 8.23 (br. s., 1H), 8.16 (s, 1H), 7.50 (br. s., 1H), 7.15-7.37 (m, 3H), 6.75 (s, 1H), 6.70 (d, J=7.6 Hz, 1H), 4.09 (br. s., 1H), 3.84 (s, 3H), 3.08 (br. s., 1H), 1.54 (br. s., 6H), 1.26 (d, J=17.0 Hz, 2H); LC-MS 381.1 [M+H]⁺.

Example 23

4-(6-(2H-1,2,3-Triazol-2-yl)pyridin-2-ylamino)-6-((1R,2S)-2-aminocyclohexylamino)pyridazine-3-carboxamide Step 1

Ethyl 4-(6-(2H-1,2,3-triazol-2-yl)pyridin-2-ylamino)-6-chloropyridazine-3-carboxylate

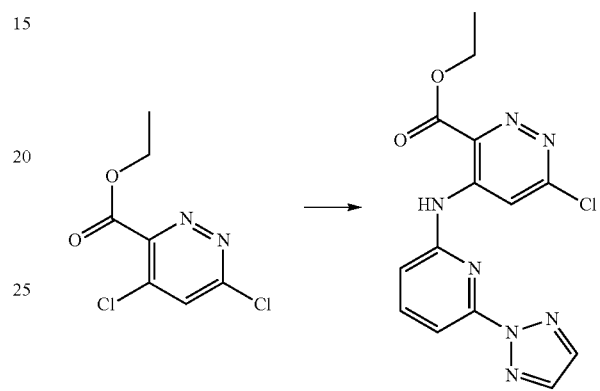

To a solution of ethyl 4,6-dichloropyridazine-3-carboxylate (154 mg, 695 µmol) in acetonitrile was added 6-(2H-1,2,3-triazol-2-yl)pyridin-2-amine (112 mg, 695 µmol) and heated to 140° C. for 72 h. The mixture was cooled and precipitated by addition of acetone. The mixture was filtered and the solid collected was washed with methanol and ether then dried to give ethyl 4-(6-(2H-1,2,3-triazol-2-yl)pyridin-2-ylamino)-6-chloropyridazine-3-carboxylate (85 mg, 246 µmol, 35%) as an off white solid. ¹H NMR (400 MHz, DMSO-d) δ ppm 10.60 (s, 1H), 9.50 (s, 1H), 8.26 (s, 2H), 8.08 (t, J=8.2 Hz, 1H), 7.74 (d, J=7.8 Hz, 1H), 7.35 (d, J=8.2 Hz, 1H), 4.48 (q, J=7.3 Hz, 2H), 1.40 (t, J=7.3 Hz, 3H); MS (EI/CI) m/z: 346.0 [M+H].

Step 2

4-(6-(2H-1,2,3-Triazol-2-yl)pyridin-2-ylamino)-6-chloropyridazine-3-carboxamide

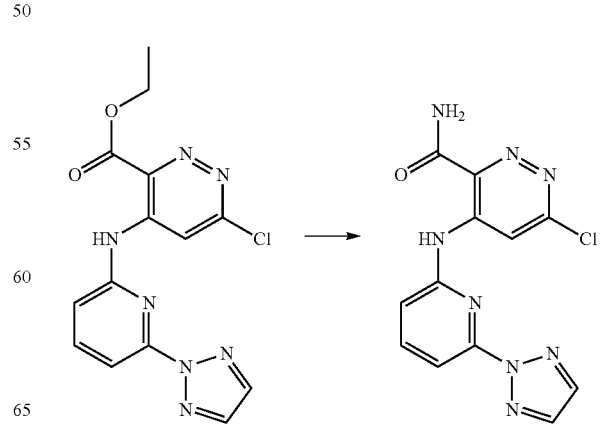

Ammonia in methanol (3.94 g, 5 mL, 35.0 mmol) was added to ethyl 4-(6-(2H-1,2,3-triazol-2-yl)pyridin-2-ylamino)-6-chloropyridazine-3-carboxylate (100 mg, 289 µmol) and stirred at 35° C. for 16 h. The mixture was concentrated in vacuo to give 4-(6-(2H-1,2,3-triazol-2-yl)pyridin-2-ylamino)-6-chloropyridazine-3-carboxamide (90 mg, 284 µmol, 98%) as an off-white solid. $^1$H NMR (400 MHz, DMSO-d) δ ppm 12.30 (s, 1H), 9.13 (s, 1H), 9.54 (s, 1H), 8.94 (s, 1H), 8.29 (s, 1H), 8.27 (s, 2H), 8.05 (t, J=8.1 Hz, 1H), 7.72 (d, J=7.9 Hz, 1H), 7.23 (d, J=8.1 Hz, 1H); MS (EI/CI) m/z: 316.9 [M+H].

Step 3 tert-Butyl (1S,2R)-2-(5-(6-(2H-1,2,3-triazol-2-yl)pyridin-2-ylamino)-6-carbamoylpyridazin-3-ylamino)cyclohexylcarbamate

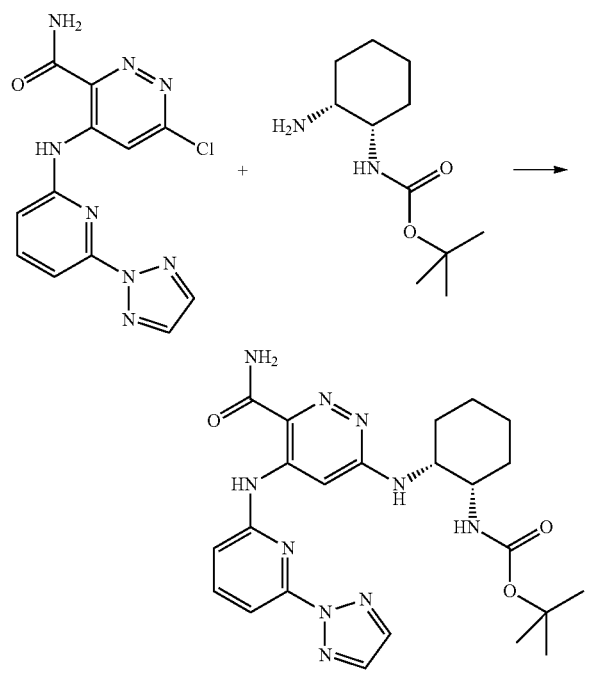

To a solution of 4-(6-(2H-1,2,3-triazol-2-yl)pyridin-2-ylamino)-6-chloropyridazine-3-carboxamide (90 mg, 284 µmol) in NMP (947 µL) was added tert-butyl (1S,2R)-2-aminocyclohexylcarbamate (122 mg, 568 µmol) and the mixture heated to 140° C. for 16 h. Additional tert-butyl (1S,2R)-2-aminocyclohexylcarbamate (61 mg, 284 µmol) was added and the mixture heated for a further 16 h. The reaction mixture was cooled, diluted with ethyl acetate and brine, then the phases were separated and the organic phase collected and washed with brine (2×). The organic layer was concentrated in vacuo then purified by chromatography (silica, 2-5% methanol in dichloromethane) to give a residue that was triturated with ethyl acetate, filtered, and washed with ether to give tert-butyl (1S,2R)-2-(5-(6-(2H-1,2,3-triazol-2-yl)pyridin-2-ylamino)-6-carbamoylpyridazin-3-ylamino)cyclohexylcarbamate (79 mg, 160 µmol, 56%) as a brown solid. MS (EI/CI) m/z: 495.1 [M+H].

Step 4

4-(6-(2H-1,2,3-Triazol-2-yl)pyridin-2-ylamino)-6-((1R,2S)-2-aminocyclohexylamino) pyridazine-3-carboxamide

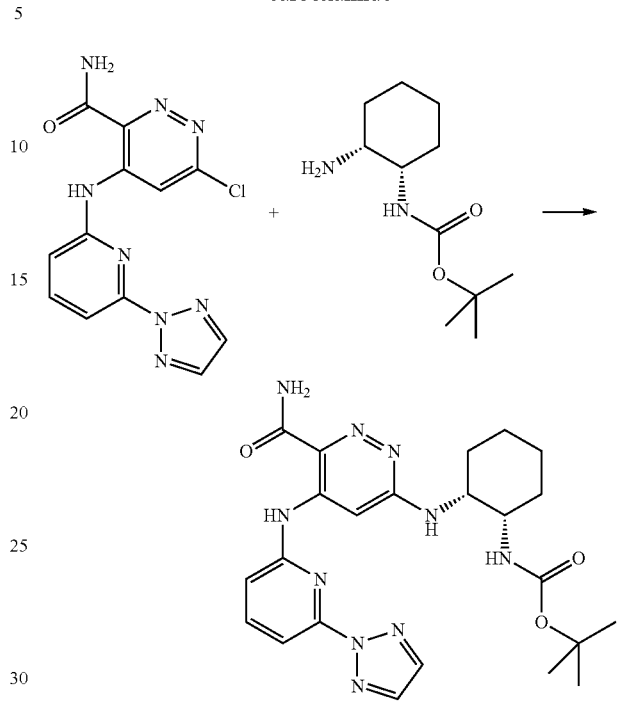

To a solution of tert-butyl (1S,2R)-2-(5-(6-(2H-1,2,3-triazol-2-yl)pyridin-2-ylamino)-6-carbamoylpyridazin-3-ylamino)cyclohexylcarbamate (79 mg, 160 µmol) in dichloromethane (2.5 mL) was added trifluoroacetic acid (364 mg, 246 µL, 3.19 mmol) and the mixture stirred at room temperature for 16 h. The mixture was diluted with dichloromethane and 1 N NaOH (2 mL), and then washed with NaHCO$_3$ and brine. The organic layer was dried over MgSO$_4$, then filtered and concentrated in vacuo. The mixture was dissolved in ethanol and concentrated (3×). The residue obtained was triturated with ether and finally filtered to give 4-(6-(2H-1,2,3-triazol-2-yl)pyridin-2-ylamino)-6-((1R,2S)-2-aminocyclohexylamino)pyridazine-3-carboxamide (5 mg, 10.8 µmol, 7%) as a light brown solid. $^1$H NMR (400 MHz, DMSO-d$_6$) δ ppm 12.12 (s, 1H), 8.46 (s, 1H), 8.38 (s, 2H), 7.99 (t, J=8.1 Hz, 1H), 7.80 (s, 1H), 7.62 (d, J=8.1 Hz, 1H), 7.11 (d, J=8.2 Hz, 1H), 6.94 (s., 1H), 1.35-1.85 (m, 8H), 1.46 (m, 2H); MS (EI/CI) m/z: 395.1 [M+H].

Example 24

6-((1R,2S)-2-aminocyclohexylamino)-4-(6,7-dihydro-5H-cyclopenta[b]pyridin-2-ylamino)pyridazine-3-carboxamide Step 1

Ethyl 6-chloro-4-(6,7-dihydro-5H-cyclopenta[b]pyridin-2-ylamino)pyridazine-3-carboxylate

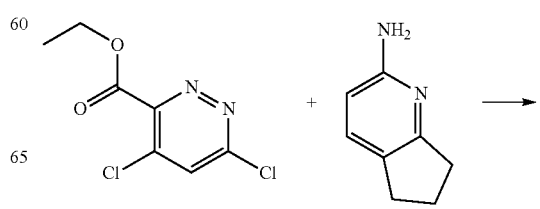

-continued

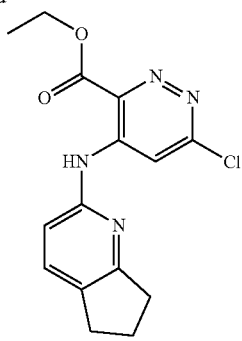

A heavy walled resealable tube was charged with ethyl 4,6-dichloropyridazine-3-carboxylate (1.5 g, 6.79 mmol), 6,7-dihydro-5H-cyclopenta[b]pyridin-2-amine (1.09 g, 8.14 mmol), acetonitrile (10 mL) and Hunig's base (877 mg, 1.19 mL, 6.79 mmol). The mixture was heated at 80° C. with stirring for 3d, after cooling to room temperature, the solvents were distilled off and the crude residue obtained was purified by chromatography (80 g column, 50 μM from Thomson, 0 to 10% acetone in dichloromethane, 20 min) to give ethyl 6-chloro-4-(6,7-dihydro-5H-cyclopenta[b]pyridin-2-ylamino)pyridazine-3-carboxylate (554 mg, 26%) as a light brown solid. $^1$H NMR (CHLOROFORM-d) δ: 10.51 (s, 1H), 8.94 (s, 1H), 7.41 (d, J=8.3 Hz, 1H), 6.60 (d, J=8.3 Hz, 1H), 4.46 (q, J=7.2 Hz, 2H), 2.92 (t, J=7.7 Hz, 2H), 2.83 (t, J=7.4 Hz, 2H), 1.87-2.24 (m, 2H), 1.42 (t, J=7.2 Hz, 3H); LC-MS 319.0 [M+H]$^+$.

Step 2

6-Chloro-4-(6,7-dihydro-5H-cyclopenta[b]pyridin-2-ylamino)pyridazine-3-carboxamide

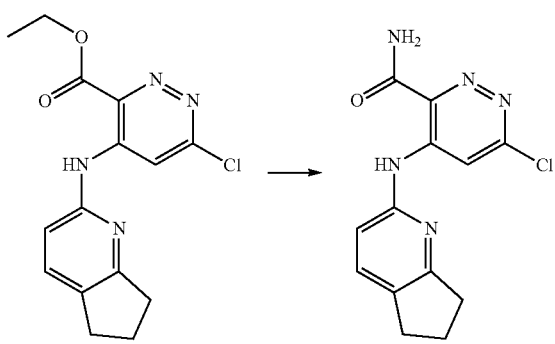 [SMILES: CCOC(=O)c1nnc(Cl)cc1Nc1ccc2c(n1)CCC2 ; NC(=O)c1nnc(Cl)cc1Nc1ccc2c(n1)CCC2]

Ethyl 6-chloro-4-(6,7-dihydro-5H-cyclopenta[b]pyridin-2-ylamino)pyridazine-3-carboxylate (554 mg, 1.74 mmol) was suspended in ammonia 7M in methanol (11.8 g, 15.0 mL, 105 mmol). The flask containing the mixture was sealed and stirred at room temperature for 18 h. The precipitated off-white solid was separated by filtration and dried under high vacuum to give 6-chloro-4-(6,7-dihydro-5H-cyclopenta[b]pyridin-2-ylamino)pyridazine-3-carboxamide (375 mg, 75%) as an off-white solid. $^1$H NMR (DMSO-d$_6$) δ: 11.92 (s, 1H), 8.95 (s, 1H), 8.83 (s, 1H), 8.18 (s, 1H), 7.63 (d, J=7.9 Hz, 1H), 6.84 (d, J=7.9 Hz, 1H), 2.78-3.00 (m, 4H), 2.07 (quin, J=7.6 Hz, 2H); LC-MS 290.0 [M+H]$^+$.

Step 3 tert-Butyl (1S,2R)-2-(6-carbamoyl-5-(6,7-dihydro-5H-cyclopenta[b]pyridin-2-ylamino)pyridazin-3-ylamino)cyclohexylcarbamate

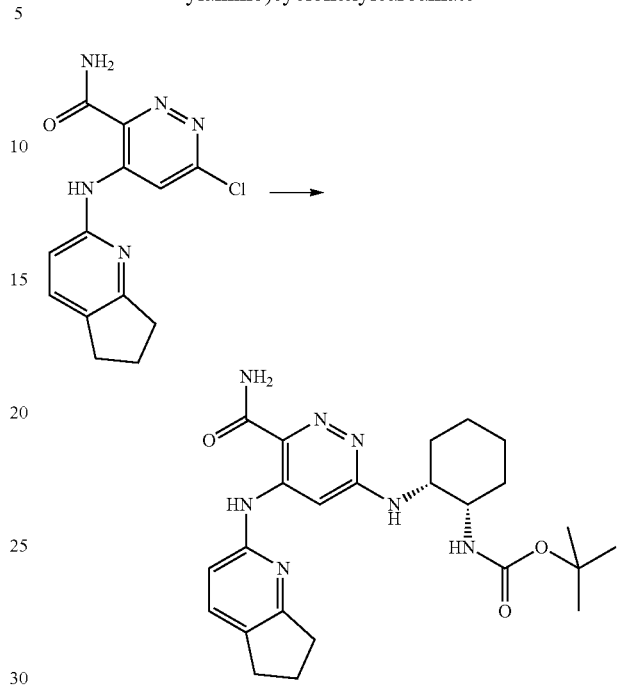

A solution of 6-chloro-4-(6,7-dihydro-5H-cyclopenta[b]pyridin-2-ylamino)pyridazine-3-carboxamide (375 mg, 1.29 mmol) and tert-butyl (1S,2R)-2-aminocyclohexylcarbamate (555 mg, 2.59 mmol) in N-methyl-2-pyrrolidinone (3 mL) was treated with tert-butyl (1S,2R)-2-aminocyclohexylcarbamate (555 mg, 2.59 mmol), The reaction mixture was heated at 120° C. for 72 h, then cooled to room temperature, concentrated under high vacuum and the residue obtained was purified by chromatography (spherical silica 20-45 μM, 80 g, Versaflash Supelco, 0 to 5% of a 9:1 MeOH:NH$_4$OH solution in CH$_2$Cl$_2$, 20 min) to give tert-butyl (1S,2R)-2-(6-carbamoyl-5-(6,7-dihydro-5H-cyclopenta[b]pyridin-2-ylamino)pyridazin-3-ylamino)cyclohexylcarbamate (444 mg, 73%) as a light brown foam. $^1$H NMR (CHLOROFORM-d) δ: 11.30 (s, 1H), 8.19 (s, 1H), 8.06 (d, J=3.4 Hz, 1H), 7.40 (d, J=8.3 Hz, 1H), 6.75-7.10 (m, 1H), 6.61 (d, J=8.3 Hz, 1H), 5.77-6.14 (m, 2H), 3.99 (m, 1H), 3.55-3.74 (m, 1H), 2.67-3.05 (m, 4H), 2.11 (quin, J=7.5 Hz, 2H), 1.18-2.01 (m, 17H); LC-MS 468.2 [M+H]$^+$.

Step 4

6-((1R,2S)-2-Aminocyclohexylamino)-4-(6,7-dihydro-5H-cyclopenta[b]pyridin-2-ylamino)pyridazine-3-carboxamide

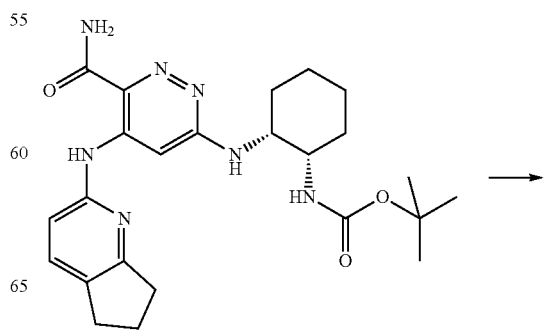

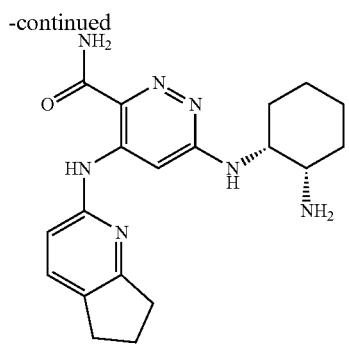

A solution of tert-butyl (1S,2R)-2-(6-carbamoyl-5-(6,7-dihydro-5H-cyclopenta[b]pyridin-2-ylamino)pyridazin-3-ylamino)cyclohexylcarbamate (444 mg, 950 μmol) in CH$_2$Cl$_2$ (5 mL) was treated with TFA (4.08 g, 2.76 mL, 35.8 mmol) and the mixture stirred at room temperature for 18 h. The solvents were evaporated and the residue purified by flash chromatography (spherical silica 20-45 μM, 80 g, Versaflash Supelco) eluting with 0 to 5% of a 9:1 MeOH:NH$_4$OH solution in CH$_2$Cl$_2$, 15 min) to give 6-((1R,2S)-2-aminocyclohexylamino)-4-(6,7-dihydro-5H-cyclopenta[b]pyridin-2-ylamino)pyridazine-3-carboxamide (80 mg, 23%) as an off-white solid. $^1$H NMR (DMSO-d$_6$) δ: 11.54 (br. s., 1H), 8.35 (br. s., 1H), 7.95 (br. s., 1H), 7.46-7.69 (m, 2H), 6.80 (d, J=7.2 Hz, 1H), 6.69 (d, J=7.6 Hz, 1H), 3.89 (br. s., 1H), 3.12 (br. s., 1H), 2.75-2.98 (m, 4H), 1.96-2.17 (m, 2H), 1.61 (d, J=11.7 Hz, 8H), 1.31 (br. s., 2H); LC-MS 368.3 [M+H]$^+$.

Example 25

6-((1R,2S)-2-Aminocyclohexylamino)-4-(6-isopropyl-5-methylpyridin-2-ylamino)pyridazine-3-carboxamide Step 1

Ethyl 6-chloro-4-(6-isopropyl-5-methylpyridin-2-ylamino) pyridazine-3-carboxylate

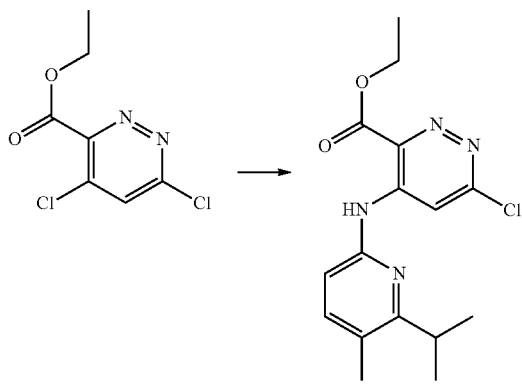 [SMILES: CCOC(=O)c1nnc(Cl)cc1Cl ; CCOC(=O)c1nnc(Cl)cc1Nc1ccc(C)c(C(C)C)n1]

A heavy walled sealable tube was charged with ethyl 4,6-dichloropyridazine-3-carboxylate (0.985 g, 4.46 mmol) and 6-isopropyl-5-methylpyridin-2-amine (1.005 g, 6.69 mmol). To the mixture was added acetonitrile (5 mL) and the yellow solution was heated (oilbath/hotplate) with stirring at 130° C. for 20 h to give a brown solution. After cooling to room temperature, the acetonitrile was removed in vacuo to obtain a dark brown solid. The residue was dissolved in dichloromethane, adsorbed on silica gel and purified by flash column (spherical silica 20-45 μm, 50 g, Versaflash from Supelco, eluting with 0% to 5% acetone in dichloromethane over 20 min, holding for 5 min. and then from 5% to 20% over 20 min, and holding for 5 min) to give ethyl 6-chloro-4-(6-isopropyl-5-methylpyridin-2-ylamino) pyridazine-3-carboxylate as yellow crystals (848 mg, 57%). $^1$H NMR (400 MHz, CHLOROFORM-d) δ ppm 10.60 (br. s., 1H), 9.36 (s, 1H), 7.44 (d, J=8.08 Hz, 1H), 6.70 (d, J=8.08 Hz, 1H), 4.58 (q, J=7.07 Hz, 2H), 3.30 (spt, J=6.70 Hz, 1H), 2.34 (s, 3H), 1.52 (t, J=7.20 Hz, 3H), 1.33 (d, J=6.82 Hz, 6H). LC-MS 335 [M+H]$^+$.

Step 2

6-Chloro-4-(6-isopropyl-5-methylpyridin-2-ylamino) pyridazine-3-carboxamide

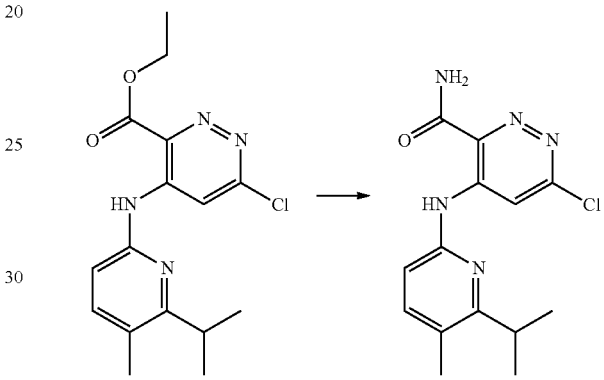

A pressure tube was charged with ethyl 6-chloro-4-(6-isopropyl-5-methylpyridin-2-ylamino) pyridazine-3-carboxylate (850 mg, 2.54 mmol) and an ammonia solution in methanol (7M, 20 mL, 140 mmol). The light yellow suspension was stirred at 50° C. for 1.5 h. After that, the reaction mixture was concentrated in vacuo to give 6-chloro-4-(6-isopropyl-5-methylpyridin-2-ylamino) pyridazine-3-carboxamide (693 mg, 89%) as an orange solid. $^1$H NMR (400 MHz, CHLOROFORM-d) δ ppm 11.48 (br. s., 1H), 9.39 (s, 1H), 8.18 (br. s., 1H), 7.42 (d, J=8.08 Hz, 1H), 6.71 (d, J=8.08 Hz, 1H), 5.67 (br. s., 1H), 3.29 (dt, J=13.52, 6.63 Hz, 1H), 2.33 (s, 3H), 2.26-2.26 (m, 1H), 1.33 (d, J=6.82 Hz, 2H). LC-MS 306 [M+H]$^+$.

Step 3

6-((1R,2S)-2-Aminocyclohexylamino)-4-(6-isopropyl-5-methylpyridin-2-ylamino)pyridazine-3-carboxamide

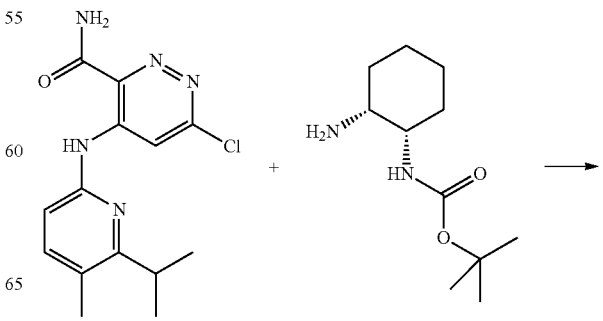

-continued

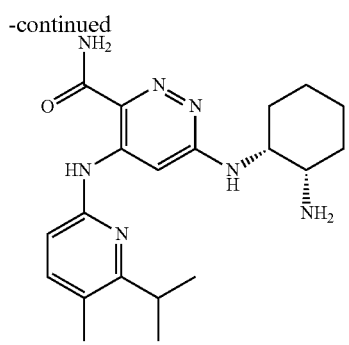

A pressure tube was charged with 6-chloro-4-(6-isopropyl-5-methylpyridin-2-ylamino)pyridazine-3-carboxamide (230 mg, 752 µmol), tert-butyl (1S,2R)-2-aminocyclohexylcarbamate (242 mg, 1.13 mmol) and NMP (4 mL). The yellow solution was stirred at 130° C. for 2.5 days. After that, the NMP was distilled off using a Kugelrohr apparatus under high vacuum to afford a light brown solid. The crude solid was dissolved in dichloromethane and MeOH and adsorbed on silica gel, then purified by flash column (spherical silica 20-45 µm, 11 g, Versaflash from Supelco, eluting with 100% dichloromethane to 88:11.4:0.6 dichloromethane:methanol:NH$_4$OH over 40 min) to give a light brown solid. The crude product was dissolved in dichloromethane (2 mL) and TFA (740 mg, 500 µL, 6.49 mmol) was added. The mixture was stirred at room temperature for 4 h. After that, the TFA and the dichloromethane were removed in vacuo, the brown solid obtained dissolved in dichloromethane, adsorbed on silica gel and then purified by flash column (spherical silica 20-45 µm, 11 g, Versaflash from Supelco, eluting with 100% dichloromethane to 88:11.4:0.6 dichloromethane:methanol:NH$_4$OH over 40 min) to give 6-((1R,2S)-2-aminocyclohexylamino)-4-(6-isopropyl-5-methylpyridin-2-ylamino)pyridazine-3-carboxamide (70 mg, 24%) as a white solid. $^1$H NMR (400 MHz, DMSO-d$_6$) δ ppm 11.65 (br. s., 1H), 8.37 (br. s., 1H), 7.92 (s, 1H), 7.61 (br. s., 1H), 7.48 (d, J=8.34 Hz, 1H), 6.71 (d, J=8.08 Hz, 1H), 6.66 (d, J=8.08 Hz, 1H), 3.24 (dt, J=13.39, 6.70 Hz, 1H), 3.08 (d, J=2.53 Hz, 1H), 2.26 (s, 3H), 1.30-1.75 (m, 11H), 1.26 (dd, J=6.70, 1.39 Hz, 6H). LC-MS 384 [M+H]$^+$.

Example 26

6-((1R,2S)-2-aminocyclohexylamino)-4-(6-propylpyridin-2-ylamino)pyridazine-3-carboxamide Step 1

Ethyl 6-chloro-4-(6-propylpyridin-2-ylamino)pyridazine-3-carboxylate

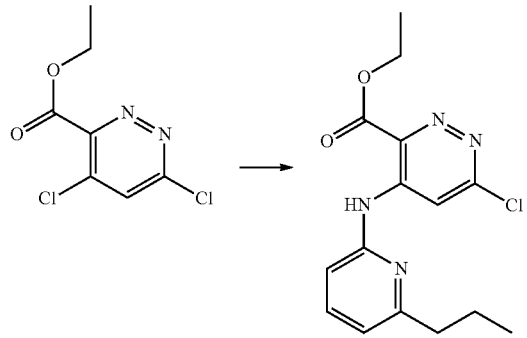 [SMILES: CCOC(=O)c1nnc(Cl)cc1Cl ; CCCc1cccc(Nc2cc(Cl)nnc2C(=O)OCC)n1]

A mixture of ethyl 4,6-dichloropyridazine-3-carboxylate (0.80 g, 3.62 mmol) and 6-propylpyridin-2-amine (739 mg, 5.43 mmol) was dissolved in acetonitrile (4 mL) and heated at 130° C. After 24 h, the reaction mixture was cooled and concentrated in vacuo, then purified by chromatography (silica, 80 g, 0 to 3% acetone in dichloromethane over 15 min, then 3 to 10% acetone in dichloromethane over another 15 min) to give ethyl 6-chloro-4-(6-propylpyridin-2-ylamino)pyridazine-3-carboxylate (335 mg, 1.04 mmol, 29%) as a pale yellow crystalline solid after drying under high vacuum at room temperature. LC-MS 321.1 [M+H]$^+$.

Step 2

6-Chloro-4-(6-propylpyridin-2-ylamino)pyridazine-3-carboxamide

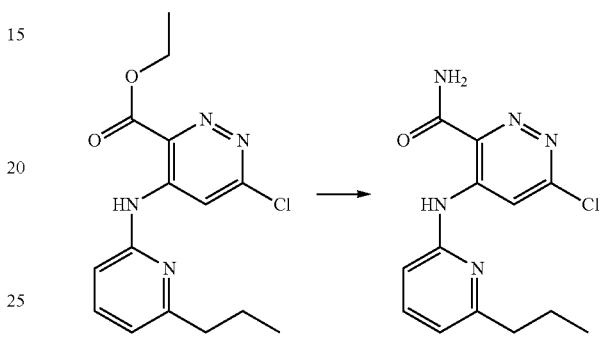

Ethyl 6-chloro-4-(6-propylpyridin-2-ylamino)pyridazine-3-carboxylate (340 mg, 1.06 mmol) was stirred with 7N methanolic ammonia (15.1 mL, 106 mmol). A colorless precipitate formed within a few minutes. After 18 h, the mixture was concentrated in vacuo to give 6-chloro-4-(6-propylpyridin-2-ylamino)pyridazine-3-carboxamide (289 mg, 991 µmol, 94%) as an off-white powder. LC-MS 292.2 [M+H]$^+$. This material was used directly without further purification.

Step 3 tert-Butyl (1S,2R)-2-(6-carbamoyl-5-(6-propylpyridin-2-ylamino)pyridazin-3-ylamino)cyclohexylcarbamate

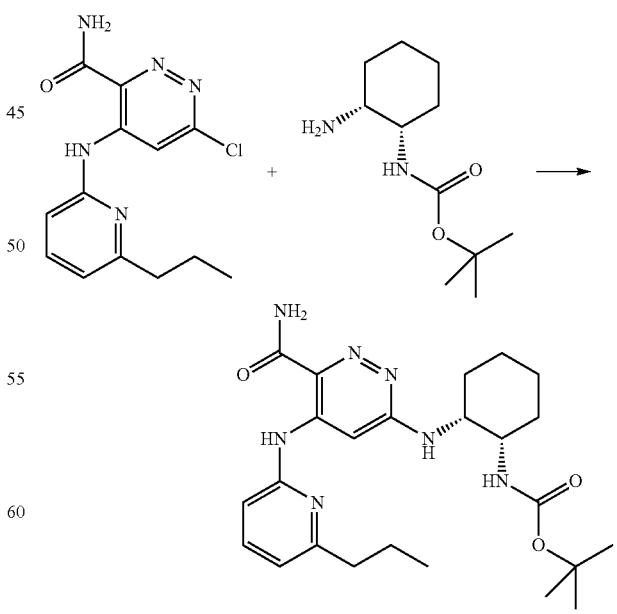

6-Chloro-4-(6-propylpyridin-2-ylamino)pyridazine-3-carboxamide (289 mg, 991 µmol) and tert-butyl (1S,2R)-2-aminocyclohexylcarbamate (425 mg, 1.98 mmol) were dissolved in N-methyl-2-pyrrolidinone (2 mL) and heated at 130° C. for 24 h. LCMS showed desired product mass, as well as starting material. A third equivalent of tert-butyl (1S,2R)-2-aminocyclohexylcarbamate was added (213 mg, 0.991 mmol) and heating continued. After 8 h, a third portion of tert-butyl (1S,2R)-2-aminocyclohexylcarbamate (0.310 g) was added. After 24 h, the mixture was cooled and concentrated in vacuo (high vacuum, 100° C.) to a brown solid residue. Purification by chromatography (silica, 0 to 10% of a 9:1 MeOH:NH$_4$OH solution in dichloromethane, 20 min) gave tert-butyl (1S,2R)-2-(6-carbamoyl-5-(6-propylpyridin-2-ylamino)pyridazin-3-ylamino)cyclohexylcarbamate (271 mg, 577 µmol, 58%) as a light brown solid. LC-MS 470.2 [M+H]$^+$.

Step 4

6-((1R,2S)-2-aminocyclohexylamino)-4-(6-propylpyridin-2-ylamino)pyridazine-3-carboxamide

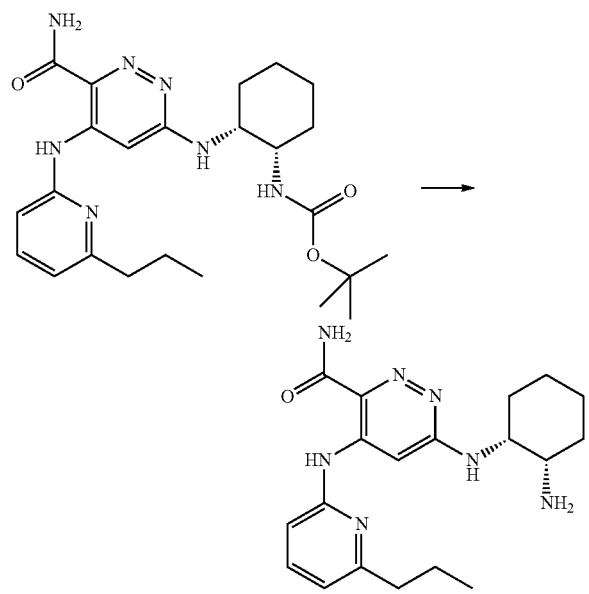

tert-Butyl (1S,2R)-2-(6-carbamoyl-5-(6-propylpyridin-2-ylamino)pyridazin-3-ylamino)cyclohexylcarbamate (260 mg, 554 µmol) was dissolved in dichloromethane (4 mL) then TFA (3.16 g, 2.13 mL, 27.7 mmol) was added. The mixture was stirred at room temperature for 12 h then the mixture was concentrated in vacuo to a brown oil, and purified by chromatography (silica, 40 g, 0 to 20% of a 9:1 MeOH:NH$_4$OH solution in dichloromethane, 30 min) to give a pale yellow foam (140 mg). This was dissolved in ethanol and concentrated in vacuo (3×20 mL) to give the desired product, pure by H nmr and LCMS except for traces of isopropyl alcohol. This was dissolved in absolute ethanol, concentrated in vacuo, and then triturated twice with ethanol (2×0 5 mL) and then dried to give 6-((1R,2S)-2-aminocyclohexylamino)-4-(6-propylpyridin-2-ylamino)pyridazine-3-carboxamide (110 mg, 295 µmol, 53%) as a white powder. $^1$H NMR (DMSO-d$_6$) δ: 11.67 (s, 1H), 8.39 (br. s., 1H), 8.08 (br. s., 1H), 7.63 (t, J=7.7 Hz, 2H), 6.85 (d, J=7.6 Hz, 1H), 6.72-6.82 (m, 2H), 3.74 (br. s., 1H), 3.12 (d, J=3.0 Hz, 1H), 2.65-2.76 (m, 2H), 1.45-1.81 (m, 10H), 1.21-1.39 (m, 2H), 0.94 (t, J=7.3 Hz, 3H); LC-MS 370.2 [M+H]$^+$.

Example 27

6-((3R,4R)-3-Aminotetrahydro-2H-pyran-4-ylamino)-4-(6-isopropyl-5-methylpyridin-2-ylamino)pyridazine-3-carboxamide

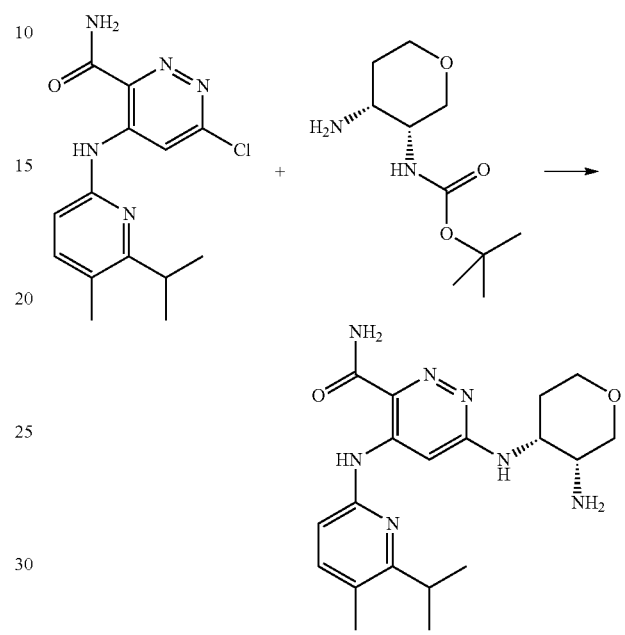

A mixture of 6-chloro-4-(6-isopropyl-5-methylpyridin-2-ylamino) pyridazine-3-carboxamide (223 mg, 729 µmol, prepared as described in example 25), tert-butyl (3R,4R)-4-aminotetrahydro-2H-pyran-3-ylcarbamate (315 mg, 1.46 mmol) and NMP (4 mL) was stirred at 140° C. for 18 h. The NMP was distilled off using a Kugelrohr apparatus under high vacuum to give a light brown solid. The crude material was dissolved in dichloromethane and MeOH and adsorbed on silica gel, then purified by chromatography (spherical silica 20-45 µm, 11 g, Versaflash from Supelco, eluting with 100% dichloromethane to 88:11.4:0.6 dichloromethane:methanol:NH$_4$OH over 40 min) to give 109 mg of intermediate as a brown solid. This intermediate was dissolved in dichloromethane (2 mL) and TFA (740 mg, 500 µL, 6.49 mmol) was added. The mixture was stirred at room temperature for 16 h. The TFA and the dichloromethane were concentrated in vacuo and the residue obtained was purified by chromatography (spherical silica 20-45 µm, 11 g, Versaflash from Supelco, eluting with 100% dichloromethane to 88:11.4:0.6 dichloromethane:methanol:NH$_4$OH over 40 min) to give a brown solid. The solid was suspended in 0.5 mL heptane and 10 drops of ethanol. The mixture was briefly sonicated and then heated, then cooled and the solvents decanted. The solid residue was dried overnight under high vacuum to give 6-((3R,4R)-3-aminotetrahydro-2H-pyran-4-ylamino)-4-(6-isopropyl-5-methylpyridin-2-ylamino)pyridazine-3-carboxamide (22 mg, 8%) as a brown solid. $^1$H NMR (400 MHz, CHLOROFORM-d) δ ppm 11.18-11.31 (m, 1H), 8.26 (s, 1H), 7.95 (br. s., 1H), 7.26 (d, J=8.34 Hz, 1H), 6.55 (d, J=8.08 Hz, 1H), 5.73 (d, J=7.33 Hz, 1H), 5.29 (br. s., 1H), 3.99 (br. s., 1H), 3.90 (d, J=8.08 Hz, 1H), 3.78 (d, J=11.37 Hz, 1H), 3.66 (q, J=7.07 Hz, 1H), 3.57 (d, J=11.37 Hz, 1H), 3.44 (t, J=11.12

Hz, 1H), 3.20 (dt, J=13.33, 6.60 Hz, 1H), 2.97 (br. s., 1H), 2.21 (s, 3H), 1.89 (d, J=11.12 Hz, 1H), 1.61-1.77 (m, 1H), 1.25 (dd, J=6.57, 3.54 Hz, 6H), 1.18 (t, J=7.07 Hz, 1H); LC-MS 386 [M+H]$^+$.

Example 28

6-((1R,2S)-2-Aminocyclohexylamino)-4-(3,5-dimethylphenylamino)pyridazine-3-carboxamide Step 1

Ethyl 6-chloro-4-(3,5-dimethylphenylamino)pyridazine-3-carboxylate

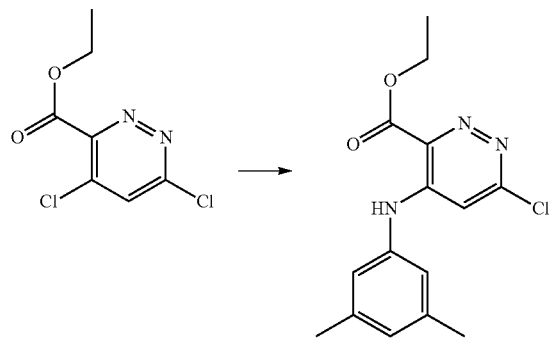 [SMILES: CCOC(=O)c1nnc(Cl)cc1Cl ; CCOC(=O)c1nnc(Cl)cc1Nc1cc(C)cc(C)c1]

To a solution of ethyl 4,6-dichloropyridazine-3-carboxylate (700 mg, 3.17 mmol) in acetonitrile (10.6 mL) was added ethyl 4,6-dichloropyridazine-3-carboxylate (700 mg, 3.17 mmol) and the mixture heated at 140° C. in a sealed vial for 48 h. The mixture was cooled and then concentrated in vacuo, then purified by chromatography (silica, 0 to 30% acetone in dichloromethane) to give ethyl 6-chloro-4-(3,5-dimethylphenylamino)pyridazine-3-carboxylate (104 mg, 340 μmol, 11%) as a light brown solid. $^1$H NMR (400 MHz, CHLOROFORM-d) δ ppm 9.70 (s, 1H), 7.03 (s, 1H), 6.99 (s, 1H), 6.88 (s, 2H), 4.57 (q, J=7.6 Hz, 2H), 2.38 (s, 6H), 1.52 (t, J=7.6 Hz, 3H); MS (EI/CI) m/z: 305.9 [M+H].

Step 2

6-Chloro-4-(3,5-dimethylphenylamino)pyridazine-3-carboxamide

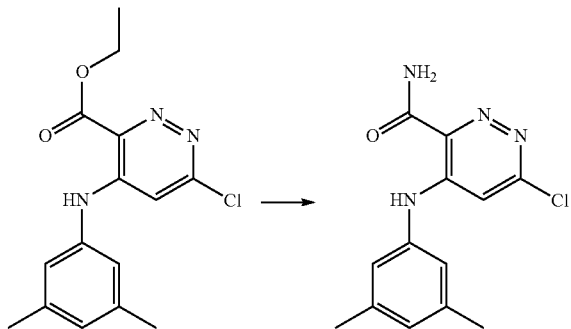 [SMILES: CCOC(=O)c1nnc(Cl)cc1Nc1cc(C)cc(C)c1 ; Cc1cc(C)cc(Nc2cc(Cl)nnc2C(N)=O)c1]

To a solution of ethyl 6-chloro-4-(3,5-dimethylphenylamino)pyridazine-3-carboxylate (104 mg, 340 μmol) in methanol was added ammonia in methanol (4.86 mL, 34.0 mmol) and stirred at 50° C. for 16 h. The mixture was concentrated to give 6-chloro-4-(3,5-dimethylphenylamino)pyridazine-3-carboxamide (90 mg, 325 μmol, 96%) as a brown solid, which was used directly without purification. $^1$H NMR (400 MHz, DMSO-d) δ ppm 10.84 (s, 1H), 8.72 (s, 1H), 8.08 (s, 1H), 7.12 (s, 1H), 6.98 (s, 2H), 6.98 (s, 1H), 6.93 (s, 1H), 2.30 (s, 6H); MS (EI/CI) m/z: 276.9 [M+H].

Step 3 tert-Butyl (1S,2R)-2-(6-carbamoyl-5-(3,5-dimethylphenylamino)pyridazin-3-ylamino)cyclohexylcarbamate

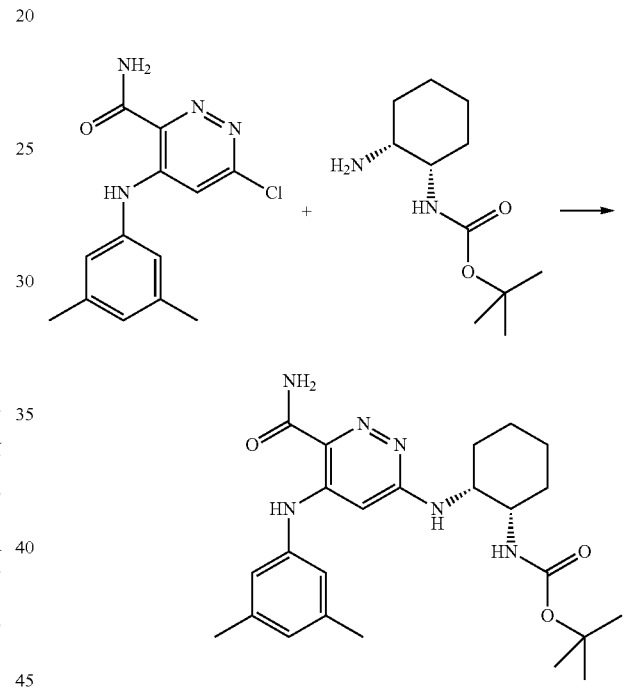

To a solution of 6-chloro-4-(3,5-dimethylphenylamino)pyridazine-3-carboxamide (44 mg, 159 μmol) in NMP (530 μL) was added tert-butyl (1S,2R)-2-aminocyclohexylcarbamate (68.2 mg, 318 μmol) and the mixture heated to 140° C. for 20 h. Additional tert-butyl (1S,2R)-2-aminocyclohexylcarbamate (68.2 mg, 318 μmol) was then added and heating continued for a further 7 h. Finally, another portion of tert-butyl (1S,2R)-2-aminocyclohexylcarbamate (34.1 mg, 159 μmol) was added and the mixture heated for 16 h. The reaction mixture was cooled, and then diluted with ethyl acetate. The phases were separated and the organic phase then washed with water and brine. The organic phase was collected, concentrated in vacuo, and the residue obtained was purified by chromatography (silica, 30 to 70% ethyl acetate in hexanes) to give tert-butyl (1S,2R)-2-(6-carbamoyl-5-(3,5-dimethylphenylamino)pyridazin-3-ylamino)cyclohexylcarbamate (30 mg, 66.0 μmol, 42%) as a brown oil. MS (EI/CI) m/z: 455.2 [M+H].

Step 4

6-((1R,2S)-2-Aminocyclohexylamino)-4-(3,5-dimethylphenylamino)pyridazine-3-carboxamide

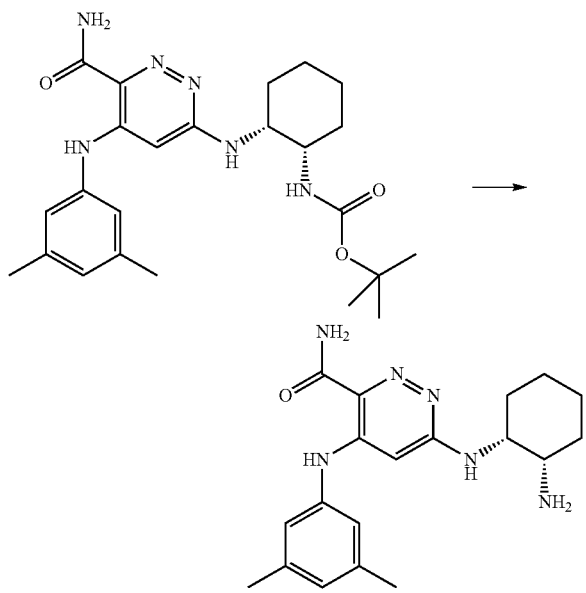

To a solution of tert-butyl (1S,2R)-2-(6-carbamoyl-5-(3,5-dimethylphenylamino)pyridazin-3-ylamino)cyclohexylcarbamate (30 mg, 66.0 mmol) in dichloromethane (1 mL) was added trifluoroacetic acid (151 mg, 102 μL, 1.32 mmol) and the mixture stirred at room temperature for 16 h. The mixture was concentrated in vacuo then diluted with dichloromethane and drops of 25% NH$_4$OH added until the pH was measured to be ~8. The weakly basic solution was washed with water, then the organic phase was concentrated in vacuo and purified by chromatography (silica, 30 to 100% of a 10:89.5:0.5 MeOH:dichloromethane:NH$_4$OH solution in dichloromethane) to give 6-((1R,2S)-2-aminocyclohexylamino)-4-(3,5-dimethylphenylamino)pyridazine-3-carboxamide (17 mg, 48.0 mmol, 73%) as a light brown solid. $^1$H NMR (400 MHz, METHANOL-d$_6$) δ ppm 6.90 (s, 2H), 6.88 (s, 1H), 6.50 (s, 1H), 4.32 (s, 1H), 1.63-1.84 (m, 6H), 1.51 (m, 2H); MS (EI/CI) m/z: 355.1 [M+H].

Example 29

6-((3R,4R)-3-aminotetrahydro-2H-pyran-4-ylamino)-4-(6-tert-butylpyridin-2-ylamino)pyridazine-3-carboxamide Step 1

Ethyl 4-(6-tert-butylpyridin-2-ylamino)-6-chloropyridazine-3-carboxylate

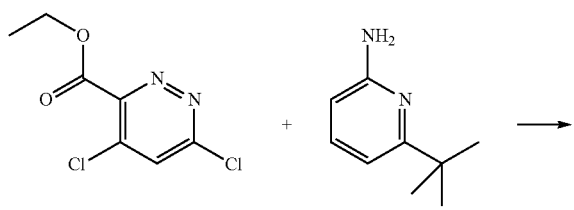

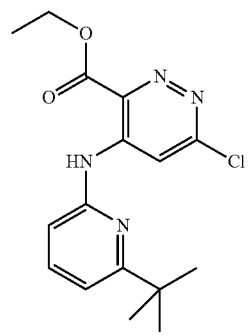

A mixture of ethyl 4,6-dichloropyridazine-3-carboxylate (0.73 g, 3.3 mmol) and 6-tert-butylpyridin-2-amine (992 mg, 6.61 mmol, available commercially from J&W PharmLab, LLC) was dissolved in acetonitrile (3.00 mL) and heated at 130° C. for 20 h. After cooling to room temperature, the mixture was concentrated and the residue purified by flash chromatography (spherical silica 20-45 μM, 50 g, Versaflash Supelco) eluting with 0 to 20% acetone in dichloromethane over 20 min to give ethyl 4-(6-tert-butylpyridin-2-ylamino)-6-chloropyridazine-3-carboxylate (539 mg, 48.7% yield) as a light brown residue. $^1$H NMR (CHLOROFORM-d) δ: 10.59 (s, 1H), 9.32 (s, 1H), 7.55 (t, J=7.9 Hz, 1H), 6.98 (d, J=7.2 Hz, 1H), 6.66 (d, J=7.9 Hz, 1H), 4.48 (q, J=7.2 Hz, 2H), 1.43 (t, J=7.2 Hz, 3H), 1.28-1.35 (m, 9H); LC-MS 335.0, 337.0 [M+H]$^+$.

Step 2

4-(6-tert-Butylpyridin-2-ylamino)-6-chloropyridazine-3-carboxamide

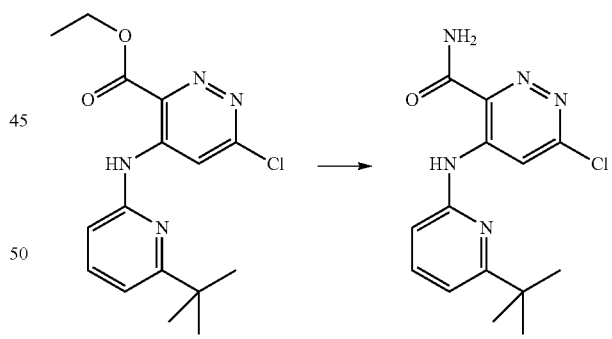

In a 100 mL round bottom flask, ethyl 4-(6-tert-butylpyridin-2-ylamino)-6-chloropyridazine-3-carboxylate (539 mg, 1.61 mmol) was suspended in ammonia 7M in methanol (7.87 g, 10.0 mL, 70.0 mmol). Sealed and stirred at room temperature for 18 h. The solvents were evaporated and the residue dried in high vacuum to give clean 4-(6-tert-butylpyridin-2-ylamino)-6-chloropyridazine-3-carboxamide (492 mg, 99.9% yield) as an off-white solid. $^1$H NMR (DMSO-d6) δ: 11.94 (s, 1H), 9.23 (s, 1H), 8.84 (s, 1H), 8.19 (s, 1H), 7.74 (t, J=7.9 Hz, 1H), 7.14 (d, J=7.6 Hz, 1H), 6.92 (d, J=7.9 Hz, 1H), 1.34 (s, 9H); LC-MS 306.1, 308.1 [M+H]$^+$.

Step 3 tert-Butyl (3R,4R)-4-(5-(6-tert-butylpyridin-2-ylamino)-6-carbamoylpyridazin-3-ylamino)tetrahydro-2H-pyran-3-ylcarbamate

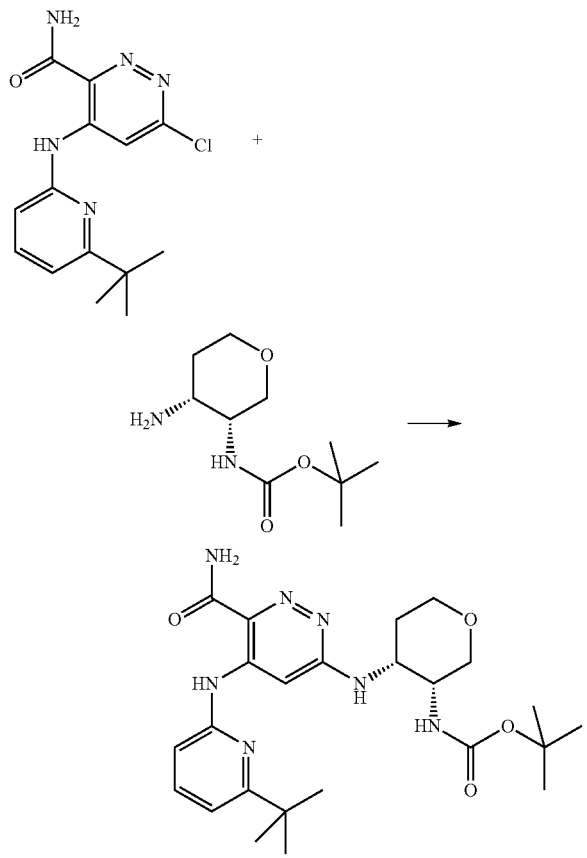

A resealable pressure tube was charged with 4-(6-tert-butylpyridin-2-ylamino)-6-chloropyridazine-3-carboxamide (100 mg, 327 μmol) dissolved in NMP (2.00 mL) To this solution was added tert-butyl (3R,4R)-4-aminotetrahydro-2H-pyran-3-ylcarbamate (70.7 mg, 327 μmol) and the reaction mixture was heated in an oil bath with stirring at 130° C. for 24 h. Added additional tert-butyl (3R,4R)-4-aminotetrahydro-2H-pyran-3-ylcarbamate (70.7 mg, 327 μmol) and reaction continued for 24 h. Added more tert-butyl (3R,4R)-4-aminotetrahydro-2H-pyran-3-ylcarbamate (70.7 mg, 327 μmol) and reaction continued for 72 h. The NMP was evaporated under high vacuum. The residue was purified by flash chromatography (silica gel 50 μm, 40 g, Analogix) eluting with 0 to 5% over 20 min (MeOH containing 10% NH$_4$OH)/CH$_2$Cl$_2$ to yield tert-butyl (3R,4R)-4-(5-(6-tert-butylpyridin-2-ylamino)-6-carbamoylpyridazin-3-ylamino)tetrahydro-2H-pyran-3-ylcarbamate (73 mg, 46.0% yield) as a yellow foam. $^1$H NMR (CHLOROFORM-d) δ: 11.45 (br. s., 1H), 8.33 (s, 1H), 8.14 (s, 1H), 8.06 (d, J=3.4 Hz, 1H), 7.52 (t, J=7.9 Hz, 1H), 6.91 (d, J=7.9 Hz, 1H), 6.66 (d, J=7.9 Hz, 1H), 5.65 (br. s., 1H), 5.37 (d, J=8.3 Hz, 1H), 3.38-4.31 (m, 6H), 1.63-2.23 (m, 2H), 1.46 (s, 9H), 1.39 (s, 9H); LC-MS 486.3 [M+H]$^+$.

Step 4

6-((3R,4R)-3-Aminotetrahydro-2H-pyran-4-ylamino)-4-(6-tert-butylpyridin-2-ylamino)pyridazine-3-carboxamide

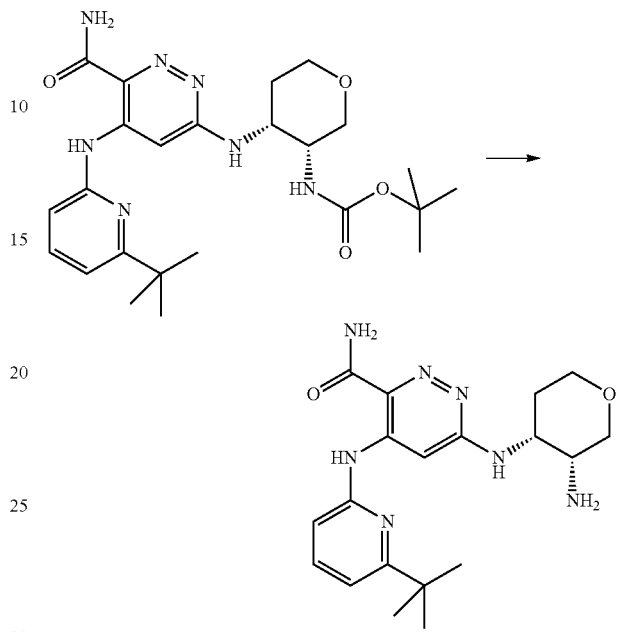

To a solution of tert-butyl (3R,4R)-4-(5-(6-tert-butylpyridin-2-ylamino)-6-carbamoylpyridazin-3-ylamino)tetrahydro-2H-pyran-3-ylcarbamate (73 mg, 150 μmol) in CH$_2$Cl$_2$ (3.00 mL) was added TFA (1.48 g, 1 mL, 13.0 mmol) and the mixture stirred to room temperature for 18 h. The solvent was evaporated and the residue purified by flash chromatography (spherical silica 20-45 μM, 23 g, Versaflash Supelco) eluting with 0 to 5% over 20 min (MeOH containing 10% NH$_4$OH)/CH$_2$Cl$_2$ to give 6-((3R,4R)-3-aminotetrahydro-2H-pyran-4-ylamino)-4-(6-tert-butylpyridin-2-ylamino)pyridazine-3-carboxamide (23.5 mg, 40.5% yield) as an off-white solid. $^1$H NMR (CHLOROFORM-d) δ: 11.45 (s, 1H), 8.38 (s, 1H), 8.03 (br. s., 1H), 7.54 (t, J=7.9 Hz, 1H), 6.93 (d, J=7.6 Hz, 1H), 6.69 (d, J=7.9 Hz, 1H), 5.83 (d, J=8.3 Hz, 1H), 5.37 (br. s., 1H), 3.91-4.13 (m, 2H), 3.86 (d, J=11.0 Hz, 1H), 3.65 (d, J=10.6 Hz, 1H), 3.41-3.58 (m, 1H), 3.04 (br. s., 1H), 1.97 (d, J=9.4 Hz, 1H), 1.63-1.85 (m, 1H), 1.55 (br. s., 3H), 1.42 (s, 9H); LC-MS 386.2 [M+H]$^+$.

Example 30

6-((1R,2S)-2-Aminocyclohexylamino)-4-(6-ethoxypyridin-2-ylamino)pyridazine-3-carboxamide Step 1

6-Ethoxypyridin-2-amine

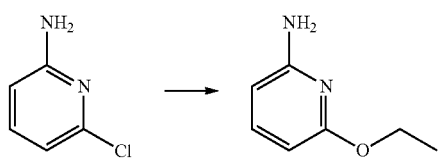

In a vial in a water bath, a 21% wt solution of sodium ethoxide in ethanol (1.08 g, 1.25 mL, 15.9 mmol) was diluted in ethanol (4 mL) and stirred at 25° C. for 10 min then 6-chloropyridin-2-amine (2.0 g, 15.6 mmol) was added in a single portion. After 3 h the reaction mixture was transferred to a sealed flask and was stirred at 130° C. for 18 h. A second portion of 21% wt solution of sodium ethoxide in ethanol (1.08 g, 1.25 mL, 15.9 mmol) was added and the reaction was stirred at 130° C. for another 36 h. Finally, a third portion of a 21% wt solution of sodium ethoxide in ethanol (3.18 g, 3.66 mL, 46.7 mmol) was added and the mixture stirred at 140° C. for 6 h then at 130° C. for 18 h. The mixture was cooled, concentrated onto silica gel, and purified by chromatography (silica, Analogix 120 g, 0 to 100% ethyl acetate in hexanes, 60 min) to give 6-ethoxypyridin-2-amine (819 mg, 36%) that was used directly without further purification. MS (EI/CI) m/z: 139 [M+H].

Step 2

Ethyl 6-chloro-4-(6-ethoxypyridin-2-ylamino)pyridazine-3-carboxylate

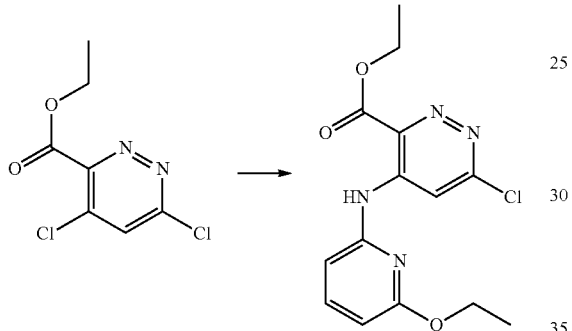

In a sealed reaction tube, 6-ethoxypyridin-2-amine (775 mg, 5.61 mmol) and ethyl 4,6-dichloropyridazine-3-carboxylate (620 mg, 2.8 mmol) were combined with acetonitrile (14 mL) and stirred at 130° C. for 36 h. The mixture was cooled, concentrated to a brown solid, and then chromatographed (80 g Silicycle column, eluent 0 to 10% acetone in dichloromethane, 20 min, then held at 10% for 10 min) to give ethyl 6-chloro-4-(6-ethoxypyridin-2-ylamino)pyridazine-3-carboxylate (40.3 mg, 125 µmol, 4%) as a white solid. MS (EI/CI) m/z: 323.2 [M+H].

Step 3

6-Chloro-4-(6-ethoxypyridin-2-ylamino)pyridazine-3-carboxamide

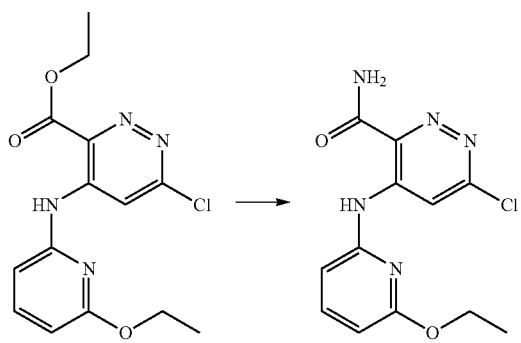 [SMILES: CCOC(=O)c1nnc(Cl)cc1Nc1cccc(OCC)n1 ; CCOc1cccc(Nc2cc(Cl)nnc2C(N)=O)n1]

Ethyl 6-chloro-4-(6-ethoxypyridin-2-ylamino)pyridazine-3-carboxylate (40.3 mg, 125 mmol) was dissolved in 7 N ammonia in methanol solution (7.01 g, 9 mL, 63.0 mmol) and stirred at 25° C. for 18 h. The reaction mixture was concentrated in vacuo to give 6-chloro-4-(6-ethoxypyridin-2-ylamino)pyridazine-3-carboxamide (33 mg, 112 µmol, 90%) as a light yellow solid that was used directly without further purification. MS (EI/CI) m/z: 294.1 [M+H].

Step 4 tert-Butyl (1S,2R)-2-(6-carbamoyl-5-(6-ethoxypyridin-2-ylamino)pyridazin-3-ylamino)cyclohexylcarbamate

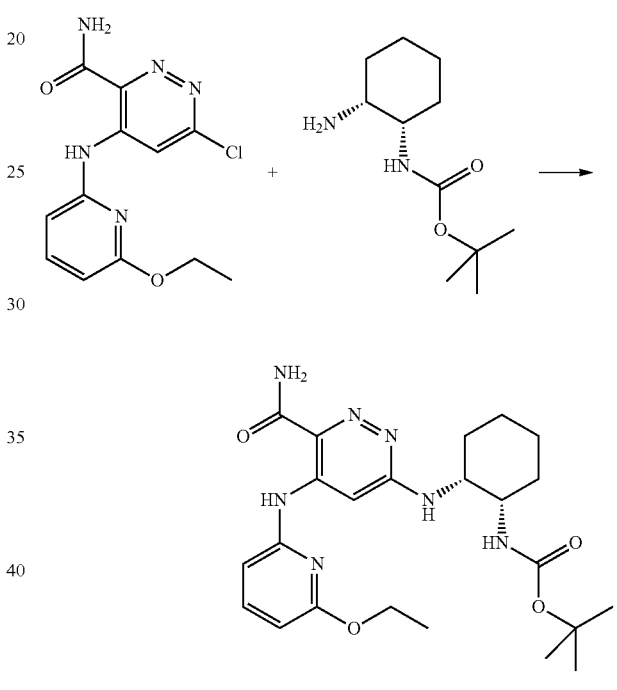

6-Chloro-4-(6-ethoxypyridin-2-ylamino)pyridazine-3-carboxamide (33 mg, 112 µmol) and tert-butyl (1S,2R)-2-aminocyclohexylcarbamate (50 mg, 233 µmol) were combined in NMP (2 mL) and stirred at 140° C. for 48 h. A second portion of tert-butyl (1S,2R)-2-aminocyclohexylcarbamate (50 mg, 233 µmol) was added and the reaction was stirred at 140° C. for 96 h, then cooled to room temperature and concentrated in vacuo. The residue obtained was partitioned between water and EtOAc. The aqueous layer was extracted with EtOAc and the organics were combined and washed with brine. The solvent was removed in vacuo to give an orange foam. The foam was concentrated onto silica and purified by chromatography (4 g RediSep Gold, 0 to 5% of a mixture of MeOH containing 0.5% NH₄OH in dichloromethane, 20 min) to give tert-butyl (1S,2R)-2-(6-carbamoyl-5-(6-ethoxypyridin-2-ylamino)pyridazin-3-ylamino)cyclohexylcarbamate (32.3 mg, 51.4 µmol, 46%) containing some dichloromethane impurity. This was used directly without further purification. MS (EI/CI) m/z: 372.3 [M+H].

Step 5

6-((1R,2S)-2-Aminocyclohexylamino)-4-(6-ethoxy-pyridin-2-ylamino)pyridazine-3-carboxamide

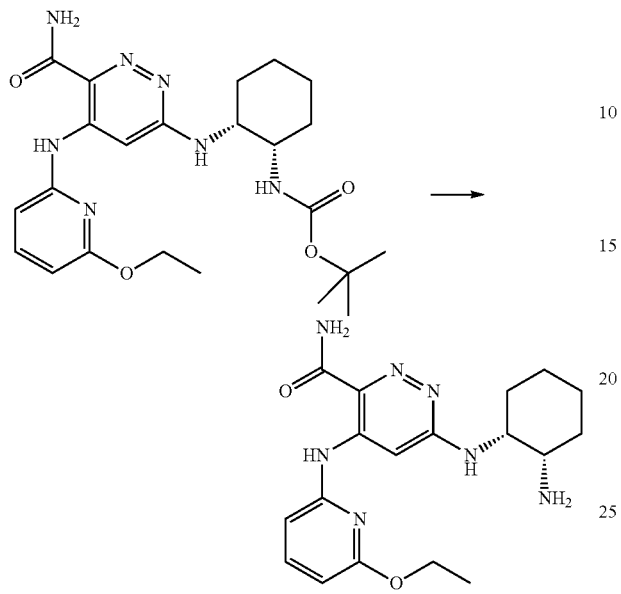

tert-Butyl (1S,2R)-2-(6-carbamoyl-5-(6-ethoxypyridin-2-ylamino)pyridazin-3-ylamino)cyclohexylcarbamate (32.2 mg, 51.2 μmol) was dissolved in dichloromethane (1 mL) and treated with trifluoroacetic acid (744 mg, 0.5 mL, 6.53 mmol). The reaction was stirred at 25° C. for 3 h then concentrated in vacuo to a brown oil. This oil was dissolved in dichloromethane, washed with 1N NaOH (3×5 mL) and brine (5 mL), then the organic phase was dried ($Na_2SO_4$), filtered and concentrated to give an off-white solid. The solid was triturated with $Et_2O$ (3×5 mL) and dried overnight in vacuo to give an off-white solid, 6-((1R,2S)-2-aminocyclohexylamino)-4-(6-ethoxypyridin-2-ylamino)pyridazine-3-carboxamide (12.6 mg, 33.6 μmol, 66% yield), $^1$H NMR (DMSO-$d_6$) δ: 11.65 (br. s., 1H), 8.40 (br. s., 1H), 7.71 (s, 1H), 7.64 (t, J=7.9 Hz, 2H), 6.77 (d, J=7.8 Hz, 1H), 6.54 (d, J=7.8 Hz, 1H), 6.36-6.42 (m, 1H), 4.35 (q, J=7.0 Hz, 2H), 3.85 (br. s., 1H), 3.09 (br. s., 1H), 1.48-1.74 (m, 6H), 1.20-1.40 (m, 5H); MS (EI/CI) m/z: 372.3 [M+H].

Example 31

6-((1R,2S)-2-aminocyclohexylamino)-4-(5-methoxy-6-propylpyridin-2-ylamino)pyridazine-3-carboxamide Step 1

2-Allyl-3-methoxy-6-nitropyridine

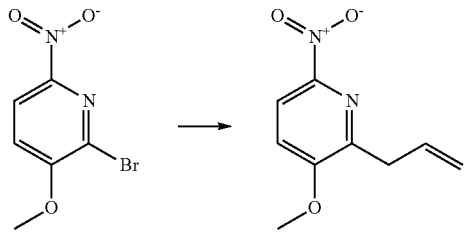

2-Bromo-3-methoxy-6-nitropyridine (3.22 g, 13.8 mmol), cesium fluoride (6.3 g, 41.5 mmol) and tetrakis(triphenylphosphine)palladium (0) (1.6 g, 1.38 mmol) were combined with 2-allyl-4,4,5,5-tetramethyl-1,3,2-dioxaborolane (2.55 g, 2.85 mL, 15.2 mmol) in THF (27 mL) and heated at 66° C. for 20 h. The mixture was cooled then diluted with water and ethyl acetate. The phases were separated then the organic phase was washed with water (2×) and brine, concentrated in vacuo and then purified by chromatography (silica, 10 to 50% ethyl acetate in hexanes) to give 2-allyl-3-methoxy-6-nitropyridine (2.0 g, 10.3 mmol, 75%) as a blue solid. MS (EI/CI) m/z: 194.8 [M+H].

Step 2

5-Methoxy-6-propylpyridin-2-amine

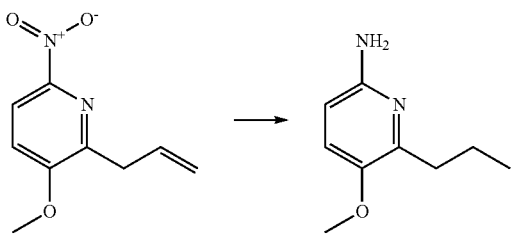

To a solution of 2-allyl-3-methoxy-6-nitropyridine (2.0 g, 10.3 mmol) in ethanol (34 mL) was added 10% palladium on carbon (219 mg, 2.06 mmol). The reaction was evacuated and back filled with hydrogen. This was repeated two more times. The reaction mixture was stirred under hydrogen at 1 atm for 16 h, then filtered through a pad of celite and the filter cake washed thoroughly with ethyl acetate. The filtrates were concentrated in vacuo and purified by chromatography (silica, 25 to 90% ethyl acetate in hexanes) to give 5-methoxy-6-propylpyridin-2-amine (1.41 g, 8.48 mmol, 82%) as an off white solid. $^1$H NMR (400 MHz, CHLOROFORM-$d_6$) δ ppm 7.09 (d, J=8.8 Hz, 1H), 6.38 (d, J=8.8 Hz, 1H), 4.28 (br. s, 2H), 3.77 (s, 3H), 2.68 (t, J=7.9 Hz, 2H), 1.69 (m, 2H), 0.99 (t, J=7.4 Hz, 3H); MS (EI/CI) m/z: 166.8 [M+H].

Step 3

Ethyl 6-chloro-4-(5-methoxy-6-propylpyridin-2-ylamino)pyridazine-3-carboxylate

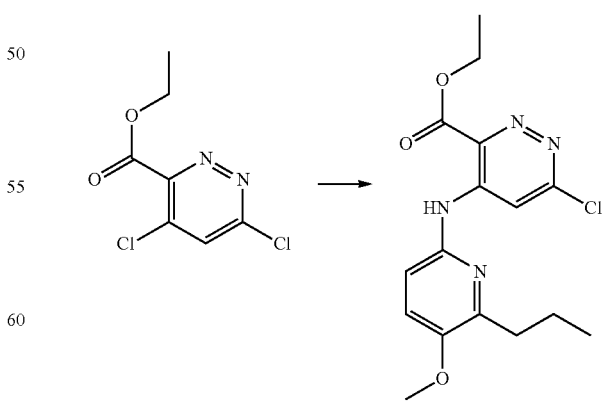

To a solution of ethyl 4,6-dichloropyridazine-3-carboxylate (1.9 g, 8.6 mmol) in acetonitrile (28.7 mL) was added 5-methoxy-6-propylpyridin-2-amine (1.43 g, 8.6 mmol) and the mixture heated at 70° C. for 72 h. The mixture was concentrated in vacuo then purified by chromatography (silica, 10 to 60% ethyl acetate in hexanes) to give ethyl 6-chloro-4-(5-methoxy-6-propylpyridin-2-ylamino)pyridazine-3-carboxylate (1.22 g, 3.48 mmol, 41%) as a yellow solid. $^1$H NMR (400 MHz, CHLOROFORM-$d_6$) δ ppm 10.58 (s, 1H), 8.84 (s, 1H), 7.25 (d, J=8.7 Hz, 1H), 6.88 (d, J=8.5 Hz, 1H), 4.58 (q, J=7.3 Hz, 2H), 3.88 (s, 3H), 2.87 (t, J=7.5 Hz, 2H), 1.84 (m, 2H), 1.52 (t, J=7.3 Hz, 3H), 1.05 (t, J=7.1 Hz, 3H); MS (EI/CI) m/z: 351.0 [M+H].
Step 4

6-Chloro-4-(5-methoxy-6-propylpyridin-2-ylamino)pyridazine-3-carboxamide

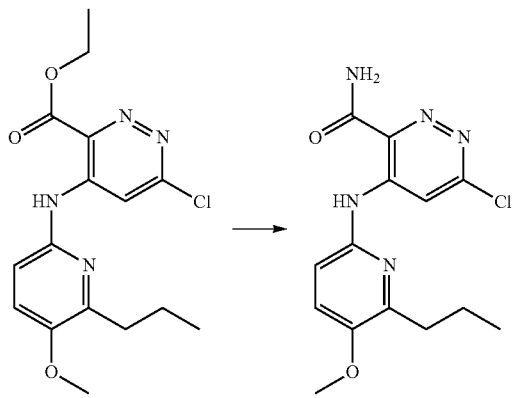 [SMILES: CCCc1nc(Nc2cc(Cl)nnc2C(=O)OCC)ccc1OC ; CCCc1nc(Nc2cc(Cl)nnc2C(N)=O)ccc1OC]

To a mixture of ethyl 6-chloro-4-(5-methoxy-6-propylpyridin-2-ylamino)pyridazine-3-carboxylate (1.22 g, 3.48 mmol) in methanol (10 mL) was added 7 N ammonia in methanol (23.6 g, 30 mL, 210 mmol) and the mixture stirred at 50° C. in a sealed tube for 16 h. The mixture was concentrated in vacuo to give 6-chloro-4-(5-methoxy-6-propylpyridin-2-ylamino)pyridazine-3-carboxamide (1.113 g, 3.46 mmol, 100%) as a yellow solid. $^1$H NMR (400 MHz, DMSO-$d_6$) δ ppm 11.72 (s, 1H), 8.89 (s, 1H), 8.77 (s, 1H), 8.13 (s, 1H), 7.47 (d, J=8.6 Hz, 1H), 7.01 (d, J=8.6 Hz, 1H), 3.81 (s, 3H), 2.74 (t, J=7.3 Hz, 2H), 1.75 (m, 2H), 0.97 (t, J=7.3 Hz, 3H); MS (EI/CI) m/z: 321.9 [M+H].
Step 5 tert-Butyl (1S,2R)-2-(6-carbamoyl-5-(5-methoxy-6-propylpyridin-2-ylamino)pyridazin-3-ylamino)cyclohexylcarbamate

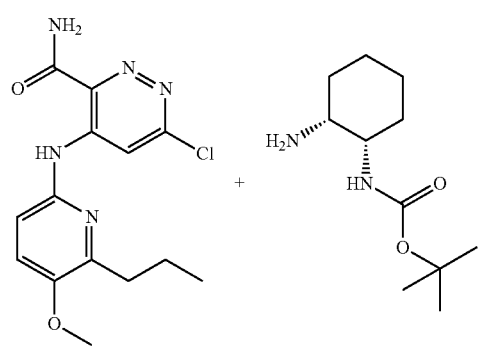

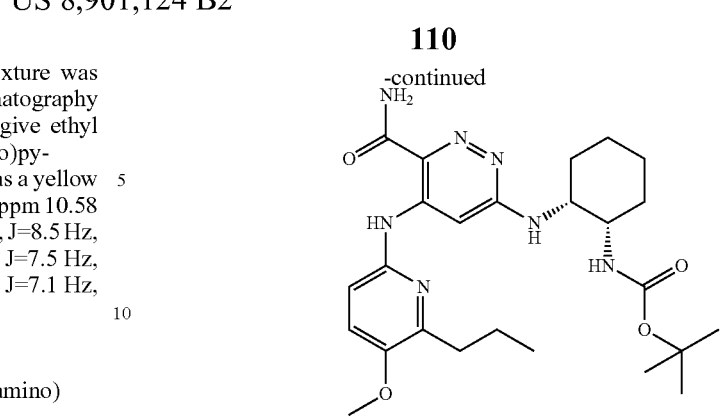

To a solution of 6-chloro-4-(5-methoxy-6-propylpyridin-2-ylamino)pyridazine-3-carboxamide (200 mg, 622 μmol) in NMP (2.07 mL) was added tert-butyl (1S,2R)-2-aminocyclohexylcarbamate (133 mg, 622 μmol) and the mixture heated at 140° C. for 20 h. A second portion of tert-butyl (1S,2R)-2-aminocyclohexylcarbamate (133 mg, 622 μmol) was added and the mixture stirred for a further 7 h. A final portion of tert-butyl (1S,2R)-2-aminocyclohexylcarbamate (133 mg, 622 μmol) was added and the mixture heated for 16 h, then cooled, diluted with ethyl acetate, and washed with brine (4×). The organic layer was collected, concentrated in vacuo, and the residue obtained was purified by chromatography (silica, 1 to 5% methanol in dichloromethane) to give tert-butyl (1S,2R)-2-(6-carbamoyl-5-(5-methoxy-6-propylpyridin-2-ylamino)pyridazin-3-ylamino)cyclohexylcarbamate (96 mg, 192 μmol, 31%) as a light brown solid. MS (EI/CI) m/z: 500.2 [M+H].
Step 6

6-((1R,2S)-2-aminocyclohexylamino)-4-(5-methoxy-6-propylpyridin-2-ylamino)pyridazine-3-carboxamide

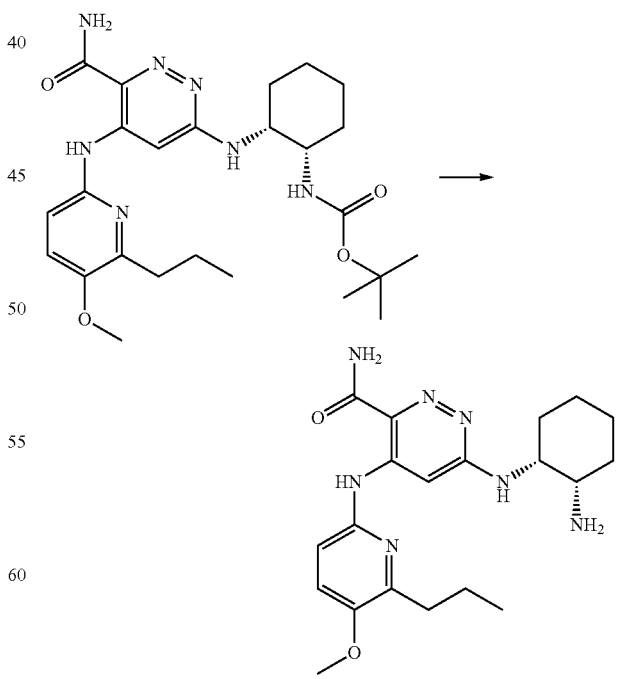

To a solution of tert-butyl (1S,2R)-2-(6-carbamoyl-5-(5-methoxy-6-propylpyridin-2-ylamino)pyridazin-3-ylamino)cyclohexylcarbamate (96 mg, 192 μmol) in dichloromethane (3 mL) was added trifluoroacetic acid (438 mg, 296 μL, 3.84 mmol) and the mixture stirred at room temperature overnight. The mixture was concentrated in vacuo then diluted with 25% aqueous NH$_4$OH and dichloromethane. The phases were separated and the organic phase washed with water. The organic layer was concentrated in vacuo then purified by chromatography (silica, 3 to 20% methanol in dichloromethane) to give 6-((1R,2S)-2-aminocyclohexylamino)-4-(5-methoxy-6-propylpyridin-2-ylamino)pyridazine-3-carboxamide (59 mg, 148 μmol, 77%) as a light brown solid. $^1$H NMR (400 MHz, DMSO-d$_6$) δ ppm 11.36 (s, 1H), 8.30 (s, 1H), 7.72 (s, 1H), 7.60 (s, 1H), 7.42 (d, J=8.8 Hz, 1H), 6.87 (d, J=8.8 Hz, 1H), 6.72 (d, J=7.6 Hz, 1H), 3.96 (s, 1H), 3.79 (s, 3H), 3.28 (s, 1H), 2.72 (t, J=7.3 Hz, 2H), 1.54-1.74 (m, 8H), 1.35 (m, 2H), 0.94 (t, J=7.4 Hz, 3H); MS (EI/CI) m/z: 400.2 [M+H].

Example 32

6-((1R,2S)-2-aminocyclohexylamino)-4-(5-methoxy-6-propylpyridin-2-ylamino)pyridazine-3-carboxamide Step 1

3-Methoxy-6-nitro-2-(prop-1-en-2-yl)pyridine

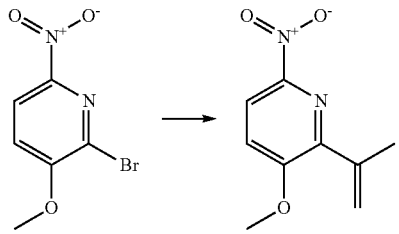

In a microwave vial was added a mixture of 2-bromo-3-methoxy-6-nitropyridine (1.5 g, 6.44 mmol), 4,4,5,5-tetramethyl-2-(prop-1-en-2-yl)-1,3,2-dioxaborolane (1.41 g, 8.37 mmol), tetrakis(triphenylphosphine)palladium (0) (744 mg, 644 μmol), potassium phosphate tribasic (2.73 g, 12.9 mmol), DMA (16.1 mL) and water (5.36 mL). The vial was sealed and heated in the microwave for 20 min at 150° C., then cooled and diluted with ethyl acetate and brine. The organic phase was separated and washed with brine (3×), then concentrated in vacuo and purified by chromatography (silica, 5 to 35% ethyl acetate in hexanes) to give 3-methoxy-6-nitro-2-(prop-1-en-2-yl)pyridine (824 mg, 4.24 mmol, 66%) as a brown solid. MS (EI/CI) m/z: 194.8 [M+H].

Step 2

6-Isopropyl-5-methoxypyridin-2-amine

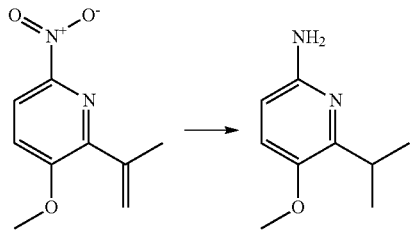

To a solution of 3-methoxy-6-nitro-2-(prop-1-en-2-yl)pyridine (824 mg, 4.24 mmol) in ethanol (14.1 mL) was added 10% palladium on carbon (45.2 mg, 424 μmol). The reaction mixture was evacuated and back filled with hydrogen. This was repeated two more times. The reaction was stirred under hydrogen at 1 atm for 16 h. The mixture was then filtered reaction through a pad of celite, the filtrate concentrated in vacuo, and then purified by chromatography (silica, 10 to 60% ethyl acetate in hexanes) to give 6-isopropyl-5-methoxypyridin-2-amine (562 mg, 3.38 mmol, 80%) as a yellow solid. $^1$H NMR (400 MHz, CHLOROFORM-d$_6$) δ ppm 7.04 (d, J=8.7 Hz, 1H), 6.33 (d, J=8.7 Hz, 1H), 4.12 (br. s, 2H), 3.78 (s, 3H), 3.36 (m, 1H), 1.22 (d, J=7.0 Hz, 6H); MS (EI/CI) m/z: 166.8 [M+H].

Step 3

6-Chloro-4-(6-isopropyl-5-methoxypyridin-2-ylamino)pyridazine-3-carboxylate

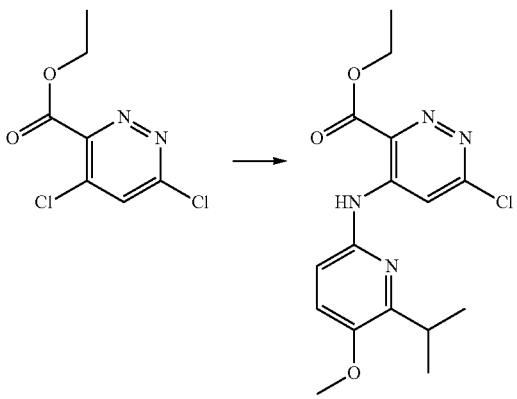 [SMILES: CCOC(=O)c1nnc(Cl)cc1Cl ; CCOC(=O)c1nnc(Cl)cc1Nc1ccc(OC)c(C(C)C)n1]

To a solution of ethyl 4,6-dichloropyridazine-3-carboxylate (747 mg, 3.38 mmol) in acetonitrile (11.3 mL) was added 6-isopropyl-5-methoxypyridin-2-amine (562 mg, 3.38 mmol) and heated to 80° C. for 20 h. The mixture was cooled and concentrated in vacuo. Purification by chromatography (silica, 10 to 50% ethyl acetate in hexanes) gave ethyl 6-chloro-4-(6-isopropyl-5-methoxypyridin-2-ylamino)pyridazine-3-carboxylate (438 mg, 1.25 mmol, 37%) as a yellow solid. $^1$H NMR (400 MHz, CHLOROFORM-d$_6$) δ ppm 10.61 (s, 1H), 9.15 (s, 1H), 7.22 (d, J=8.7 Hz, 1H), 6.61 (d, J=8.7 Hz, 1H), 4.57 (q, J=7.6 Hz, 2H), 3.88 (s, 3H), 3.53 (m, 1H), 1.53 (t, J=7.0 Hz, 3H), 1.31 (d, J=6.7 Hz, 6H); MS (EI/CI) m/z: 351.0 [M+H].

Step 4

Ethyl 6-chloro-4-(6-isopropyl-5-methoxypyridin-2-ylamino)pyridazine-3-carboxylate

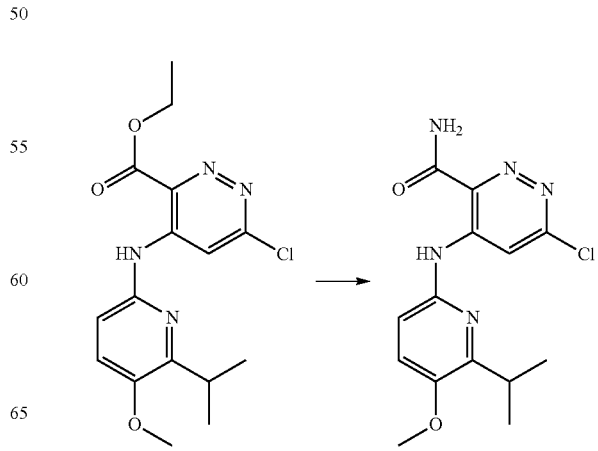

A mixture of ethyl 6-chloro-4-(6-isopropyl-5-methoxypyridin-2-ylamino)pyridazine-3-carboxylate (438 mg, 1.25 mmol) and ammonia in methanol (7 N, 8.92 mL, 62.4 mmol) in methanol (1 mL) was warmed at 40° C. for 16 h. The mixture was then concentrated in vacuo to give ethyl 6-chloro-4-(6-isopropyl-5-methoxypyridin-2-ylamino)pyridazine-3-carboxylate (438 mg, 1.25 mmol, 100%) as an off-white solid. $^1$H NMR (400 MHz, DMSO-d$_6$) δ ppm 11.75 (s, 1H), 9.03 (s, 1H), 8.78 (s, 1H), 8.13 (s, 1H), 7.48 (d, J=8.5 Hz, 1H), 7.00 (d, J=8.5 Hz, 1H), 3.82 (s, 3H), 3.44 (m, 1H), 1.22 (d, J=6.6 Hz, 6H); MS (EI/CI) m/z: 321.9 [M+H].

Step 5 tert-Butyl (1S,2R)-2-(6-carbamoyl-5-(6-isopropyl-5-methoxypyridin-2-ylamino)pyridazin-3-ylamino)cyclohexylcarbamate

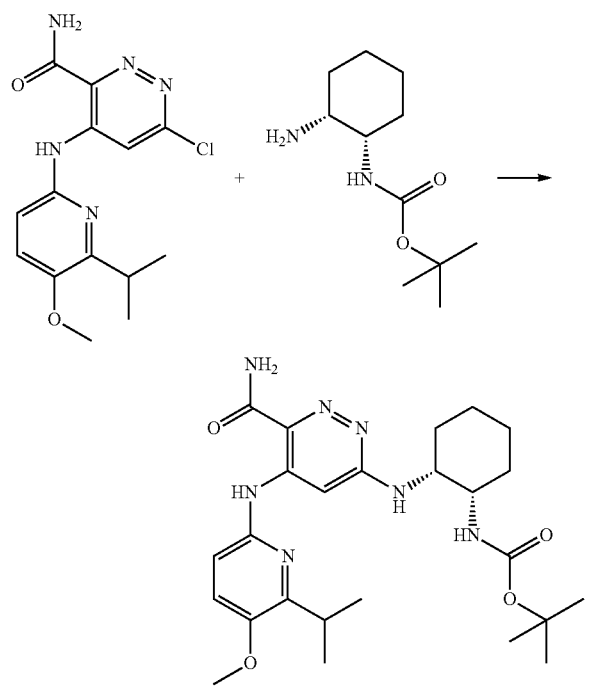

To a solution of 6-chloro-4-(6-isopropyl-5-methoxypyridin-2-ylamino)pyridazine-3-carboxamide (199 mg, 618 μmol) in NMP (2.06 mL) was added tert-butyl (1S,2R)-2-aminocyclohexylcarbamate (532 mg, 2.47 mmol) in four portions approximately every 12 h while heating at 140° C. After a total heating time of 48 h, the mixture was cooled, diluted with ethyl acetate and brine, then the phases were separated and the organic phase washed twice more with brine. The organic phase was concentrated in vacuo then purified by chromatography (silica, 1 to 5% methanol in dichloromethane) to give tert-butyl (1S,2R)-2-(6-carbamoyl-5-(6-isopropyl-5-methoxypyridin-2-ylamino)pyridazin-3-ylamino)cyclohexylcarbamate (100 mg, 200 μmol, 32%) as a brown solid. MS (EI/CI) m/z: 500.4 [M+H].

Step 6

6-((1R,2S)-2-Aminocyclohexylamino)-4-(6-isopropyl-5-methoxypyridin-2-ylamino)pyridazine-3-carboxamide

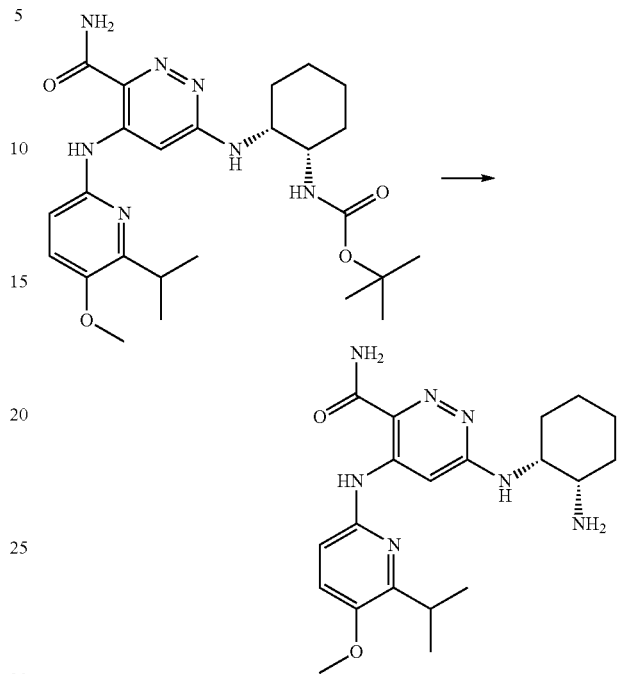

To a solution of tert-butyl (1S,2R)-2-(6-carbamoyl-5-(6-isopropyl-5-methoxypyridin-2-ylamino)pyridazin-3-ylamino)cyclohexylcarbamate (100 mg, 200 μmol) in dichloromethane (3 mL) was added trifluoroacetic acid (456 mg, 308 μL, 4.00 mmol) and the mixture stirred at room temperature for 16 h. The mixture was concentrated in vacuo then 25% aqueous NH$_4$OH solution added. This was then diluted with dichloromethane and water, the phases separated, and the organic phase washed twice with water. The organic layer was dried over anhydrous magnesium sulfate then purified by chromatography (silica, 0 to 15% methanol in dichloromethane) to give 6-((1R,2S)-2-aminocyclohexylamino)-4-(6-isopropyl-5-methoxypyridin-2-ylamino)pyridazine-3-carboxamide (43 mg, 108 μmol, 54%) as an off-white solid. $^1$H NMR (400 MHz, DMSO-d$_6$) δ ppm 11.45 (s, 1H), 8.31 (s, 1H), 7.69 (s, 1H), 7.58 (s, 1H), 7.42 (d, J=8.7 Hz, 1H), 6.85 (d, J=8.7 Hz, 1H), 6.63 (d, J=8.0 Hz, 1H), 3.80 (s, 3H), 3.42 (m, 1H), 3.15 (s, 1H), 1.52-1.69 (m, 8H), 1.32 (m, 2H), 1.24 (d, J=6.4 Hz, 6H); MS (EI/CI) m/z: 400.3 [M+H].

Example 33

4-(6-(1H-Pyrazol-1-yl)pyridin-2-ylamino)-6-((1R,2S)-2-aminocyclohexylamino)pyridazine-3-carboxamide Step 1

6-(1H-Pyrazol-1-yl)pyridin-2-amine

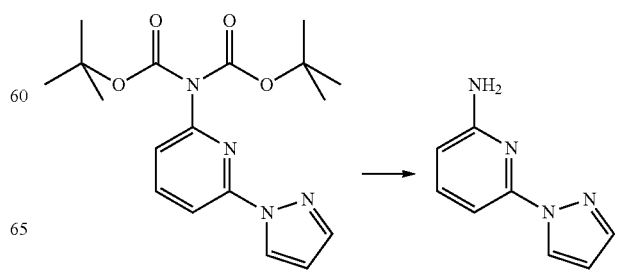

6-(Di-Boc-amino)-2-bromopyridine (1.0 g, 2.68 mmol, ChronTech), copper (341 mg, 5.36 mmol), potassium hydroxide (301 mg, 5.36 mmol), and 1H-pyrazole (1.82 g, 26.8 mmol, Eq: 10) were combined and stirred at 160° C. for 18 h. The reaction mixture was cooled, diluted with EtOAc (50 mL) and the solids removed by filtration. The dark blue filtrate was washed with saturated aqueous NaHCO$_3$ and brine then concentrated onto silica gel and purified by chromatography (40 g RediSep column, 20 to 100% ethyl acetate in hexanes, 20 min) to give 6-(1H-pyrazol-1-yl)pyridin-2-amine (365 mg, 2.28 mmol, 85%) as a white solid. MS (EI/CI) m/z: 161.2 [M+H].

Step 2

4-(6-(1H-Pyrazol-1-yl)pyridin-2-ylamino)-6-chloropyridazine-3-carboxylate

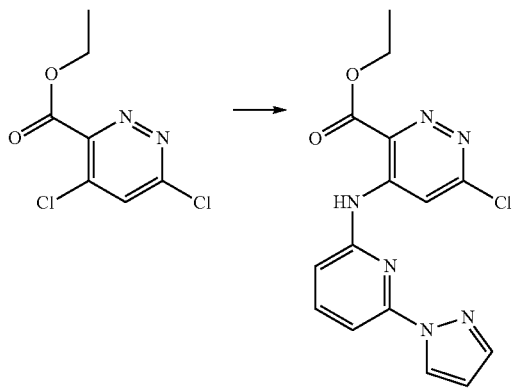 [SMILES: CCOC(=O)c1nnc(Cl)cc1Cl ; CCOC(=O)c1nnc(Cl)cc1Nc1cccc(-n2cccn2)n1]

A solution of ethyl 4,6-dichloropyridazine-3-carboxylate (230 mg, 1.04 mmol) and 6-(1H-pyrazol-1-yl)pyridin-2-amine (332.3 mg, 2.07 mmol) in acetonitrile (11.8 mL) was heated at 130° C. in a sealed tube for 48 h, then cooled concentrated in vacuo and then purified by chromatography (silica, Analogix 24 g RediSep Gold column 0 to 20% acetone in dichloromethane, 20 min) to give ethyl 4-(6-(1H-pyrazol-1-yl)pyridin-2-ylamino)-6-chloropyridazine-3-carboxylate (107 mg, 258 µmol, 25%) as a white solid. This material was 83% pure and was used directly in the next step without further purification. MS (EI/CI) m/z: 345.1 [M+H].

Step 3

4-(6-(1H-pyrazol-1-yl)pyridin-2-ylamino)-6-chloropyridazine-3-carboxamide

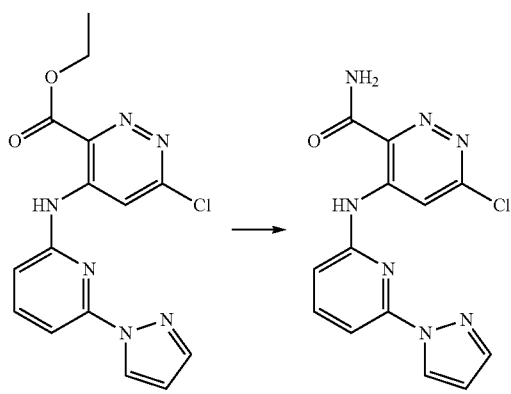 [SMILES: CCOC(=O)c1nnc(Cl)cc1Nc1cccc(-n2cccn2)n1 ; NC(=O)c1nnc(Cl)cc1Nc1cccc(-n2cccn2)n1]

To a solution of ethyl 4-(6-(1H-pyrazol-1-yl)pyridin-2-ylamino)-6-chloropyridazine-3-carboxylate (107 mg of ~83% purity, 258 µmol) in methanol (1 mL) was added ammonia in methanol (2.5 mL, 17.5 mmol) and the mixture warmed at 25° C. for 18 h. The mixture was cooled, filtered, and the collected solid dried in vacuo to give 4-(6-(1H-pyrazol-1-yl)pyridin-2-ylamino)-6-chloropyridazine-3-carboxamide (45 mg, 141 µmol, 55%) as a white solid.

Step 4 tert-Butyl (1S,2R)-2-(5-(6-(1H-pyrazol-1-yl)pyridin-2-ylamino)-6-carbamoylpyridazin-3-ylamino)cyclohexylcarbamate

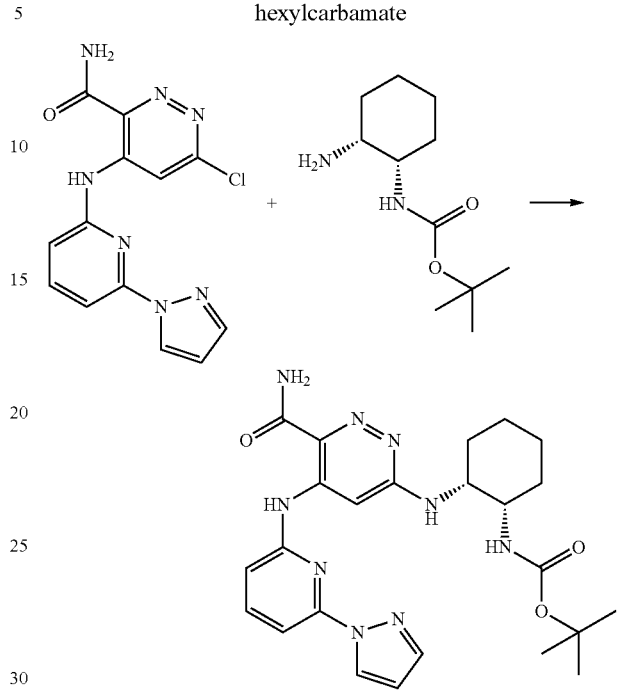

To a solution of 4-(6-(1H-pyrazol-1-yl)pyridin-2-ylamino)-6-chloropyridazine-3-carboxamide (131 mg, 415 µmol) in NMP (5 mL) was added tert-butyl (1S,2R)-2-aminocyclohexylcarbamate (133 mg, 622 µmol) and the mixture stirred at 140° C. for 24 h. A second portion of tert-butyl (1S,2R)-2-aminocyclohexylcarbamate (162 mg, 756 µmol) was added and the mixture heated at 140° C. for a further 24 h. The reaction mixture was cooled, and then diluted with water. The mixture was extracted with ethyl acetate (3×50 mL) then the combined organic phases were washed with brine (50 mL), then concentrated in vacuo, and finally purified by chromatography (silica, 12 g RediSep Gold, 2 to 6% of a 99.5:0.5 methanol:ammonium hydroxide solution in dichloromethane, 20 min) to give tert-butyl (1S,2R)-2-(5-(6-(1H-pyrazol-1-yl)pyridin-2-ylamino)-6-carbamoylpyridazin-3-ylamino)cyclohexylcarbamate (70 mg, 142 µmol, 34%) as a beige solid. MS (EI/CI) m/z: 494.3 [M+H].

Step 5

4-(6-(1H-Pyrazol-1-yl)pyridin-2-ylamino)-6-((1R,2S)-2-aminocyclohexylamino)pyridazine-3-carboxamide

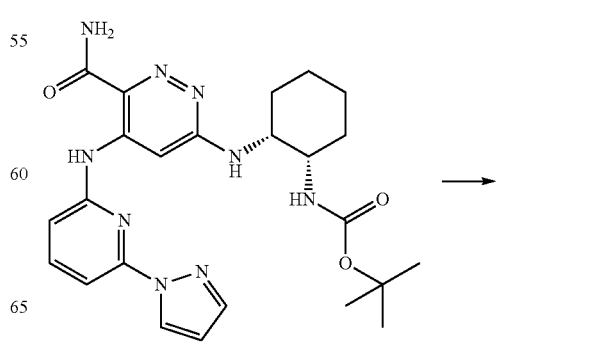

117

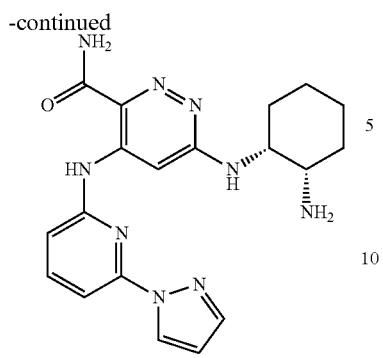

To a solution of tert-butyl (1S,2R)-2-(5-(6-(1H-pyrazol-1-yl)pyridin-2-ylamino)-6-carbamoylpyridazin-3-ylamino)cyclohexylcarbamate (70 mg, 142 μmol) in dichloromethane (2.5 mL) was added trifluoroacetic acid (2.01 g, 1.35 mL, 17.6 mmol) and the mixture stirred at 25° for 2 h. The mixture was concentrated in vacuo and then diluted with dichloromethane and then washed successively with 1N NaOH (3×5 mL) and brine (5 mL). The organic phase was dried over sodium sulfate, concentrated in vacuo and then dried in vacuo to give 4-(6-(1H-pyrazol-1-yl)pyridin-2-ylamino)-6-((1R,2S)-2-aminocyclohexylamino)pyridazine-3-carboxamide (14.2 mg, 36.1 μmol, 25%) as a white solid. $^1$H NMR (DMSO-d$_6$) δ: 11.93 (s, 1H), 8.63-8.71 (m, 1H), 8.45 (br. s., 1H), 7.78-7.94 (m, 3H), 7.71 (br. s., 1H), 7.51 (d, J=7.8 Hz, 1H), 7.05 (d, J=7.5 Hz, 1H), 6.92 (d, J=8.0 Hz, 1H), 6.63 (dd, J=2.5, 1.8 Hz, 1H), 4.02 (br. s., 1H), 3.18 (br. s., 1H), 1.46-1.79 (m, 7H), 1.20-1.41 (m, 3H); MS (EI/CI) m/z: 394.3 [M+H].

Example 34

6-((3R,4R)-3-aminotetrahydro-2H-pyran-4-ylamino)-4-(6-isopropyl-5-methoxypyridin-2-ylamino)pyridazine-3-carboxamide Step 1 tert-Butyl (3R,4R)-4-(6-carbamoyl-5-(6-isopropyl677-5-methoxypyridin-2-ylamino)pyridazin-3-ylamino)tetrahydro-2H-pyran-3-ylcarbamate

118

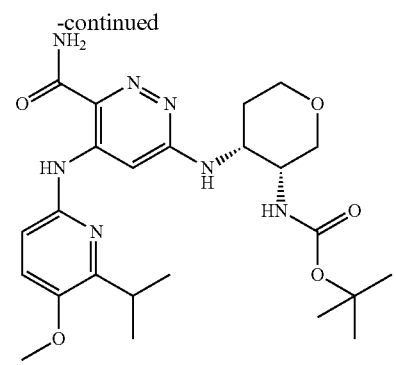

To a solution of 6-chloro-4-(6-isopropyl-5-methoxypyridin-2-ylamino)pyridazine-3-carboxamide (199 mg, 618 μmol, prepared as described in example 32) in NMP (2.06 mL) was added tert-butyl (3R,4R)-4-aminotetrahydro-2H-pyran-3-ylcarbamate (536 mg, 2.47 mmol) in four portions approximately every 12 h and the mixture heated at 140° C. After 48 h total heating time the mixture was cooled and then diluted with ethyl acetate and brine. The phases were separated then the organic phase was washed with brine (2×), then concentrated in vacuo and the residue obtained was purified by chromatography (silica, 10 to 50% methanol in dichloromethane) to give 6-chloro-4-(6-isopropyl-5-methoxypyridin-2-ylamino)pyridazine-3-carboxamide (199 mg, 618 μmol, quantitative) as a light brown solid. MS (EI/CI) m/z: 502.2 [M+H].

Step 2

6-((3R,4R)-3-Aminotetrahydro-2H-pyran-4-ylamino)-4-(6-isopropyl-5-methoxypyridin-2-ylamino)pyridazine-3-carboxamide

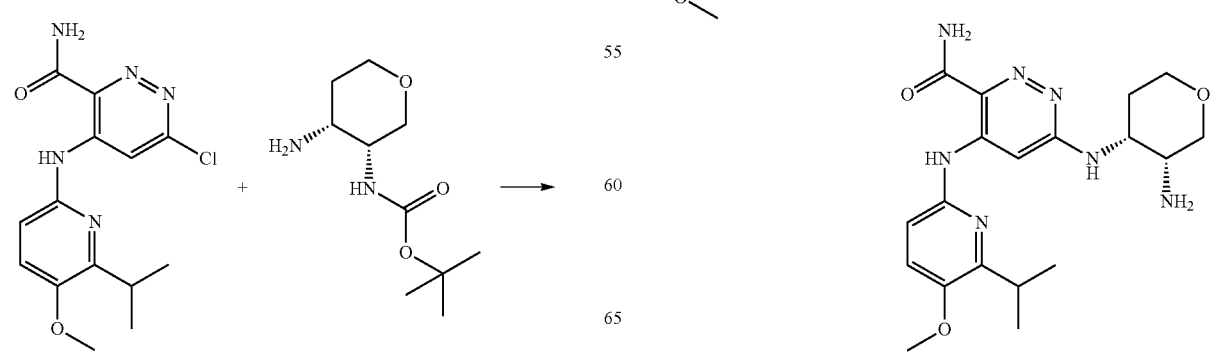

To a solution of tert-butyl (3R,4R)-4-(6-carbamoyl-5-(6-isopropyl-5-methoxypyridin-2-ylamino)pyridazin-3-ylamino)tetrahydro-2H-pyran-3-ylcarbamate (86 mg, 171 µmol) in dichloromethane (2.7 mL) was added trifluoroacetic acid (391 mg, 264 µL, 3.43 mmol) and stirred at room temperature for 16 h. The reaction mixture was then diluted with dichloromethane, concentrated in vacuo, and purified by chromatography (silica, 0 to 12% of a 99.5:0.5 methanol: NH$_4$OH solution in dichloromethane) to give 6-((3R,4R)-3-aminotetrahydro-2H-pyran-4-ylamino)-4-(6-isopropyl-5-methoxypyridin-2-ylamino)pyridazine-3-carboxamide (51 mg, 127 µmol, 74%) as a yellow solid. $^1$H NMR (400 MHz, METHANOL-d$_6$) δ ppm 8.08 (s, 1H), 7.42 (d, J=8.6 Hz, 1H), 6.91 (d, J=8.9 Hz, 1H), 4.35 (m, 1H), 4.12 (dd, J=12.1, 3.4 Hz, 1H), 4.07 (d, J=12.6 Hz, 1H), 3.89 (s, 1H), 3.88 (s, 3H), 3.80 (d, J=12.8 Hz, 1H), 3.65 (m, 1H), 3.52 (m, 1H), 2.12 (m, 1H), 1.96 (d, J=13.1 Hz, 1H), 1.32 (d, J=5.8 Hz, 6H); MS (EI/CI) m/z: 402.3 [M+H].

Example 35

6-((1R,2S)-2-Aminocyclohexylamino)-4-(6-isopropyl-4-methylpyridin-2-ylamino)pyridazine-3-carboxamide Step 1

6-Chloro-4-(6-isopropyl-4-methylpyridin-2-ylamino)pyridazine-3-carboxylate

To a solution of ethyl 4,6-dichloropyridazine-3-carboxylate (260 mg, 1.18 mmol) in acetonitrile (3.9 mL) was added 6-isopropyl-4-methylpyridin-2-amine (265 mg, 1.76 mmol) and then the mixture heated at 140° C. for 48 h. The mixture was cooled, concentrated in vacuo, and then purified by chromatography (silica, 5 to 30% ethyl acetate in hexanes) to give ethyl 6-chloro-4-(6-isopropyl-4-methylpyridin-2-ylamino)pyridazine-3-carboxylate (117 mg, 349 µmol, 30%) as an off white solid. $^1$H NMR (400 MHz, CHLOROFORM-d$_6$) δ ppm 10.60 (s, 1H), 9.39 (s, 1H), 6.76 (s, 1H), 6.59 (s, 1H), 4.58 (q, J=7.0 Hz, 2H), 3.04 (m, 1H), 2.35 (s, 3H), 1.53 (t, J=7.1 Hz, 3H), 1.35 (d, J=7.0 Hz, 6H), MS (EI/CI) m/z: 335.0 [M+H].

Step 2

6-Chloro-4-(6-isopropyl-4-methylpyridin-2-ylamino)pyridazine-3-carboxamide

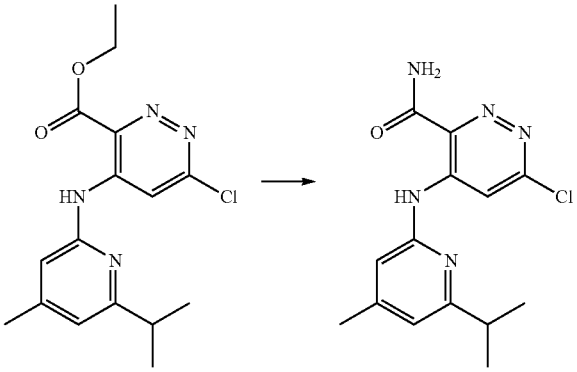 [SMILES: CCOC(=O)c1nnc(Cl)cc1Nc1cc(C)cc(C(C)C)n1 ; Cc1cc(Nc2cc(Cl)nnc2C(N)=O)nc(C(C)C)c1]

To a solution of ethyl 6-chloro-4-(6-isopropyl-4-methylpyridin-2-ylamino)pyridazine-3-carboxylate (115 mg, 343 µmol) in methanol (1 mL) was added ammonia in methanol (7 N, 4.91 mL, 34.3 mmol) and then the mixture heated at 45° C. for 20 h. The mixture was concentrated in vacuo to give 6-chloro-4-(6-isopropyl-4-methylpyridin-2-ylamino)pyridazine-3-carboxamide (105 mg, 343 µmol, 100%) as a white solid. $^1$H NMR (400 MHz, DMSO-d$_6$) δ ppm 11.91 (s, 1H), 9.25 (s, 1H), 8.85 (s, 1H), 8.21 (s, 1H), 6.87 (s, 1H), 6.77 (s, 1H), 3.01 (m, 1H), 2.31 (s, 3H), 1.28 (d, J=6.6 Hz, 6H); MS (EI/CI) m/z: 305.9 [M+H].

Step 3 tert-Butyl (1S,2R)-2-(6-carbamoyl-5-(6-isopropyl-4-methylpyridin-2-ylamino)pyridazin-3-ylamino)cyclohexylcarbamate

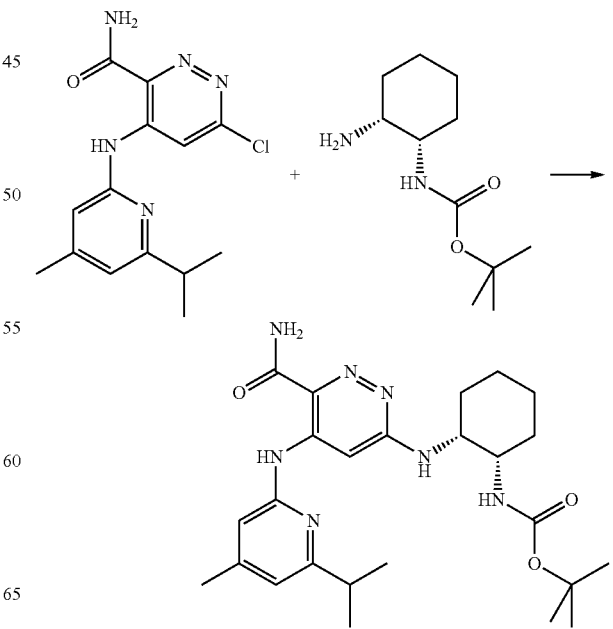

To a stirred solution of 6-chloro-4-(6-isopropyl-4-methylpyridin-2-ylamino)pyridazine-3-carboxamide (54 mg, 177 µmol) in NMP (590 µL) was added tert-butyl (1S,2R)-2-aminocyclohexylcarbamate (227.1 mg, 883 µmol) in three portions approximately every 12 h and while heating the mixture (in the periods between additions) at 140° C. After a total of 36 h, the mixture was cooled and then diluted with ethyl acetate and water. The organic phase was separated and then washed with water and brine. The organic phase was then concentrated in vacuo and finally purified by chromatography (silica, 30 to 80% ethyl acetate in hexanes) to give tert-butyl (1S,2R)-2-(6-carbamoyl-5-(6-isopropyl-4-methylpyridin-2-ylamino)pyridazin-3-ylamino)cyclohexylcarbamate (35 mg, 72.4 µmol, 41.0%) as a brown oil. MS (EI/CI) m/z: 484.3 [M+H].

Step 4

6-((1R,2S)-2-Aminocyclohexylamino)-4-(6-isopropyl-4-methylpyridin-2-ylamino)pyridazine-3-carboxamide

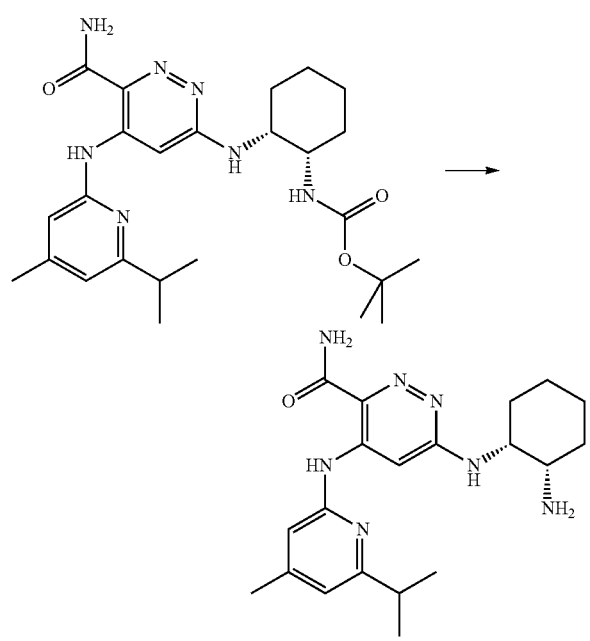

To a solution of tert-butyl (1S,2R)-2-(6-carbamoyl-5-(6-isopropyl-4-methylpyridin-2-ylamino)pyridazin-3-ylamino)cyclohexylcarbamate (35 mg, 72.4 µmol) in dichloromethane (1.1 mL) was added trifluoroacetic acid (165 mg, 112 µL, 1.45 mmol) and the mixture stirred at room temperature for 20 h. The mixture was concentrated in vacuo and then the residue diluted with dichloromethane and a few drops of 25% aqueous NH₄OH added until the mixture was measured at pH~8. The mixture was then washed with water, the organic phase collected, concentrated in vacuo, and finally purified by chromatography (silica, 3 to 10% of a 99.5:0.5 methanol:NH₄OH solution in dichloromethane) to give 6-((1R,2S)-2-aminocyclohexylamino)-4-(6-isopropyl-4-methylpyridin-2-ylamino)pyridazine-3-carboxamide (15 mg, 39.1 µmol, 54%) as a light brown solid. ¹H NMR (400 MHz, DMSO-$d_6$) δ ppm 11.64 (s, 1H), 8.36 (s, 1H), 8.07 (s, 1H), 7.64 (s, 1H), 6.79 (d, J=4.3 Hz, 1H), 6.73 (s, 1H), 6.60 (s, 1H), 3.90 (s, 1H), 2.98 (m, 1H), 2.27 (s, 3H), 1.52-1.76 (m, 6H), 1.38 (m, 2H), 1.27 (d, J=7.0 Hz, 6H); MS (EI/CI) m/z: 384.1 [M+H].

Example 36

6-((1R,2S)-2-aminocyclohexylamino)-4-(6-(2-cyanopropan-2-yl)pyridin-2-ylamino)pyridazine-3-carboxamide Step 1

2-(6-Bromopyridin-2-yl)-2-methylpropanenitrile

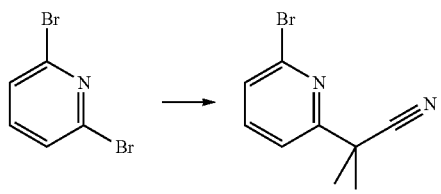

A dried 500 mL round bottom flask was charged with a solution of iso-butyronitrile (3.29 g, 4.27 mL, 47.6 mmol) in toluene (100 mL), the solution was cooled down to 0° C. and KHMDS 0.5 m in toluene (100 mL, 50.0 mmol) was added slowly. After complete addition, the reaction mixture was allowed to warm up to room temperature over 1 hour. The resulting mixture was added to a solution of 2,6-dibromopyridine (28.2 g, 119 mmol, available commercially from Aldrich) in toluene (100 mL) While adding, the light yellow solution became quickly dark reddish. The reaction mixture was stirred at room temperature for 18 hours. The crude mixture was diluted with ether, washed with a saturated aqueous solution of ammonium chloride and brine. The organic phase was dried over magnesium sulfate, filtered and concentrated in vacuo. The semi-solid residue was suspended in a small amount of toluene and filtered off, the light brown solid corresponded to 2,6-dibromopyridine recovered. Filtrate was purified by flash chromatography (silica gel 50 µm, 220 g, Rediflash Teledyne-Isco) eluting with 0 to 50% over 20 min dichloromethane/hexanes to give 2-(6-bromopyridin-2-yl)-2-methylpropanenitrile (7.608 g, 28.4% yield) as a light yellow oil that solidified into a white solid upon standing. ¹H NMR (CHLOROFORM-d) δ: 7.58-7.61 (m, 2H), 7.42-7.46 (m, 1H), 1.76 (s, 6H); LC-MS 225.0 226.9 [M+H]⁺.

Step 2

2-(6-Aminopyridin-2-yl)-2-methylpropanenitrile

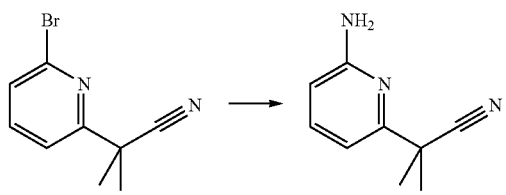

A heavy walled resealable tube was loaded, under an argon atmosphere, with copper (I) oxide (159 mg, 1.11 mmol), 2-(6-bromopyridin-2-yl)-2-methylpropanenitrile (5000 mg, 22.2 mmol), ammonium hydroxide 28% solution (26.9 mL, 444 mmol), K$_2$CO$_3$ (614 mg, 4.44 mmol), N,N-dimethylethylenediamine (196 mg, 244 µA, 2.22 mmol) and ethyleneglycol (44.4 mL). The reaction was heated to 60° C. with stirring for 6 h. After cooling down, the reaction mixture was extracted with dichloromethane (3×25 mL), combined organics dried over magnesium sulfate and evaporated. The residue was purified by flash chromatography (silica gel 50 µm, 40 g, Analogix) eluting with 0 to 5% over 20 min (10% ammonium hydroxide in methanol)/dichloromethane, obtained 2-(6-aminopyridin-2-yl)-2-methylpropanenitrile (3.2 g, 89.4% yield) as a white solid. $^1$H NMR (CHLOROFORM-d) δ: 7.34-7.46 (m, 1H), 6.81 (d, J=7.2 Hz, 1H), 6.40 (d, J=7.9 Hz, 1H), 4.67 (br. s., 2H), 1.63-1.68 (m, 6H); LC-MS 162.1 [M+H]$^+$.

Step 3

Ethyl 6-chloro-4-(6-(2-cyanopropan-2-yl)pyridin-2-ylamino)pyridazine-3-carboxylate

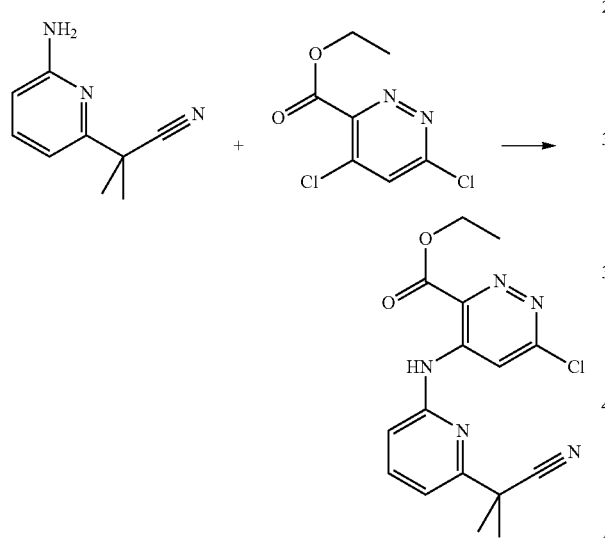

A mixture of ethyl 4,6-dichloropyridazine-3-carboxylate (1.4 g, 6.33 mmol) and 2-(6-aminopyridin-2-yl)-2-methylpropanenitrile (2.04 g, 12.7 mmol) was dissolved in acetonitrile (3.00 mL) and heated to 130° C. for 18 h. The mixture was cooled, concentrated, the residue was adsorbed on silica gel and purified by flash chromatography (silica gel 45 µM, 160 g, Thomson) eluting with 0 to 20% acetone in dichloromethane over 20 min, impure desired product was isolated, all fractions containing desired product were concentrated and the residue dissolved in a dichloromethane and evaporated to a small volume where a solid precipitated, filtered and dried and corresponded to the desired ethyl 6-chloro-4-(6-(2-cyanopropan-2-yl)pyridin-2-ylamino)pyridazine-3-carboxylate (792 mg, 36.2% yield). $^1$H NMR (CHLOROFORM-d) δ: 10.86 (s, 1H), 9.27 (s, 1H), 7.75 (t, J=7.9 Hz, 1H), 7.26 (d, J=7.9 Hz, 1H), 6.90 (d, J=7.9 Hz, 1H), 4.58 (q, J=7.2 Hz, 2H), 1.81 (s, 6H), 1.52 (t, J=7.2 Hz, 3H); LC-MS 346.1 [M+H]$^+$.

Step 4

6-Chloro-4-(6-(2-cyanopropan-2-yl)pyridin-2-ylamino)pyridazine-3-carboxamide

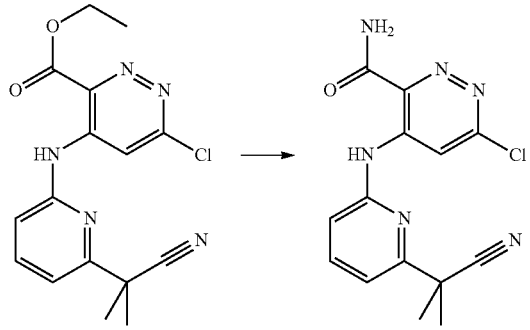 [SMILES: CCOC(=O)c1nnc(Cl)cc1Nc1cccc(C(C)(C)C#N)n1 ; CC(C)(C#N)c1cccc(Nc2cc(Cl)nnc2C(N)=O)n1]

In a 50 mL round bottom flask, ethyl 6-chloro-4-(6-(2-cyanopropan-2-yl)pyridin-2-ylamino)pyridazine-3-carboxylate (792 mg, 2.29 mmol) was suspended in ammonia 7M in methanol (7.87 g, 10.0 mL, 70.0 mmol). Sealed and stirred at room temperature for 18 h. The abundant solid formed during the reaction was separated by filtration, filter cake rinsed with fresh methanol and dried in high vacuum to give clean 6-chloro-4-(6-(2-cyanopropan-2-yl)pyridin-2-ylamino)pyridazine-3-carboxamide (581 mg, 80.1% yield) as an off-white solid. $^1$H NMR (DMSO-d$_6$) δ: 12.14 (s, 1H), 9.22 (s, 1H), 8.89 (s, 1H), 8.23 (s, 1H), 7.87 (t, J=7.9 Hz, 1H), 7.27 (d, J=7.6 Hz, 1H), 7.10 (d, J=7.9 Hz, 1H), 1.73 (s, 6H); LC-MS 316.9 [M+H]$^+$.

Step 5 tert-Butyl (1S,2R)-2-(6-carbamoyl-5-(6-(2-cyanopropan-2-yl)pyridin-2-ylamino)pyridazin-3-ylamino)cyclohexylcarbamate

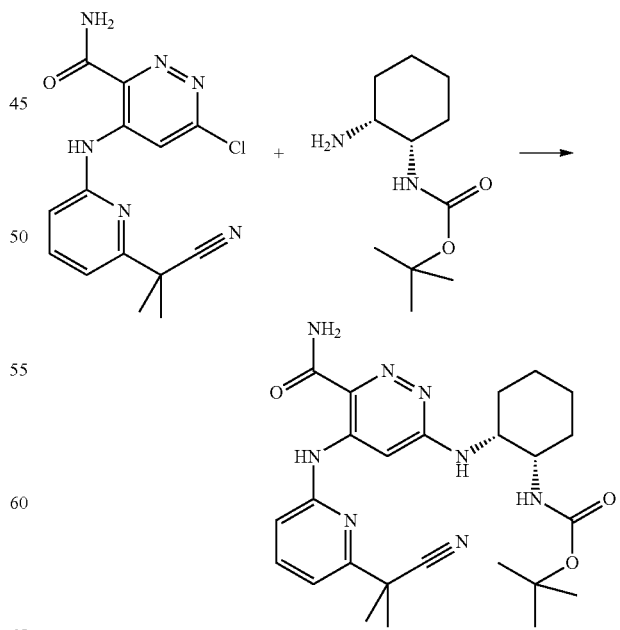

A resealable pressure tube was charged with 6-chloro-4-(6-(2-cyanopropan-2-yl)pyridin-2-ylamino)pyridazine-3- carboxamide (200 mg, 631 µmol) and tert-butyl (1S,2R)-2-aminocyclohexylcarbamate (135 mg, 631 µmol) in NMP (2.00 mL). The reaction mixture was heated in an oil bath with stirring at 120° C. for 18 h. Then added more tert-butyl (1S,2R)-2-aminocyclohexylcarbamate (135 mg, 631 µmol) in small portions during 7 hours and reaction continued for 18 h. The solvent was distilled off under high vacuum. The residue was dissolved in dichloromethane containing few drops of methanol and then purified by flash column (spherical silica 20-45 µM, 50 g, Versaflash Supelco) eluting with 0 to 5% over 20 min (MeOH containing 10% NH$_4$OH)/CH$_2$Cl$_2$ to yield tert-butyl (1S,2R)-2-(6-carbamoyl-5-(6-(2-cyanopropan-2-yl)pyridin-2-ylamino)pyridazin-3-ylamino)cyclohexylcarbamate (110 mg, 222 µmol, 35.2% yield) as a yellow foam. $^1$H NMR (CHLOROFORM-d) δ: 11.48 (s, 1H), 8.82 (br. s., 1H), 8.00-8.11 (m, 1H), 7.62 (t, J=7.9 Hz, 1H), 6.89 (d, J=7.6 Hz, 1H), 6.79 (d, J=8.3 Hz, 1H), 5.53-5.85 (m, 2H), 5.06 (d, J=8.3 Hz, 1H), 4.47 (br. s., 1H), 3.80-3.99 (m, 1H), 1.24-1.93 (m, 23H); LC-MS 495.1 [M+H]$^+$.

It was also recovered some starting material 6-chloro-4-(6-(2-cyanopropan-2-yl)pyridin-2-ylamino)pyridazine-3-carboxamide (130 mg, 65.0% yield).

Step 6

6-((1R,2S)-2-Aminocyclohexylamino)-4-(6-(2-cyanopropan-2-yl)pyridin-2-ylamino)pyridazine-3-carboxamide

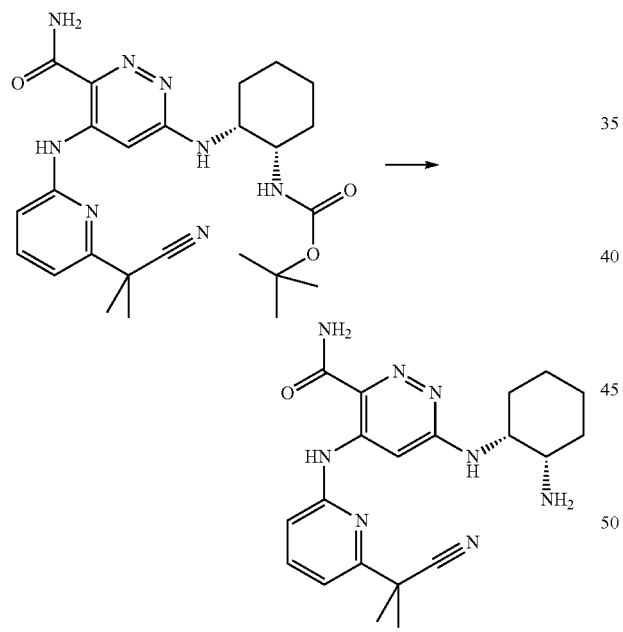

To a solution of tert-butyl (1S,2R)-2-(6-carbamoyl-5-(6-(2-cyanopropan-2-yl)pyridin-2-ylamino)pyridazin-3-ylamino)cyclohexylcarbamate (110 mg, 222 µmol) in CH$_2$Cl$_2$ (3.00 mL) was added TFA (1.48 g, 1.00 mL, 13.0 mmol) and the reaction mixture stirred to room temperature for 18 h. Solvents evaporated and residue purified by flash column (spherical silica 20-45 µM, 23 g, Versaflash Supelco) eluting with 0 to 5% over 20 min (MeOH containing 10% NH$_4$OH)/CH$_2$Cl$_2$ to give 6-((1R,2S)-2-aminocyclohexylamino)-4-(6-(2-cyanopropan-2-yl)pyridin-2-ylamino)pyridazine-3-carboxamide (50 mg, 57% yield) as an off-white solid. $^1$H NMR (CHLOROFORM-d) δ: 11.47 (s, 1H), 8.76 (s, 1H), 8.06 (d, J=3.0 Hz, 1H), 7.60 (t, J=7.9 Hz, 1H), 6.86 (d, J=7.6 Hz, 1H), 6.78 (d, J=7.9 Hz, 1H), 5.60-5.77 (m, 2H), 4.25 (br. s., 1H), 3.11-3.24 (m, 1H), 1.32-1.92 (m, 16H); LC-MS 395.1 [M+H]$^+$.

Example 37

6-((1R,2S)-2-aminocyclohexylamino)-4-(6-(2-hydroxypropan-2-yl)pyridin-2-ylamino)pyridazine-3-carboxamide Step 1

2-(6-Bromopyridin-2-yl)propan-2-ol

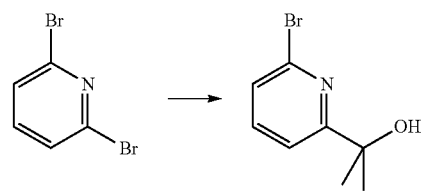

A dry 250 mL round bottomed flask fitted with a stir bar and septum was charged with n-buthyllithium 1.6 M in hexane (30.3 mL, 48.5 mmol), the flask was cooled in a dry-ice acetone bath to −76° C. and added THF (30 mL) to the solution, then added a solution of 2,6-dibromopyridine (11.5 g, 48.5 mmol) in THF (60 mL) slowly via cannula over 15 min. The dark yellow-brown solution was stirred for 30 minutes in the dry-ice bath, then added propan-2-one (4.75 g, 6 mL, 81.7 mmol). The deep green solution was stirred in the dry-ice bath for 15 minutes and then allowed to warm to room temperature. After an hour, added carefully a saturated aqueous solution of ammonium chloride (100 mL) and product extracted with dichloromethane (3×200), combined organics dried over magnesium sulfate and evaporated. The residue was purified by flash chromatography (silica gel 50 µm, 150 g, Analogix) eluting with 0 to 50% over 20 min dichloromethane/hexanes, obtained 2-(6-bromopyridin-2-yl)propan-2-ol (9.9 g, 94.3% yield) as a light yellow clear liquid. $^1$H NMR (CHLOROFORM-d) δ: 7.52-7.59 (m, 1H), 7.33-7.40 (m, 2H), 4.05 (br. s., 1H), 1.55 (s, 6H); LC-MS 216.1, 218.1 [M+H]$^+$.

Step 2

2-(6-Aminopyridin-2-yl)propan-2-ol

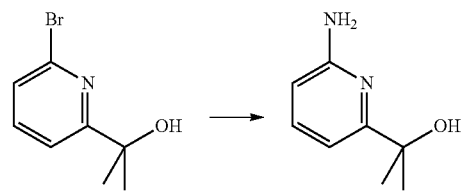

A heavy walled resealable tube was loaded under an argon atmosphere with copper (I) oxide (53.0 mg, 370 µmol), 2-(6-bromopyridin-2-yl)propan-2-ol (1600 mg, 7.4 mmol), ammonium hydroxide 28% solution (16.5 M) (8.98 mL, 148 mmol), K$_2$CO$_3$ (205 mg, 1.48 mmol), N,N-dimethylethylenediamine (65.3 mg, 81.3 µA, 740 µmol) and ethyleneglycol (14.8 mL). The reaction was stirred for 6 h at 60° C. After cooling to room temperature, the reaction mixture was extracted with dichloromethane (3×25 mL), combined organics dried over magnesium sulfate and evaporated. The residue was purified by flash chromatography (spherical silica 20-45

µM, 23 g, Versaflash Supelco) eluting with 0 to 5% over 20 min (10% ammonium hydroxide in methanol)/dichloromethane to give 2-(6-aminopyridin-2-yl)propan-2-ol (626 mg, 55.5% yield) as a light yellow liquid. $^1$H NMR (CHLOROFORM-d) δ: 7.44 (t, J=7.7 Hz, 1H), 6.67 (d, J=7.6 Hz, 1H), 6.38 (d, J=7.9 Hz, 1H), 5.12 (s, 1H), 4.38-4.55 (m, 2H), 1.49 (s, 6H); LC-MS 153.1, 155.1 [M+H]$^+$.

Step 3

Ethyl 6-chloro-4-(6-(2-hydroxypropan-2-yl)pyridin-2-ylamino)pyridazine-3-carboxylate

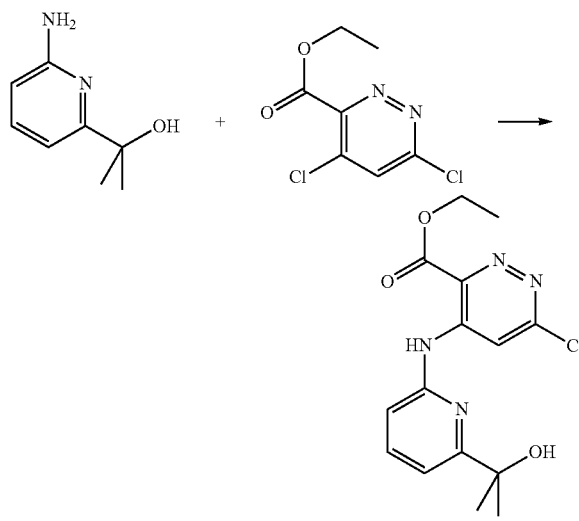

A mixture of ethyl 4,6-dichloropyridazine-3-carboxylate (0.45 g, 2.04 mmol) and 2-(6-aminopyridin-2-yl)propan-2-ol (620 mg, 4.07 mmol) was dissolved in acetonitrile (3.00 mL) and heated at 130° C. for 18 h. The mixture was cooled, concentrated, the residue was adsorbed on silica gel and purified by flash chromatography (silica gel 45 µM, 160 g, Thomson) eluting with 0 to 100% hexanes/ethyl acetate over 40 min, to yield ethyl 6-chloro-4-(6-(2-hydroxypropan-2-yl)pyridin-2-ylamino)pyridazine-3-carboxylate (405 mg, 59.1% yield). $^1$H NMR (CHLOROFORM-d) δ: 10.72 (s, 1H), 9.00 (s, 1H), 7.76 (t, J=7.9 Hz, 1H), 7.34 (d, J=7.9 Hz, 1H), 6.89 (d, J=7.9 Hz, 1H), 5.21 (br. s., 1H), 4.60 (q, J=7.2 Hz, 2H), 1.67 (s, 6H), 1.54 (t, J=7.9 Hz, 3H); LC-MS 337.0, 339.0 [M+H]$^+$.

Step 4

6-Chloro-4-(6-(2-hydroxypropan-2-yl)pyridin-2-ylamino)pyridazine-3-carboxamide

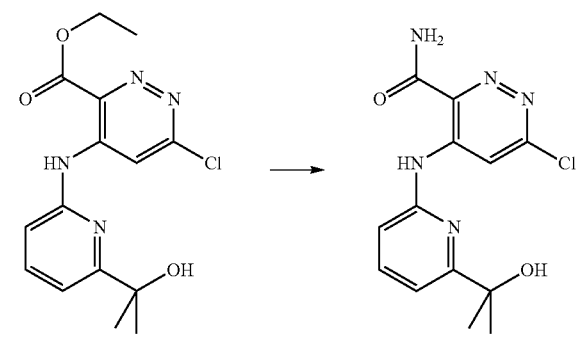 [SMILES: CCOC(=O)c1nnc(Cl)cc1Nc1cccc(C(C)(C)O)n1 ; CC(C)(O)c1cccc(Nc2cc(Cl)nnc2C(N)=O)n1]

In a 50 mL round bottom flask, ethyl 6-chloro-4-(6-(2-hydroxypropan-2-yl)pyridin-2-ylamino)pyridazine-3-carboxylate (792 mg, 2.35 mmol) was suspended in ammonia 7M in methanol (7.87 g, 10.0 mL, 70.0 mmol). Sealed and stirred at room temperature for 5 h. The solvents were evaporated and the residue purified by flash chromatography (spherical silica 20-45 µM, 50 g, Versaflash Supelco) eluting with 0 to 5% over 20 min (MeOH containing 10% NH$_4$OH)/CH$_2$Cl$_2$ to give 6-chloro-4-(6-(2-hydroxypropan-2-yl)pyridin-2-ylamino)pyridazine-3-carboxamide (241 mg, 33.3% yield) as an off-white solid. $^1$H NMR (CHLOROFORM-d) δ: 11.64 (s, 1H), 8.96 (s, 1H), 8.18 (br. s., 1H), 7.71 (t, J=7.9 Hz, 1H), 7.25 (d, J=7.6 Hz, 1H), 6.86 (d, J=8.3 Hz, 1H), 5.70 (br. s., 1H), 1.64 (s, 6H); LC-MS 308.0, 310.0 [M+H]$^+$.

Step 5 tert-Butyl (1S,2R)-2-(6-carbamoyl-5-(6-(2-hydroxypropan-2-yl)pyridin-2-ylamino)pyridazin-3-ylamino)cyclohexylcarbamate

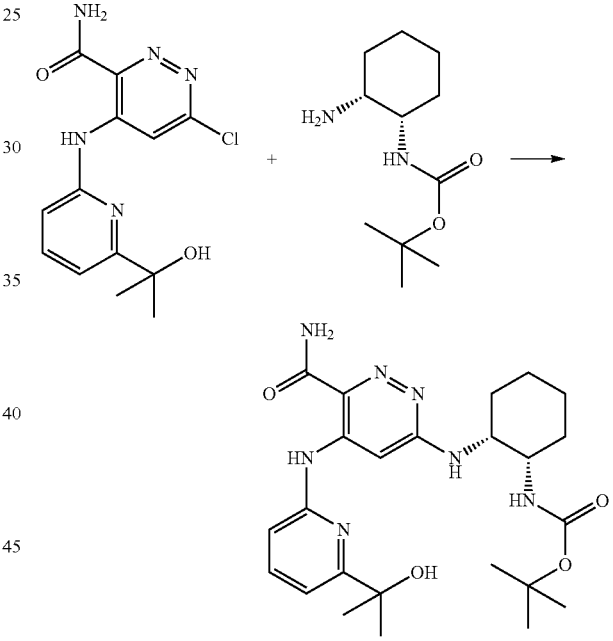

A dry 50 mL round bottom flask was charged with 6-chloro-4-(6-(2-hydroxypropan-2-yl)pyridin-2-ylamino)pyridazine-3-carboxamide (241 mg, 783 µmol) dissolved in NMP (2.00 mL) To this solution was added tert-butyl (1S,2R)-2-aminocyclohexylcarbamate (168 mg, 783 µmol) and the reaction mixture was heated in an oil bath with stirring at 120° C. for 18 h. After that, it was added more tert-butyl (1S,2R)-2-aminocyclohexylcarbamate (168 mg, 783 µmol) in small portions during 7 hours. After last addition, the reaction was continued for 18 h. After cooling to room temperature, the solvent was distilled off under high vacuum, the residue was dissolved in dichloromethane containing few drops of methanol and then purified by flash chromatography (spherical silica 20-45 µM, 50 g, Versaflash Supelco) eluting with 0 to 5% over 20 min (MeOH containing 10% NH$_4$OH)/CH$_2$Cl$_2$ to yield tert-butyl (1S,2R)-2-(6-carbamoyl-5-(6-(2- hydroxypropan-2-yl)pyridin-2-ylamino)pyridazin-3-ylamino)cyclohexylcarbamate (179 mg, 47.1% yield) as a yellow foam. ¹H NMR (CHLOROFORM-d) δ: 11.54 (br. s., 1H), 8.16 (br. s., 1H), 8.04 (s, 1H), 7.60 (t, J=7.9 Hz, 1H), 7.05 (d, J=7.6 Hz, 1H), 6.76 (d, J=8.3 Hz, 1H), 6.53-6.70 (m, 1H), 5.81 (d, J=3.4 Hz, 1H), 5.43 (br. s., 1H), 3.71-4.14 (m, 3H), 1.23-1.90 (m, 23H); LC-MS 486.2 [M+H]⁺.

Step 6

6-((1R,2S)-2-Aminocyclohexylamino)-4-(6-(2-hydroxypropan-2-yl)pyridin-2-ylamino)pyridazine-3-carboxamide

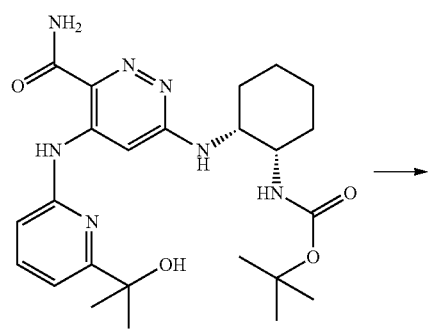

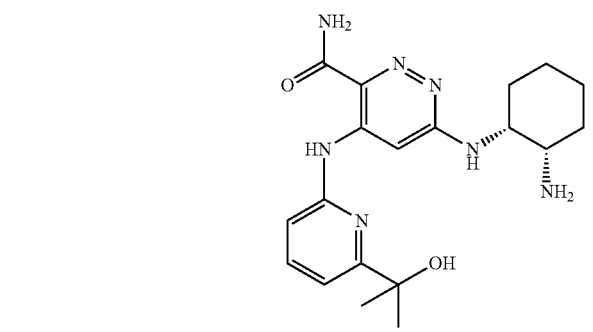

To a solution of tert-butyl (1S,2R)-2-(6-carbamoyl-5-(6-(2-hydroxypropan-2-yl)pyridin-2-ylamino)pyridazin-3-ylamino)cyclohexylcarbamate (179 mg, 369 µmol) in CH₂Cl₂ (3.00 mL) was added TFA (1.48 g, 1.00 mL, 13.0 mmol) and mixture stirred to room temperature for 18 h. The solvent was evaporated and the residue purified by flash chromatography (spherical silica 20-45 µM, 23 g, Versaflash Supelco) eluting with 0 to 5% over 20 min (MeOH containing 10% NH₄OH)/CH₂Cl₂ to give 6-((1R,2S)-2-aminocyclohexylamino)-4-(6-(2-hydroxypropan-2-yl)pyridin-2-ylamino)pyridazine-3-carboxamide (80 mg, 56.3% yield) as an off-white foam. ¹H NMR (DMSO-d₆) δ: 11.76 (s, 1H), 8.38 (br. s., 1H), 7.90 (s, 1H), 7.60-7.78 (m, 2H), 7.23 (d, J=7.6 Hz, 1H), 6.70-6.83 (m, 2H), 5.18 (s, 1H), 3.70 (br. s., 1H), 3.09 (br. s., 1H), 1.21-1.77 (m, 16H); LC-MS 386.1 [M+H]⁺.

Example 38

6-((1R,2S)-2-aminocyclohexylamino)-4-(4-methyl-6-propylpyridin-2-ylamino)pyridazine-3-carboxamide Step 1

(E)-4-Methyl-6-(prop-1-enyl)pyridin-2-amine

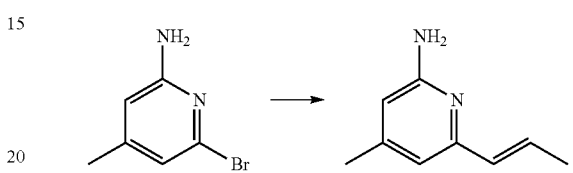

6-bromo-4-methylpyridin-2-amine (500 mg, 2.67 mmol), (E)-6-methyl-2-(prop-1-enyl)-1,3,6,2-dioxazaborocane-4,8-dione (1.05 g, 5.35 mmol), cesium carbonate (2.61 g, 8.02 mmol) and tetrakis(triphenylphosphine)palladium (0) (309 mg, 267 µmol) were combined with dioxane (7.4 mL and water (1.5 mL) and the mixture was heated to 150° C. for 60 min in the microwave. The reaction mixture was cooled and then diluted with ethyl acetate and water. The phases were separated and the organic phase was washed with water and brine. The organic phase was concentrated in vacuo and then purified by chromatography (silica, 20% to 60% ethyl acetate in hexanes) to give a residue that was triturated with methanol to obtain a yellow precipitate. This precipitate was collected by filtration and dried to give (E)-4-methyl-6-(prop-1-enyl)pyridin-2-amine (235 mg, 1.59 mmol, 59%) as a yellow oil. MS (EI/CI) m/z: 148.8 [M+H].

Step 2

4-Methyl-6-propylpyridin-2-amine

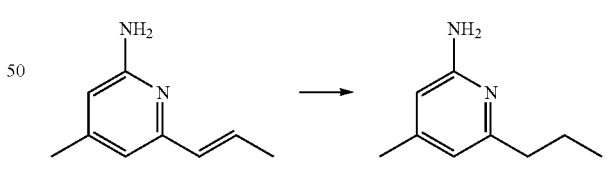

To a solution of (E)-4-methyl-6-(prop-1-enyl)pyridin-2-amine (235 mg, 1.59 mmol) in ethanol (5.29 mL) was added 10% palladium on carbon (169 mg, 159 µmol). The reaction mixture was evacuated and back filled with H₂ three times. The mixture was stirred under an atmosphere of hydrogen (balloon at 1 atm) for 16 h, then filtered through a pad of celite. The filtrate was collected, concentrated in vacuo and purified by chromatography (silica, 30 to 60% ethyl acetate in hexanes gradient) to give 4-methyl-6-propylpyridin-2-amine (135 mg, 899 µmol, 57%) as a colorless oil. MS (EI/CI) m/z: 150.8 [M+H].

Step 3

Ethyl 6-chloro-4-(4-methyl-6-propylpyridin-2-ylamino)pyridazine-3-carboxylate

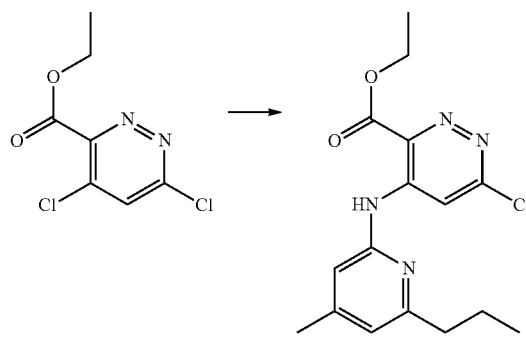

To a solution of ethyl 4,6-dichloropyridazine-3-carboxylate (335 mg, 1.52 mmol) in acetonitrile (5 mL) was added 4-methyl-6-propylpyridin-2-amine (342 mg, 2.27 mmol) and the mixture heated in a sealed tube at 130° C. for 72 h. The mixture was cooled, concentrated in vacuo, and then purified by chromatography (silica, 10 to 35% ethyl acetate in hexanes) to give ethyl 6-chloro-4-(4-methyl-6-propylpyridin-2-ylamino)pyridazine-3-carboxylate (147 mg, 439 mmol, 29%) as a light brown solid. $^1$H NMR (400 MHz, CHLOROFORM-$d_6$) δ ppm 10.61 (s, 1H), 9.26 (s, 1H), 6.74 (s, 1H), 6.61 (s, 1H), 4.58 (q, J=7.1 Hz, 2H), 2.76 (t, J=7.5 Hz, 1H), 2.35 (s, 3H), 1.84 (m, 2H), 1.53 (t, J=6.9 Hz, 3H), 1.03 (t, J=7.3 Hz, 3H), MS (EI/CI) m/z: 335.0 [M+H].

Step 4

6-Chloro-4-(4-methyl-6-propylpyridin-2-ylamino)pyridazine-3-carboxamide

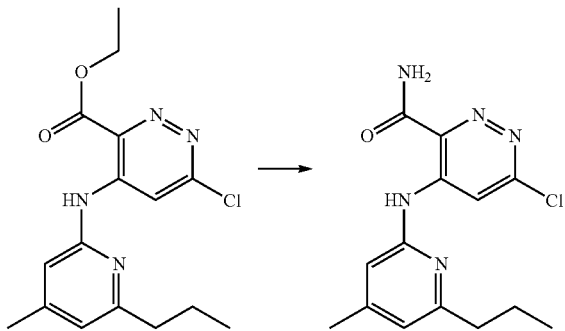 [SMILES: CCCc1cc(C)cc(Nc2cc(Cl)nnc2C(=O)OCC)n1 ; CCCc1cc(C)cc(Nc2cc(Cl)nnc2C(N)=O)n1]

A mixture of ethyl 6-chloro-4-(4-methyl-6-propylpyridin-2-ylamino)pyridazine-3-carboxylate (147 mg, 439 μmol) in ammonia in methanol (7 N, 6.27 mL, 43.9 mmol) was heated to 40° C. for 16 h. The mixture was concentrated in vacuo to give 6-chloro-4-(4-methyl-6-propylpyridin-2-ylamino)pyridazine-3-carboxamide (134 mg, 438 μmol, 100%) as a white solid. $^1$H NMR (400 MHz, DMSO-$d_6$) δ ppm 11.88 (s, 1H), 9.16 (s, 1H), 8.82 (s, 1H), 8.18 (s, 1H), 6.83 (s, 1H), 6.76 (s, 1H), 2.69 (t, J=7.3 Hz, 2H), 2.29 (s, 3H), 1.76 (m, 1H), 0.95 (t, J=7.3 Hz, 3H); MS (EI/CI) m/z: 305.9 [M+H].

Step 5 tert-Butyl (1S,2R)-2-(6-carbamoyl-5-(4-methyl-6-propylpyridin-2-ylamino)pyridazin-3-ylamino)cyclohexylcarbamate To a solution of 6-chloro-4-(4-methyl-6-propylpyridin-2-ylamino)pyridazine-3-carboxamide (134 mg, 438 μmol) in NMP (1.5 mL) was added tert-butyl (1S,2R)-2-aminocyclohexylcarbamate (376 mg, 1.75 mmol) in 3 portions approximately every 12 h over 36 h, with heating at 140° C. in the periods between additions. The mixture was then diluted with ethyl acetate and brine. The phases were separated and the organic phase washed twice with brine. The organic phase was concentrated in vacuo and then purified by chromatography (silica, 30 to 100% ethyl acetate in hexanes) to give tert-butyl (1S,2R)-2-(6-carbamoyl-5-(4-methyl-6-propylpyridin-2-ylamino)pyridazin-3-ylamino)cyclohexylcarbamate (91 mg, 188 μmol, 43%) as a light brown solid. MS (EI/CI) m/z: 484.3 [M+H].

Step 6

6-((1R,2S)-2-Aminocyclohexylamino)-4-(4-methyl-6-propylpyridin-2-ylamino)pyridazine-3-carboxamide

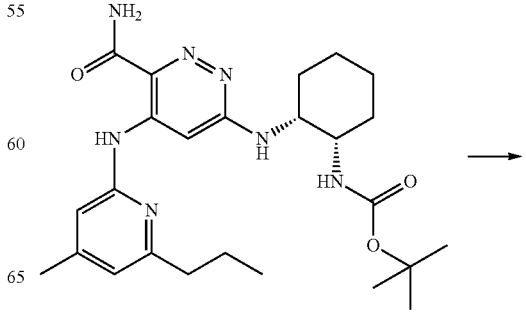

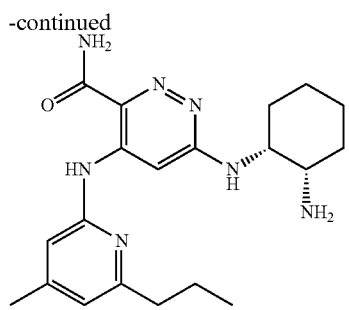

To a solution of tert-butyl (1S,2R)-2-(6-carbamoyl-5-(4-methyl-6-propylpyridin-2-ylamino)pyridazin-3-ylamino)cyclohexylcarbamate (91 mg, 188 μmol) in dichloromethane (2.9 mL) was added trifluoroacetic acid (429 mg, 290 μL, 3.76 mmol) and the mixture stirred at room temperature for 16 h. The mixture was concentrated in vacuo then diluted with NH₄OH and dichloromethane. The mixture was washed with water, then the organic phase was concentrated in vacuo and purified by chromatography (silica, 3 to 15% methanol in dichloromethane) to give 6-((1R,2S)-2-aminocyclohexylamino)-4-(4-methyl-6-propylpyridin-2-ylamino)pyridazine-3-carboxamide (46 mg, 120 μmol, 64%) as an off-white solid. ¹H NMR (400 MHz, DMSO-d₆) δ ppm 11.59 (s, 1H), 8.34 (s, 1H), 8.08 (s, 1H), 7.63 (s, 1H), 6.80 (d, J=7.2 Hz, 1H), 6.70 (s, 1H), 6.60 (s, 1H), 3.88 (s, 1H), 3.25 (s, 1H), 2.67 (t, J=7.4 Hz, 1H), 2.26 (s, 3H), 1.71 (m, 2H), 1.54-1.71 (m, 6H), 1.35 (s, 2H), 0.93 (t, J=7.2 Hz, 3H); MS (EI/CI) m/z: 384.1 [M+H].

Example 39

6-((3R,4R)-3-aminotetrahydro-2H-pyran-4-ylamino)-4-(4-methyl-6-propylpyridin-2-ylamino)pyridazine-3-carboxamide Step 1 tert-Butyl (3R,4R)-4-(6-carbamoyl-5-(4-methyl-6-propylpyridin-2-ylamino)pyridazin-3-ylamino)tetrahydro-2H-pyran-3-ylcarbamate

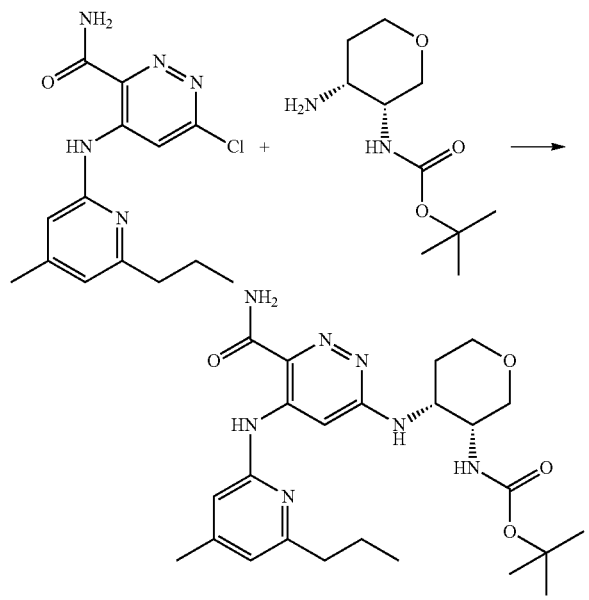

To a solution of 6-chloro-4-(4-methyl-6-propylpyridin-2-ylamino)pyridazine-3-carboxamide (73 mg, 239 μmol, prepared as described in example 38) in NMP (796 μL) was added tert-butyl (3R,4R)-4-aminotetrahydro-2H-pyran-3-ylcarbamate (206.4 mg, 956 μmol) in 4 portions approximately every 12 h over 48 h and heated at 140° C. in the periods between additions. After 48 h, the mixture was diluted with ethyl acetate and brine. The phases were separated then the organic phase was washed with brine (3×), concentrated in vacuo, and purified by chromatography (silica, 1 to 5% methanol in dichloromethane) to give tert-butyl (3R,4R)-4-(6-carbamoyl-5-(4-methyl-6-propylpyridin-2-ylamino)pyridazin-3-ylamino)tetrahydro-2H-pyran-3-ylcarbamate (27 mg, 56 μmol, 23%) as a light brown solid. MS (EI/CI) m/z: 486.2 [M+H].

Step 2

6-((3R,4R)-3-Aminotetrahydro-2H-pyran-4-ylamino)-4-(4-methyl-6-propylpyridin-2-ylamino)pyridazine-3-carboxamide

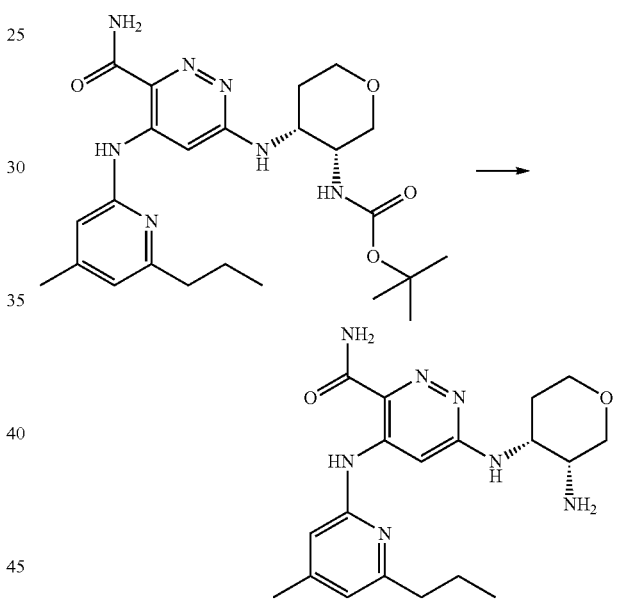

To a solution of tert-butyl (3R,4R)-4-(6-carbamoyl-5-(4-methyl-6-propylpyridin-2-ylamino)pyridazin-3-ylamino)tetrahydro-2H-pyran-3-ylcarbamate (27 mg, 55.6 μmol) in dichloromethane (1 mL) was added trifluoroacetic acid (127 mg, 85.7 μL, 1.11 mmol) and the mixture stirred at room temperature for 16 h. The mixture was concentrated in vacuo and then the residue was diluted with dichloromethane and 25% aqueous NH₄OH. The mixture was washed with water (2×), then the organic phase was collected, concentrated in vacuo, and purified by chromatography (silica, 1 to 10% of a 99.5:0.5 methanol:NH₄OH solution in dichloromethane) to give 6-((3R,4R)-3-aminotetrahydro-2H-pyran-4-ylamino)-4-(4-methyl-6-propylpyridin-2-ylamino)pyridazine-3-carboxamide (7 mg, 18.2 μmol, 33%) as an off-white solid. ¹H NMR (400 MHz, DMSO-d₆) δ ppm 11.61 (s, 1H), 8.38 (s, 1H), 8.10 (s, 1H), 7.68 (s, 1H), 6.98 (d, J=5.8 Hz, 1H), 6.71 (s, 1H), 6.61 (s, 1H), 4.08 (q, J=5.5 Hz, 1H), 3.92 (d, J=9.9 Hz, 1H), 3.81 (d, J=12.2 Hz, 1H), 3.59 (d, J=11.7 Hz, 1H), 3.47 (t, J=11.8 Hz, 1H), 3.28 (s, 1H), 3.17 (d, J=5.0 Hz, 2H), 2.67 (t, J=7.8 Hz, 1H), 2.33 (s, 1H), 2.26 (s, 3H), 1.72 (m, 3H), 1.23 (s, 1H), 0.93 (t, J=7.4 Hz, 3H); MS (EI/CI) m/z: 386.2 [M+H].

Example 40

6-((3R,4R)-3-aminotetrahydro-2H-pyran-4-ylamino)-4-(5-methoxy-6-propylpyridin-2-ylamino)pyridazine-3-carboxamide Step 1 tert-Butyl (3R,4R)-4-(6-carbamoyl-5-(5-methoxy-6-propylpyridin-2-ylamino)pyridazin-3-ylamino)tetrahydro-2H-pyran-3-ylcarbamate

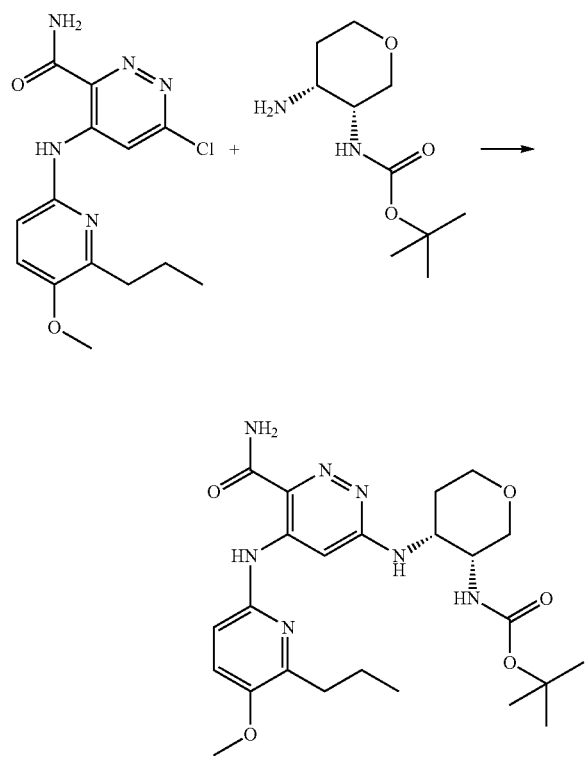 [SMILES: CCCc1nc(Nc2cc(Cl)nnc2C(N)=O)ccc1OC ; CC(C)(C)OC(=O)N[C@H]1COCC[C@H]1N ; CCCc1nc(Nc2cc(N[C@@H]3CCOC[C@@H]3NC(=O)OC(C)(C)C)nnc2C(N)=O)ccc1OC]

To a solution of 6-chloro-4-(5-methoxy-6-propylpyridin-2-ylamino)pyridazine-3-carboxamide (200 mg, 622 µmol, prepared as described in example 31) in NMP (2.1 mL) was added tert-butyl (3R,4R)-4-aminotetrahydro-2H-pyran-3-ylcarbamate (402 mg, 1.86 mmol) in 3 portions approximately every 12 h and heated to 140° C. in the periods between additions. After a total of 36 h, the mixture was cooled, diluted with ethyl acetate and brine, then the organic phase separated and washed with brine (3×). The organic phase was then concentrated in vacuo and the residue obtained was purified by chromatography (silica, 1 to 5% methanol in dichloromethane) to give tert-butyl (3R,4R)-4-(6-carbamoyl-5-(5-methoxy-6-propylpyridin-2-ylamino)pyridazin-3-ylamino)tetrahydro-2H-pyran-3-ylcarbamate (77 mg, 154 µmol, 25%) as a light brown solid. MS (EI/CI) m/z: 502.2 [M+H].

Step 2

6-((3R,4R)-3-aminotetrahydro-2H-pyran-4-ylamino)-4-(5-methoxy-6-propylpyridin-2-ylamino)pyridazine-3-carboxamide

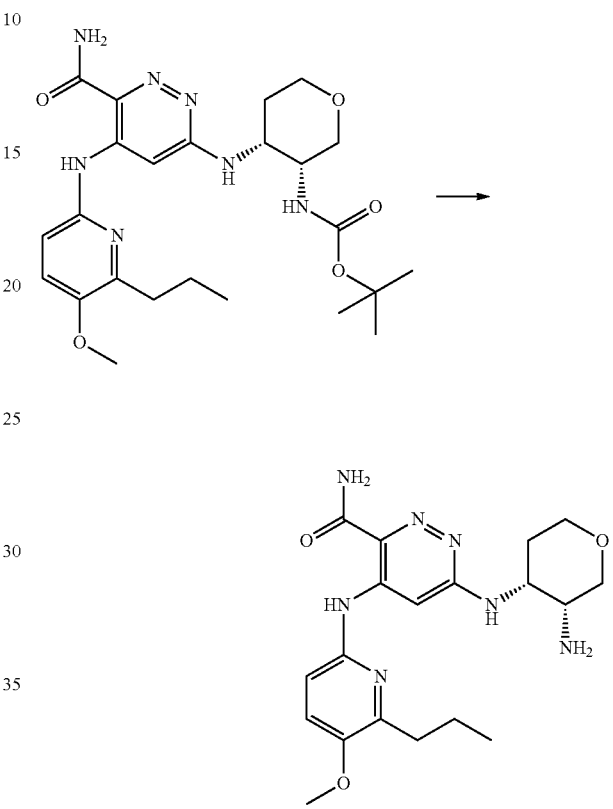

To a solution of tert-butyl (3R,4R)-4-(6-carbamoyl-5-(5-methoxy-6-propylpyridin-2-ylamino)pyridazin-3-ylamino)tetrahydro-2H-pyran-3-ylcarbamate (77 mg, 154 µmol) in dichloromethane (2.4 mL) was added trifluoroacetic acid (350 mg, 237 µL, 3.07 mmol) and the mixture stirred at room temperature. After 16 h the mixture was concentrated in vacuo then diluted with 25% aqueous NH$_4$OH and dichloromethane. The mixture was washed with water, then the organic phase was concentrated in vacuo and purified by chromatography (silica, 3 to 10% methanol in dichloromethane) to give 6-((3R,4R)-3-aminotetrahydro-2H-pyran-4-ylamino)-4-(5-methoxy-6-propylpyridin-2-ylamino)pyridazine-3-carboxamide (33 mg, 82.2 µmol, 54%) as a an off-white solid. $^1$H NMR (400 MHz, DMSO-d$_6$) δ ppm 11.37 (s, 1H), 8.33 (s, 1H), 7.74 (s, 1H), 7.58 (s, 1H), 7.41 (d, J=8.7 Hz, 1H), 6.87 (d, J=8.8 Hz, 1H), 6.76 (d, J=7.6 Hz, 1H), 3.98 (br. s, 1H), 3.84 (m, 1H), 3.79 (s, 3H), 3.70 (d, J=11.3 Hz, 1H), 3.51 (d, J=11.5 Hz, 1H), 3.40 (t, J=11.2 Hz, 1H), 2.99 (s, 1H), 2.72 (t, J=7.4 Hz, 2H), 1.81 (m, 1H), 1.72 (m, 2H), 1.72 (m, 3H), 0.94 (t, J=7.3 Hz, 3H); MS (EI/CI) m/z: 402.2 [M+H].

Example 41

6-((3R,4R)-3-Aminotetrahydro-2H-pyran-4-ylamino)-4-(5-fluoro-6-isopropylpyridin-2-ylamino)pyridazine-3-carboxamide Step 1

(6-Bromo-5-fluoro-pyridin-2-yl)-carbamic acid tert-butyl ester

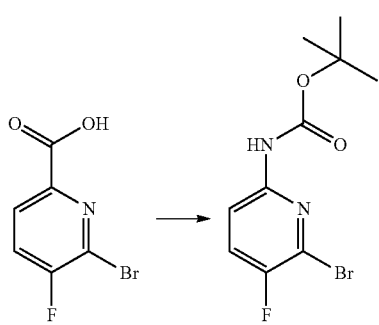 [SMILES: O=C(O)c1ccc(F)c(Br)n1 ; CC(C)(C)OC(=O)Nc1ccc(F)c(Br)n1]

To a solution of 6-bromo-5-fluoro-2-picolinic acid (2 g, 9.09 mmol) in tert-butanol (46 mL) and triethylamine (1.27 mL, 9.09 mmol, Eq: 1.00) was added DPPA (1.97 mL, 9.09 mmol). The slurry was stirred at room temperature until all solids dissolved (~15 min), after which it was heated to 85° C. for 2 h. Upon cooling the mixture was concentrated onto silica gel and chromatographed (silica, 5% to 30% EtOAc in hexanes) to give slightly impure (6-bromo-5-fluoro-pyridin-2-yl)-carbamic acid tert-butyl ester (1.55 g, 59%). $^1$H NMR (400 MHz, CHLOROFORM-$d_6$) δ ppm 7.97 (d, J=8.6 Hz, 1H), 7.43 (d, J=8.6 Hz, 1H), 1.53 (s, 9H).

Step 2

6-Bromo-5-fluoro-pyridin-2-ylamine

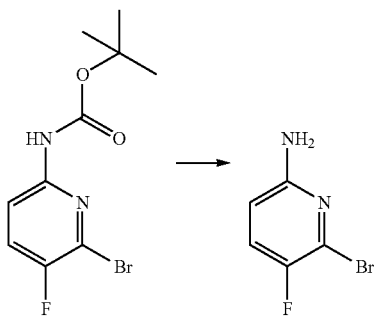 [SMILES: CC(C)(C)OC(=O)Nc1ccc(F)c(Br)n1 ; Nc1ccc(F)c(Br)n1]

To a solution of (6-bromo-5-fluoro-pyridin-2-yl)-carbamic acid tert-butyl ester (1.43 g, 4.91 mmol) in DCM (25 mL) was added TFA (3.78 mL, 49.1 mmol, Eq: 10.0). The mixture was stirred at room temperature for 2 h, after which it was concentrated in vacuo, and redissolved in EtOAc. The organic layer was washed with sat. aq. NaHCO$_3$ followed by water and brine. The resulting organic layer was concentrated on to silica gel and chromatographed (10% to 40% EtOAc/hexanes) to give 6-bromo-5-fluoro-pyridin-2-ylamine (850 mg, 91%). $^1$H NMR (400 MHz, CHLOROFORM-$d_6$) δ ppm 7.23 (dd, J=8.6, 7.5 Hz, 1H), 6.41 (dd, J=8.6, 2.6 Hz, 1H), 4.40 (br. s, 2H).

Step 3

5-Fluoro-6-isopropenyl-pyridin-2-ylamine

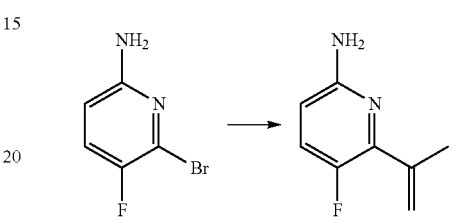

To a solution 6-bromo-5-fluoro-pyridin-2-ylamine (850 mg, 4.45 mmol) in dimethylacetamide (13.5 mL) was added 4,4,5,5-tetramethyl-2-(prop-1-en-2-yl)-1,3,2-dioxaborolane (1.09 mL, 5.79 mmol), palladium tetrakis(triphenylphosphine) (514 mg, 445 μmol) and tribasic potassium phosphate (1.89 g, 8.9 mmol) in water (4 mL, 223 mmol). The mixture was sealed in a microwave vial and heated at 150° C. in a microwave for 15 min. Upon cooling, the mixture was diluted with EtOAc, washed with water and brine, concentrated on to silica gel, and chromatographed (20% to 100% EtOAc in hexanes) to give 5-fluoro-6-isopropenyl-pyridin-2-ylamine contaminated with catalyst-derived impurities (~800 mg) that was used directly in the next step without further purification.

Step 4

5-Fluoro-6-isopropylpyridin-2-amine

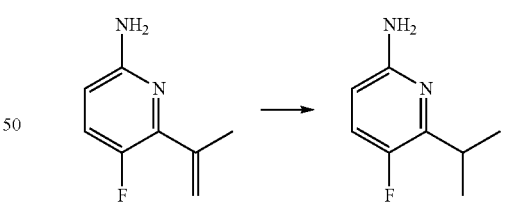

To a solution of 5-fluoro-6-isopropenyl-pyridin-2-ylamine (crude from last step, 4.45 mmol) in methanol (13.5 mL) was added 10% palladium on carbon (95 mg) at room temperature. A hydrogen balloon (1 atm) was attached and the mixture was stirred overnight. After 18 h, the mixture was filtered over Celite, concentrated on to silica gel, and chromatographed (10% to 40% EtOAc in hexanes) to give 5-fluoro-6-isopropylpyridin-2-amine (470 mg, 69% over two steps). $^1$H NMR (400 MHz, CHLOROFORM-$d_6$) δ ppm 7.12 (t, J=9.2 Hz, 1H), 6.30 (dd, J=8.5, 3.0 Hz, 1H), 4.31 (br. s, 2H), 4.15 (m, 1H), 1.26 (d, J=7.2 Hz, 6H).

Step 5

Ethyl 6-chloro-4-(5-fluoro-6-isopropylpyridin-2-ylamino)pyridazine-3-carboxylate

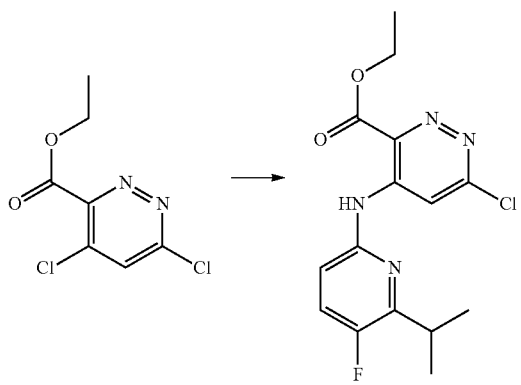 [SMILES: CCOC(=O)c1nnc(Cl)cc1Cl ; CCOC(=O)c1nnc(Cl)cc1Nc1ccc(F)c(C(C)C)n1]

To a solution of ethyl 4,6-dichloropyridazine-3-carboxylate (674 mg, 3.05 mmol) in acetonitrile (10 mL) was added 5-fluoro-6-isopropylpyridin-2-amine (470 mg, 3.05 mmol) and heated at 130° C. in a sealed tube for 18 h. Upon completion, the mixture was concentrated on to silica gel and purified by chromatography (silica. 10% to 33% EtOAc in hexanes) to give recovered aniline (300 mg) and ethyl 6-chloro-4-(5-fluoro-6-isopropylpyridin-2-ylamino)pyridazine-3-carboxylate (150 mg, 22%). $^1$H NMR (400 MHz, CHLOROFORM-$d_6$) δ ppm 10.72 (s, 1H), 9.23 (s, 1H), 7.38 (t, J=8.4 Hz, 1H), 6.79 (dd, J=8.5, 2.8 Hz, 1H), 4.57 (m, 2H), 3.45 (m, 1H), 1.53 (m, 3H), 1.36 (d, J=6.9 Hz, 6H).

Step 6

6-Chloro-4-(5-fluoro-6-isopropylpyridin-2-ylamino)pyridazine-3-carboxamide

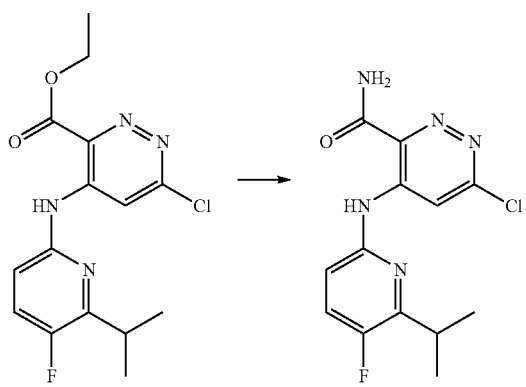 [SMILES: CCOC(=O)c1nnc(Cl)cc1Nc1ccc(F)c(C(C)C)n1 ; CC(C)c1nc(Nc2cc(Cl)nnc2C(N)=O)ccc1F]

To a solution of ethyl 6-chloro-4-(5-fluoro-6-isopropylpyridin-2-ylamino)pyridazine-3-carboxylate (290 mg, 856 µmol) was added 7N ammonia in MeOH (12.2 mL, 85.6 mmol). The mixture was stirred at 40° C. for 18 h, after which the solvent was removed to give 6-chloro-4-(5-fluoro-6-isopropylpyridin-2-ylamino)pyridazine-3-carboxamide (250 mg, 94%) as an off-white solid. $^1$H NMR (400 MHz, CHLOROFORM-$d_6$) δ ppm 11.86 (s, 1H), 9.26 (s, 1H), 8.19 (br. s, 1H), 7.36 (t, J=8.8 Hz, 1H), 6.79 (dd, J=8.5, 2.8 Hz, 1H), 5.70 (br. s, 1H), 3.45 (m, 1H), 1.37 (d, J=6.7 Hz, 6H).

Step 7 tert-Butyl (3R,4R)-4-(6-carbamoyl-5-(5-fluoro-6-isopropylpyridin-2-ylamino)pyridazin-3-ylamino)tetrahydro-2H-pyran-3-ylcarbamate

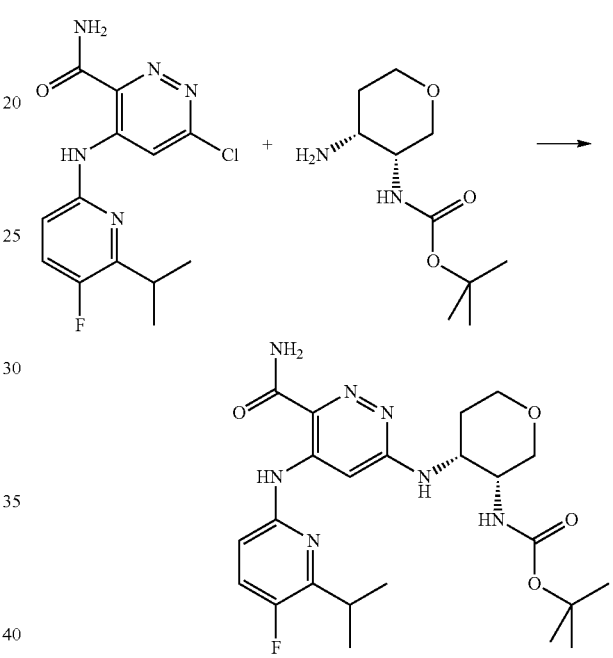

To a solution of 6-chloro-4-(5-fluoro-6-isopropylpyridin-2-ylamino)pyridazine-3-carboxamide (250 mg, 807 µmol) in NMP (3.2 mL) was added tert-butyl (3R,4R)-4-aminotetrahydro-2H-pyran-3-ylcarbamate (174 mg, 807 µmol) and the mixture heated to 140° C. Over the next 36 h three additional portions of tert-butyl (3R,4R)-4-aminotetrahydro-2H-pyran-3-ylcarbamate (174 mg, 807 µmol) were added at 12 h intervals. At 48 h the mixture was cooled, diluted with EtOAc, and washed with water and brine (2×). The organic layer was concentrated onto silica and purified by chromatography (70% to 100% EtOAc in hexanes) to give tert-butyl (3R,4R)-4-(6-carbamoyl-5-(5-fluoro-6-isopropylpyridin-2-ylamino)pyridazin-3-ylamino)tetrahydro-2H-pyran-3-ylcarbamate (100 mg, 25%). $^1$H NMR (400 MHz, CHLOROFORM-$d_6$) δ ppm 11.49 (s, 1H), 8.22 (s, 1H), 8.06 (br. s, 1H), 7.29 (t, J=9.4 Hz, 1H), 6.70 (dd, J=8.9, 3.0 Hz, 1H), 6.07 (br. s, 1H), 5.50 (br. s, 1H), 5.35 (br. s, 1H), 4.26 (br. s, 1H), 4.03 (m, 2H), 3.92 (d, J=11.4 Hz, 1H), 3.68 (d, J=11.5 Hz, 1H), 3.61 (t, J=11.8 Hz, 1H), 3.41 (m, 1H), 2.24 (d, J=11.2 Hz, 1H), 1.81 (m, 1H), 1.49 (s, 9H), 1.35 (d, J=6.9 Hz, 6H).

141
Step 8

6-((3R,4R)-3-aminotetrahydro-2H-pyran-4-ylamino)-4-(5-fluoro-6-isopropylpyridin-2-ylamino)pyridazine-3-carboxamide

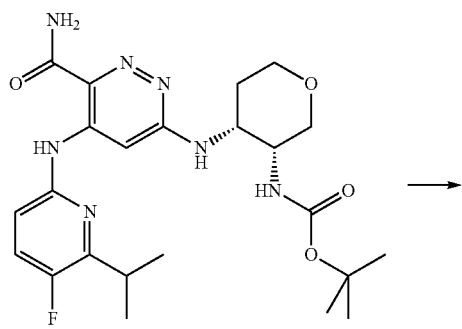

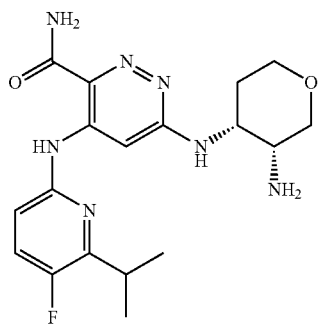

To a solution of tert-butyl (3R,4R)-4-(6-carbamoyl-5-(5-fluoro-6-isopropylpyridin-2-ylamino)pyridazin-3-ylamino)tetrahydro-2H-pyran-3-ylcarbamate (100 mg, 204 μmol) in dichloromethane (3 mL) was added trifluoroacetic acid (466 mg, 315 μL, 4.1 mmol) and the mixture stirred at room temperature for 16 h. The mixture was diluted with 25% aqueous NH₄OH, dichloromethane, and water. The organic phase was separated and washed with water (2×), then concentrated in vacuo and purified by chromatography (silica, 3 to 10% methanol in dichloromethane) to give 6-((3R,4R)-3-aminotetrahydro-2H-pyran-4-ylamino)-4-(5-fluoro-6-isopropylpyridin-2-ylamino)pyridazine-3-carboxamide (39 mg, 100 μmol, 49%) as a white solid. $^1$H NMR (400 MHz, DMSO-$d_6$) δ ppm 11.76 (s, 1H), 8.39 (s, 1H), 7.85 (s, 1H), 7.65 (s, 1H), 7.60 (t, J=9.2 Hz, 1H), 6.88 (dd, J=8.9, 2.9 Hz, 1H), 6.78 (d, J=7.7 Hz, 1H), 3.96 (br. s, 1H), 3.80 (m, 1H), 3.70 (dd, J=11.4, 2.8 Hz, 1H), 3.49 (dd, J=11.4. 1.7 Hz, 1H), 3.37 (m, 2H), 2.96 (s, 1H), 1.80 (m, 1H), 1.69 (m, 2H), 1.29 (d, J=6.8 Hz, 6H); MS (EI/CI) m/z: 390.2 [M+H].

142
Example 42

6-((3R,4R)-3-Aminotetrahydro-2H-pyran-4-ylamino)-4-(5-isopropyl-6-methoxypyridin-2-ylamino)pyridazine-3-carboxamide Step 1

6-Methoxy-5-(prop-1-en-2-yl)pyridin-2-amine

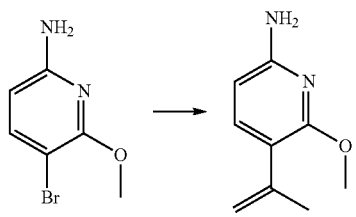

To a solution 5-bromo-6-methoxypyridin-2-amine (1.72 g, 8.47 mmol) in dimethylacetamide (26 mL) was added 4,4,5,5-tetramethyl-2-(prop-1-en-2-yl)-1,3,2-dioxaborolane (2.07 mL, 11.0 mmol), palladium tetrakis(triphenylphoshine) (979 mg, 847 μmol) and tribasic potassium phosphate (3.6 g, 16.9 mmol) in water (7.63 mL, 424 mmol). The mixture was sealed in a microwave vial and heated at 150° C. in a microwave for 15 min. Upon cooling, the mixture was diluted with EtOAc and Et₂O, washed with water and brine, concentrated on to silica gel, and chromatographed (10% to 40% EtOAc in hexanes) to give 6-methoxy-5-(prop-1-en-2-yl)pyridin-2-amine contaminated with catalyst-derived impurities (~950 mg). $^1$H NMR (400 MHz, CHLOROFORM-$d_6$) δ ppm 7.34 (d, J=8.0 Hz, 1H), 6.06 (d, J=8.1 Hz, 1H), 5.19 (m, 1H), 5.09 (m, 1H), 4.29 (br. s, 2H), 3.91 (s, 3H), 2.10 (s, 3H).

Step 2

5-Isopropyl-6-methoxypyridin-2-amine

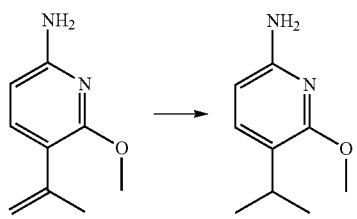

To a solution of 5-fluoro-6-isopropenyl-pyridin-2-ylamine (crude from Step 1, 8.47 mmol) in methanol (17.5 mL) was added 10% palladium on carbon (123 mg) at room temperature. A hydrogen balloon (1 atm) was attached and the mixture was stirred overnight. After 18 hours, the mixture was filtered over Celite, concentrated onto silica gel, and chromatographed (10% to 40% ethyl acetate in hexanes) to give 5-isopropyl-6-methoxypyridin-2-amine (740 mg, 53% over two steps). $^1$H NMR (400 MHz, CHLOROFORM-$d_6$) δ ppm 7.26 (d, J=7.8 Hz, 1H), 6.07 (d, J=8.1 Hz, 1H), 4.19 (br. s, 2H), 3.90 (s, 3H), 3.08 (m, 1H), 1.17 (d, J=6.9 Hz, 6H).

Step 3

Ethyl 6-chloro-4-(5-isopropyl-6-methoxypyridin-2-ylamino)pyridazine-3-carboxylate

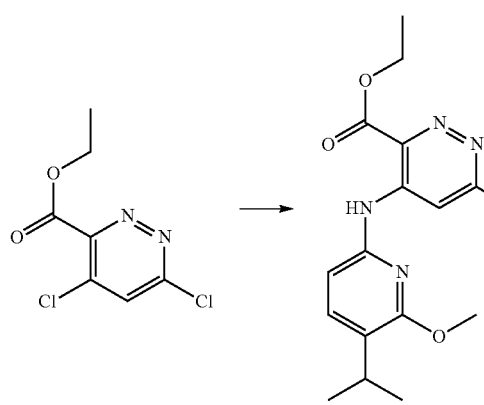

To a solution of ethyl 4,6-dichloropyridazine-3-carboxylate (1.47 g, 6.64 mmol) in acetonitrile (7.6 mL) was added 5-isopropyl-6-methoxypyridin-2-amine (830 mg, 4.99 mmol) and the mixture heated at 100° C. in a sealed tube for 18 h. Upon completion, the mixture was concentrated onto silica gel and purified by chromatography (silica, 10% to 80% ethyl acetate in hexanes) to give ethyl 6-chloro-4-(5-isopropyl-6-methoxypyridin-2-ylamino)pyridazine-3-carboxylate (500 mg, 28.5%). MS (EI/CI) m/z: 351.2 [M+H].

Step 4

6-Chloro-4-(5-isopropyl-6-methoxypyridin-2-ylamino)pyridazine-3-carboxamide

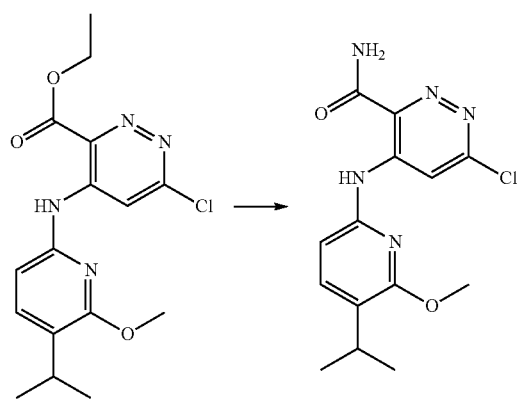 [SMILES: CCOC(=O)c1nnc(Cl)cc1Nc1ccc(C(C)C)c(OC)n1 ; COc1nc(Nc2cc(Cl)nnc2C(N)=O)ccc1C(C)C]

To a solution of ethyl 6-chloro-4-(5-isopropyl-6-methoxy-pyridin-2-ylamino)pyridazine-3-carboxylate (500 mg, 1.43 mmol) was added 7N ammonia in MeOH (20.5 mL, 143 mmol). The mixture was stirred at 40° C. for 18 h, after which the solvent was removed to give 6-chloro-4-(5-isopropyl-6-methoxy-pyridin-2-ylamino)-pyridazine-3-carboxylic acid amide (450 mg, 98%) as an off-white solid. $^1$H NMR (400 MHz, CHLOROFORM-d$_6$) δ ppm 11.47 (s, 1H), 9.10 (s, 1H), 8.17 (s, 1H), 7.48 (d, J=8.0 Hz, 1H), 6.53 (d, J=7.7 Hz, 1H), 5.71 (s, 1H), 4.04 (s, 3H), 3.18 (m, 1H), 1.23 (d, J=7.1 Hz, 6H).

Step 5 tert-Butyl (3R,4R)-4-(6-carbamoyl-5-(5-isopropyl-6-methoxypyridin-2-ylamino)pyridazin-3-ylamino)tetrahydro-2H-pyran-3-ylcarbamate

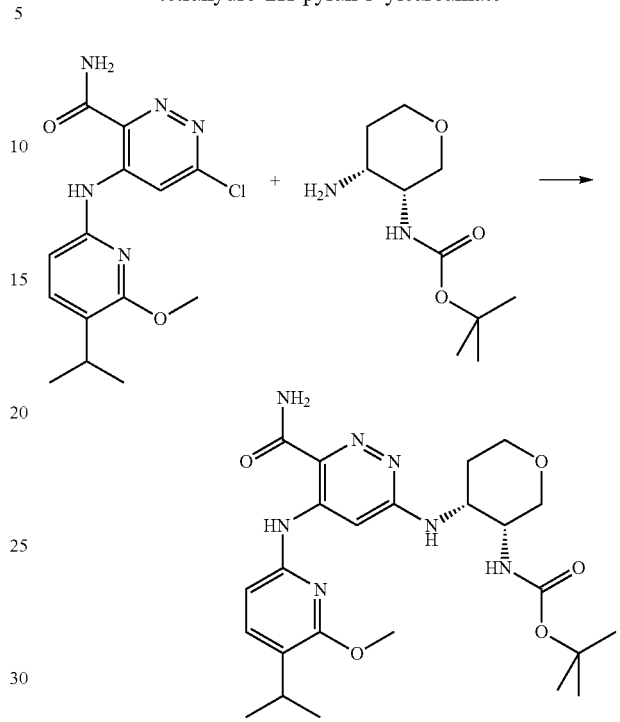

To a solution of 6-chloro-4-(5-isopropyl-6-methoxypyridin-2-ylamino)pyridazine-3-carboxamide (250 mg, 777 μmol) in NMP (2.6 mL) was added tert-butyl (3R,4R)-4-aminotetrahydro-2H-pyran-3-ylcarbamate (672 mg, 2.33 mmol) in four portions approximately every 12 h and heated to 140° C. in the periods between additions. After a total of 48 h, the mixture was cooled then diluted with ethyl acetate and brine. The phases were separated then the organic phase was washed with brine (2×), concentrated in vacuo and purified by chromatography (silica, 0 to 4% of a 99.5:0.5 methanol:NH$_4$OH solution in dichloromethane) to give tert-butyl (3R,4R)-4-(6-carbamoyl-5-(5-isopropyl-6-methoxypyridin-2-ylamino)pyridazin-3-ylamino)tetrahydro-2H-pyran-3-ylcarbamate (141 mg, 281 μmol, 36%) as light brown solid. MS (EI/CI) m/z: 502.3 [M+H].

Step 6

6-((3R,4R)-3-Aminotetrahydro-2H-pyran-4-ylamino)-4-(5-isopropyl-6-methoxypyridin-2-ylamino)pyridazine-3-carboxamide

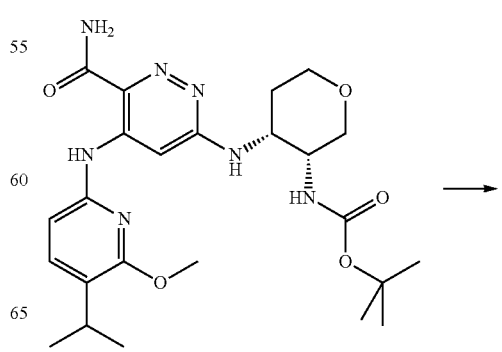

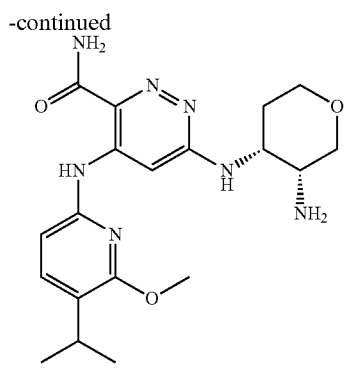

To a solution of tert-butyl (3R,4R)-4-(6-carbamoyl-5-(5-isopropyl-6-methoxypyridin-2-ylamino)pyridazin-3-ylamino)tetrahydro-2H-pyran-3-ylcarbamate (141 mg, 281 µmol) in dichloromethane (4.3 mL) was added trifluoroacetic acid (641 mg, 433 µL, 5.62 mmol) and the mixture stirred at room temperature for 16 h. The mixture was diluted with 25% aqueous NH$_4$OH, dichloromethane, and water. The organic phase was separated and washed with water (2×), then concentrated in vacuo and purified by chromatography (silica, 3 to 10% of a 99.5:0.5 methanol:NH$_4$OH solution in dichloromethane) to give 6-((3R,4R)-3-aminotetrahydro-2H-pyran-4-ylamino)-4-(5-isopropyl-6-methoxypyridin-2-ylamino)pyridazine-3-carboxamide (35 mg, 87 µmol, 31%) as an off-white solid. $^1$H NMR (400 MHz, DMSO-d$_6$) δ ppm 11.53 (s, 1H), 8.37 (s, 1H), 7.70 (s, 1H), 7.62 (s, 1H), 7.54 (d, J=8.1 Hz, 1H), 6.80 (d, J=7.8 Hz, 1H), 6.54 (d, J=8.0 Hz, 1H), 4.05 (br. s, 1H), 3.81 (d, J=11.9 Hz, 1H), 3.67 (dd, J=10.9, 3.5 Hz, 1H), 3.49 (dd, J=11.1. 1.9 Hz, 1H), 3.37 (m, 2H), 3.08 (m, 1H), 2.97 (s, 1H), 1.81 (m, 1H), 1.65 (m, 1H), 1.16 (d, J=6.8 Hz, 6H); MS (EI/CI) m/z: 402.3 [M+H].

Example 43

6-((3R,4R)-3-aminotetrahydro-2H-pyran-4-ylamino)-4-(6-isopropoxypyridin-2-ylamino)pyridazine-3-carboxamide Step 1

Ethyl 6-chloro-4-(6-isopropoxypyridin-2-ylamino)pyridazine-3-carboxylate

To a solution of ethyl 4,6-dichloropyridazine-3-carboxylate (1.63 g, 7.36 mmol) in acetonitrile (25 mL) was added 6-isopropoxypyridin-2-amine (1.12 g, 7.36 mmol) and the mixture heated at 130° C. in a sealed tube for 60 h. Upon completion, the mixture was concentrated on to silica gel and purified by chromatography (20% to 66% EtOAc in hexanes) to give ethyl 6-chloro-4-(6-isopropoxypyridin-2-ylamino)pyridazine-3-carboxylate (330 mg, 13%). MS (EI/CI) m/z: 337.1 [M+H].

Step 2

6-Chloro-4-(6-isopropoxypyridin-2-ylamino)pyridazine-3-carboxamide

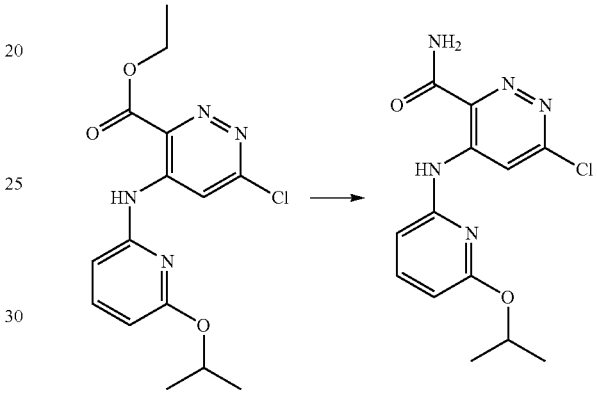

To a solution of give ethyl 6-chloro-4-(6-isopropoxypyridin-2-ylamino)pyridazine-3-carboxylate (530 mg, 1.57 mmol) was added 7N ammonia in MeOH (16.9 mL, 118 mmol). The mixture was stirred at 40° C. for 18 h, after which the solvent was removed to give 6-chloro-4-(6-isopropoxypyridin-2-ylamino)pyridazine-3-carboxamide (470 mg, 97%) as an off-white solid. $^1$H NMR (400 MHz, CHLOROFORM-d$_6$) δ ppm 11.57 (s, 1H), 9.08 (s, 1H), 8.17 (s, 1H), 7.58 (t, J=7.8 Hz, 1H), 6.50 (d, J=7.3 Hz, 1H), 6.44 (d, J=8.0 Hz, 1H), 5.69 (s, 1H), 5.23 (m, 1H), 1.47 (d, J=6.3 Hz, 6H).

Step 3

(3R,4R)-4-(6-Carbamoyl-5-(6-isopropoxypyridin-2-ylamino)pyridazin-3-ylamino)tetrahydro-2H-pyran-3-ylcarbamate

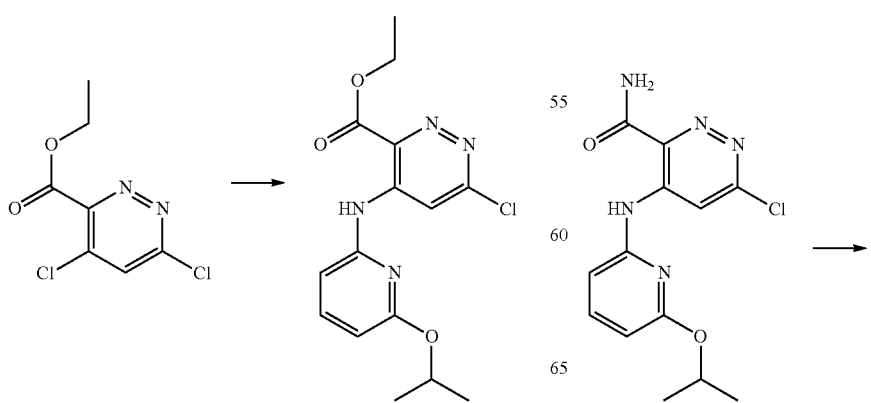

-continued

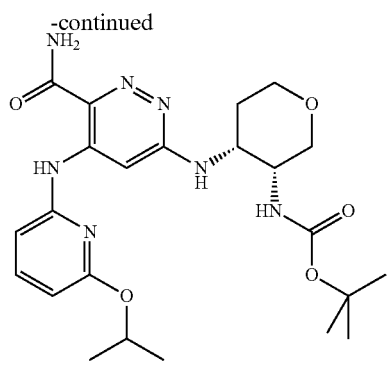

To a solution of 6-chloro-4-(6-isopropoxypyridin-2-ylamino)pyridazine-3-carboxamide (270 mg, 877 μmol, Eq: 1.00) in NMP (3.51 mL) was added tert-butyl (3R,4R)-4-aminotetrahydro-2H-pyran-3-ylcarbamate (190 mg, 877 μmol, Eq: 1.00) and the mixture heated to 140° C. Over the next 36 hrs three additional portions of amine were added at 12 h intervals. At 48 hrs the mixture was cooled, diluted with EtOAc, and washed with water and brine (2×). The organic layer was concentrated onto silica and purified by chromatography (70% to 100% EtOAc/hexanes) to (3R,4R)-4-(6-carbamoyl-5-(6-isopropoxypyridin-2-ylamino)pyridazin-3-ylamino)tetrahydro-2H-pyran-3-ylcarbamate (190 mg, 44.4%). $^1$H NMR (400 MHz, CHLOROFORM-$d_6$) δ ppm 11.37 (s, 1H), 8.06 (s, 1H), 7.92 (s, 1H), 7.49 (t, J=7.5 Hz, 1H), 6.44 (d, J=8.0 Hz, 1H), 6.31 (d, J=8.2 Hz, 1H), 5.91 (s, 1H), 5.67 (s, 1H), 5.38 (d, J=8.5 Hz, 1H), 5.15 (m, 1H), 4.30 (m, 1H), 4.05 (s, 1H), 4.00 (d, J=12.5 Hz, 1H), 3.90 (d, J=12.3 Hz, 1H), 3.68 (d, J=11.3 Hz, 1H), 3.61 (t, J=10.8 Hz, 1H), 2.27 (s, 1H), 1.79 (m, 1H), 1.44 (m, 15H).

Step 4

6-((3R,4R)-3-Aminotetrahydro-2H-pyran-4-ylamino)-4-(6-isopropoxypyridin-2-ylamino)pyridazine-3-carboxamide

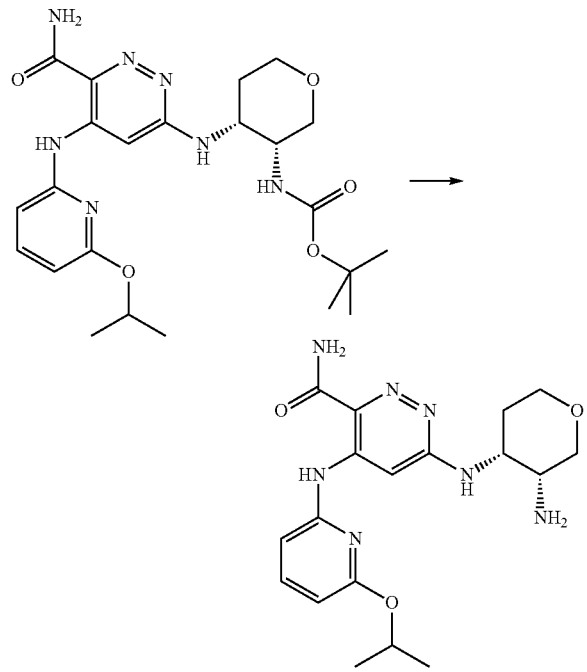

To a solution of tert-butyl (3R,4R)-4-(6-carbamoyl-5-(6-isopropoxypyridin-2-ylamino)pyridazin-3-ylamino)tetrahydro-2H-pyran-3-ylcarbamate (185 mg, 379 μmol) in dichloromethane (5.9 mL) was added trifluoroacetic acid (865 mg, 585 μL, 7.59 mmol) and the mixture stirred at r.t. for 16 h. The mixture was diluted with 25% aqueous NH$_4$OH, dichloromethane, and water. The organic phase was separated and washed with water (2×), then concentrated in vacuo and purified by chromatography (silica, 3 to 10% of a 99.5:0.5 methanol:NH$_4$OH solution in dichloromethane) to give 6-((3R,4R)-3-aminotetrahydro-2H-pyran-4-ylamino)-4-(6-isopropoxypyridin-2-ylamino)pyridazine-3-carboxamide (68 mg, 176 μmol, 46%) as an off-white solid. $^1$H NMR (400 MHz, DMSO-$d_6$) δ ppm 11.56 (s, 1H), 8.38 (s, 1H), 7.62 (m, 3H), 6.76 (d, J=7.7 Hz, 1H), 6.54 (d, J=7.8 Hz, 1H), 6.35 (d, J=8.2 Hz, 1H), 5.18 (m, 1H), 4.07 (br. s, 1H), 3.80 (d, J=11.3 Hz, 1H), 3.67 (dd, J=11.6, 3.8 Hz, 1H), 3.50 (dd, J=11.9. 2.3 Hz, 1H), 3.39 (m, 2H), 2.96 (s, 1H), 1.78 (m, 1H), 1.68 (m, 2H), 1.33 (dd, J=6.3, 1.7 Hz, 6H); MS (EI/CI) m/z: 388.3 [M+H].

Biological Examples

SYK Assay Information

Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 μL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)

Streptavidin coated beads: Streptavidin Sepharose™, suspension 5.0 mL, in 50 mM EDTA/PBS diluted (1:100), (Amersham, Cat. No.: 17-5113-01)

Compounds: 10 mM in 100% dimethylsulfoxide (DMSO), final conc.: compound 0.003-100 uM in 10% DMSO Enzyme: Recombinant human full length SYK protein (Invitrogen Cat. No.: PV4089) dephosphorylated by protein tyrosine phosphatase PTP1B, working solution 8.89 nM, final conc.:0.004 μM.

Peptide 1: biotinylated peptide is derived from a naturally occurring phosphor-acceptor consensus sequence (Biotin-EPEGDYEEVLE), special order from QCB, stock solution 20 mM, final conc.: 10 μM.

ATP: Adenosine-5'-triphosphate 20 mM, (ROCHE Cat. No.: 93202720), final concentration: 20 μM Buffer: HEPES: 2-Hydroxyethyl piperazine-2-ethanesulfonic acid (Sigma, Cat. No.: H-3375) final concentration: 50 mM HEPES pH7.5

BSA: Bovine Serum Albumin Fraction V, fatty acid free (Roche Diagnostics GmbH, Cat. No. 9100221) diluted to a final concentration of 0.1%

EDTA: EDTA stock solution 500 mM, (GIBCO, Cat. No.: 15575-038) final concentration: 0.1 mM DTT: 1,4-Dithiothreitol (Roche Diagnostics GmbH, Cat. No.: 197777), final conc.: 1 mM MgCl$_2$×6H$_2$O: MERCK, Cat. No.: 105833.1000, final concentration: 10 mM Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0.1% BSA, pH 7.5

Bead wash buffer: 10 g/L PBS (Phosphate buffered saline) with 2M NaCl+ 1% phosphoric acid.

Experimental Method:

In 20 µL volume, 18 µL of recombinant human full length SYK [8.89 nM] was mixed with 2 µL of 10× concentrations of the test compounds, [usually 100 µM-0.003 µM] in [10%] DMSO and the mixture was incubated for 15 min at RT.

The kinase reaction was initiated by the addition of 20 µL 2× substrate cocktail containing the Biotin-peptide substrate [20 µM], ATP [40 µM] and $^{33}$PγATP [2 µCi/rxn]. After incubation at RT for 30 min, the reaction was terminated by the transfer of 25 µL of the reaction sample to a 96 well 0.65 µm Millipore MADVNOB membrane/plate containing 100 µL 5 mM EDTA and 10% Streptavidine coated beads in PBS.

The unbound radionucleotides were washed under vacuum with 3×250 µL 2M NaCl; 2×250 µL 2M NaCl+ 1% phosphoric acid and 1×250 µL H$_2$O. After the last wash, membrane/plates were transferred to an adaptor plate, heat dried for 1 hour min at 60° C., and 60 µL scintillation cocktail was added to each well and the amount of radioactivity was counted in a top counter.

The percent inhibition was calculated based on the uninhibited enzyme rate:

% Inhibition=(1−((Test−Positive Control)/(Negative Control−Positive Control)))*100

The IC$_{50}$ was calculated using a non-linear curve fit with XLfit software (ID Business Solution Ltd., Guilford, Surrey, UK).

| Compound | ENZYME FILTRATION IC$_{50}$ (M) | Ic50: HUMAN WHOLE BLOOD (M) |
| --- | --- | --- |
| I-1 | 0.019 | |
| I-2 | 0.011 | |
| I-3 | 0.065 | |
| I-4 | 0.090 | |
| I-5 | 0.098 | |
| I-6 | 0.464 | |
| I-7 | 0.004 | |
| I-8 | 0.015 | |
| I-9 | 0.367 | |
| I-10 | 0.011 | |
| I-11 | 0.003 | |
| I-12 | 0.003 | |
| I-13 | 0.020 | |
| I-14 | 0.003 | |
| I-15 | 0.00558 | 0.0315 |
| I-16 | 0.01697 | 0.15965 |
| I-17 | 0.00428 | 0.0306 |
| I-18 | 0.0047 | 0.07053 |
| I-19 | 0.04302 | 1.04462 |
| I-20 | 0.1449 | 31.7963 |
| I-21 | 0.0051 | 0.4492 |
| I-22 | 0.264 | 21.4529 |
| I-23 | 0.0089 | 0.8098 |
| I-24 | 0.01145 | 0.2365 |
| I-25 | 0.00325 | 0.81055 |
| I-26 | 0.005 | 0.4327 |
| I-27 | 0.0057 | 0.3126 |
| I-28 | 0.25245 | 1.5861 |
| I-29 | 0.04595 | 1.79665 |
| I-30 | 0.0222 | 0.4866 |
| I-31 | 0.0054 | 0.1964 |
| I-32 | 0.0109 | 0.2349 |
| I-33 | | 1.4157 |
| I-34 | 0.01035 | 0.31625 |
| I-35 | 0.00205 | 0.92335 |
| I-36 | 0.1766 | 2.0892 |
| I-37 | 0.24205 | 2.3446 |
| I-38 | 0.00175 | 0.6416 |
| I-39 | | 0.818 |
| I-40 | | 0.3321 |
| I-41 | | 0.4944 |
| I-42 | | 0.9093 |
| I-43 | | 0.3718 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of Formula I:

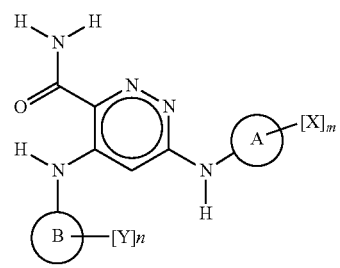

wherein:
 A is cycloalkyl or heterocycloalkyl;
  each X is independently amino, C(=O)NHR, C(=O)R, C(=O)OR, OR, NHC(=O)R, CH$_2$NHR, lower alkyl, hydroxy lower alkyl, or hydroxy lower alkyl amino;
  each R is independently H, or R';
  each R' is independently lower alkyl, heterocycloalkyl, phenyl, heteroaryl, or heteroaryl lower alkyl, optionally substituted with one or more R";
  each R" is independently hydroxy, lower alkyl amido, carboxy, oxo, lower alkoxy, lower alkyl amino, or lower dialkyl amino;
 m is 0, 1, or 2;
 B is phenyl or mono- or bicyclic heteroaryl;
 each Y is independently halo, lower alkyl, lower alkoxy, lower haloalkyl, lower hydroxyalkyl, heteroaryl, lower alkyl sulfonyl, cycloalkyl, or heterocycloalkyl; and
 n is 0, 1, or 2;
or a pharmaceutically acceptable salt thereof.

2. The compound of claim 1, wherein B is pyridyl.

3. The compound of claim 2, wherein A is cyclohexyl or tetrahydropyranyl.

4. The compound of claim 3, wherein m is 1.
5. The compound of claim 4, wherein X is amino.
6. The compound of claim 5, wherein n is 1.
7. The compound of claim 6, wherein Y is lower alkyl, cycloalkyl, heteroaryl, or lower alkyl sulfonyl.
8. The compound of claim 7, wherein Y is lower alkyl.
9. The compound of claim 5, wherein n is 2.
10. The compound of claim 9, wherein one Y is lower alkyl and the other is halo or lower alkyl.
11. The compound of claim 1, wherein B is pyrrolo[2,3-b]pyridyl or pyrazolyl.
12. A pharmaceutical composition comprising the compound of claim 1 admixed with at least one pharmaceutically acceptable carrier, excipient or diluent.
13. A compound selected from the group consisting of:
    6-(cis-2-Amino-cyclohexylamino)-4-(6-methyl-pyridin-2-ylamino)-pyridazine-3-carboxylic acid amide;
    6-(cis-2-Amino-cyclohexylamino)-4-(6-ethyl-pyridin-2-ylamino)-pyridazine-3-carboxylic acid amide;
    6-((3R,4R)-3-Amino-tetrahydro-pyran-4-ylamino)-4-(6-methyl-pyridin-2-ylamino)-pyridazine-3-carboxylic acid amide;
    6-((1S,2R)-2-Amino-cyclohexylamino)-4-(6-[1,2,3]triazol-1-yl-pyridin-2-ylamino)-pyridazine-3-carboxylic acid amide;
    6-(cis-2-Amino-cyclohexylamino)-4-(5-methanesulfonyl-pyridin-2-ylamino)-pyridazine-3-carboxylic acid amide;
    6-((1R,2S)-2-Amino-cyclohexylamino)-4-p-tolylamino-pyridazine-3-carboxylic acid amide;
    6-((1R,2S)-2-Amino-cyclohexylamino)-4-(6-isopropyl-pyridin-2-ylamino)-pyridazine-3-carboxylic acid amide;
    6-((3R,4R)-3-Amino-tetrahydro-pyran-4-ylamino)-4-(5,6-dimethyl-pyridin-2-ylamino)-pyridazine-3-carboxylic acid amide;
    6-((1R,2S)-2-Amino-cyclohexylamino)-4-(1-methyl-1H-pyrazol-3-ylamino)-pyridazine-3-carboxylic acid amide;
    6-((1R,2S)-2-Amino-cyclohexylamino)-4-(6-methyl-pyridin-2-ylamino)-pyridazine-3-carboxylic acid amide;
    6-((1R,2S)-2-Amino-cyclohexylamino)-4-(1-methyl-1H-pyrrolo[2,3-b]pyridin-6-ylamino)-pyridazine-3-carboxylic acid amide;
    6-((1R,2S)-2-Amino-cyclohexylamino)-4-(6-cyclopropyl-pyridin-2-ylamino)-pyridazine-3-carboxylic acid amide;
    6-((1R,2S)-2-Amino-cyclohexylamino)-4-(5-fluoro-6-methyl-pyridin-2-ylamino)-pyridazine-3-carboxylic acid amide;
    6-((1S,2R)-2-Amino-cyclohexylamino)-4-(6-ethyl-pyridin-2-ylamino)-pyridazine-3-carboxylic acid amide;
    6-((1R,2S)-2-Amino-cyclohexylamino)-4-(5,6-dimethyl-pyridin-2-ylamino)-pyridazine-3-carboxylic acid amide;
    6-((1R,2S)-2-Amino-cyclohexylamino)-4-(5-chloro-6-methyl-pyridin-2-ylamino)-pyridazine-3-carboxylic acid amide;
    6-((1R,2S)-2-Amino-cyclohexylamino)-4-(5,6-dimethoxy-pyridin-2-ylamino)-pyridazine-3-carboxylic acid amide;
    6-((1R,2S)-2-aminocyclohexylamino)-4-(4,6-dimethylpyridin-2-ylamino)pyridazine-3-carboxamide 2,2,2-trifluoroacetate;
    6-((1R,2S)-2-aminocyclohexylamino)-4-(6-tert-butylpyridin-2-ylamino)pyridazine-3-carboxamide;
    6-(cyclohexylamino)-4-(6-cyclopropylpyridin-2-ylamino)pyridazine-3-carboxamide;
    6-((1R,2S)-2-aminocyclohexylamino)-4-(6-cyclobutylpyridin-2-ylamino)pyridazine-3-carboxamide;
    6-((1R,2S)-2-aminocyclohexylamino)-4-(1-methyl-1H-benzo[d]imidazol-4-ylamino)pyridazine-3-carboxamide;
    4-(6-(2H-1,2,3-triazol-2-yl)pyridin-2-ylamino)-6-((1R,2S)-2-aminocyclohexylamino)pyridazine-3-carboxamide;
    6-((1R,2S)-2-aminocyclohexylamino)-4-(6,7-dihydro-5H-cyclopenta[b]pyridin-2-ylamino)pyridazine-3-carboxamide;
    6-((1R,2S)-2-Amino-cyclohexylamino)-4-(6-isopropyl-5-methyl-pyridin-2-ylamino)-pyridazine-3-carboxylic acid amide;
    6-((1R,2S)-2-aminocyclohexylamino)-4-(6-propylpyridin-2-ylamino)pyridazine-3-carboxamide;
    6-((3R,4R)-3-Amino-tetrahydro-pyran-4-ylamino)-4-(6-isopropyl-5-methyl-pyridin-2-ylamino)-pyridazine-3-carboxylic acid amide;
    6-((1R,2S)-2-aminocyclohexylamino)-4-(3,5-dimethylphenylamino)pyridazine-3-carboxamide;
    6-((3R,4R)-3-aminotetrahydro-2H-pyran-4-ylamino)-4-(6-tert-butylpyridin-2-ylamino)pyridazine-3-carboxamide;
    6-((1R,2S)-2-aminocyclohexylamino)-4-(6-ethoxypyridin-2-ylamino)pyridazine-3-carboxamide;
    6-((1R,2S)-2-aminocyclohexylamino)-4-(5-methoxy-6-propylpyridin-2-ylamino)pyridazine-3-carboxamide;
    6-((1R,2S)-2-aminocyclohexylamino)-4-(6-isopropyl-5-methoxypyridin-2-ylamino)pyridazine-3-carboxamide;
    4-(6-(1H-pyrazol-1-yl)pyridin-2-ylamino)-6-((1R,2S)-2-aminocyclohexylamino)pyridazine-3-carboxamide;
    6-((3R,4R)-3-aminotetrahydro-2H-pyran-4-ylamino)-4-(6-isopropyl-5-methoxypyridin-2-ylamino)pyridazine-3-carboxamide;
    6-((1R,2S)-2-aminocyclohexylamino)-4-(6-isopropyl-4-methylpyridin-2-ylamino)pyridazine-3-carboxamide;
    6-((1R,2S)-2-aminocyclohexylamino)-4-(6-(2-cyanopropan-2-yl)pyridin-2-ylamino)pyridazine-3-carboxamide;
    6-((1R,2S)-2-aminocyclohexylamino)-4-(6-(2-hydroxypropan-2-yl)pyridin-2-ylamino)pyridazine-3-carboxamide;
    6-((1R,2S)-2-aminocyclohexylamino)-4-(4-methyl-6-propylpyridin-2-ylamino)pyridazine-3-carboxamide;
    6-((3R,4R)-3-aminotetrahydro-2H-pyran-4-ylamino)-4-(4-methyl-6-propylpyridin-2-ylamino)pyridazine-3-carboxamide;
    6-((3R,4R)-3-aminotetrahydro-2H-pyran-4-ylamino)-4-(5-methoxy-6-propylpyridin-2-ylamino)pyridazine-3-carboxamide;
    6-((3R,4R)-3-aminotetrahydro-2H-pyran-4-ylamino)-4-(5-fluoro-6-isopropylpyridin-2-ylamino)pyridazine-3-carboxamide;
    6-((3R,4R)-3-aminotetrahydro-2H-pyran-4-ylamino)-4-(5-isopropyl-6-methoxypyridin-2-ylamino)pyridazine-3-carboxamide; and
    6-((3R,4R)-3-aminotetrahydro-2H-pyran-4-ylamino)-4-(6-isopropoxypyridin-2-ylamino)pyridazine-3-carboxamide.

* * * * *